(12) United States Patent
Krohn et al.

(10) Patent No.: US 7,510,718 B2
(45) Date of Patent: Mar. 31, 2009

(54) EXPRESSION VECTORS AND USES THEREOF

(75) Inventors: Kai Krohn, Salmentaka (FI); Vesna Blazevic, Tampere (FI); Marja Tahtinen, Tampere (FI); Mart Ustav, Tartu (EE); Urve Toots, Tartu (EE); Andres Mannik, Tartu (EE); Annamari Ranki, Helsinki (FI); Ene Ustav, Tartu (EE)

(73) Assignee: Fit Biotech Oyj PLC, Tampere (FI)

( * ) Notice: Subject to any disclaimer, the term of this patent is extended or adjusted under 35 U.S.C. 154(b) by 653 days.

(21) Appl. No.: 10/476,615

(22) PCT Filed: May 3, 2002

(86) PCT No.: PCT/FI02/00379

§ 371 (c)(1),
(2), (4) Date: Nov. 3, 2003

(87) PCT Pub. No.: WO02/090558

PCT Pub. Date: Nov. 14, 2002

(65) Prior Publication Data

US 2005/0026137 A1 Feb. 3, 2005

(30) Foreign Application Priority Data

May 3, 2001 (FI) .................................. 20010922

(51) Int. Cl.
*A61K 39/00* (2006.01)
*A61K 39/40* (2006.01)
*A61K 39/42* (2006.01)
*A61K 39/295* (2006.01)
*A61K 39/385* (2006.01)
*A61K 49/00* (2006.01)
*C12Q 1/70* (2006.01)
*C12N 15/00* (2006.01)

(52) U.S. Cl. .................. 424/204.1; 424/9.2; 424/159.1; 424/164.1; 424/192.1; 424/193.1; 435/5; 435/320.1

(58) Field of Classification Search ........................ None
See application file for complete search history.

(56) References Cited

U.S. PATENT DOCUMENTS

| | | | |
|---|---|---|---|
| 5,093,246 | A | 3/1992 | Cech et al. |
| 5,366,729 | A | 11/1994 | Marklund et al. |
| 5,788,961 | A | 8/1998 | Marklund et al. |
| 6,130,066 | A | 10/2000 | Tartaglia et al. |
| 6,339,065 | B1 | 1/2002 | Cooper |
| 6,479,279 | B2 | 11/2002 | Ustav |
| 6,951,928 | B1 | 10/2005 | Peltonen et al. |
| 7,118,751 | B1 | 10/2006 | Ledbetter et al. |
| 2002/0103145 | A1 | 8/2002 | Bot et al. |
| 2003/0129169 | A1 | 7/2003 | Krohn et al. |

FOREIGN PATENT DOCUMENTS

| | | |
|---|---|---|
| EP | 0 918 874 | 3/2001 |
| WO | WO 88/04300 | 6/1988 |
| WO | WO 90/11364 | 10/1990 |
| WO | WO 92/06180 | 4/1992 |
| WO | WO 92/20316 | 11/1992 |
| WO | WO 92/22635 | 12/1992 |
| WO | WO 93/14188 | 7/1993 |
| WO | WO 93/20221 | 10/1993 |
| WO | WO 94/12629 | 6/1994 |
| WO | WO 97/24451 | 7/1997 |
| WO | WO 98/02548 | 1/1998 |
| WO | 98/07876 | 2/1998 |
| WO | WO 99/43841 | 9/1999 |

OTHER PUBLICATIONS

Ilves et al., Long-Term Episomal Maintainence of Bovine Papillomavirus Type 1 Plasmids Is Determined by Attachment to Host Chromosomes, Which Is Mediated by the Viral E2 Protein and Its Binding Sites, Journal of Virology, May 1999, vol. 73, No. 5, pp. 4404-4412.*

Van Craenenbroeck et al., Episomal vectors for gene expression in mammalian cells, European Journal of Biochemistry, FEBS 2000, vol. 267, pp. 5665-5678.*

Liljeqvist et al. Surface display of functional fibronectin-binding domains on *Staphylococcus carnosus*., FEBS Letters, 1999, vol. 446, pp. 299-304.*

Jiang et al., Coadministration of Interluekin 12 Expression Vector with Antigen 2 cDNA Enhances Induction of Protective Immunity against *Coccidoides immitis*, Infection and Immunity, Nov. 1999, vol. 67, No. 11, pp. 5848-5853.*

(Continued)

*Primary Examiner*—Bruce Campell
*Assistant Examiner*—Sharon Hurt
(74) *Attorney, Agent, or Firm*—Buchanan Ingersoll & Rooney, P.C.

(57) ABSTRACT

The present invention relates to novel vectors, to DNA vaccines and gene therapeutics containing the vectors, to methods for the preparation of the vectors and DNA vaccines and gene therapeutics containing the vectors, and to therapeutic uses of the vectors. The novel vectors comprise (a) an expression cassette of a gene of a nuclear-anchoring protein, which contains (i) a DNA binding domain capable of binding to a specific DNA sequence and (ii) a functional domain capable of binding to a nuclear component and (b) a multimerized DNA sequence forming a binding site for the anchoring protein, and optionally (c) one or more expression cassettes of a DNA sequence of interest. The vectors lack a papilloma virus origin of replication.

26 Claims, 102 Drawing Sheets

OTHER PUBLICATIONS

Strasser et al., Herpes Simplex Virus DNA Vaccine Efficacy: Effect of Glycoprotein D Plasmid Constructs, Journal of Infectious Diseases, 2000, vol. 182, pp. 1304-1310.*

Farci et al., Lack of Protective Immunity Against Reinfection with Hepatitis C Virus, Sceince, 1992, vol. 258, pp. 135-140.*

Lusky et al. The bovine papillomavirus E2 protein modulates the assembly of but is not stably maintained ina replication-competent multimeric E1-replication origin complex. Proceedings of the National Academy of Sciences of the United States of America, Sep. 1994, vol. 91, pp. 8895-8899.*

Kennard et al. Expression of Cell Surface GPI-Anchored Human p97 Baculovirus-Infected Insect Cells. Biotechnology and Bioengineering, Jul. 1997, vol. 55, No. 1, pp. 41-53.*

Collings et al. Humoral and cellular immune responses to HIV-1 Nef in mice DNA-immunised with non-replicating or self-replicating expression vectors. Vaccine, 2000 (available Oct. 14, 1999), vol. 18, No. 5-6, pp. 460-467.*

Abroi et al., 1996, "Transcriptional and replicational activation functions in the bovine papillomavirus type 1 E2 protein are encoded by different structural determinants", J Virol. 70(9):6169-6179.

Androphy et al., 1987, "Bovine papillomavirus E2 trans-activating gene product binds to specific sites in papillomavirus DNA", Nature 325(6099):70-73.

Antson et al., 2000, "Structure of the intact transactivation domain of the human papillomavirus E2 protein", Nature 403(6771):805-809.

Boyer et al., 2000, "Vaccination of seronegative volunteers with a human immunodeficiency virus type 1 env/rev DNA vaccine induces antigen-specific proliferation and lymphocyte production of beta-chemokines", J Infect Dis. 181(2):476-483.

Brokaw et al., 1996, "Amino Acids Critical for the Functions of the Bovine Papillomavirus Type 1 E2 Transactivator", J. Virol. 71:23-29.

Dostatni et al., 1988, "A dimer of BPV-1 E2 containing a protease resistant core interacts with its DNA target", EMBO J. 7(12):3807-3816.

Ferguson et al., 1996, "Genetic analysis of the activation domain of bovine papillomavirus protein E2: its role in transcription and replication", J Virol. 70(7):4193-4199.

Grossel et al., 1996, "Transcriptional activation function is not required for stimulation of DNA replication by bovine papillomavirus type 1 E2", J Virol. 70(10):7264-7269.

Harris et al., 1999, "Crystal structure of the human papillomavirus type 18 E2 activation domain", Science. 284(5420):1673-1677.

Haugen et al., 1988, "Sequence-specific and general transcriptional activation by the bovine papillomavirus-1 E2 trans-activator require an N-terminal amphipathic helix-containing E2 domain", EMBO J. 7(13):4245-453.

Hegde et al., 1992, "Crystal structure at 1.7 A of the bovine papillomavirus-1 E2 DNA-binding domain bound to its DNA target", . Nature. 359(6395):505-512.

Hegde et al., 1995, "Structure of the BPV-1 E2 DNA-binding domain bound to its DNA target", J Nucl Med. 36(6 Suppl):25S-27S.

Holt et al., 1994, "DNA binding specificity of the bovine papillomavirus E1 protein is determined by sequences contained within an 18-base-pair inverted repeat element at the origin of replication", J Virol. 68(2):1904-1102.

Holt et al., 1995, "Mutational analysis of the 18-base-pair inverted repeat element at the bovine papillomavirus origin of replication: identification of critical sequences for E1 binding and in vivo replication", J Virol. 69(10):6525-6532.

Howley et al., 1996, Papillomavirinae: the viruses and their replication, Virology, Fields et al. eds. Philadelphia, Lippincott-Raven Publishers, p. 2045-2076.

Lambert et al., 1988, "The genetics of bovine papillomavirus type 1", Annu Rev Genet. 22:235-258.

Lusky et al., 1994, "The bovine papillomavirus E2 protein modulates the assembly of but is not stably maintained in a replication-competent multimeric E1-replication origin complex", Proc Natl Acad Sci U S A. 91(19):8895-8899.

McBride et al., 1989, E2 polypeptides encoded by bovine papillomavirus type 1 form dimers through the common carboxyl-terminal domain: transactivation is mediated by the conserved amino-terminal domain. Proc Natl Acad Sci U S A. 86(2):510-514.

Ohe et al., 1995, "Construction of a Novel Bovine Papillomavirus Vector Without Detectable Transforming Activity Suitable for Gene Transfer", Human Gene Therapy 6:325-333.

Sedman et al., 1997, "Binding of the E1 and E2 proteins to the origin of replication of bovine papillomavirus", J Virol. 71(4):2887-2896.

Ulmer et al., 1993, "Heterologous protection against influenza by injection of DNA encoding a viral protein", Science 259(5102):1745-1749.

Ustav et al., 1991, "Identification of the origin of replication of bovine papillomavirus and characterization of the viral origin recognition factor", EMBO J. 10(13):4321-4329.

Ustav et al., 1993, "The bovine papillomavirus origin of replication requires a binding site for the E2 transcriptional activator", PNAS USA 90:898-902.

Ustav et al., 1991, "Transient replication of BPV-1 requires two viral polypeptides encoded by the E1 and E2 open reading frames", EMBO J. 10(2):449-457.

Ivar Ilves et al., "Long-Term Episomal Maintenance of Bovine Papillomavirus Type 1 Plasmids is Determined by Attachement to Host Chromosomes, which is Mediated by the Viral E2 Protein and Its Binding Sites," Journal of Virology, V. 73, 1999, pp. 4404-4412.

Kathleen Van Craenenbroeck et al., "Episomal Vectors for Gene Expression in Mammalian Cells," Eur. J. Biochem., V. 267, 2000, pp. 5665-5678.

Auni Collings et al., "Humoral and Cellular Immune Responses to HIV-1 Nef in Mice DNA-Immunised with Non-Replicating or Self-Replicating Expression Vectors," Vaccine, V. 18, 2000, pp. 460-467.

S. Mücke et al., "Suitability of Epstein-Barr Virus-Based Episomal Vectors for Expression of Cytokine Genes in Human Lymphoma Cells," Gene Therapy, V. 4, 1997, pp. 82-92.

Siu Chun Hung et al., "Maintenance of Epstein-Barr Virus (EBV) *OriP*- Based Episomes Requires EBV-Encoded Nuclear Antigen-1 Chromosome-Binding Domains, which can be Replaced by High-Mobility Group-I or Histone H1," PNAS, V. 98, 2001, pp. 1865-1870.

Nathalie Bastien et al., "Interaction of the Papillomavirus E2 Protein with Mitotic Chromosomes," Virology, V. 270, 2000, pp. 124-134.

Tu et al., "Non-replicating Epstein-Barr Virus-based Plasmids Extend Gene Expression and Can Improve Gene Therapy *in Vivo*", The Journal of Biological Chemistry, Sep. 2000, vol. 275, No. 39, pp. 30408-30416.

Ayyavoo et al., "Immunogenicity of a Novel DNA Vaccine Cassette Expressing Multiple Human Immunodeficiency Virus (HIV-1) Accessory Genes", AIDS 2000, vol. 14 pp. 1-9.

Zheng et al., "Conditional Mutations in the Mitotic Chromosome Binding Function of the Bovine Papillomavirus Type 1 E2 Protein", Journal of Virology, Feb. 2005, vol. 79, No. 3, pp. 1500-1509.

Skeiky et al., "T Cell Expression Cloning of a *Mycrobacterium tuberculosis* Gene Encoding a Protective Antigen Associated with the Early Control of Infection", Journal of Immunology, Sep. 2000, vol. 165, pp. 7140-7149.

Warren et al., "Method for Identifying Microbial Antigens that Stimulate Specific Lymphocyte Responses: Application to *Salmonella*", Proc. Natl. Acad. Sci., Dec. 1990, vol. 87, pp. 9823-9827.

Reeves, "Molecular Biology of HMGA Proteins: hubs of nuclear function", Gene, 2001, vol. 277, pp. 63-81.

Pierce et al., "Construction of a Directed Hammerhead Ribozyme Library: Towards the Identification of Optimal Target Sites for Antisense-Mediated Gene Inhibition", Nucleic Acids Research, 1998, vol. 26, No. 22, pp. 5093-5101.

Johnston et al., "Genetic to Genomic Vaccination", Vaccine, 1997, vol. 15, No. 8, pp. 806-809.

Han et al., "Biochemical Characterization of *Candida albicans* Epitopes that can Elicit Protective and Nonprotective Antibodies", Infection and Immunology, Oct. 1997, vol. 65, No. 10, pp. 4100-4107.

Edwards et al., "Origin DNA-Binding Proteins", Current Opinion in Structural Biology, 1998, pp. 49-53.

Galperin et al., "Who's Your Neighbore? New Computational Approaches for Functional Genomics", Nature Biotechnology, Jun. 2000, vol. 18, pp. 609-613.

Berendsen et al., "A Glimpse of the Holy Grail?", Science, Oct. 1998, vol. 282, Issue 5389.

Marechal et al., "Mapping EBNA-1 Domains Involved in Binding to Metaphase Chromosomes", Journal of Virology, May 1999, vol. 73, No. 5, pp. 4385-4392.

Grossman et al., "EBNA1 and E2: A New Paradigm for Origin-Binding Proteins?", Trends in Microbiology, Mar. 1996, vol. 4, No. 3, pp. 87-89.

Bochkarev et al., Crystal Structure of the DNA-Binding Domain of the Epstein-Barr Virus Origin-Binding Protein, EBNA1, Bound to DNA, Cell, Mar. 1996, vol. 84, pp. 791-800.

Parker et al., "The Bovine Papillomavirus E2 Transactivator is Stimulated by the E1 Initiator Through the E2 Activation Domain", Virology, 2000, vol. 270, pp. 430-433.

Doyle et al., "A New Source of Endothelial Progenitor Cells—Vascular Biology Redefined?", Trends in Biotechnology, Sep. 2005, vol. 23, No. 9, pp. 444-446.

Krysan et al., "Isolation of Human Sequences that Replicate Autonomously in Human Cells", Molecular ad Cellular Biology, Mar. 1989, vol. 9, No. 3, pp. 1026-1033.

Heinzel et al., "Autonomous DNA Replication in Human Cells is Affected by the Size and the Source of the DNA", Molecular ad Cellular Biology, Apr. 1991, vol. 11, No. 4, pp. 2263-2272.

Haase et al., "Replication Control of Autonomously Replicating Human Sequences", Nucleic Acids Research, vol. 19, No. 18, pp. 5053-5058. 1991.

Krysan et al., "Autonomous Replication in Human Cells of Multimers of Specific Human and Bacterial DNA Seqquences"; Molecular ad Cellular Biology, May 1993, vol. 13, No. 5, pp. 2688-2696.

Stoll et al., "Epstein-Barr Virus/Human Vector Provides High-Level, Long-Term Expression of $\alpha_1$-Antitrypsin in Mice", Molecular Therapy, Aug. 2001, vol. 4, No. 2, pp. 122-129.

Haase et al., "Transcription Inhibits the Replication of Autonomously Replicating Plasmids in Human Cells", Molecular ad Cellular Biology, Apr. 1994, vol. 14, No. 4, pp. 2516-2524.

* cited by examiner

Nef →

Plasmid pEBO LPP

Plasmid s6E2d1EGFP

EXPRESSION VECTORS AND USES THEREOF

1. FIELD OF THE INVENTION

The present invention relates to novel vectors, to DNA vaccines and gene therapeutics containing said vectors, to methods for the preparation of the vectors and DNA vaccines and gene therapeutics containing the vectors, and to therapeutic uses of said vectors. More specifically, the present invention relates to novel vectors comprising (a) an expression cassette of a gene of a nuclear-anchoring protein, which contains (i) a DNA binding domain capable of binding to a specific DNA sequence and (ii) a functional domain capable of binding to a nuclear component and (b) a multimerized DNA forming a binding site for the anchoring protein of a nuclear-anchoring protein, and optionally (c) one or more expression cassettes of a DNA sequence of interest. In particular the invention relates to vectors that lack a papilloma virus origin of replication. The invention also relates to vectors that lack an origin of replication functional in a mammalian cell. The invention further relates to methods for expressing a DNA sequence of interest in a subject.

2. BACKGROUND OF THE INVENTION

Transfer of autologous or heterologous genes into animal or human organisms with suitable vectors is emerging as a technique with immense potential to cure diseases with a genetic background or to prevent or cure infectious diseases. Several types of viral and non-viral vectors have been developed and tested in animals and in human subjects to deliver a gene/genes that are defective by mutations and therefore nonfunctional. Examples of such vectors include Adenovirus vectors, Herpes virus vectors, Retrovirus vectors, Lentivirus vectors and Adeno-associated vectors.

Vaccination has proven to be a highly effective and economical method to prevent a disease caused by infectious agents. Since the introduction of the Vaccinia virus as an attenuated vaccine against the smallpox virus (Variola), vaccines against a multitude of human pathogens have been developed and taken into routine use. Today small pox has been eradicated by vaccinations and the same is to be expected shortly for the poliovirus. Several childhood diseases, such as pertussis, diphtheria and tetanus, can be effectively prevented by vaccinations.

In general, the most successful viral vaccines are live avirulent mutants of the disease-causing viruses. The key to the success of this approach is the fact that a living virus targets the same organs, the same type and similar number of cells, and therefore, by multiplying in the recipient, elicits a long-lasting immune response without causing the disease or causing only a mild disease. In effect, a live attenuated vaccine produces a subclinical infection, the nature's own way of immunizing. As a result, a full immune response will be induced, including humoral, cellular and innate responses, providing a long lasting and sometimes a life-long immune protection against the pathogen.

Although live attenuated vaccines are most potent, they can cause harmful side effects. Thus, an attenuated viral vaccine can revert to a virulent strain or in cases where the attenuated virus is apathogenic in adults it can still cause a disease in infants or in disabled persons. This is true in the case of viruses causing chronic infections, such as Human Immunodeficiency Virus type 1 and 2. Vaccines composed of viral and bacterial proteins or immunogenic peptides are less likely to cause unwanted side effects but may not be as potent as the live vaccines. This is especially the case with vaccines against microbes causing chronic infections, such as certain viruses and intracellular bacteria.

The strength and type of immune response is, however, also dependent on how the viral proteins are processed and how they are presented to the immune system by antigen presenting cells (APCs), such as macrophages and dendritic cells. Protein and peptide antigens are taken up by APCs via endocytosis, processed to small immunogenic peptides through an endosomal pathway and presented to T-lymphocytes (T-cells) by MHC (major histocompatibility complex) class II antigens [in man HLAs (human leukocyte antigens) class II]. In contrast, proteins synthesized de novo in APCs or in possible target cells for an immune response, will be processed through a cytoplasmic pathway and presented to T-cells by MHC class I antigens (in man HLAs class I). In general, the presentation of immunogenic peptides through the class II pathway will lead to the activation of the helper/inducer T-cells, which in turn will lead to the activation of B-cells and to antibody response. In contrast, presentation through class I MHC favors the induction of cytotoxic T-lymphocytes (CTLs), which are capable of recognition and destruction of virally infected cells.

In early 1990's, a method to mimic the antigen processing and presentation that was normally achieved by live attenuated vaccines was introduced [Ulmer, J. B. et al Science 259 (1993) 1745-1749]. It was shown that an injection of eukaryotic expression vectors in the form of circular DNA into the muscle induced take-up of this DNA by the muscle cells (and probably others) and was able to induce the expression of the gene of interest, and to raise an immune response, especially a cellular immune response in the form of CTLs, to the protein encoded by the inserted gene. Since that observation, DNA immunization has become a standard method to induce immune responses to foreign proteins in experimental animals and human studies with several DNA vaccines are underway.

Generally, the DNA vectors used in these vaccine studies contain a cloning site for the gene of interest, a strong viral promoter, such as the immediate early promoter of the CMV virus, in order to drive the expression of the gene of interest, a polyadenylation region, and an antibiotic resistance gene and a bacterial replication origin for the propagation of the DNA vector (plasmid) in bacterial cells.

With the vectors described above it is possible to obtain a detectable level of expression of the gene of interest after administering the vector to experimental animals or to humans, either by a direct injection to muscle or to skin with a particle bombardment technique or by applying the vector in a solution directly to mucous membranes. However, the expression obtained by these vectors is short lived: the vectors tend to disappear from the transfected cells little by little and are not transferred to daughter cells in a dividing cell population. The short-term expression of the gene of interest and limited number of cells targeted are probably the major reasons, why only temporary immune responses are observed in subjects immunized with DNA vectors described above. Thus, for example, Boyer et al. observed only temporary immune responses to HIV-1 Env and Rev proteins in human subjects, who were immunized several times with a vector similar to the those described above [Boyer, J. D., J Infect Dis 181 (2000) 476-483].

There is a growing interest in developing novel products useful in gene therapy and DNA vaccination. For instance papilloma virus vectors carrying the expression cassette for the gene of interest have been suggested to be useful candidates.

To date more than 70 subtypes of human papilloma viruses (HPVs) and many different animal papilloma viruses have been identified [zur Hausen, H. and de Villiers E., Annu Rev Microbiol 48 (1994) 427-447; Bernard, H., et al., Curr Top Microbiol Immunol 186 (1994) 33-54]. All papilloma viruses share a similar genome organization and the positioning of all of the translational open reading frames (ORFs) is highly conserved.

Papilloma viruses infect squamous epithelial cells of skin or mucosa at different body sites and induce the formation of benign tumors, which in some cases can progress to malignancy. The papilloma virus genomes are replicated and maintained in the infected cells as multicopy nuclear plasmids. The replication, episomal maintenance, expression of the late genes and virus assembly are tightly coupled to the differentiation of the epithelial tissue: the papilloma virus DNA episomal replication takes place during the initial amplificational replication and the second, i.e. latent, and the third, i.e. vegetative, replications in the differentiating epithelium [Howley, P. M.; Papillomavirinae: the viruses and their replication. In Virology, Fields, B. C., Knipe, D. M., Howley, P. M., Eds., Lippincott-Raven Publishers, Philadelphia, USA, 1996, 2. Edition, p. 2045-2076].

Two viral factors encoded by the E1 and E2 open reading frames have been shown to be necessary and sufficient for the initiation of the DNA replication from the papilloma virus origin in the cells [Ustav, M. and Steniund, A., EMBO J 10 (1991) 449-57; Ustav, M., et al., EMBO J 10 (1991) 4321-4329; Ustav, E., et al., Proc Natl Acad Sci USA 90 (1993) 898-902].

Functional origins for the initiation of the DNA replication have been defined for BPV1 [Ustav, M., et al., EMBO J 10 (1991) 4321-4329], HPV1a [Gopalakrishnan, V. and Khan, S., supra], HPV11 [Russell, J., Botchan, M., J Virol 69 (1995) 651-660], HPV18 [Sverdrup, F. and Khan, S., J Virol 69 (1995) 1319-1323:Sverdrup, F. and Khan, S., J Virol 68 (1994) 505-509] and many others. Characteristically, all these origin fragments have a high A/T content, and they contain several overlapping individual E1 protein recognition sequences, which together constitute the E1 binding site [Ustav, M., et al., EMBO J 10 (1991) 4321-4329; Holt, S., et al., J Virol 68 (1994) 1094-1102; Holt, S. and Wilson, V., J Virol 69 (1995) 6525-3652; Sedman, T., et al. J Virol 71 (1997) 2887-2996]. In addition, these functional origin fragments contain an E2 binding site, which is essential for the initiation of DNA replication in vivo in most cases (Ustav, E., et al., supra). The E2 protein facilitates the first step of the origin recognition by E1. After the initial binding of monomeric E1 to the origin the multimerization of E1 is initiated. This leads to the formation of the complex with the ori melting activity. It has been suggested that E2 has no influence on the following stages of the initiation of the DNA replication [Lusky, M., et al., Proc Natl Acad Sci USA 91 (1994) 8895-8899].

The BPV1 E2 ORF encodes three proteins that originate from selective promoter usage and alternative mRNA splicing [Lambert, P., et al., Annu Rev Genet 22 (1988) 235-258]. All these proteins can form homo- and heterodimers with each other and bind specifically to a 12 bp interrupted palindromic sequence 5'-ACCNNNNNNGGT-3' [Androphy, E., et al., Nature 325 (1987) 70-739].

There are 17 E2 binding sites in the BPV1 genome and up to four sites in the HPV genomes, which play a crucial role in the initiation of viral DNA replication (Ustav, E., et al., supra) and in the regulation of viral gene expression (Howley, P. M., Papillomavirinae: the viruses and their replication, in Virology, Fields, B. C., Knipe, D. M., Howley, P. M., Eds., Philadelphia: Lippincott-Raven Publishers, 1996. 2. edition, p. 2045-2076). Structural and mutational analyses have revealed three distinct functional domains in the full size E2 protein. The N-terminal part (residues 1 to 210) is an activation domain for transcription and replication. It is followed by the unstructured hinge region (residues 211 to 324) and the carboxy-terminal DNA binding-dimerization domain (residues 325 to 410) [Dostatni, N., et al., EMBO J 7 (1988) 3807-3816; Haugen, T., et al. EMBO J 7 (1988) 4245-4253; McBride, A., et al., EMBO J 7 (1988) 533-539; McBride, A., et al., Proc Natl Acad Sci USA 86 (1989) 510-514]. On the basis of X-ray crystallographical data, the DNA binding-dimerization domain of E2 has a structure of a dyad-symmetric eight-stranded antiparallel beta barrel, made up of two identical "half-barrel" subunits [Hegde, R., et al., Nature 359 (1992) 505-512; Hegde, R., J Nucl Med 36(6 Suppl) (1995) 25S-27S]. The functional elements of the transactivation domain of E2 have a very high structural integrity as confirmed by mutational analysis [Abroi, A., et al., J Virol 70 (1996) 6169-6179; Brokaw, J., et al., J Virol 71 (1996) 23-29; Grossel, M., et al., J Virol 70 (1996) 7264-7269; Ferguson, M. and Botchan, M., J Virol 70 (1996) 4193-4199] and by X-ray crystallography [Harris, S., and Botchan, M. R., Science 284 (1999) 1673-1677 and Antson, A. et al., Nature 403 (2000) 805-809]. In addition, X-ray crystallography shows that the N-terminal domain of the E2 protein forms a dimeric structure, where Arg 37 has an important function in dimer formation (Antson, A., et al., supra).

As has been described previously, bovine papillomavirus type 1 E2 protein in trans and its multiple binding sites in cis are both necessary and sufficient for the chromatin attachment of the episomal genetic elements. The phenomenon is suggested to provide a mechanism for partitioning viral genome during viral infection in the dividing cells [Ilves, I., et al., J Virol. 73 (1999) 4404-4412].

None of the papilloma vectors or other vectors disclosed so far fulfills the criteria and requirements set forth for an optimal vaccine, which are the same for DNA vaccines and for conventional vaccines. (It should be noted that these requirements are preferred but not necessary for use as a vaccine.) First, an optimal vaccine must produce protective immunity with minimal adverse effects. Thus the vaccine should be devoid of components, which are toxic and/or cause symptoms of the disease to the recipient. Second, an optimal vaccine must induce a pathogen-specific immune response, i.e. it must elicit a strong and measurable immune response to the desired pathogen without causing an immune response to other components of the vaccine. These two requirements imply that a vector to be used as a DNA vaccine should optimally only express the desired gene(s) and optimally should not replicate in the host or contain any sequences homologous with those of the recipient, since nucleotide sequences that are homologous between the vector and the host's genome may effect the integration of the vector into the host's genome. Third, an optimal vaccine must induce a right type of immune response; i.e. it must raise both humoral and cellular immune responses in order to act on the intracellular and extracellular pathogen. Finally, an optimal vaccine must be stable, i.e. it must retain its potency for a sufficiently long time in the body to raise the immune response in a vaccine formulation for use in various demanding circumstances during storage and preparation. Additionally, vaccines should be of reasonable price. Further, the route and the method of inoculation are important considerations for optimizing a DNA immunization.

When developing a DNA vaccine the stability of the expression of the desired gene is sometimes a major problem.

Thus, the maintenance function or the persistance of the vector in the recipient cell has been focused on in the prior art, however, often at the cost of the safety. For example, Ohe, Y., et al. ][Hum Gene Ther 6(3) (1995) 325-333] disclose a papilloma virus vector capable of stable, high-level gene expression, which is suggested for use in gene therapy. Transforming early genes E5, E6, and E7 have been deleted from said vector, but it still contains nucleotide sequences encoding other papilloma viral genes, such as the E1 and E2 genes, which are involved in the replication of the virus. Thus, the vector produces several other papilloma proteins, which may elicit undesired immune responses and which induce a risk of the vector's integration in the recipient. Also, the vector is replicable, since it contains the E1 gene. Additionally, it is large in size and therefore subject to bacterial modification during preparation.

International Patent Application PCT/EE96/00004 (WO 97/24451) discloses vectors capable of a long-term maintenance in a host cell and methods using such vectors for obtaining long-term production of a gene product of interest in a mammalian host cell, which expresses E1 and E2. These vectors contain a minimal origin of replication of a papilloma virus (MO), a Minichromosome Maintenance Element (MME) of a papilloma virus and a gene encoding said gene product, the MO and MME consisting of a DNA sequence different from the natural papilloma virus sequence, and in some embodiments the E1 gene. Additionally, vectors containing an MME consisting essentially of ten E2 binding sites are disclosed in some examples. These vectors require the presence of the E1 protein either in the host or in the vector for the expression. This imparts the replication function to the vectors. These vectors also express the E1 protein in addition to the gene of interest and the E2 protein and contain sequences, such as rabbit β-globin sequences, which are partially homologous to human sequences causing a serious risk of integration to human genome, which reduces the potential of these vectors as DNA vaccines. Additionally, the vectors are unstable due to their size (ca 15 kb): at the preparation stage in a bacterial cell, the bacterial replication machinery tends to modify the vector by random slicing of the vector, which leads to unsatisfactory expression products including products totally lacking the gene of interest.

International Patent Application PCT/EE96/00004 (WO 97/24451) further discloses that E1 and E2 are the only viral proteins necessary for the episomal long-term replication of the vectors. Additionally, the maintenance function of the BPV1 genome is associated with the presence of minimal ori (MO), which is stated to be necessary, although not sufficient, for the long-term persistence or the stable maintenance of the vectors the cells. In addition, the cis-elements, i.e. the Minichromosome Maintenance Elements of the BPV1, are stated to be required for the stable replication of BPV1. In particular, multimeric E2 binding sites (E2BS) are stated to be necessary for the stable maintenance of the vectors.

There is a clear need for improved novel vectors, which would be useful as DNA vaccines.

An object of the invention is therefore to provide novel vectors, which are capable of a long-term maintenance in a large and increasing number of different cells of the host's body and thereby capable of providing a stable expression of the desired antigen(s).

Another object of the invention is to provide novel vectors, which are maintained for a long period of time in the cells that originally received the vector and transferred it to the daughter cells after mitotic cell division.

Yet another object of the invention is to provide novel vectors, which express in addition to the gene or genes of interest preferably only a gene necessary for a long-term maintenance in the recipient cells and thus are devoid of components that are toxic or cause symptoms of the disease to the recipient.

A further object of the invention is to provide novel vectors, which mimic attenuated live viral vaccines, especially in their function of multiplying in the body, without inducing any considerable signs of disease and without expressing undesired proteins, which may induce adverse reactions in a host injected with the DNA vaccine.

Still a further object of the invention is to provide novel vectors, which do not replicate in the recipient.

Still another object of the invention is to provide novel vectors, which induce both humoral and cellular immune responses when used as DNA vaccines.

Yet another object of the invention is to provide novel vectors, which are suitable for a large-scale production in bacterial cell.

Yet another object of the invention is to provide novel vectors, which are not host specific and thus enable the production in various bacterial cells.

An additional object of the invention is to provide novel vectors, which are useful as carrier vectors for a gene or genes of interest, A further object of the invention is to provide novel vectors, which are useful in gene therapy and as gene therapeutic agents and for the production of macromolecular drugs in vivo.

3. SUMMARY OF THE INVENTION

The present invention discloses novel vectors, which meet the requirements of a carrier vector of a gene or genes of interest or of an optimal DNA vaccination vector and which are preferably devoid of drawbacks and side effects of prior art vectors.

The present invention is based on the surprising finding that a vector (plasmid) carrying (i) an expression cassette of a DNA sequence encoding a nuclear-anchoring protein, and (ii) multiple copies of high affinity binding sites for said nuclear-anchoring protein spreads in proliferating cells. As a result, the number of vector-carrying cells increases even without the replication of the vector. When the vector additionally carries a gene or genes of interest, the number of such cells that express a gene or genes of interest similarly increases without the replication of the vector. Thus, the vector of the invention lacks a papilloma virus origin of replication. In a preferred embodiment, the vector of the invention lacks an origin of replication that functions in a mammalian cell.

Accordingly, the present invention discloses novel vectors useful as carrier vectors of a gene or genes of interest, in DNA vaccination and gene therapy and as gene therapeutic agents. In a specific embodiment, said vectors are capable of spreading and, if desired, of expressing a gene or genes of interest in an increasing number of cells for an extended time. The vectors of the present invention preferably express only a nuclear-anchoring protein, and, if desired, the gene or genes of interest, and optionally a selectable marker. However, they preferably lack any redundant, oncogenically transforming or potentially toxic sequences, thereby avoiding a severe drawback of the vectors previously disclosed or suggested for use as DNA vaccines, i.e. hypersensitivity reactions against other viral components. In certain embodiments of the invention, this is achieved by low level of the expressed nuclear-anchoring protein in the cells. At the same time, the vectors of the present invention induce both humoral and cellular immune responses, where the gene or genes of interest is included in the vector.

The vectors of the present invention are advantageous for use both in vitro (e.g., in the production level) and in vivo (e.g., vaccination).

The present invention relates to the subject matter of the invention as set forth in the attached claims.

The-present invention relates to expression vectors comprising: (a) a DNA sequence encoding a nuclear-anchoring protein operatively linked to a heterologous promoter, said nuclear-anchoring protein comprising (i) a DNA binding domain which binds to a specific DNA sequence, and (ii) a functional domain that binds to a nuclear component, or a functional equivalent thereof; and (b) a multimerized DNA sequence forming a binding site for the nuclear anchoring protein, wherein said vector lacks a papilloma virus origin of replication. In a preferred embodiment a vector of the invention lacks an origin of replication functional in a mammalian cell.

In certain embodiments, the nuclear component is mitotic chromatin, the nuclear matrix, nuclear domain 10 (ND10), or nuclear domain POD.

In certain specific embodiments, the nuclear anchoring-protein is a chromatin-anchoring protein, and said functional domain binds mitotic chromatin.

In certain embodiments, the nuclear-anchoring protein contains a hinge or linker region.

In certain embodiments, the nuclear-anchoring protein is a natural protein of eukaryotic, prokaryotic, or viral origin. In certain specific embodiments, the natural protein is of viral origin.

In certain embodiments, the nuclear-anchoring protein is a natural protein of eukaryotic origin.

In certain embodiments, the nuclear-anchoring protein is that of a papilloma virus or an Epstein-Barr virus.

In specific embodiments, the nuclear-anchoring protein is the E2 protein of Bovine Papilloma Virus type 1 or Epstein-Barr Virus Nuclear Antigen 1.

In a specific embodiment, the nuclear-anchoring protein is the E2 protein of Bovine Papilloma Virus type 1.

In specific embodiments, the nuclear-anchoring protein is a High Mobility Group protein.

In certain embodiments, the nuclear-anchoring protein is a non-natural protein.

In certain embodiments, the nuclear-anchoring protein is a recombinant protein, a fusion protein, or a protein obtained by molecular modeling techniques.

In specific embodiments, the recombinant protein, fusion protein, or protein obtained by molecular modeling techniques contains any combination of a DNA binding domain which binds to said specific DNA sequence and a functional domain which binds to a nuclear component, wherein said functional domain which binds to a nuclear component is that of a papilloma virus, an Epstein-Barr-Virus, or a High Mobility Group protein.

In certain specific embodiments, the recombinant protein, fusion protein, or protein obtained by molecular modeling techniques contains any combination of a DNA binding domain which binds to said specific DNA sequence and a functional domain which binds to a nuclear component, wherein said functional domain which binds to a nuclear component is that of E2 protein of Bovine Papilloma Virus type 1, Epstein-Barr Virus Nuclear Antigen 1, or a High Mobility Group protein.

In certain embodiments, the vector further comprises one or more expression cassettes of a DNA sequence of interest.

In certain embodiments, the DNA sequence of interest is that of an infectious pathogen. In certain embodiments, the infectious pathogen is a virus. In certain specific embodiments, the virus is selected from the group consisting of Human Immunodeficiency Virus (HIV), Herpex Simplex Virus (HSV), Hepatitis C Virus, Influenzae Virus, and Enterovirus.

In certain embodiments, the DNA sequence of interest is that of a bacterium. In certain embodiments, the bacterium is selected from the group consisting of *Chlamydia trachomatis, Mycobacterium tuberculosis*, and *Mycoplasma pneumonia*. In a specific embodiment, the bacterium is *Salmonella*.

In certain embodiments, the DNA sequence of interest is that of a fungal pathogen. In certain embodiments, the fungal pathogen is *Candida albigans*.

In certain embodiments, the DNA sequence of interest is of HIV origin.

In specific embodiments, the DNA sequence of interest encodes a non-structural regulatory protein of HIV. In more specific embodiments, the non-structural regulatory protein of HIV is Nef, Tat and/or Rev. In a specific embodiment, the non-structural regulatory protein of HIV is Nef.

In certain embodiments, the DNA sequence of interest encodes a structural protein of HIV. In a specific embodiment, the DNA sequence of interest is the gene encoding HIV gp120/gp160.

In certain embodiments, the vector of the invention comprises a first expression cassette comprising a DNA sequence of interest which encodes Nef, Tat and/or Rev, and a second expression cassette comprising a DNA sequence of interest which encodes Nef, Tat and/or Rev.

In certain embodiments, the vector of the invention comprises a first expression cassette comprising a DNA sequence of interest which encodes Nef, Tat and/or Rev, and a second expression cassette comprising a DNA sequence of interest which encodes a structural protein of HIV.

In certain embodiments, the DNA sequence of interest encodes a protein associated with cancer.

In certain embodiments, the DNA sequence of interest encodes a protein associated with immune maturation, regulation of immune responses, or regulation of autoimmune responses. In a specific embodiment, the protein is APECED.

In a specific embodiment, the DNA sequence of interest is the Aire gene.

In certain embodiments, the DNA sequence of interest encodes a protein that is defective in any hereditary single gene disease.

In certain embodiments, the DNA sequence of interest encodes a macromolecular drug.

In certain embodiments, the DNA sequence of interest encodes a cytokine. In certain specific embodiments, the cytokine is an interleukin selected from the group consisting of IL1, IL2, IL4, IL6 and IL12. In certain other specific embodiments, the DNA sequence of interest encodes an interferon.

In certain embodiments, the DNA sequence of interest encodes a biologically active RNA molecule. In certain specific embodiments, the biologically active RNA molecule is selected from the group consisting of inhibitory antisense and ribozyme molecules. In certain specific embodiments, the inhibitory antisense or ribozyme molecules antagonize the function of an oncogene.

A vector of the invention is suitable for the use for the production of a therapeutic macromolecular agent in vivo.

In certain embodiments, the invention provides a vector for use as a medicament.

In certain embodiments, the invention provides a vector for use as a carrier vector for a gene, genes, or a DNA sequence or DNA sequences of interest, such as a gene, genes, or a DNA sequence or DNA sequences encoding a protein or peptide of an infectious agent, a therapeutic agent, a macromolecular drug, or any combination thereof.

In certain specific embodiments, the invention provides a vector for use as a medicament for treating inherited or acquired genetic defects.

In certain embodiments, the invention provides a vector for use as a therapeutic DNA vaccine against an infectious agent.

In certain embodiments, the invention provides a vector for use as a therapeutic agent.

The invention further relates to methods for providing a protein to a subject, said method comprising administering to the subject a vector of the invention, wherein said vector (i) further comprises a second DNA sequence encoding the protein to be provided to the subject, which second DNA sequence is operably linked to a second promoter, and (ii) does not encode Bovine Papilloma Virus protein E1, and wherein said subject does not express Bovine Papilloma Virus protein E1.

The invention further relates to methods for inducing an immune response to a protein in a subject, said method comprising administering to the subject a vector of the invention wherein said vector (i) further comprises a second DNA sequence encoding said protein, which second DNA sequence is operably linked to a second promoter, and (ii) does not encode Bovine Papilloma Virus protein E1, and wherein said subject does not express Bovine Papilloma Virus protein E1.

The invention further relates to methods for treating an infectious disease in a subject in need of said treatment, said method comprising administering to said subject a therapeutically effective amount of a vector of the invention, wherein the DNA sequence of interest encodes a protein comprising an immunogenic epitope of an infectious agent.

The invention further relates to methods for treating an inherited or acquired genetic defect in a subject in need of said treatment, said method comprising: administering to said subject a therapeutically effective amount of a vector of the invention, wherein said DNA sequence of interest encodes a protein which is affected by said inherited or acquired genetic defect.

The invention further relates to methods for expressing a DNA sequence in a subject, said method comprising administering a vector of the invention to said subject.

The invention further relates to methods for expressing a DNA sequence in a subject, treating an inherited or acquired genetic defect, treating an infectious disease, inducing an immune-response to a protein, and providing a protein to a subject, wherein the vector of the invention does not encode Bovine Papilloma Virus protein E1, and wherein said subject does not express Bovine Papilloma Virus protein E1.

In certain embodiments, a vector of the invention is used for production of a protein encoded by said DNA sequence of interest in a cell or an organism.

The invention further provides a method for the preparation of a vector of claim 1, 2, or 17 comprising: (a) cultivating a host cell containing said vector and (b) recovering the vector. In a specific embodiment, the method for preparing a vector of the invention further comprises before step (a) a step of transforming said host cell with said vector. In certain specific embodiments, the host cell is a prokaryotic cell. In a specific embodiment, the host cell is an *Escherichia coli*.

The invention further relates to a host cell that is characterized by containing a vector of the invention. In certain embodiments, the host cell is a bacterial cell. In a certain other embodiments, the host cell is a mammalian cell.

The invention further relates to carrier vectors containing a vector of the invention.

The invention further relates to a pharmaceutical composition comprising a vector of the invention and a suitable pharmaceutical vehicle.

The invention further relates to a DNA vaccine containing a vector of the invention.

The invention further relates to a gene therapeutic agent containing a vector of the invention.

The invention further relates to a method for the preparation of a DNA vaccine, said method comprising combining a vector of the invention with a suitable pharmaceutical vehicle.

The invention further relates to a method for the preparation of an agent for use in gene therapy, said method comprising combining a vector of the invention with a suitable pharmaceutical vehicle.

4. DESCRIPTION OF THE FIGURES

FIG. 6A shows the schematic map of the plasmids NNV-1 and NNV-2 and FIG. 6B shows the schematic map of plasmid and NNV-2wt.

FIG. 7 shows the expression of the Nef protein from the plasmids NNV-1, NNV-2, NNV-1wt, NNV-2-wt, super6, and super6wt in Jurkat cells.

FIG. 11 shows the expression of the Nef protein from the plasmids NNV-2-wt, NNV-2-wtFS, and product I in RD cells.

Figure 26:
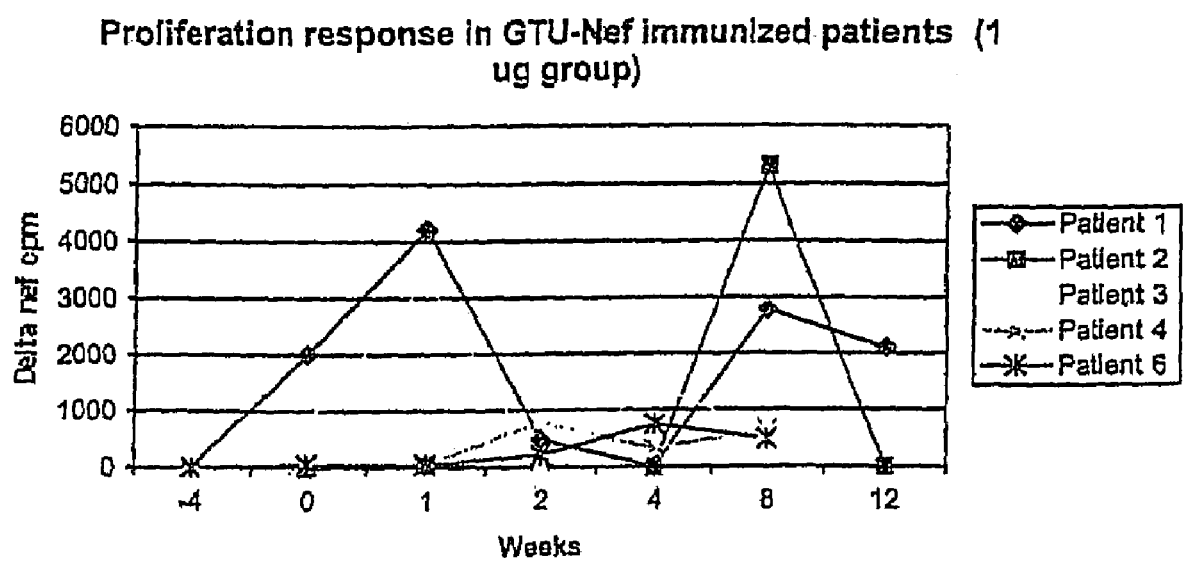

FIG. 26. T-cell responses towards recombinant Nef proteins (5 micrograms/well), measured by T-cell proliferation in five patients immunized with 1 microgram of GTU-Nef.

Figure 27:
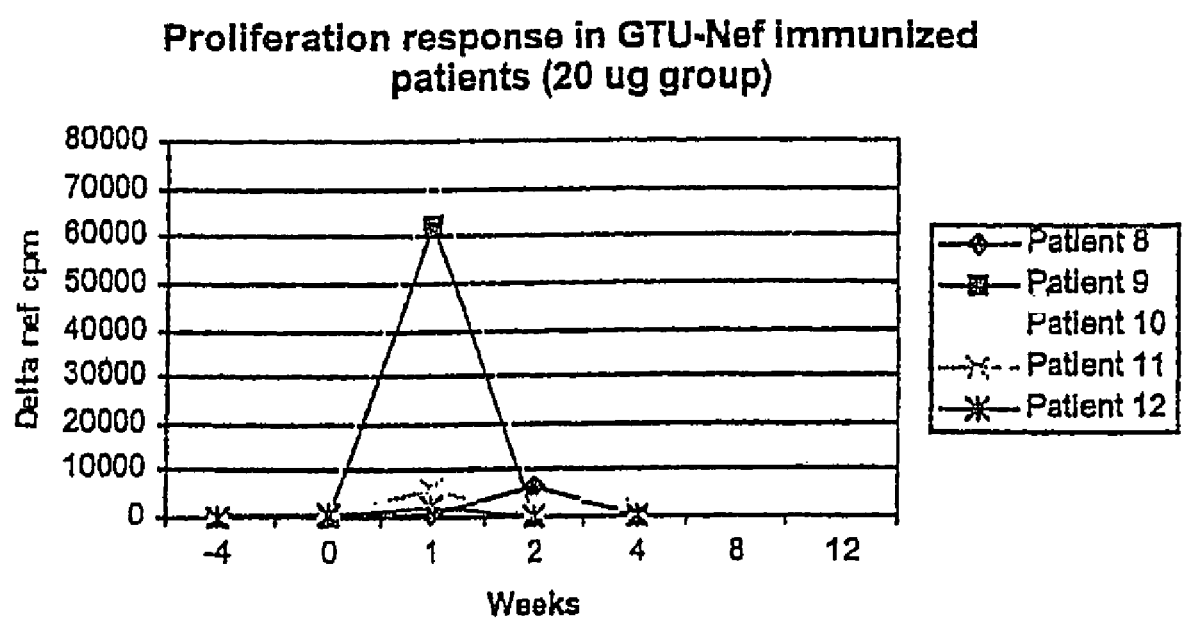

FIG. 27. T-cell responses towards recombinant Nef proteins (5 micrograms/well), measured by T-cell proliferation in five patients immunized with 20 micrograms of GTU-Nef.

Figure 28:
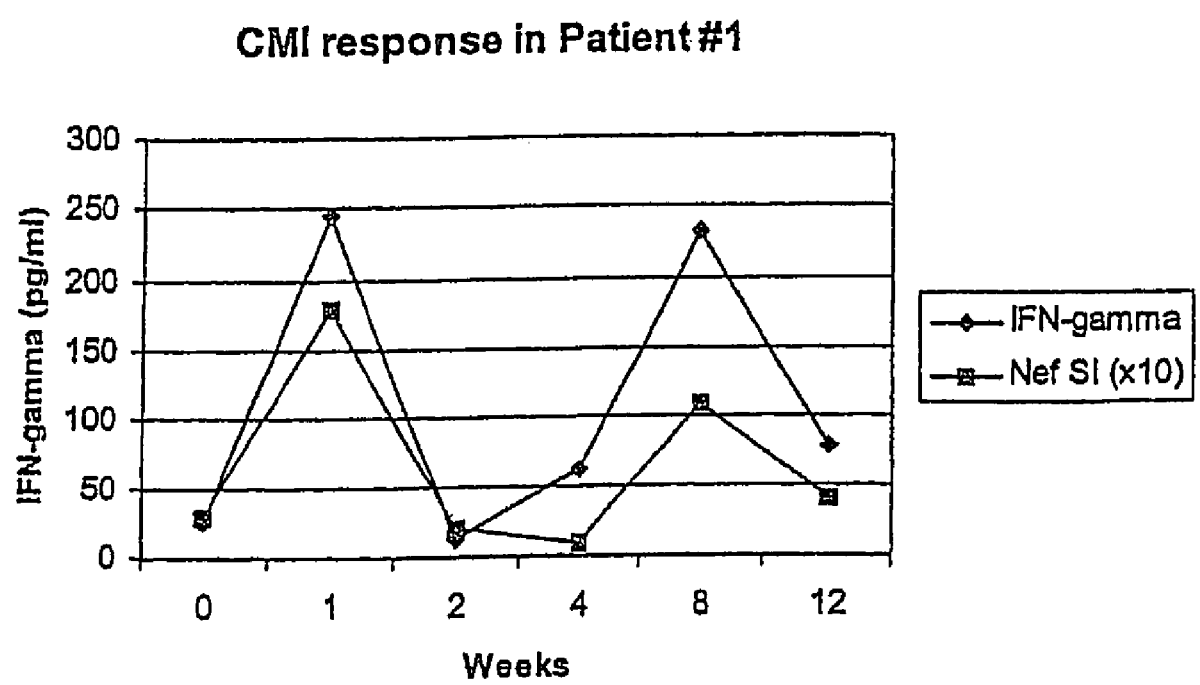

FIG. 28. T-cell responses towards recombinant Nef proteins (5 micrograms/well), measured by T-cell proliferation in patient # 1 immunized with 1 microgram of GTU-Nef. The results are given as stimulation index of the T-cell proliferation assay (Nef SI) and as IFN-Gamma secretion to the supernatant.

Figure 29A:
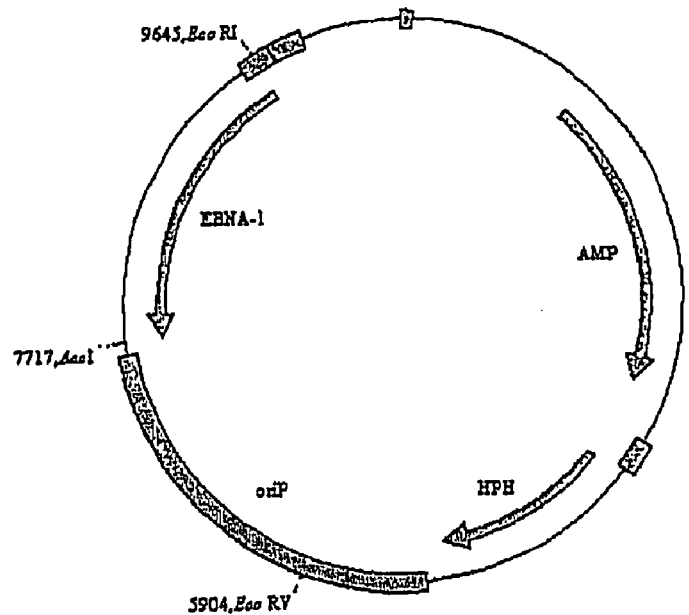
Figure 29B:
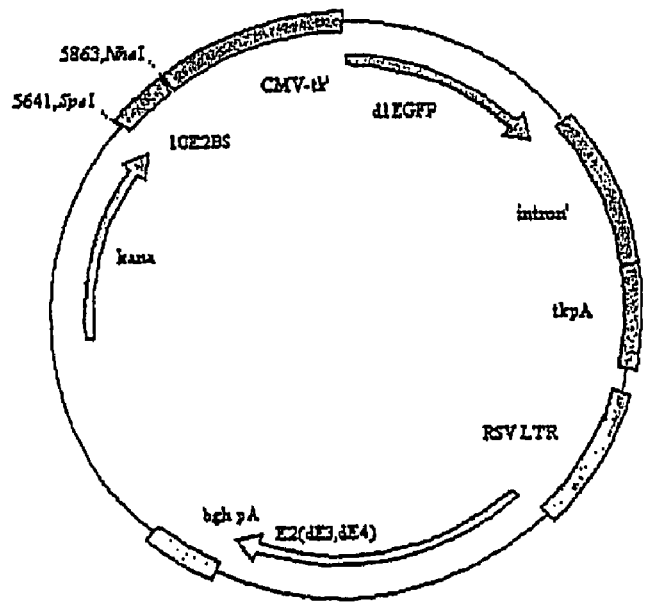
Figure 29C:
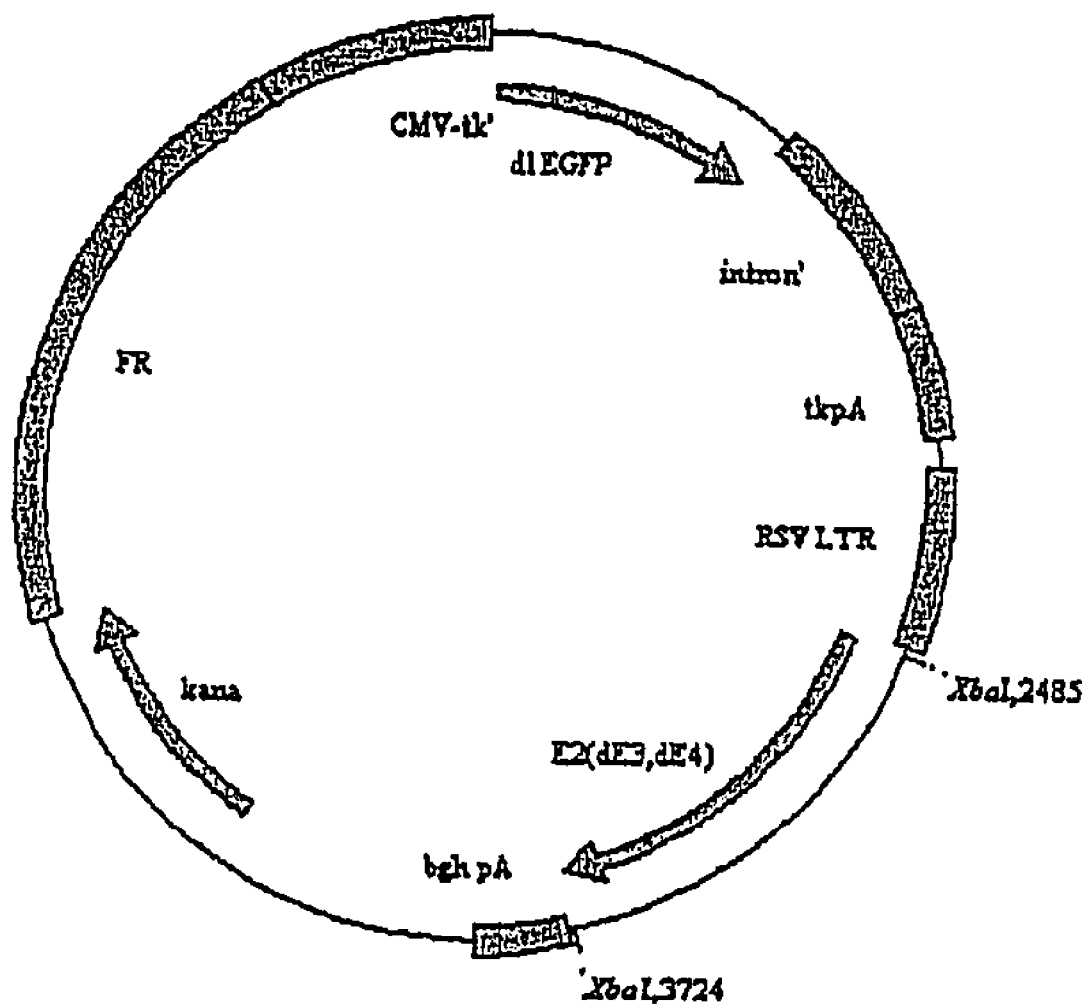

FIG. 29. (A) plasmid pEBO LPP; (B) plasmid s6E2d1EGFP; (C) plasmid FRE2d1EGFP

Figure 30:
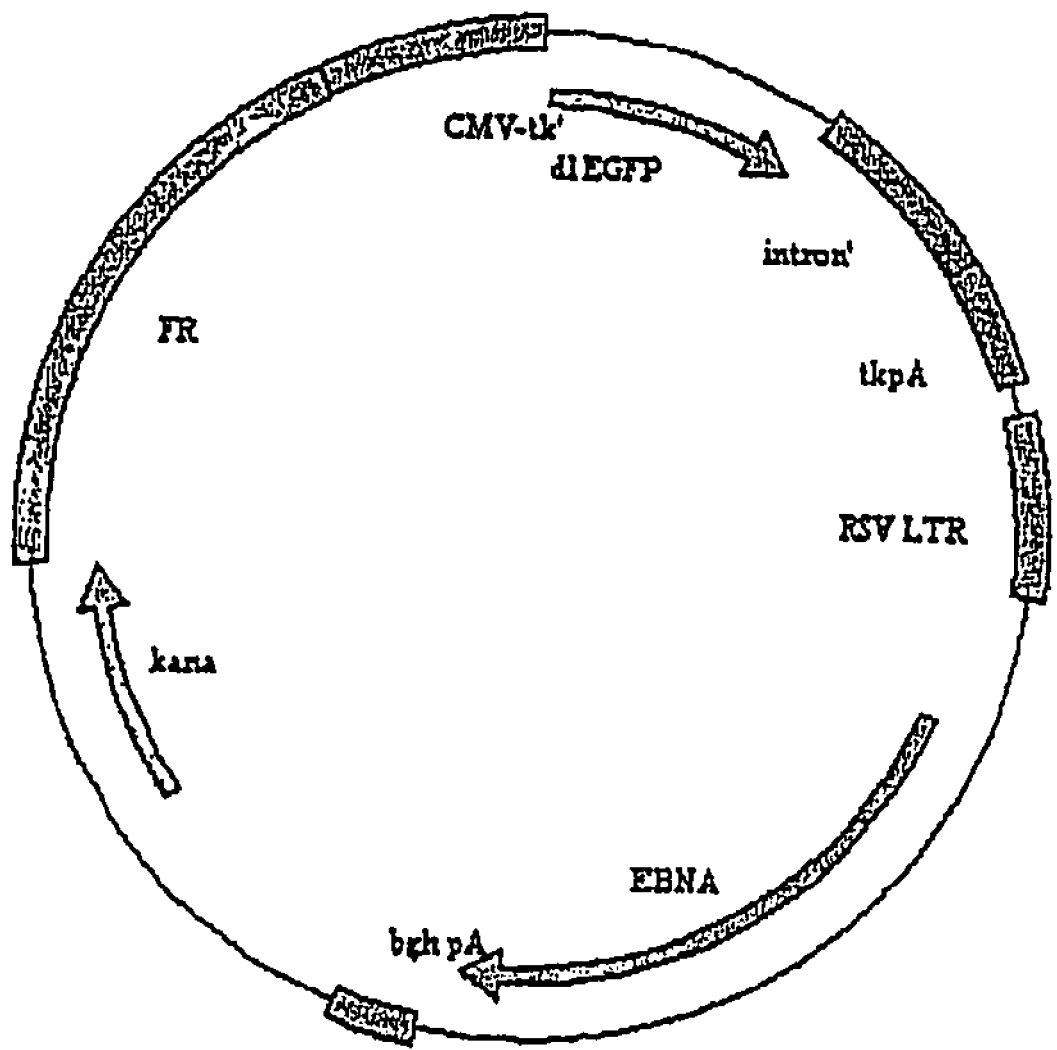

FIG. 30. Plasmid FREBNAd1EGFP

Figure 31:
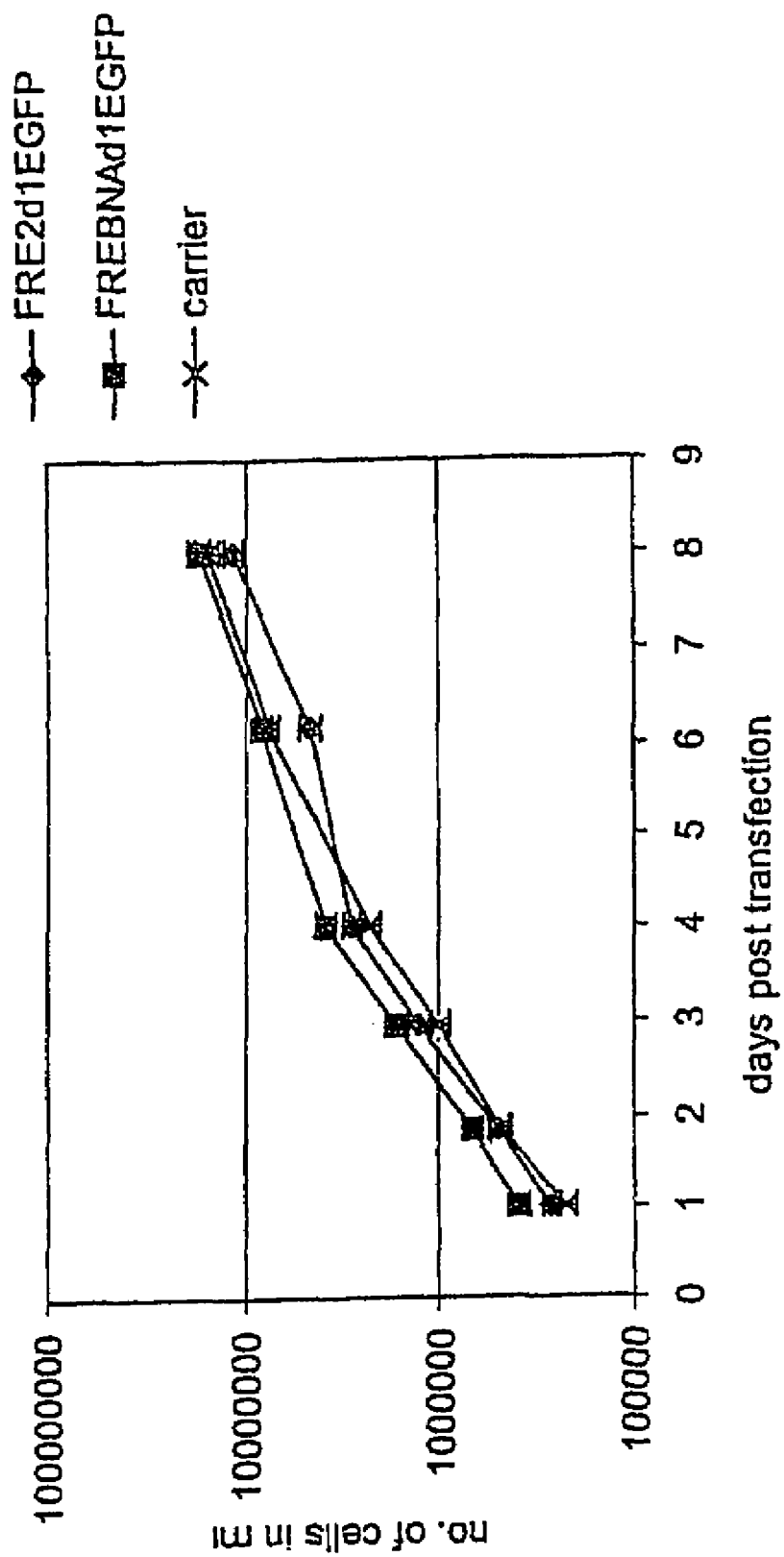

FIG. 31. Vectors did not interfere with cell proliferation

Figure 32:
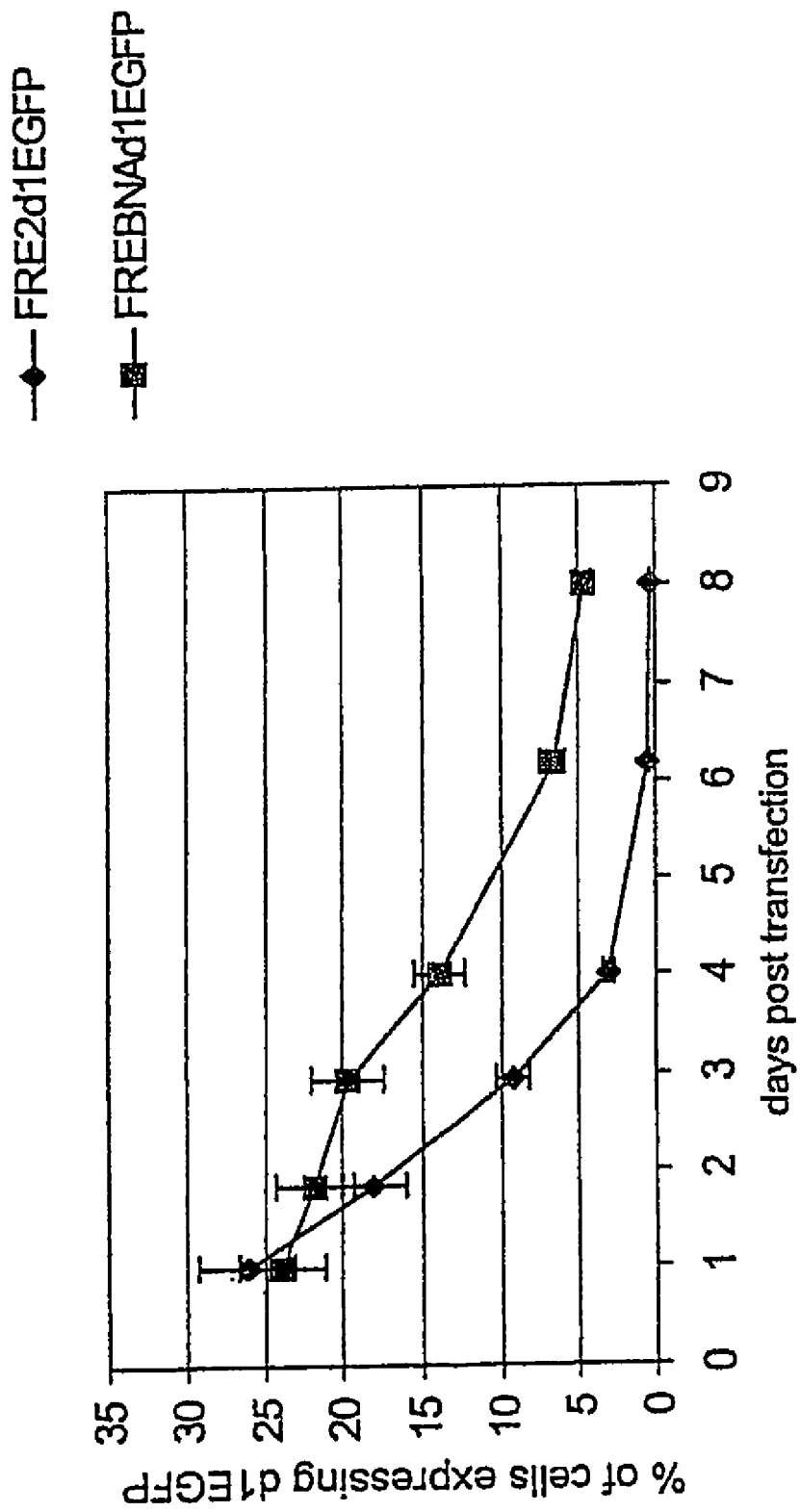

FIG. 32. Vectors were maintained in the cells with different kinetics

Figure 33:
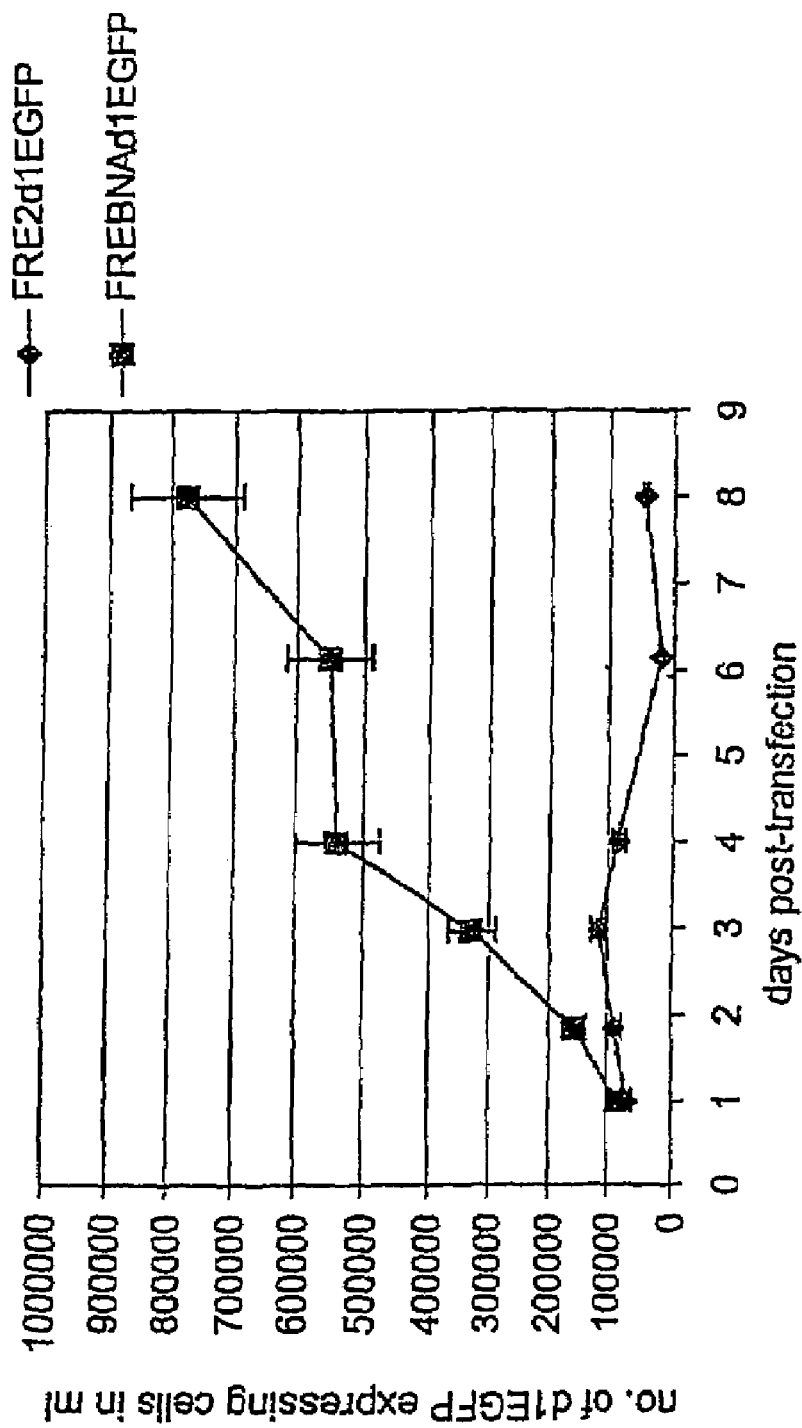

FIG. 33. Change of the number of d1EGFP expressing cells in time in transfected total population of cells FIG. 34. Change of the number of d1EGFP expressing cells in time in transfected total population of cells. (A) human embryonic cell line 293; (B) mouse cell line 3T6

Figure 35:
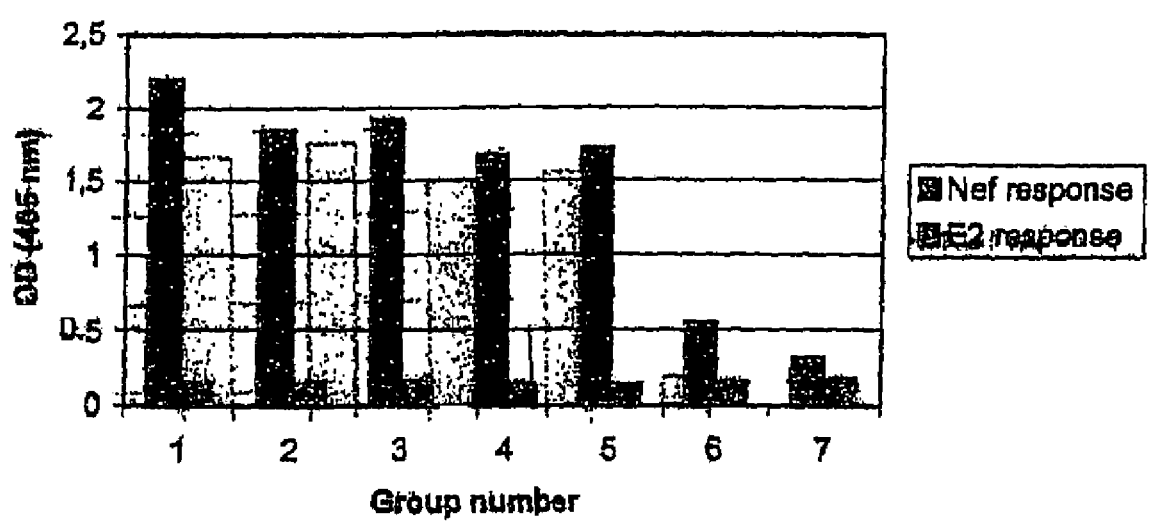

FIG. 35. Nef and E2 antibody response

Figure 36:
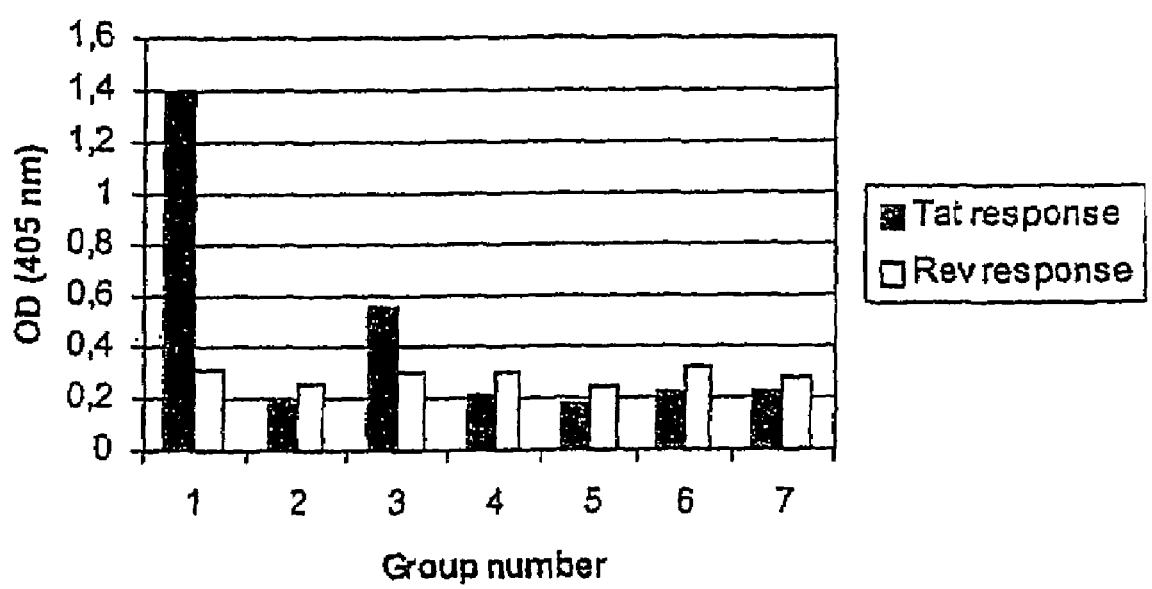

FIG. 36. Rev and Tat antibody response

Figure 37:
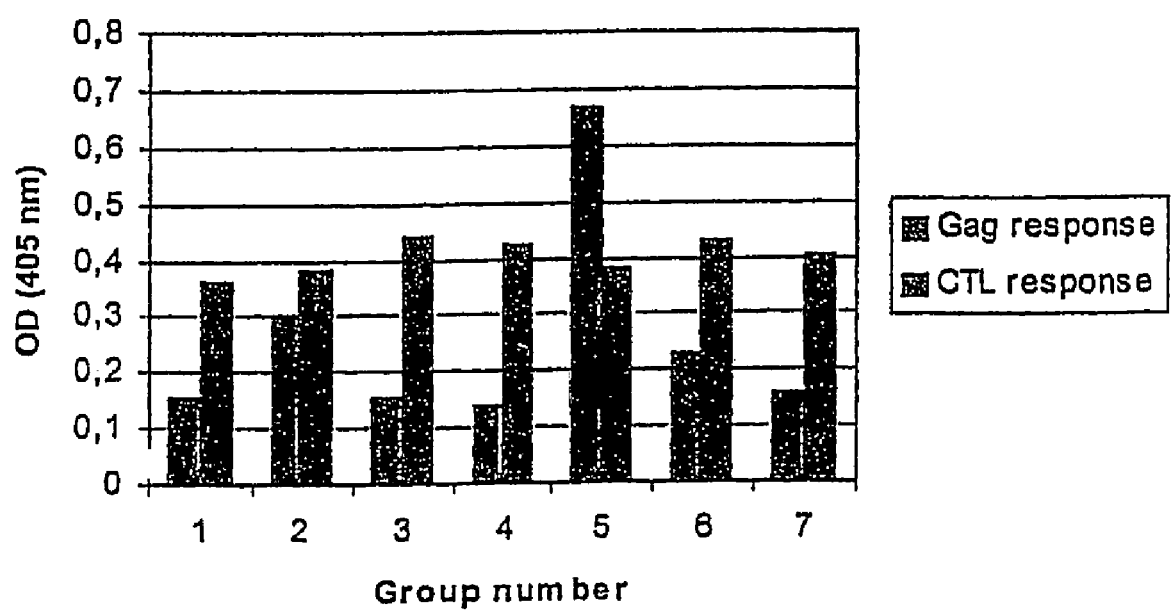

FIG. 37. Gag and CTL response

FIG. 38. (A) GTU-1; (B) GTU-2Nef; (C) GTU-3Nef; (D) super6wtd1EGFP; (E) FREBNAd1EGFP; (F) E2BSEBNAd1EGFP; (G) NNV-Rev FIG. 39. (A) pNRT; (B) pTRN; (C) pRTN; (D) pTNR; (E) PRNT; (F) p2TRN; (G) p2RNT; (H) p3RNT; (I) pTRN-iE2-GMCSF; (J) pTRN-iMG-GMCSF FIG. 40. (A) pMV1NTR; (B) pMV2NTR; (C) pMV1N11TR; (D) pMV2N11TR FIG. 41. (A) pCTL; (B) pdgag; (C) psynp17/24; (D) poptp17/24; (E) p2mCTL; (F) p2optp17/24; (G) p3mCTL; (H) p3optp17/24

Figure 42A:
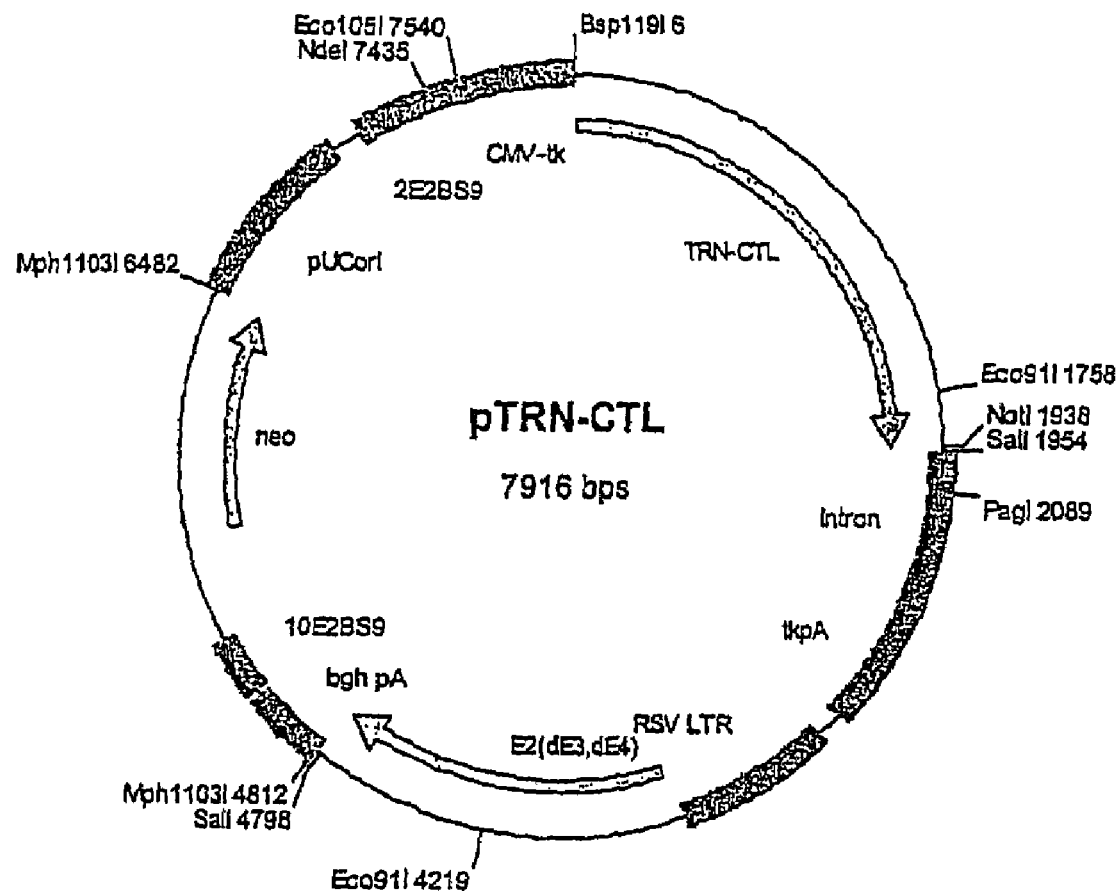
Figure 42B:
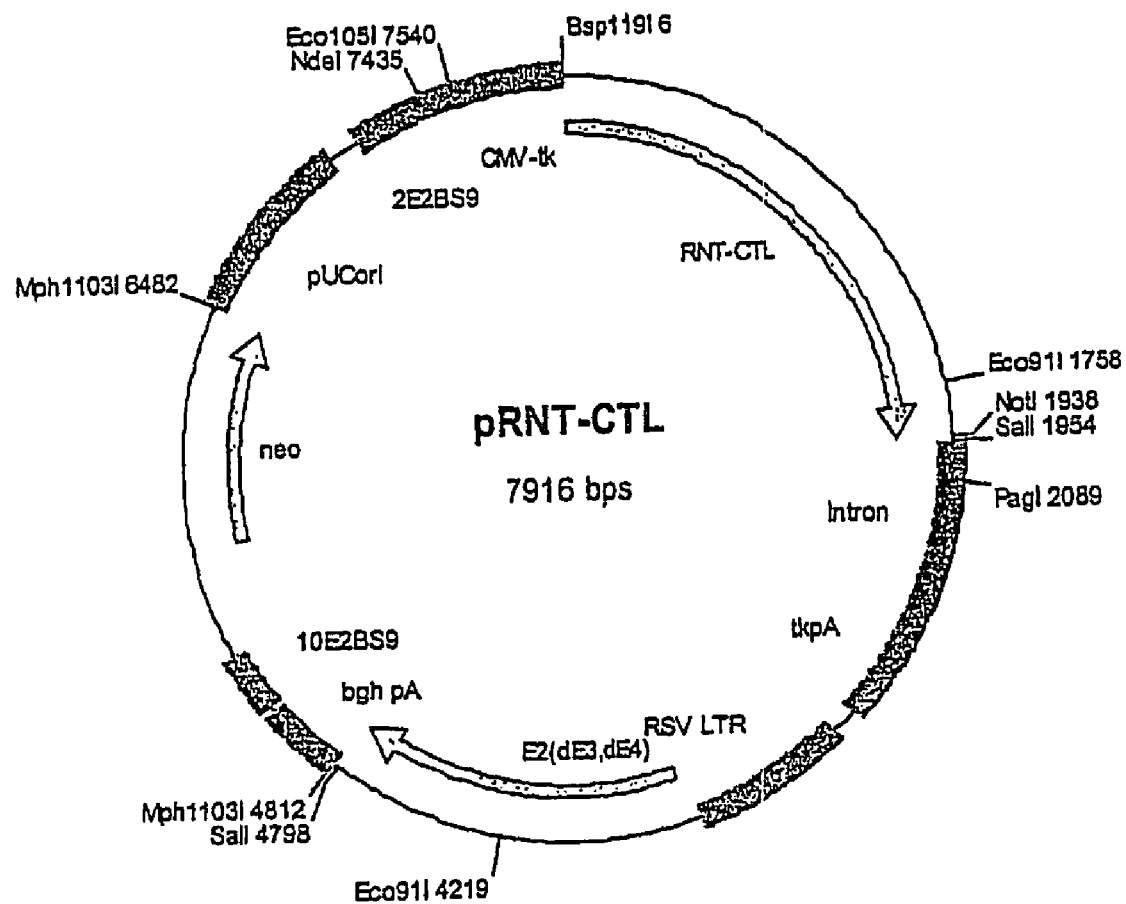
Figure 42C:
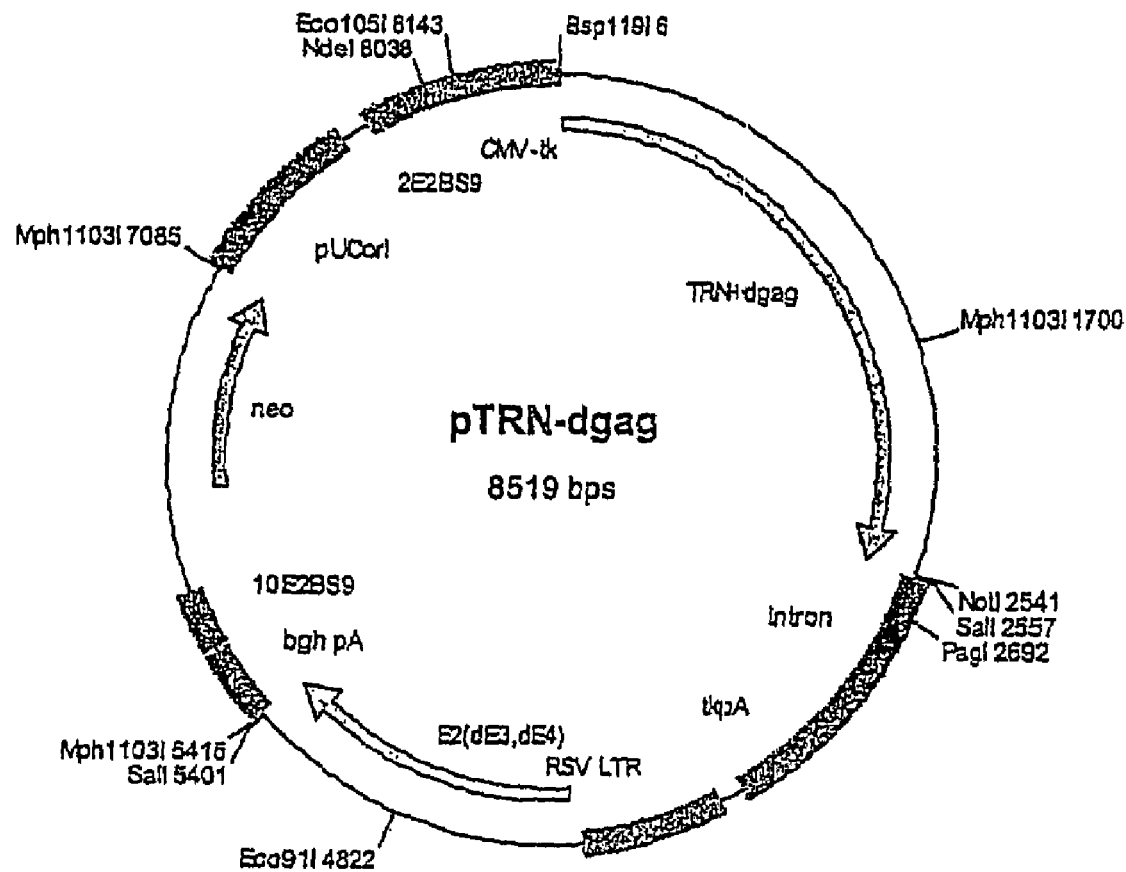
Figure 42D:
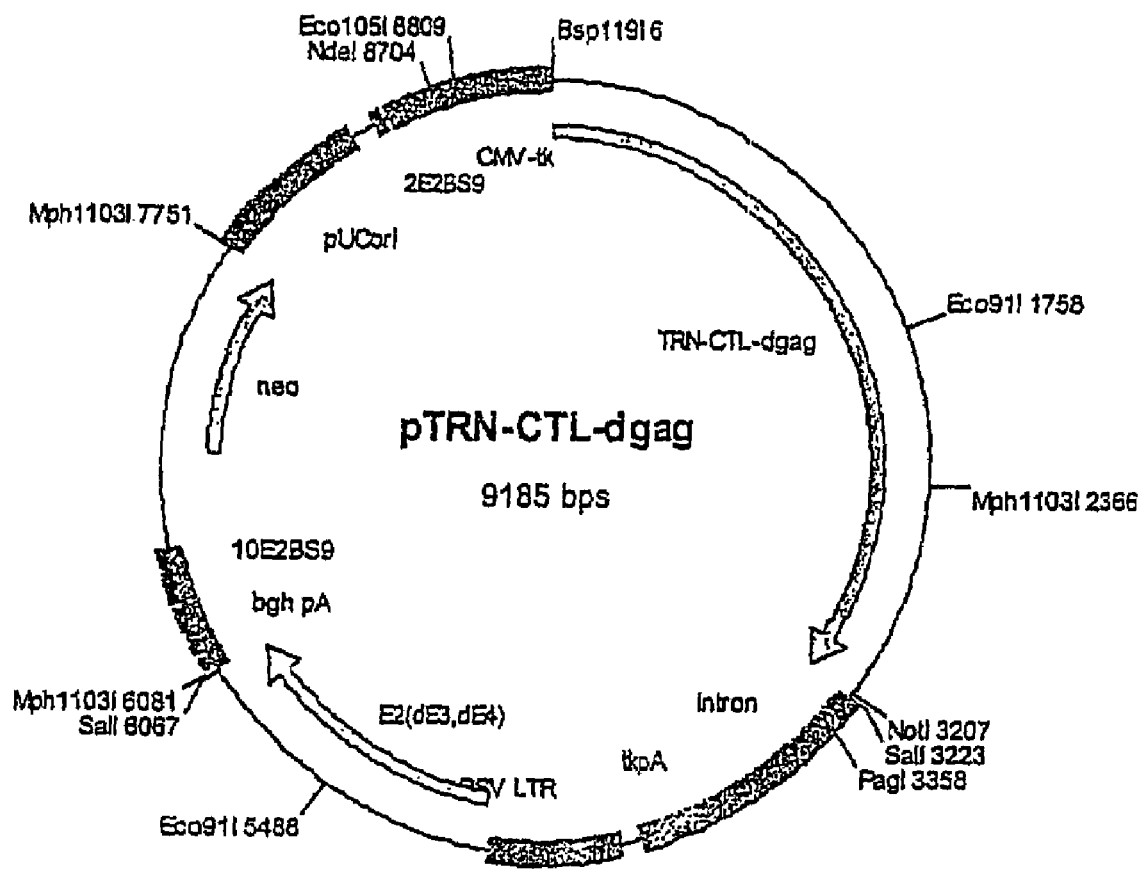
Figure 42E:
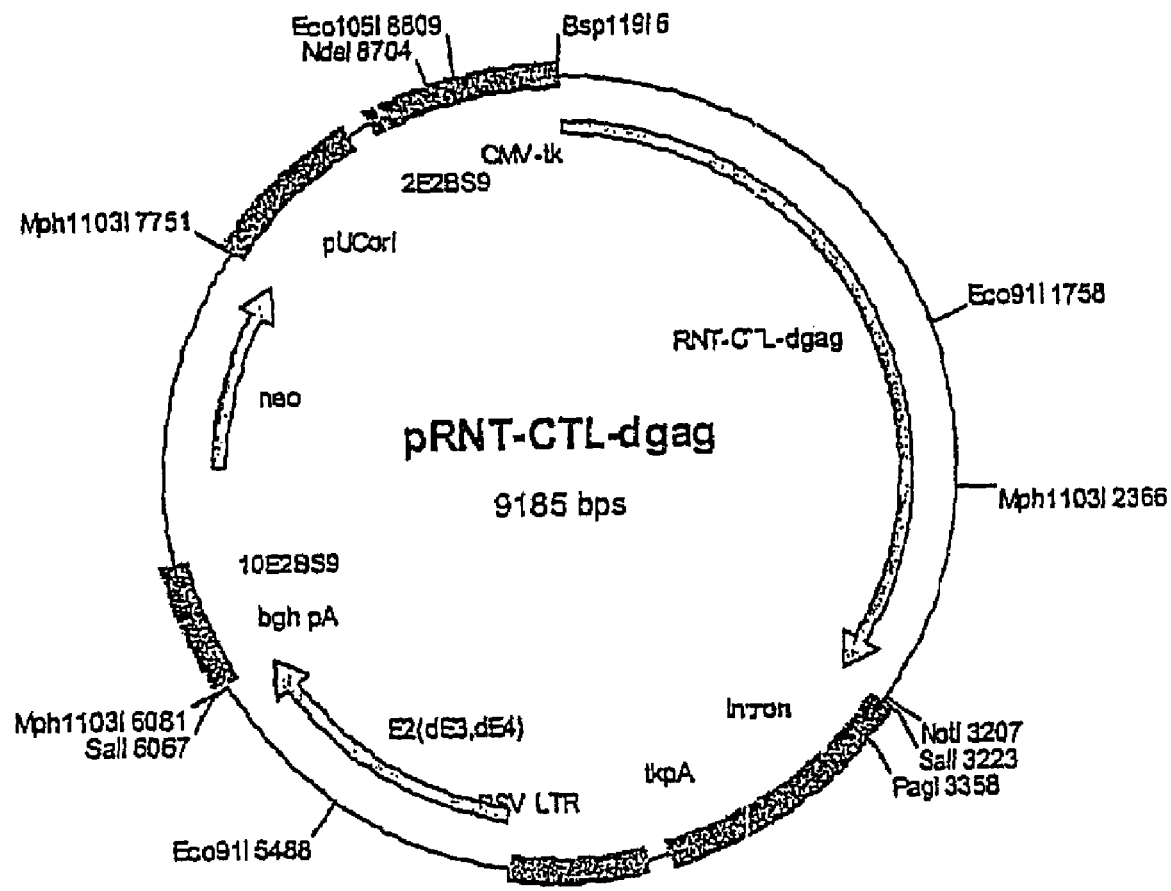
Figure 42F:
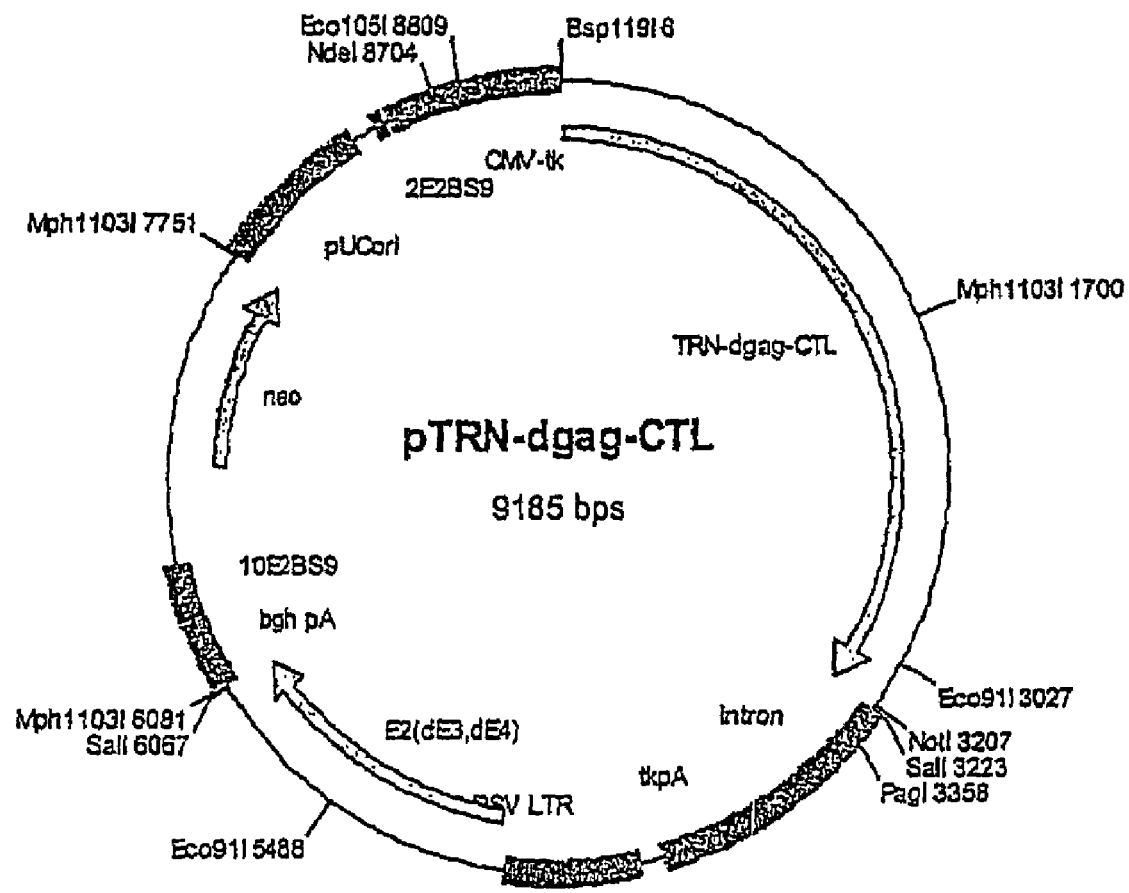
Figure 42G:
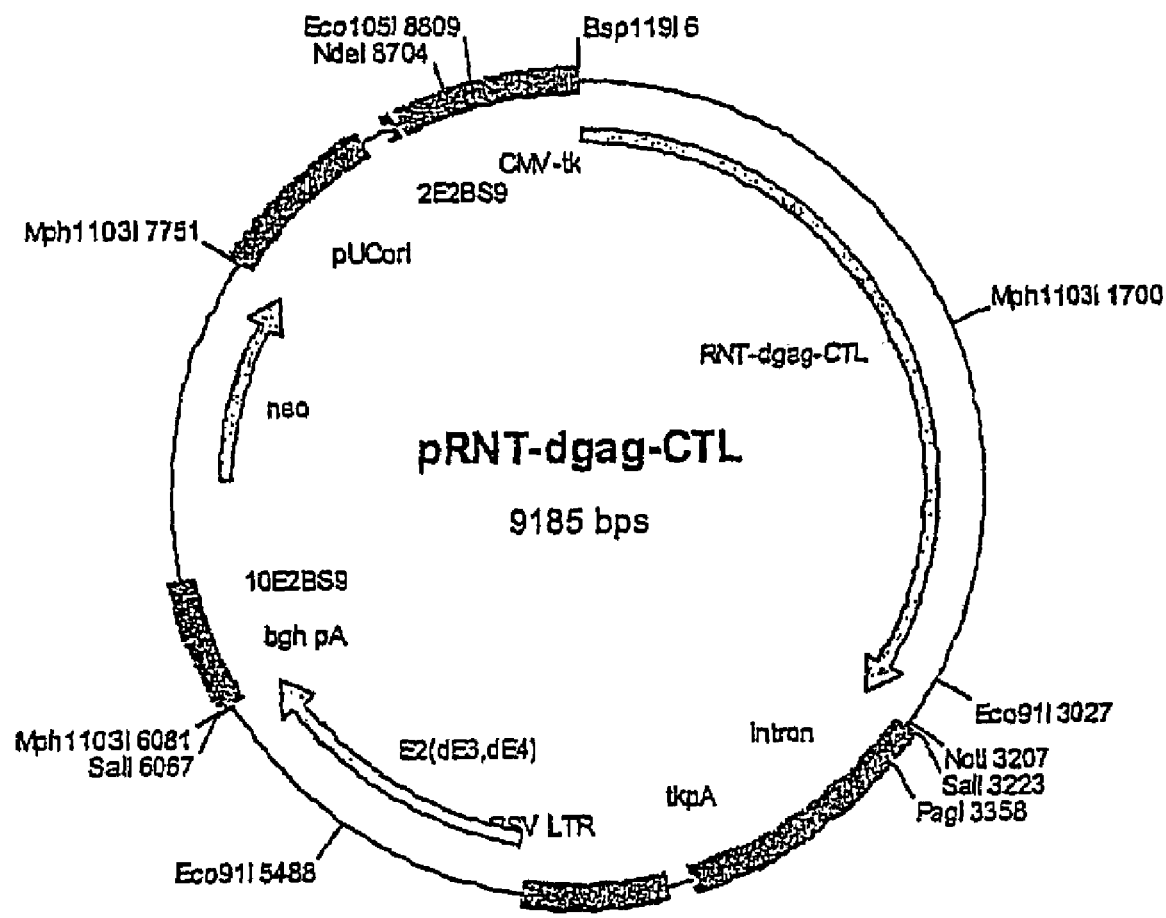
Figure 42H:
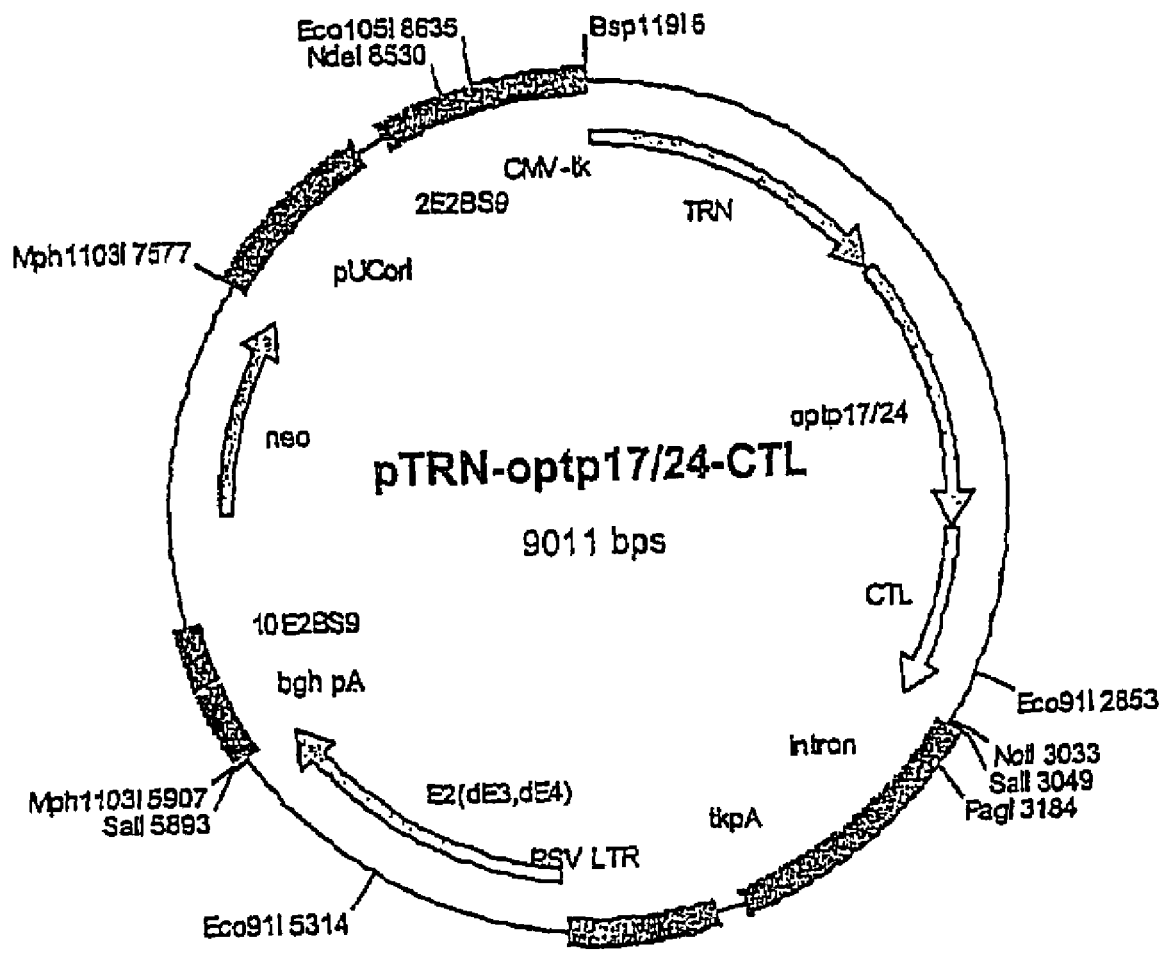
Figure 42:
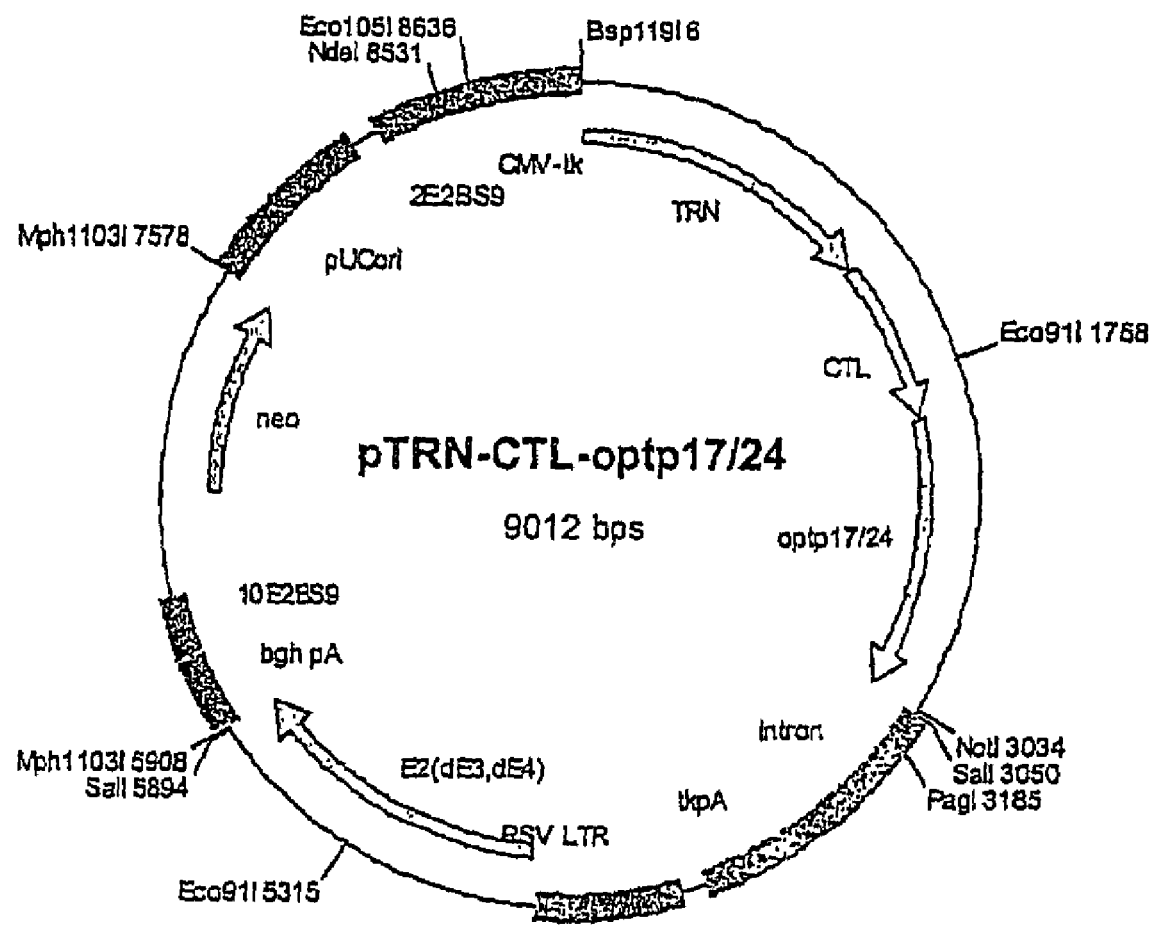
Figure 42J:
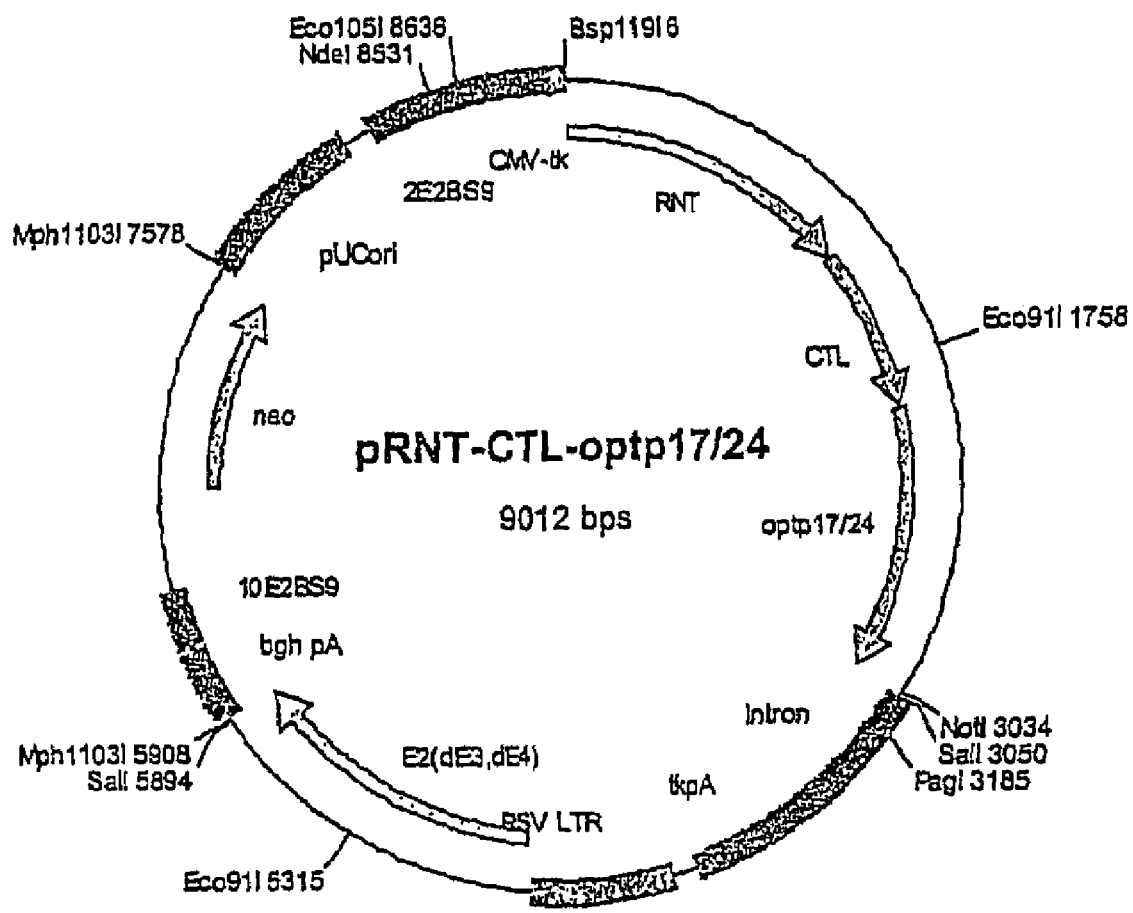
Figure 42K:
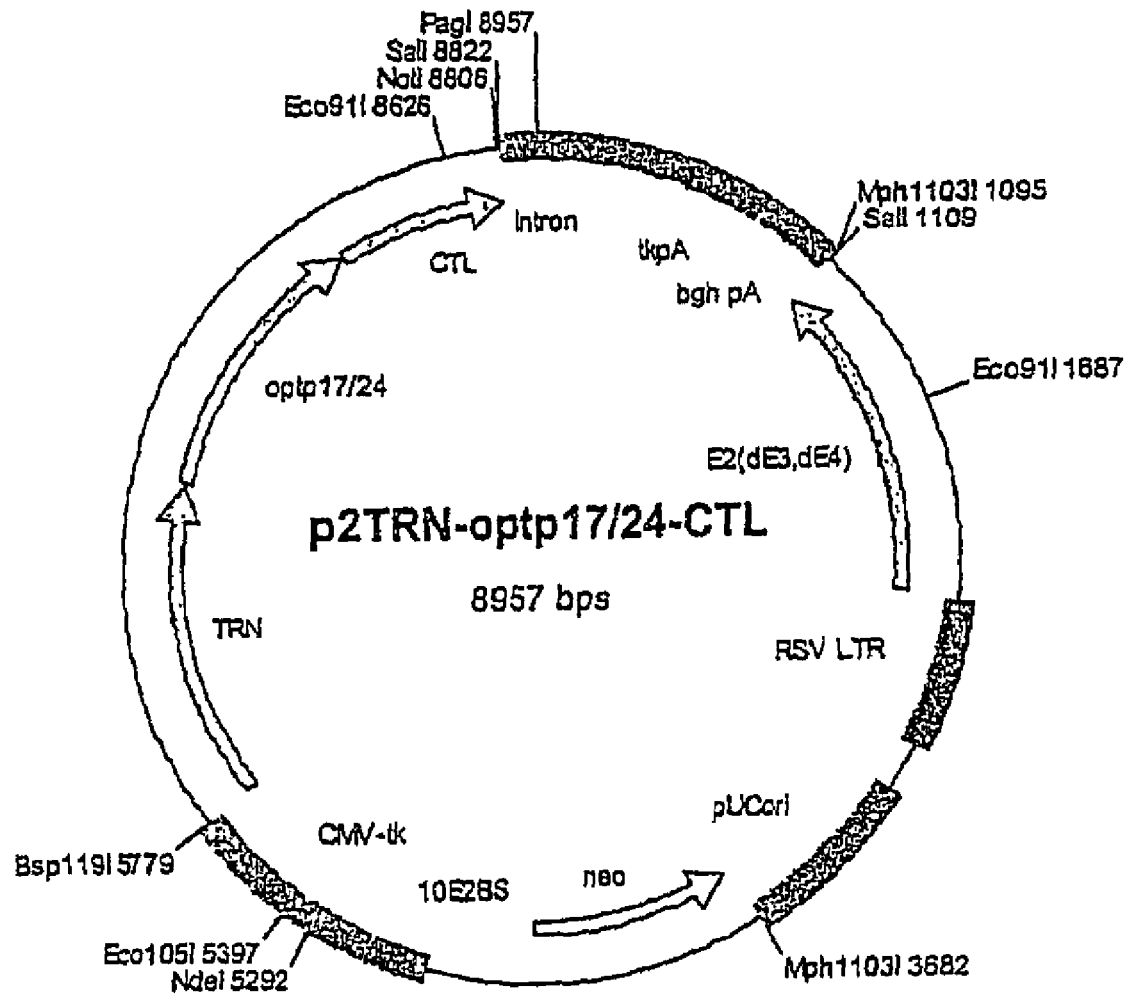
Figure 42L:
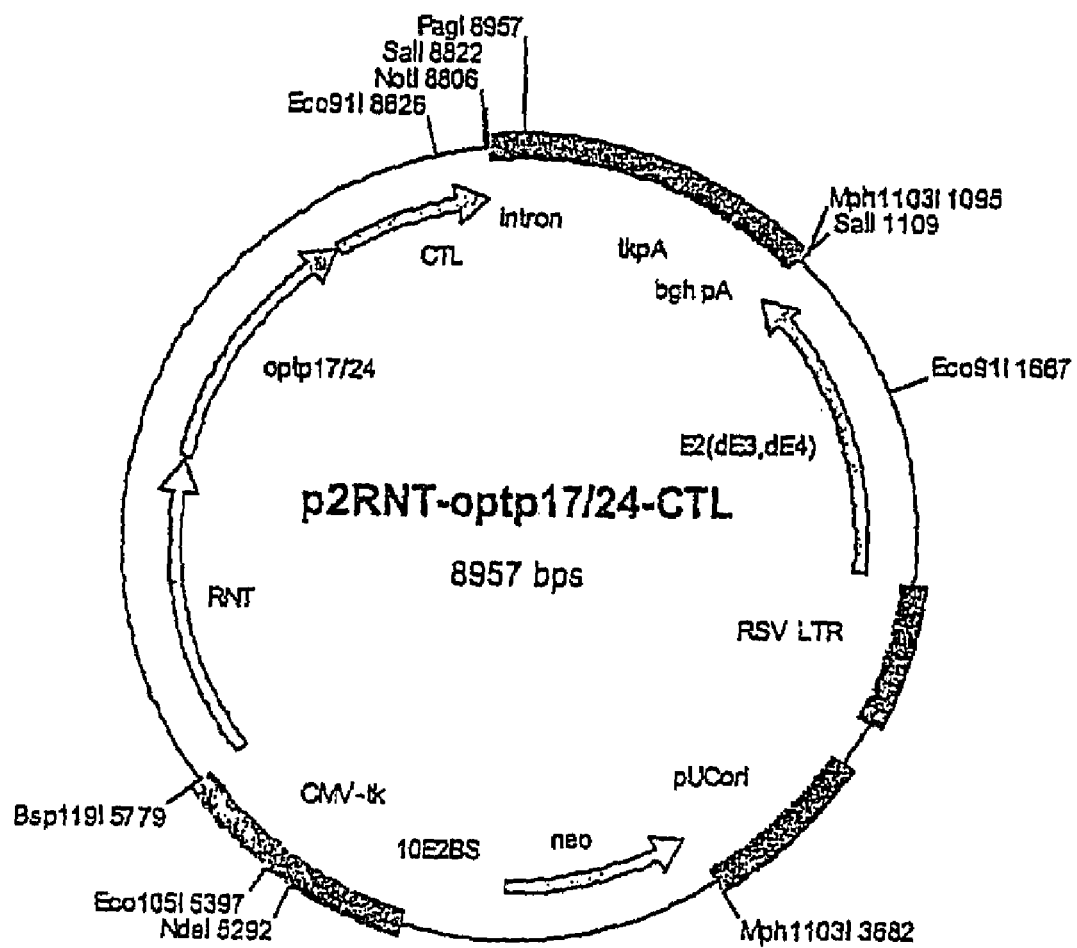
Figure 42M:
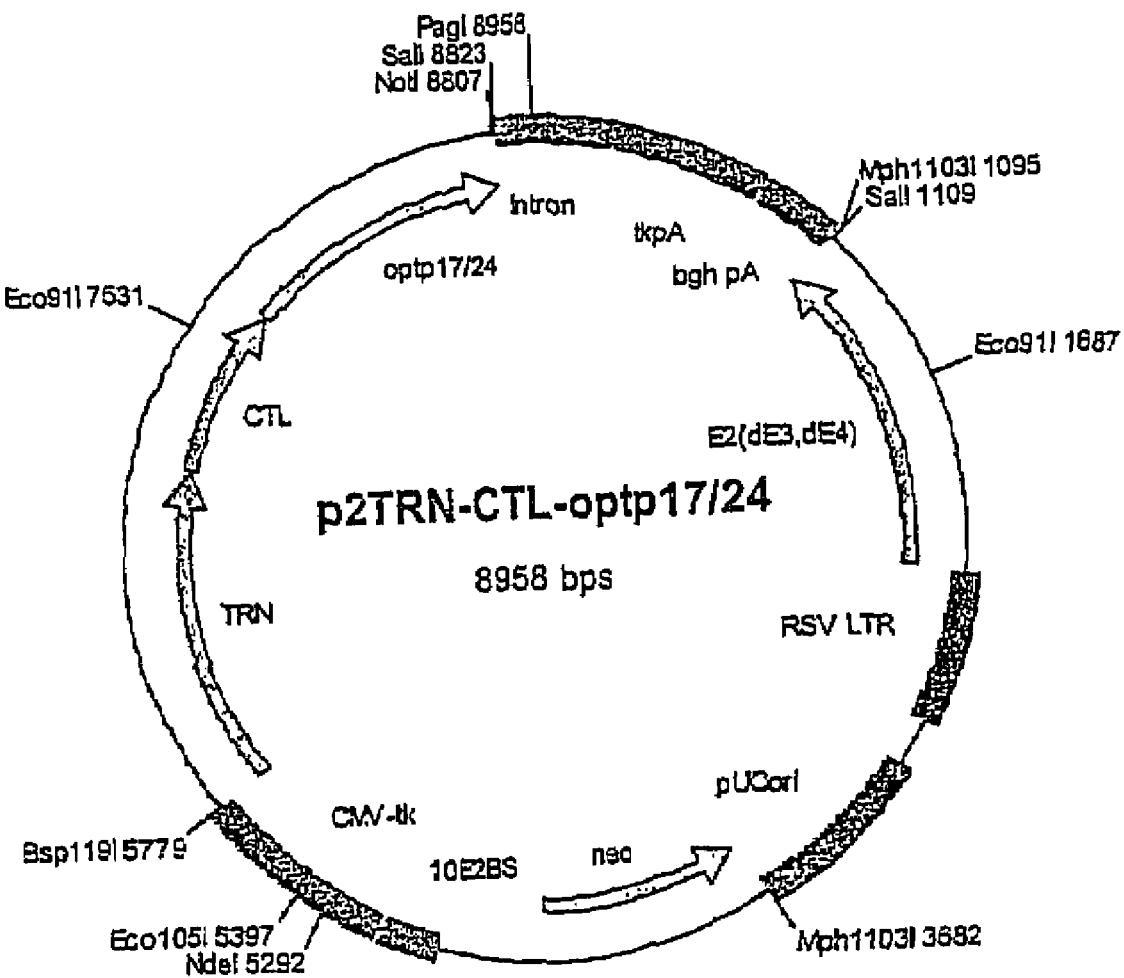
Figure 42N:
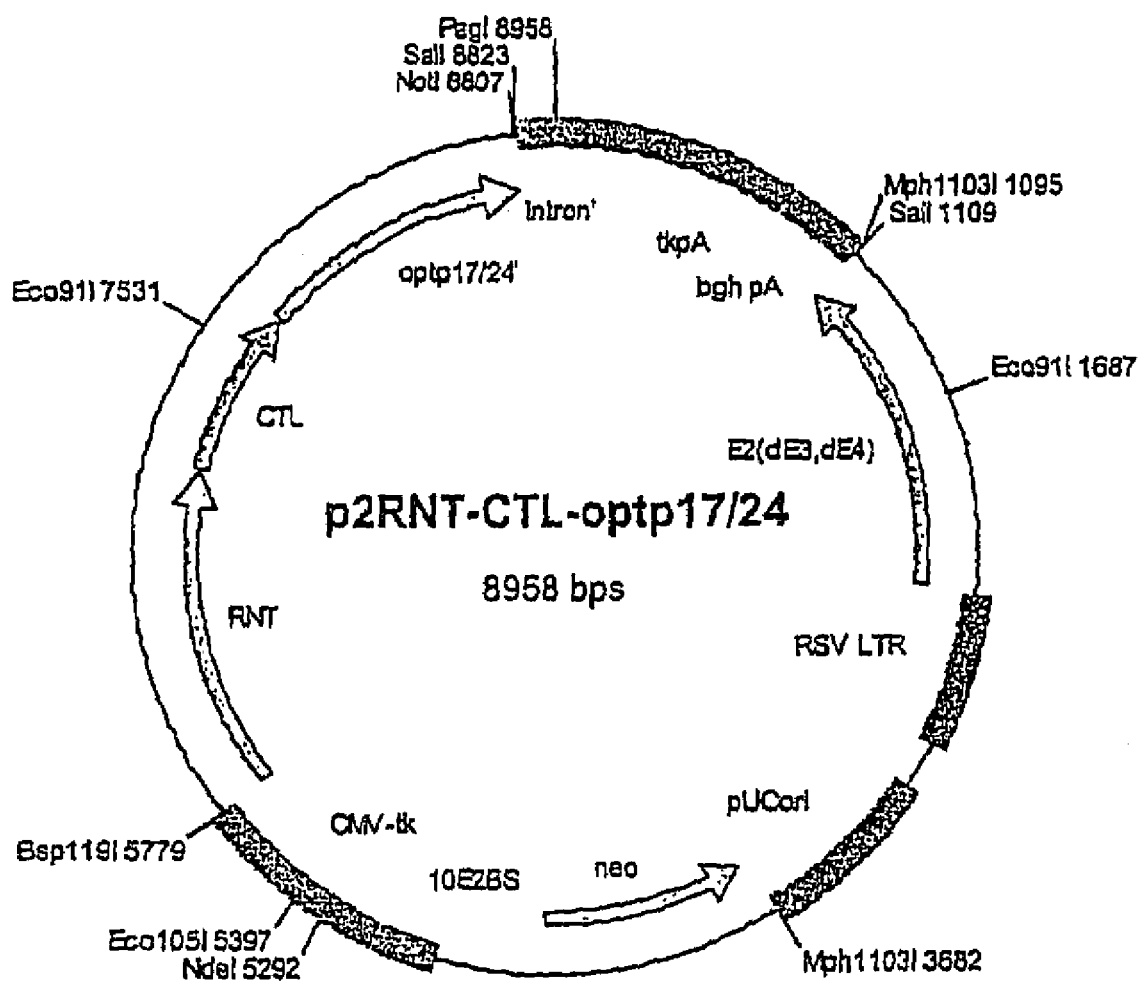
Figure 42:
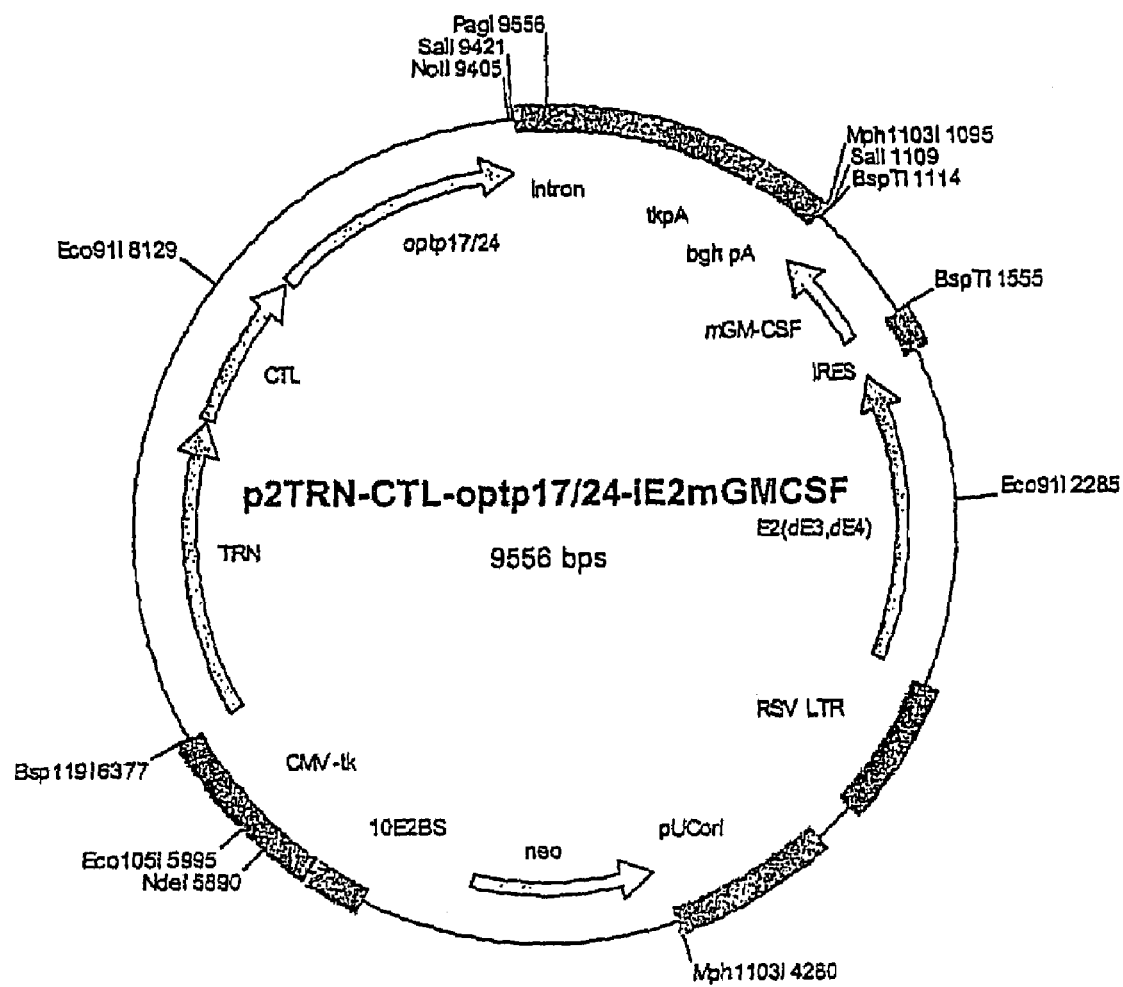
Figure 42P:
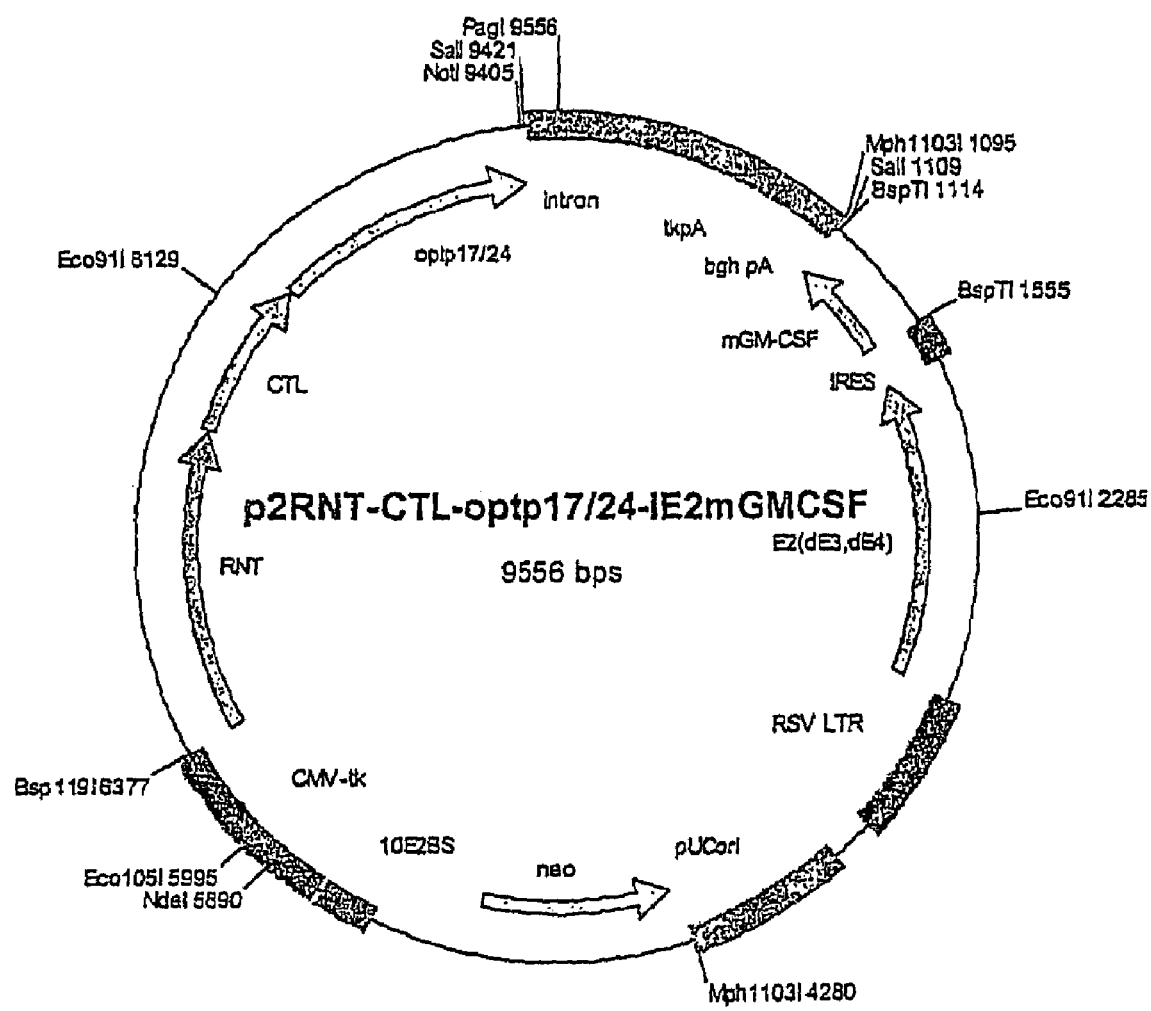
Figure 42Q:
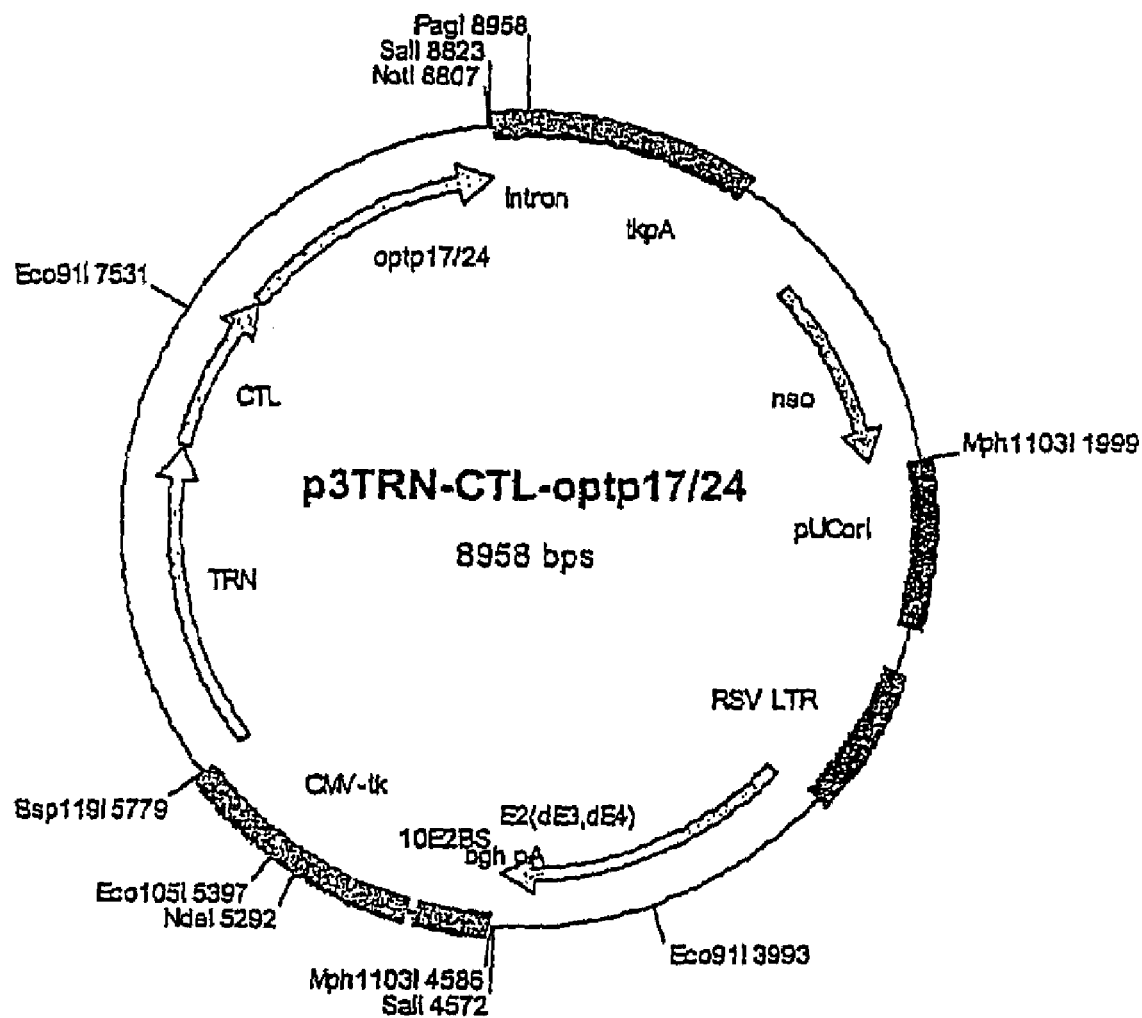
Figure 42R:
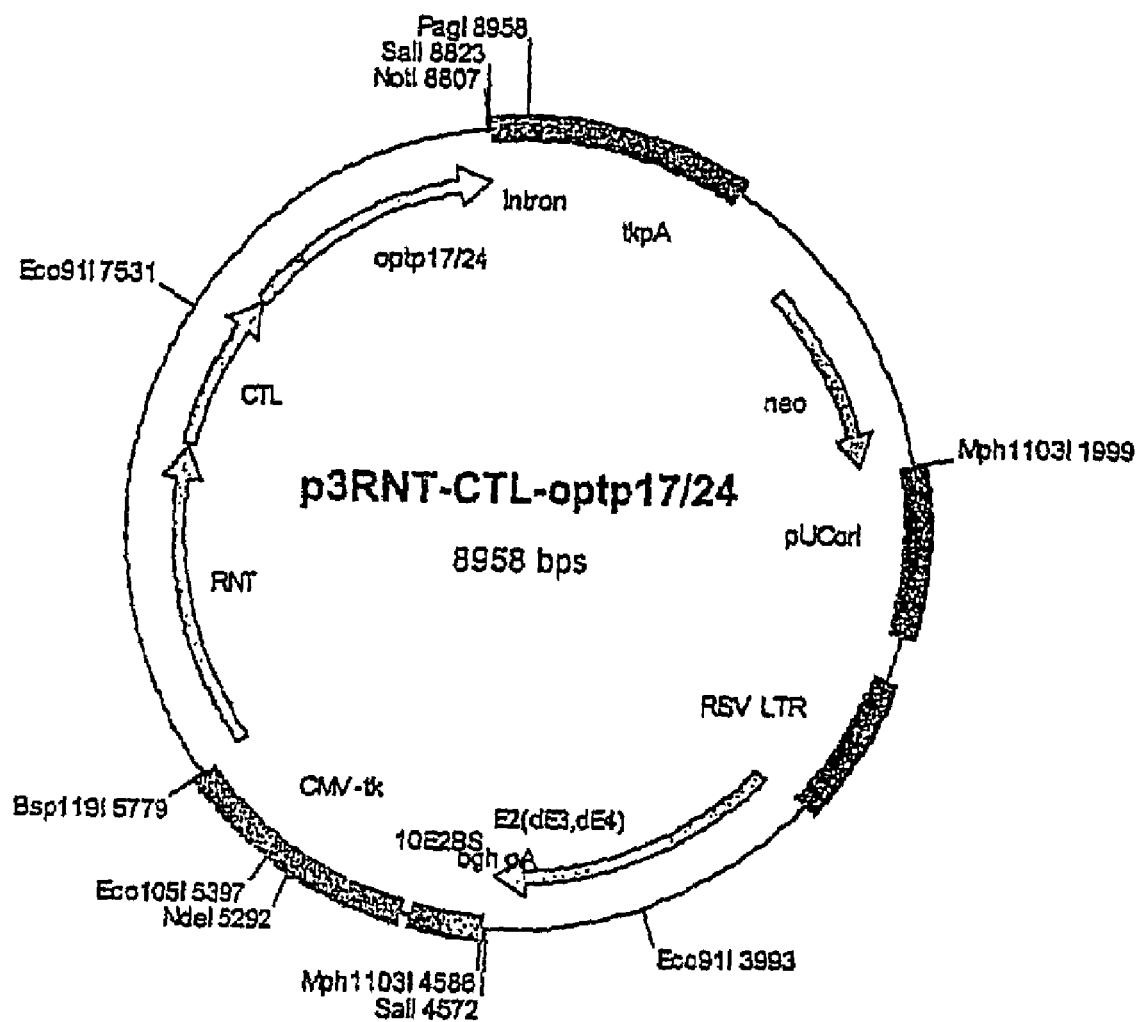
Figure 42S:
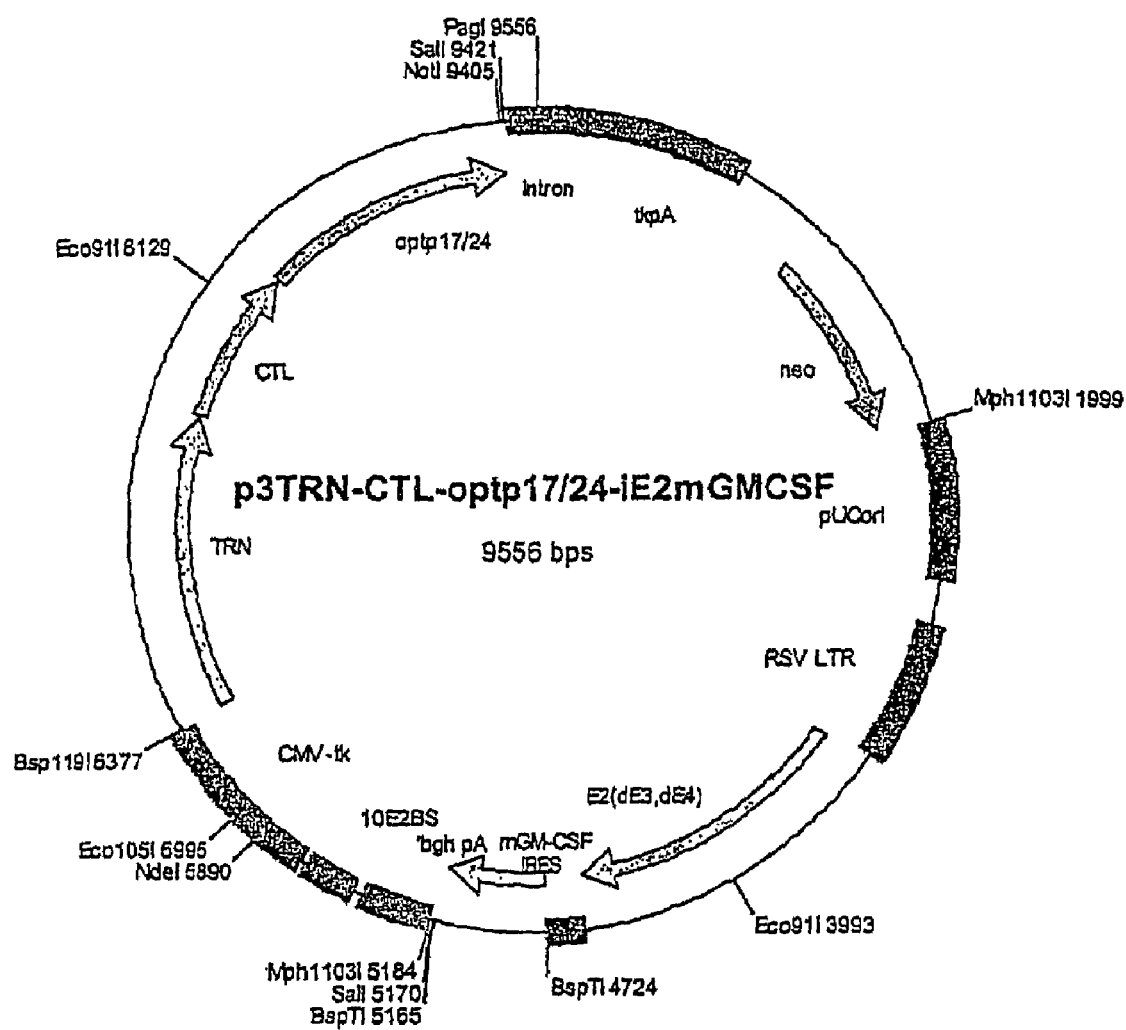

FIG. 42. (A) pTRN-CTL; (B) pRNT-CTL; (C) pTRN-dgag; (D) pTRN-CTL-dgag; (E) pRNT-CTL-dgag; (F) pTRN-dgag-CTL; (G) pRNT-dgag-CTL; (H) pTRN-optp17/24-CTL; (I) pTRN-CTL-optp17/24; (J) pRNT-CTL-optp17/24; (K) p2TRN-optp17/24-CTL; (L) p2RNT-optp17/24-CTL; (M) p2TRN-CTL-optp17/24; (N) p2RNT-CTL-optp17/24; (O) p2TRN-CTL-optp17/24-iE2-mGMCSF; (P) p2RNT-CTL-optp17/24-iE2-mGMCSF; (Q) p3TRN-CTL-optp17/24; (R) p3RNT-CTL-optp17/24, (S) p3TRN-CTL-optp17/24-iE2-mGMCSF; (T) p3RNT-CTL-optp17/24-iE2-mGMCSF; (U) FREBNA-RNT-CTL-optp17/24; (V) super6wt-RNT-CTL-optp17/24; (W) E2BSEBNA-RNT-CTL-optp17/24; (X) pCMV-RNT-CTL-optp17/24

Figure 43:

FIG. 43. Analysis of expression of the multireg antigens.

Figure 44:
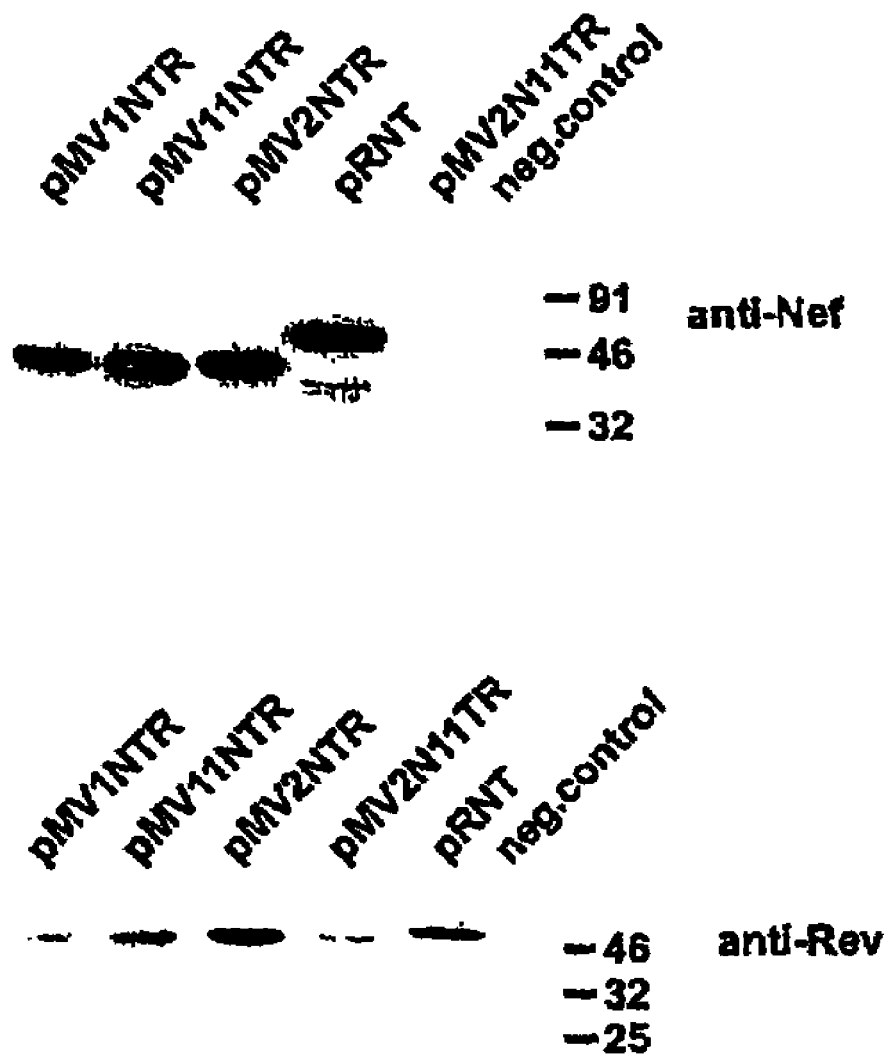
Figure 43:
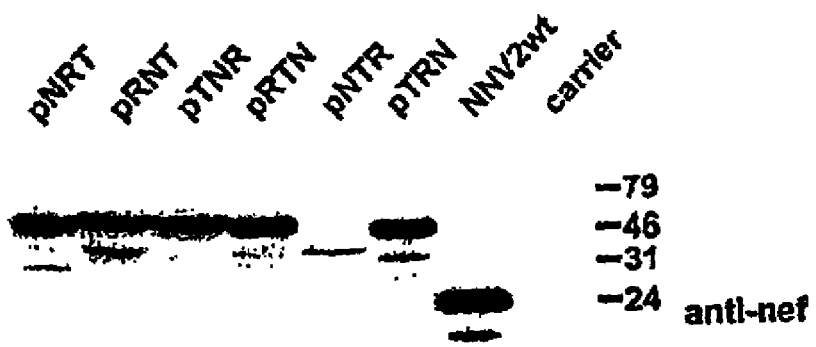
Figure 43:
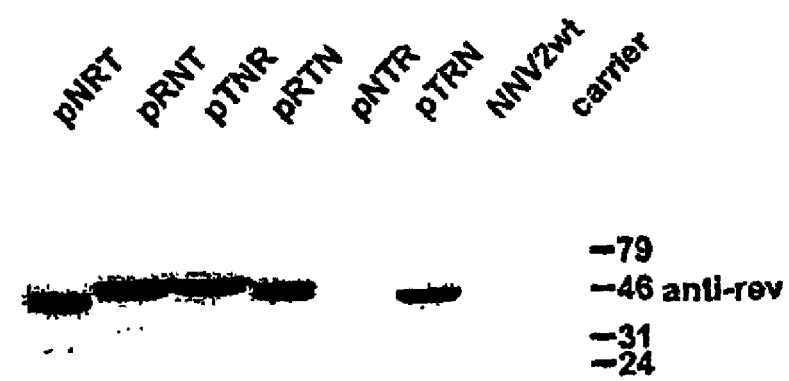
Figure 43:
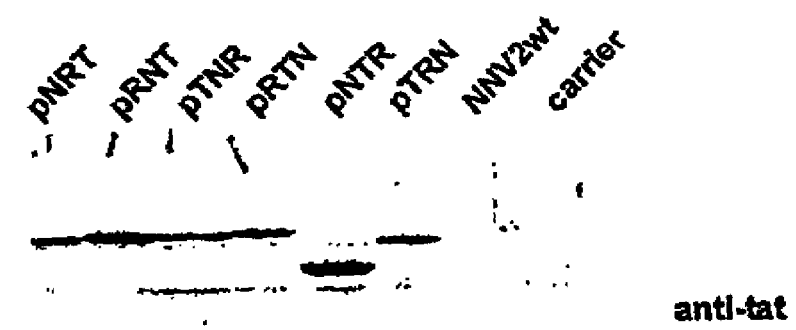
Figure 44:
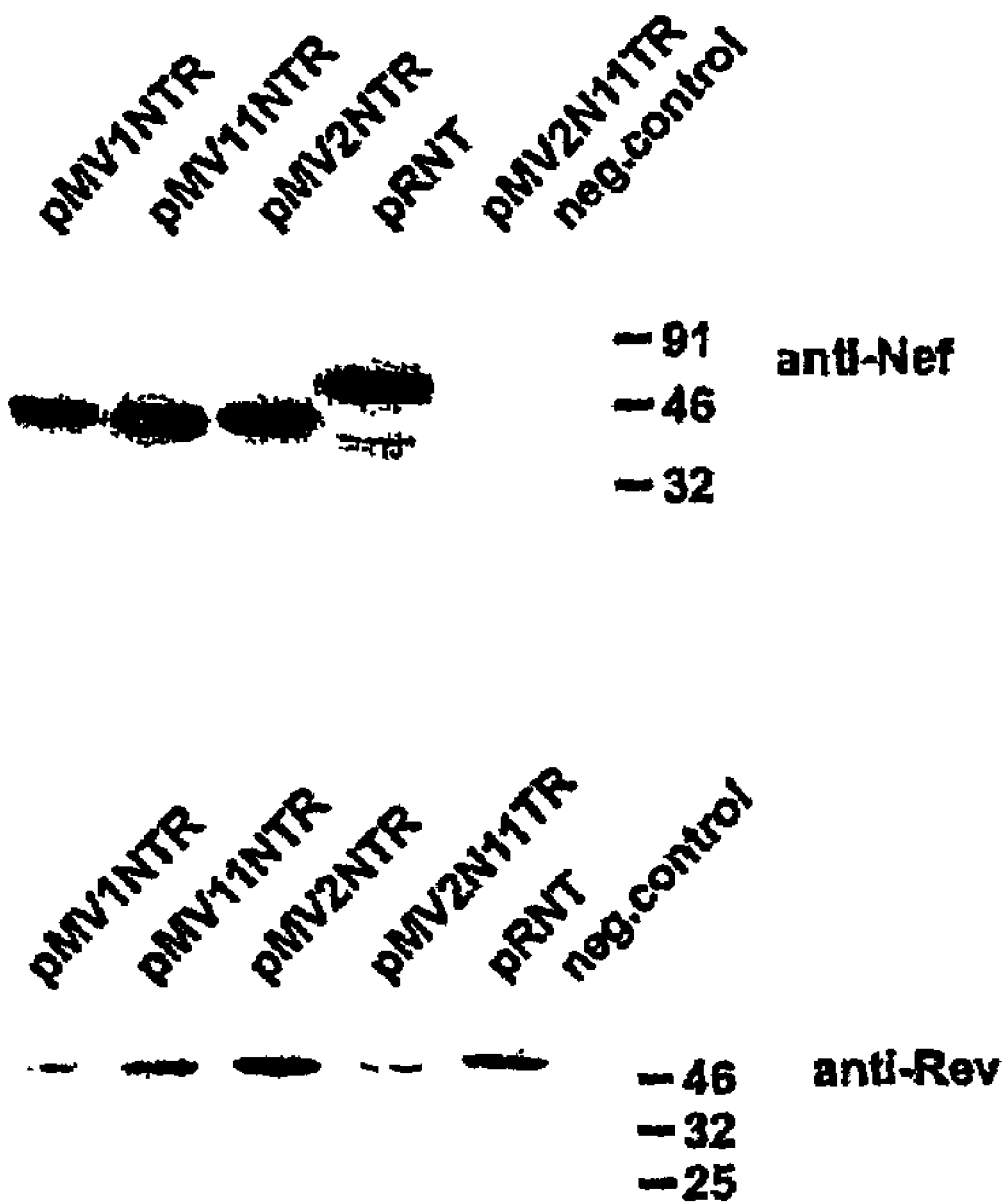

FIG. 44. Analysis of expression of the multireg antigens comprised of immunodominant parts of the proteins.

Figure 45:
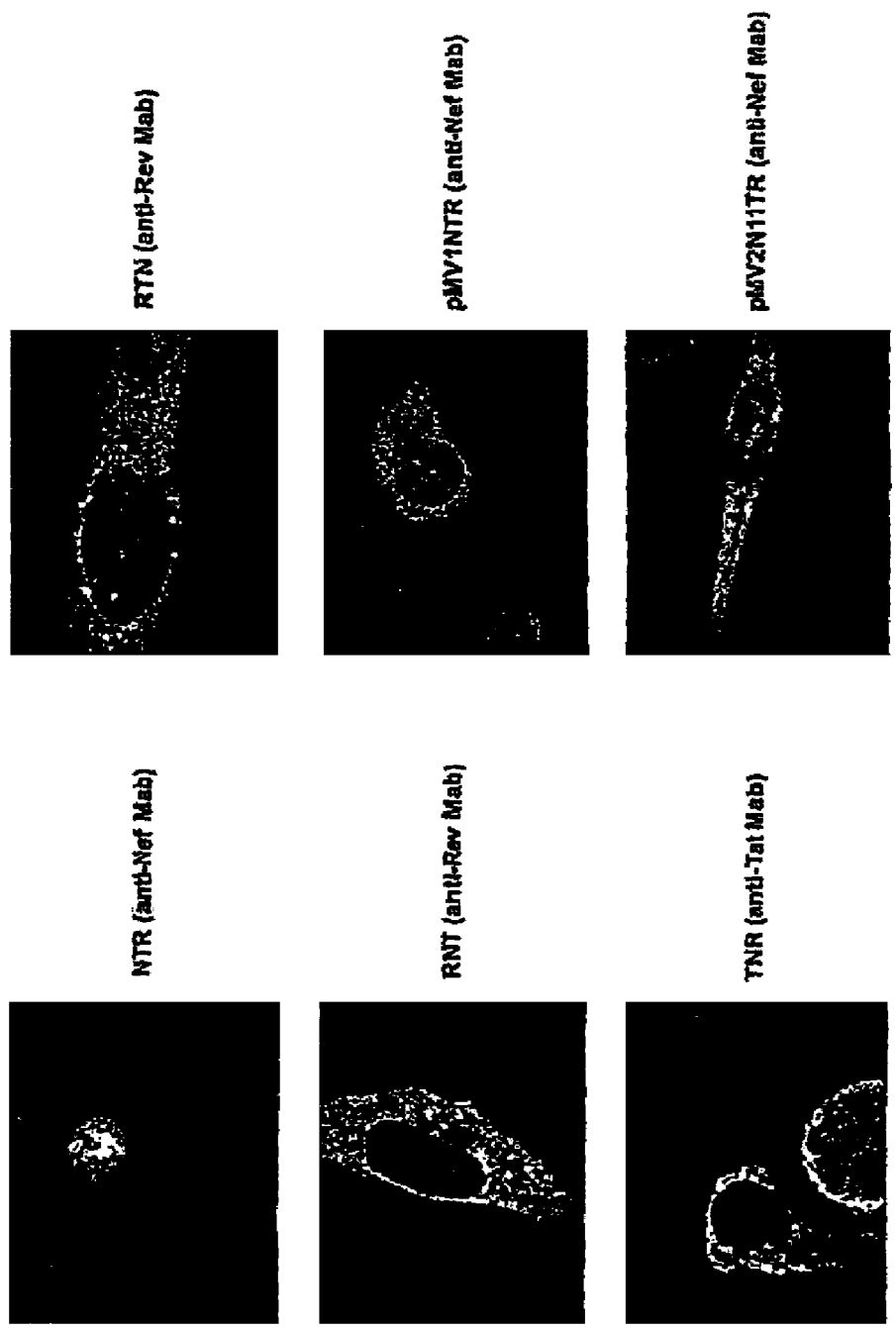

FIG. 45. Analysis of intracellular localization of multireg antigens by immunofluorescence.

Figure 46:
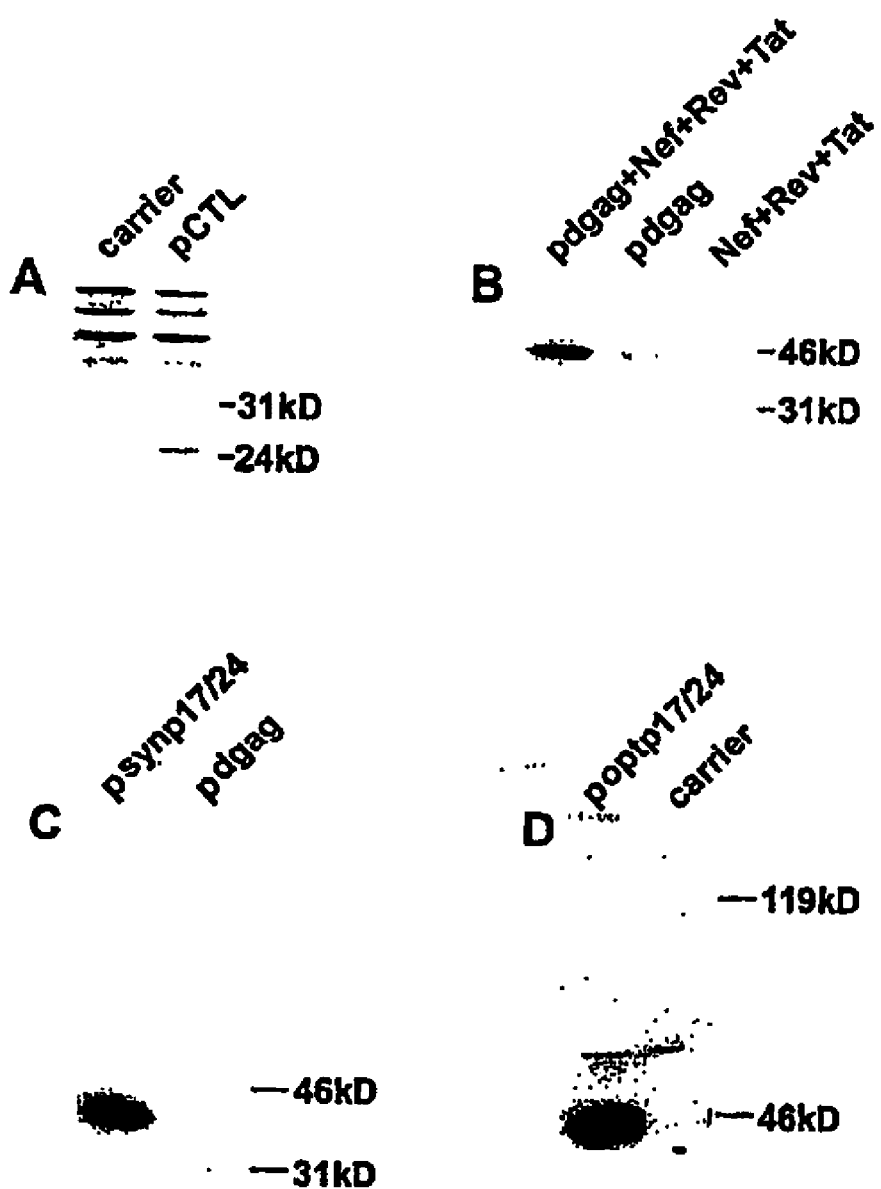

FIG. 46. Analysis of expression of the gag coded structural proteins and the CTL multi-epitope.

Figure 47:
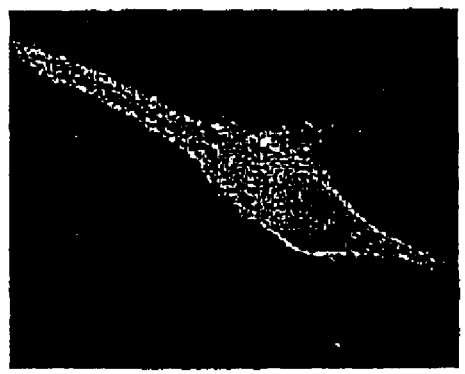

FIG. 47. The p17/24 protein localization in membranes of RD cells.

Figure 48:
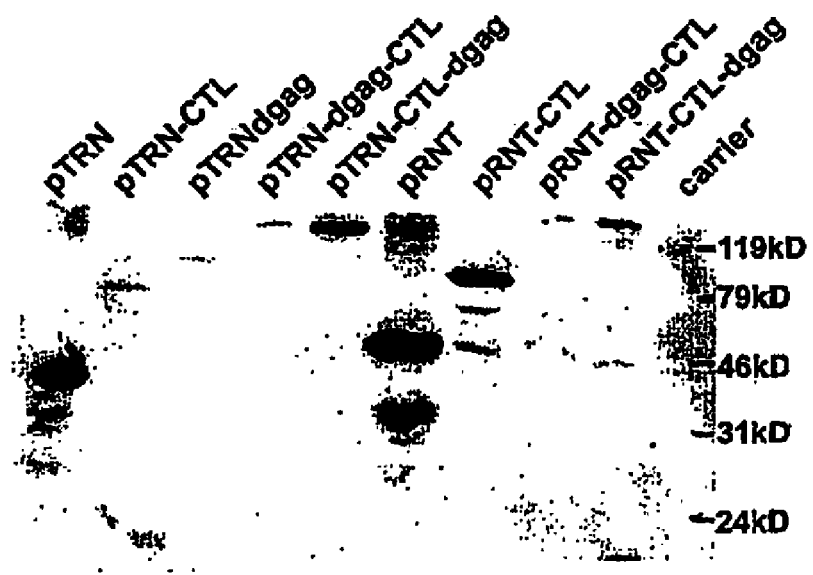

FIG. 48. Analysis expression of the dgag and CTL containing multigenes in Cos-7 cells.

Figure 49:
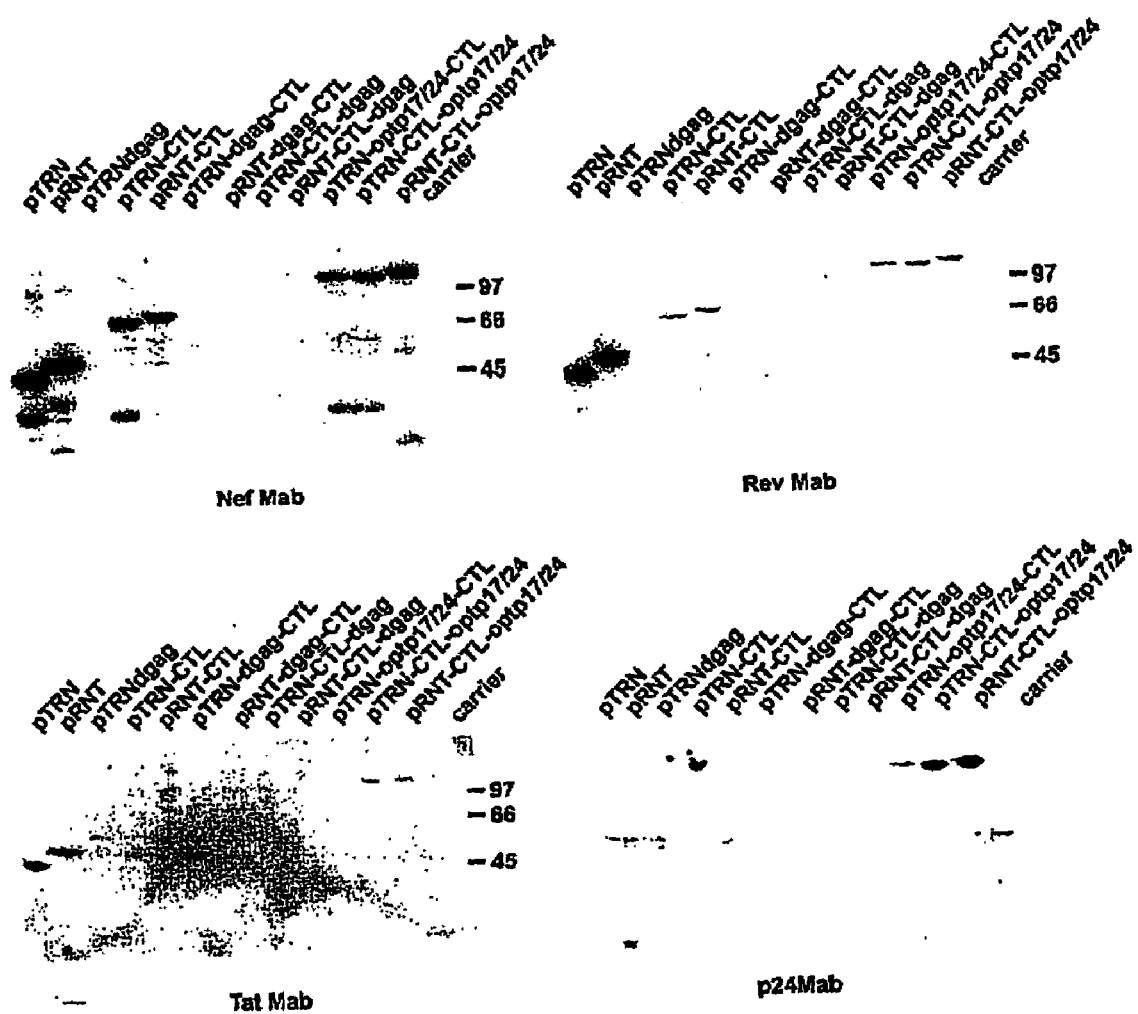

FIG. 49. Western blot analyses of multiHIV antigens expressed in Jurkat cells.

Figure 50:
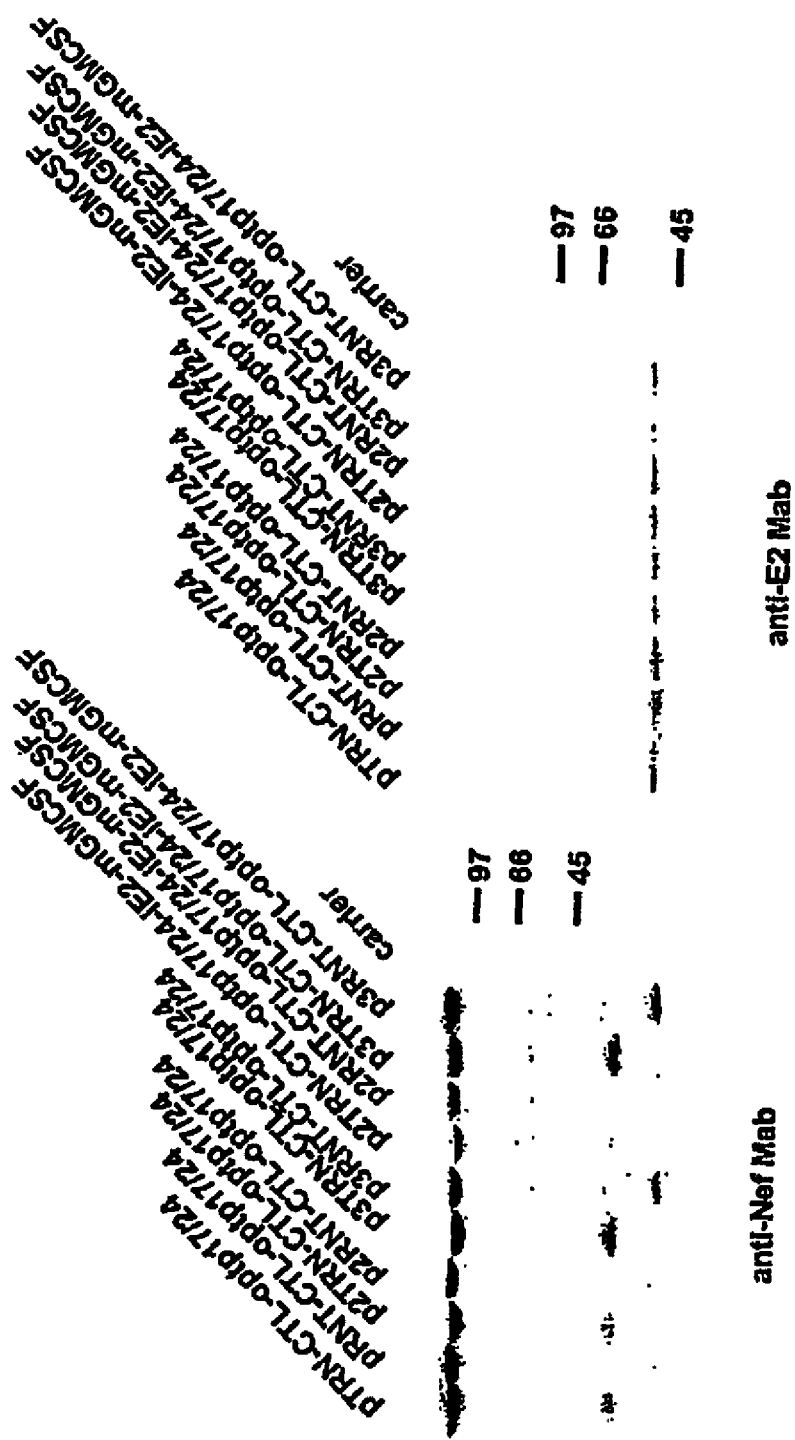

FIG. 50. Analysis of the expression of the TRN-CTL-optp17/24 and RNT-CTL-optp17/24 antigens as well E2 protein from the GTU-1, GTU-2 and GTU-3 vector.

Figure 51:
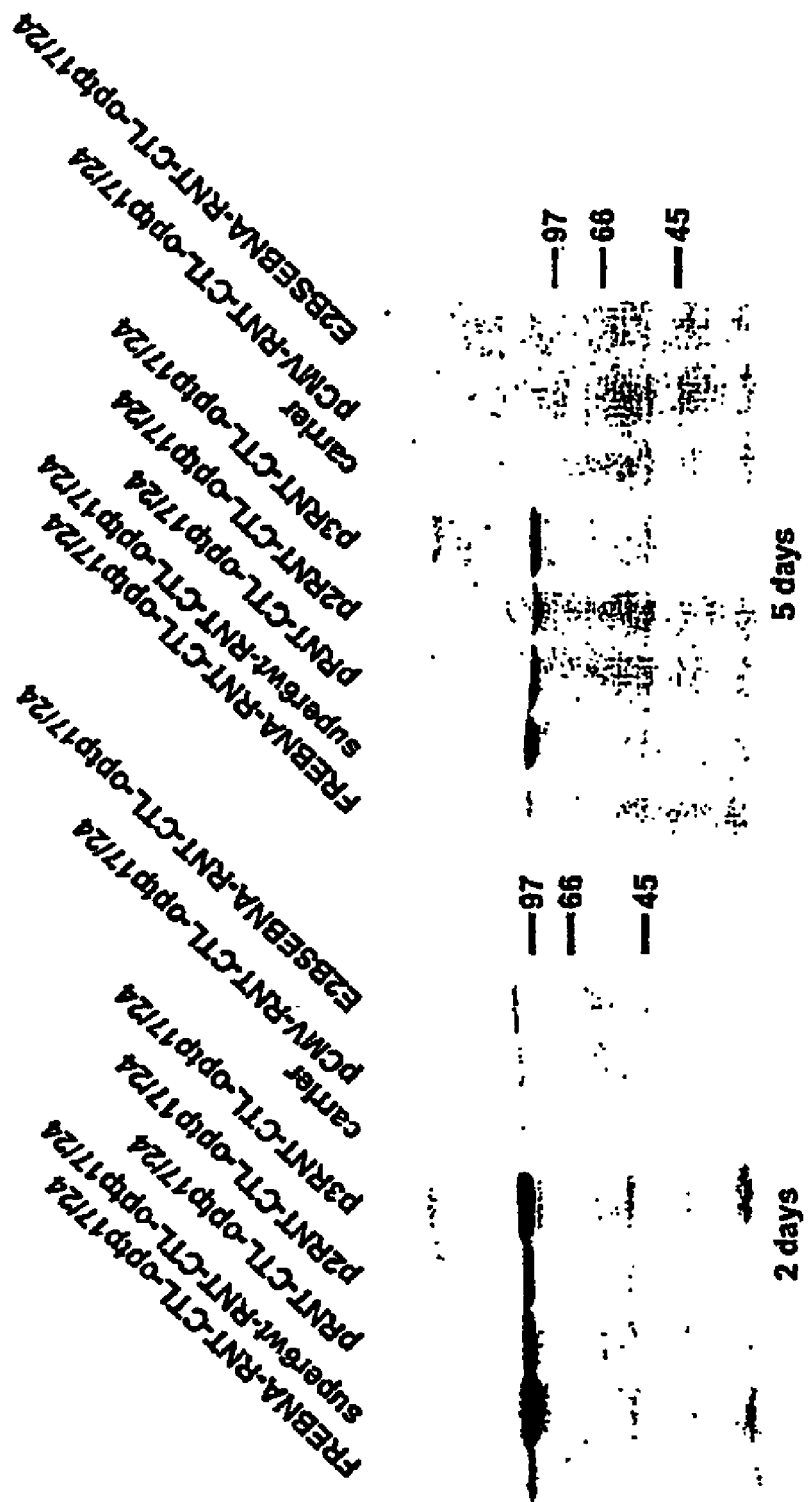

FIG. 51. The maintenance of the multiHIV antigen expression from different vectors.

Figure 52:
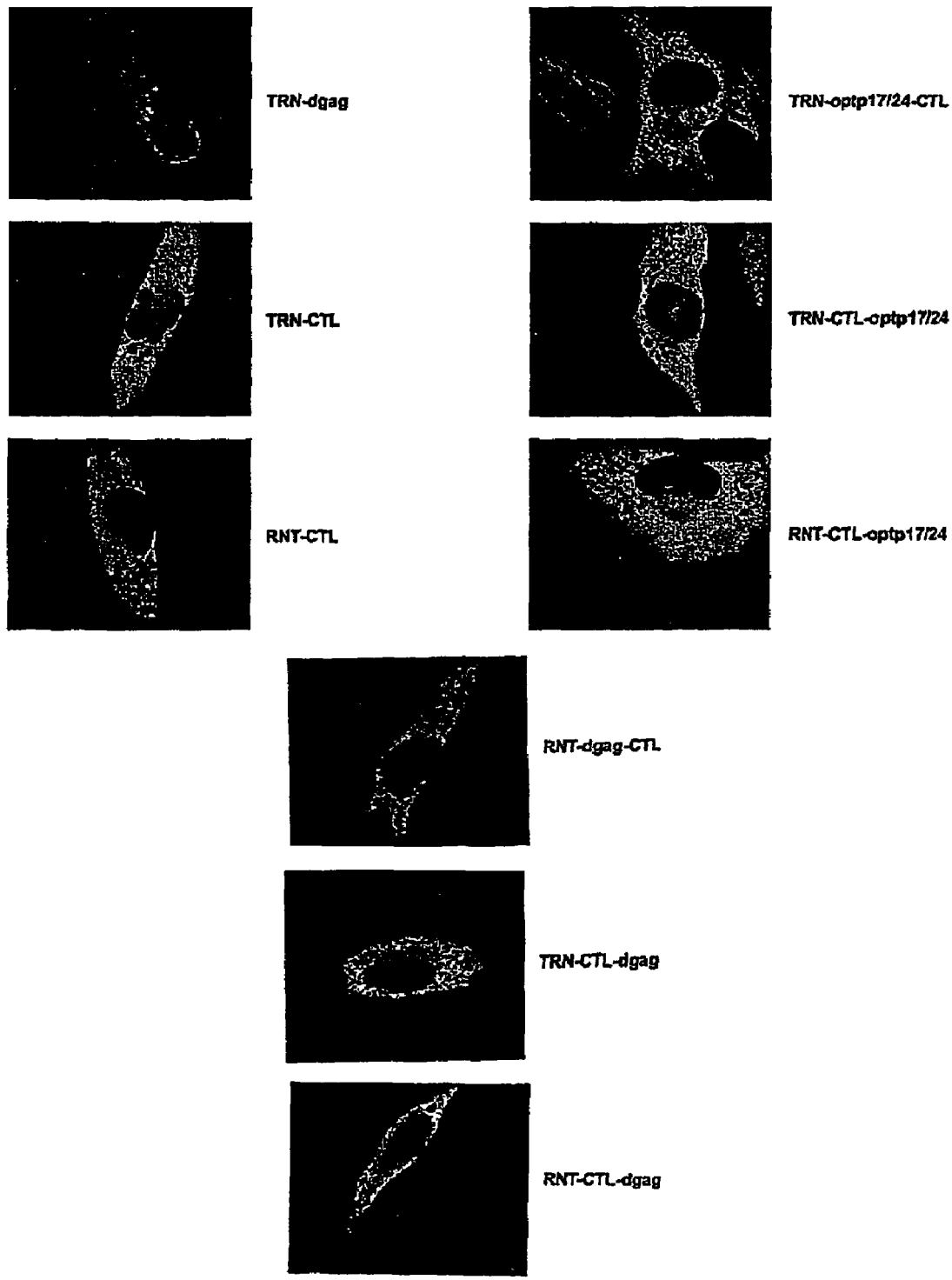

FIG. 52. Intracellular localization of the multiHIV antigens in RD cells.

5. DETAILED DESCRIPTION OF THE INVENTION

5.1 Vectors of the Invention

The present invention is based on the unexpected finding that expression vectors, which carry (A) an expression cassette of a gene of a nuclear-anchoring protein that binds both to (i) a specific DNA sequence and (ii) to a suitable nuclear component and (B) a multimerized DNA binding sequence for said nuclear-anchoring protein are capable of spreading in a proliferating cell population. Such nuclear-anchoring proteins include, but are not limited to, chromatin-anchoring proteins, such as the Bovine Papilloma Virus type 1 E2 protein (BPV1 E2; SEQ ID NO: 50). The DNA binding sequences can be, but are not limited to, multimerized E2 binding sites. On the basis of prior art, it could not be expected that a segregation/partitioning function of, for instance, the papilloma viruses could be expressed separately and that an addition of such segregation/partitioning function to the vaccine vectors would assure the distribution of the vector in the proliferating cell population. Additionally, on the basis of the prior art, it could not have been expected that functional vectors acting independently of the replication origin can be constructed.

The term "nuclear-anchoring protein" as used in the present invention refers to a protein, which binds to a specific DNA sequence and capable of providing a nuclear compartmentalization function to the vector, i.e., to a protein, which is capable of anchoring or attaching the vector to a specific nuclear compartment. In certain embodiments of the invention, the nuclear-anchoring protein is a natural protein. Examples of such nuclear compartments are the mitotic chromatin or mitotic chromosomes, the nuclear matrix, nuclear domains like ND10 and POD etc. Examples of nuclear-anchoring proteins are the Bovine Papilloma Virus type 1 (BPV1) E2 protein, EBNA1 (Epstein-Barr Virus Nuclear Antigen 1; SEQ ID NO: 52), and High Mobility Group (HMG) proteins etc. The term "functional equivalent of a nuclear-anchoring protein" as used in the present invention refers to a protein or a polypeptide of natural or non-natural origin having the properties of the nuclear-anchoring protein.

In certain other embodiments of the invention, the nuclear-anchoring protein of the invention is a recombinant protein. In certain specific embodiments of the invention, the nuclear-anchoring protein is a fusion protein, a chimeric protein, or a protein obtained by molecular modeling. A fusion protein, or a protein obtained by molecular modeling in connection with the present invention is characterized by its ability to bind to a nuclear component and by its ability to bind sequence-specifically to DNA. In a preferred embodiment of the invention, such a fusion protein is encoded by a vector of the invention which also contains the specific DNA sequence to which the fusion/chimeric protein binds. Nuclear components include, but are not limited to chromatin, the nuclear matrix, the ND10 domain and POD. In order to reduce the risk of interference with the expression of genes endogenous to the host cell, the DNA binding domain and the corresponding DNA sequence is preferably non-endogenous to the host cell/host organism. Such domains include, but are not limited to, the DNA binding domain of the Bovine Papilloma Virus type 1 (BPV1) E2 protein (SEQ ID NO: 50), Epstein-Barr Virus Nuclear Antigen 1 (EBNA1; SEQ ID NO: 52), and High Mobility Group (HMG) proteins (HMG box).

The vector of the invention can further comprise a "DNA sequence of interest", that encodes a protein (including a peptide or polypeptide), e.g., that is an immunogen or a therapeutic. In certain embodiments of the invention, the DNA sequence of interest encodes a biologically active RNA molecule, such as an antisense RNA molecule or a ribozyme.

The expression vectors of the invention carrying an expression cassette for a gene of a nuclear-anchoring protein and multimerized binding sites for said nuclear-anchoring protein spread in a proliferating host cell population. This means that a high copy-number of vectors or plasmids are delivered into the target cells and the use of the segregation/partitioning function of the nuclear-anchoring protein and its multimerized binding sites assures the distribution of the vector to the daughter cells during cell division.

The vector of the invention lacks a papilloma virus origin of replication. Further, in a preferred embodiment, the vector of the invention lacks an origin of replication functional in a mammalian cell. The omission of a papilloma virus origin of replication or a mammalian origin of replication constitutes an improvement over prior art vectors for several reasons. (1) Omission of the origin of replication reduces the size of the vector of the invention compared to prior art vectors. Such a reduction in size increases the stability of the vector and facilitates uptake by the host cell. (2) Omission of the origin of replication reduces the risk for recombination with the host cell's genome, thereby reducing the risk of unwanted side effects. (3) The omission of the origin of replication allows to control the dosage simply by adjusting the amount of vector administered. In contrast, with a functioning origin of replication, replication of the vector has to be taken into consideration when determining the required dosage. (4) If the vector is not administered to a host organism continually, the lack of an origin of replication allows the host organism to clear itself of the vector, thus providing more control over the levels of DNA sequences to be expressed in the host organism. Further, the ability of the organism to clear itself of the vector will be advantageous if the presence of the vector is required only during the course of a therapy but is undesirable in a healthy individual.

The gene of a nuclear-anchoring protein useful in the vectors of the present invention can be any suitable DNA sequence encoding a natural or artificial protein, such as a recombinant protein, a fusion protein or a protein obtained by molecular modeling techniques, having the required properties. Thus the gene of a natural nuclear-anchoring protein, which contains a DNA binding domain capable of binding to a specific DNA sequence and a functional domain capable of binding to a nuclear component, can be that of a viral protein, such as the E2 protein of Bovine Papilloma Virus or the EBNA1 (Epstein-Barr Virus Nuclear Antigen 1) of the Epstein-Barr Virus, a eukaryotic protein such a one of the High Mobility Group (HMG) proteins or a like protein, or a prokaryotic protein. Alternatively, the gene of a nuclear-anchoring protein, which contains a DNA binding domain capable of binding to a specific DNA sequence and a functional domain capable of binding to a nuclear component, can also be comprised of DNA sequences, which encode a domain from a cellular protein having the ability to attach to a suitable nuclear structure, such as to mitotic chromosomes, the nuclear matrix or nuclear domains like ND10 or POD.

Alternatively, the DNA sequence, which encodes a non-natural or artificial protein, such as a recombinant protein or a fusion protein or a protein obtained by molecular modeling, which contains a DNA binding domain capable of binding to a specific DNA sequence of, e.g., a papilloma virus, such as the DNA binding domain of the E2 protein of the BPV1, but in which the N-terminus of the nuclear-anchoring protein, e.g. that of the E2 protein, has been replaced with domains of any suitable protein of similar capacity, for example, with the N-terminal domain of Epstein-Barr Virus Nuclear Antigen 1 sequence, can be used. Similarly, DNA sequences, which encode a recombinant protein or a fusion protein, which contains a functional domain capable of binding to a nuclear component, e.g., the N-terminal functional domain of a papilloma virus, such as the E2 protein of the BPV1, but in which the C-terminal DNA-binding dimerization domain of the nuclear-anchoring protein, e.g., that of the E2 protein, has been replaced with domains of any protein of a sufficient DNA-binding strength, e.g., the DNA binding domain of the BPV-1 E2 protein and the EBNA-1, can be used.

In a preferred embodiment of the invention, the nuclear-anchoring protein is a chromatin-anchoring protein, which contains a DNA binding domain, which binds to a specific DNA sequence, and a functional domain capable of binding to mitotic chromatin. A preferred example of such a chromatin-anchoring protein and its multimerized binding sites useful in the present invention are the E2 protein of Bovine Papilloma Virus type 1 and E2 protein multimerized binding sites. In the case of E2, the mechanism of the spreading function is due to the dual function of the E2 protein: the capacity of the E2 protein to attach to mitotic chromosomes through the N-terminal domain of the protein and the sequence-specific binding capacity of the C-terminal domain of the E2 protein, which assures the tethering of vectors, which contain a multimerized E2 binding site, to mitotic chromosomes. A segregation/partitioning function is thus provided to the vectors.

In another preferred embodiment of the invention, the expression cassette of a gene of the chromatin-anchoring protein comprises a gene of any suitable protein of cellular, viral or recombinant origin having analogous properties to E2 of the BPV1, i.e., the ability to attach to the mitotic chromatin through one domain and to cooperatively bind DNA through another domain to multimerized binding sites specific for this DNA binding domain.

In a specific embodiment, sequences obtained from BPV1, are used in the vectors of the present invention, they are extensively shortened in size to include just two elements from BPV1. First, they include the E2 protein coding sequence transcribed from a heterologous eukaryotic promoter and polyadenylated at the heterologous polyadenylation site. Second, they include E2 protein multiple binding sites incorporated into the vector as a cluster, where the sites can be as head-to-tail structures or can be included into the vector by spaced positioning. Both of these elements are necessary and, surprisingly, sufficient for the function of the vectors to spread in proliferating cells. Similarly, when DNA sequences based of other suitable sources are used in the vectors of the present invention, the same principles are applied.

According to the present invention, the expression cassette of a gene of a nuclear-anchoring protein, which contains a DNA binding domain capable of binding to a specific DNA sequence and a functional domain capable of binding to a nuclear component, such as an expression cassette of a gene of a chromatin-anchoring protein, like BPV1 E2, comprises a heterologous eukaryotic promoter, the nuclear-anchoring protein coding sequence, such as a chromatin-anchoring protein coding sequence, for instance the BPV1 E2 protein coding sequence, and a poly A site. Different heterologous, eukaryotic promoters, which control the expression of the nuclear-anchoring protein, can be used. Nucleotide sequences of such heterologous, eukaryotic promoters are well known in the art and are readily available. Such heterologous eukaryotic promoters are of different strength and tissue-specificity. In a preferred embodiment, the nuclear anchoring protein is expressed at low levels.

The multimerized DNA binding sequences, i.e., DNA sequences containing multimeric binding sites, as defined in the context of the present invention, are the region, to which the DNA binding dimerization domain binds. The multimerized DNA binding sequences of the vectors of the present invention can contain any suitable DNA binding site, provided that it fulfills the above requirements.

In a preferred embodiment, the multimerized DNA binding sequence of a vector of the present invention can contain any one of known 17 different affinity E2 binding sites as a hexamer or a higher oligomer, as a octamer or a higher oligomer, as a decamer or higher oligomer. Oligomers containing different E2 binding sites are also applicable. Specifically preferred E2 binding sites useful in the vectors of the present invention are the BPV1 high affinity sites 9 and 10, affinity site 9 being most preferred. When a higher oligomer is concerned, its size is limited only by the construction circumstances and it may contain from 6 to 30 identical binding sites. Preferred vectors of the invention contain 10 BPV-1 E2 binding sites 9 in tandem. When the multimerized DNA binding sequences are comprised of different E2 binding sites, their size and composition is limited only by the method of construction practice. Thus they may contain two or more different E2 binding sites attached to a series of 6 to 30, most preferably 10, E2 binding sites. The Bovine Papilloma Virus type 1 genome (SEQ ID NO: 49) contains 17 E2 protein binding sites which differ in their affinity to E2. The E2 binding sites are described in Li et al. [Genes Dev 3(4) (1989) 510-526], which is incorporated by reference in its entirety herein.

Alternatively, the multimerized DNA binding sequences may be composed of any suitable multimeric specific sequences capable of inducing the cooperative binding of the protein to the plasmid, such as those of the EBNA1 or a suitable HMG protein. 21×30 bp repeats of binding sites for EBNA-1 are localized in the region spanning from nucleotide position 7421 to nucleotide position 8042 of the Epstein-Barr virus genome (SEQ ID NO:51). These EBNA-1 binding sites are described in the following references: Rawlins et al., Cell 42(3) (1985) 859-868; Reisman et al., Mol Cell Biol 5(8) (1985) 1822-1832; and Lupton and Levine, Mol Cell Biol 5(10) (1985) 2533-2542, all three of which are incorporated by reference in their entireties herein.

The position of the multimerized DNA binding sequences relative to the expression cassette for the DNA binding dimerization domain is not critical and can be any position in the plasmid. Thus the multimerized DNA binding sequences can be positioned either downstream or upstream relative to the expression cassette for the gene of interest, a position close to the promoter of the gene of interest being preferred.

The vectors of the invention also contain, where appropriate, a suitable promoter for the transcription of the gene or genes or the DNA sequences of interest, additional regulatory sequences, polyadenylation sequences and introns. Preferably the vectors may also include a bacterial plasmid origin of replication and one or more genes for selectable markers to facilitate the preparation of the vector in a bacterial host and a suitable promoter for the expression the gene for antibiotic selection.

The selectable marker can be any suitable marker allowable in DNA vaccines, such a kanamycin or neomycin, and others. In addition, other positive and negative selection markers can be included in the vectors of the invention, where applicable.

The vectors of the present invention only comprise the DNA sequences, for instance BPV1 DNA sequences, which are necessary and sufficient for longterm maintenance. All superfluous sequences, which may induce adverse reactions, such as oncogenic sequences, have been deleted. Thus in preferred vectors of the invention the E2 coding sequence is modified by mutational analysis so that this expresses only E2 protein and overlapping E3, E4 and E5 sequences have been inactivated by the introduction of mutations, which inactivate the translation from Open Reading Frames for E3, E4 and E5. The vector of the invention does not contain a papilloma virus origin of replication. Preferably, the vector of the invention further does not contain an origin of replication functional in a mammalian cell or a mammal.

Furthermore, the vectors of the present invention are not host specific, since the expression of the nuclear-anchoring protein, such as the E2 protein, is controlled by non-native or heterologous promoters. Depending on the particular promoter chosen, these promoters may be functional in a broad range of mammalian cells or they can be cell or tissue specific. Examples of promoters for the nuclear-anchoring protein, such as for the E2 protein, useful in the vectors of the present invention are thymidine kinase promoters, Human Cytomegalovirus Immediate Early Promoter, Rous Sarcoma Virus LTR and like. For the expression of the gene of interest, preferred promoters are strong promoters assuring high levels of expression of the gene of interest, an example for such a promoter is the Human Cytomegalovirus Immediate Early Promoter.

5.2 The Vectors of the Invention as Vehicles for Expression of a DNA Sequence of Interest A gene, genes or a DNA sequence or DNA sequences to be expressed via a vector of the invention can be any DNA sequence of interest, whose expression is desired. Thus the vectors may contain a gene or genes or a DNA sequence or DNA sequences from infectious microbial pathogens, such as viruses, against which live attenuated vaccines or inactivated vaccines cannot be prepared or used. Such DNA sequences of interest include genes or DNA sequences from viruses, such as Human Immunodeficiency Virus (HIV), Herpex Simplex Virus (HSV), Hepatitis C Virus, Influenzae Virus, Enteroviruses etc.; intracellular bacterial, such as *Chlamydia trachomatis, Mycobacterium tuberculosis, Mycoplasma pneumonia* etc.; extracellular bacteria, such as *Salmonella*; or fungi, such as *Candida albigans*.

In a preferred embodiment of the invention, the vectors contain a gene encoding early regulatory proteins of HIV, i.e. the nonstructural regulatory proteins Nef, Tat or Rev, preferably Nef. In another preferred embodiment of the invention the vectors of the invention contain genes encoding structural proteins of the HIV. In another preferred embodiment the vectors of the present invention contain two or more genes encoding any combination of early regulatory proteins and/or structural proteins of HIV. Illustrative examples of such combinations are a combination of a gene encoding the Nef protein and a DNA sequence encoding the Tat protein, possibly together with a DNA sequence encoding outer envelope glycoprotein of HIV, gp 120/gp 160 or a combination of any immunogenic epitopes of the proteins of pathogens incorporated into artificial recombinant protein.

Alternatively, the vectors of the invention may contain genes or DNA sequences for inherited or acquired genetic defects, such as sequences of differentiation antigens for melanoma, like a Tyrosinase A coding sequence or a coding sequence of beta-catenins.

In a preferred embodiment of the invention, the vectors contain a gene encoding proteins relating to cancer or other mutational diseases, preferably diseases related to immune maturation and regulation of immune response towards self and nonself, such as the APECED gene.

In another preferred embodiment of the invention, the vectors contain any DNA sequence coding for a protein that is defective in any hereditary single gene hereditary disease.

In another preferred embodiment of the invention, the vectors contain any DNA sequence coding for a macromolecular drug to be delivered and produced in vivo.

The method of the invention for the preparation of the vectors of the invention comprises the following steps: (A) cultivating a host cell containing a vector of the invention, and (B) recovering the vector. In certain specific embodiments, step (A) is preceded by transforming a host cell with a vector of the invention.

The vectors of the invention are preferably amplified in a suitable bacterial host cell, such as *Escherichia coli*. The vectors of the invention are stable and replicate at high copy numbers in bacterial cells. If a vector of the invention is to be amplified in a bacterial hast cell, the vector of the invention contains a bacterial origin of replication. Nucleotide sequences of bacterial origins of replication are well known to the skilled artisan and can readily be obtained.

Upon transfection into a mammalian host in high copy number, the vector spreads along with cell divisions and the number of cells carrying the vector increases without the replication of the vector, each cell being capable of expressing the protein of interest.

The vectors of the invention result in high expression of the desired protein. For instance, as demonstrated in Examples 4, 7-10: a high expression of the Nef protein of the HIV, green fluorescent protein (EGFP) and the AIRE protein could be demonstrated in many different cell lines and the data indicate that not only the number of positive cells, but the quantity of the protein encoded by the gene of interest is increasing in time.

The vectors of the invention also induce both humoral and cellular response as demonstrated in Examples 9 and 10. The results indicate that the vectors of the present invention can effectively be used as DNA vaccines.

The vaccines of the present invention contain a vector of the present invention or a mixture of said vectors in a suitable pharmaceutical carrier. The vaccine may for instance contain a mixture of vectors containing genes for the three different regulatory proteins of the HIV and/or structural proteins of the HIV.

The vaccines of the invention are formulated using standard methods of vaccine formulation to produce vaccines to be administered by any conventional route of administration, i.e. intramuscularily, intradermally and like.

The vectors of the invention may contain the ISS stimulatory sequences in order to activate the immune response of the body.

The vaccines of the invention can be used in a conventional preventive manner to protect an individual from infections, Alternatively, the vaccines of the invention can be used as therapeutical vaccines, especially in the case of viral infections, together with a conventional medication.

As mentioned above, the vectors of the present invention carrying the mechanism of spreading in the host cell find numerous applications as vaccines, in gene therapy, in gene transfer and as therapeutic immunogens. The vectors of the invention can be used to deliver a normal gene to a host having a gene defect, thus leading to a cure or therapy of a genetic disease. Furthermore, the vectors can deliver genes of immunogenic proteins of foreign origin, such as those from microbes or autologous tumor antigens, to be used in the development of vaccines against microbes or cancer. Furthermore, the vectors of the invention can deliver suitable genes of marker substances to nucleus, to be used in studies of cellular function or in diagnostics. Finally, the vectors of the invention can be used to specifically deliver a gene of macromolecular drug to the nucleus, thus enabling the development of novel therapeutic principles to treat and cure diseases, where the expression of the drug in the site of action, the cell nucleus, is of importance. These drugs can be chemical macromolecules, such as any proteins or polypeptides with therapeutic or curative effect, which interfere with any of the nuclear mechanisms, such as the replication or transcription or the transport of substances to and from the nucleus.

Specifically, the vectors of the present invention can be used for the expression of the specific cytokines, like interleukines (IL1, IL2, IL4, IL6, IL12 and others) or interferon, with the aim of modulating the specific immune responses of the organism (immunotherapy) against foreign antigens or boosting of the activity of the immune system against the mutated self-antigens. The vectors of the present invention are also useful in complementing malfunctioning of the brain due to the loss of specific dopamine-ergic neurons leading to the irreversible neurodegeneration, which is cause for Parkinson's disease, by expressing genes involved into synthesis of dopamine, like tyrosine hydroxylase, as well as other genes deficiency of which would have the similar effect. The vectors of the present invention are also useful for the expression of proteins and peptides regulating the brain activity, like dopamine receptors, CCK-A and CCK-B receptors, as well as neurotrophic factors, like GDNF, BDNF and other proteins regulating the brain activity. Further, the vectors of the present invention are usefulfor a longterm expression of factor IX in hepatocytes and alfa1-antitrypsin in muscle cells with the aim of complementing respective deficiencies of the organism.

5.3 Target Diseases and Disorders

In certain embodiments, a vector of the invention is used as a vaccine. In certain embodiments, a vector of the invention contains a DNA sequence of interest that encodes a protein or a peptide. Upon administering of such a vector to a subject, the protein or peptide encoded by the DNA sequence of interest is expressed and stimulates an immune response specific to the protein or peptide encoded by the DNA sequence of interest.

In specific embodiments, the vector of the invention is used to treat and/or prevent an infectious disease and/or a condition caused by an infectious agent. Such diseases and conditions include, but are not limited to, infectious diseases caused by bacteria, viruses, fungi, protozoa, helminths, and the like. In a more specific embodiment of the invention, the infectious disease is Acquired Immuno-deficiency Syndrome.

Preferably, where it is desired to treat or prevent viral diseases, DNA sequences encoding molecules comprising epitopes of known viruses are used. For example, such DNA sequences encoding antigenic epitopes may be prepared from viruses including, but not limited to, hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeiciency virus type II (HIV-II).

Preferably, where it is desired to treat or prevent bacterial infections, DNA sequences encoding molecules comprising epitopes of known bacteria are used. For example, such DNA sequences encoding antigenic epitopes may be prepared from bacteria including, but not limited to, *mycobacteria rickettsia, Mycoplasma, neisseria* and *legionella*.

Preferably, where it is desired to treat or prevent protozoal infections, DNA sequences encoding molecules comprising epitopes of known protozoa are used. For example, such DNA sequences encoding antigenic epitopes may be prepared from protozoa including, but not limited to, *leishmania, kokzidioa*, and *trypanosoma*.

Preferably, where it is desired to treat or prevent parasitic infections, DNA sequences encoding molecules comprising epitopes of known parasites are used. For example, such DNA sequences encoding antigenic epitopes may be prepared from parasites including, but not limited to, *chlamydia* and *rickettsia*.

In other specific embodiments, the vector of the invention is used to treat and/or prevent a neoplastic disease in a subject. In these embodiments, the DNA sequence of interest encodes a protein or peptide that is specific to or associated with the neoplastic disease. By way of non-limiting example, the neoplastic disease can be a fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease, etc.

In certain other embodiments of the invention, the DNA sequence of interest encodes a protein that is non-functional or malfunctioning due to an inherited disorder or an acquired mutation in the gene encoding the protein. Such genetic diseases include, but are not limited to, metabolic diseases, e.g., Atherosclerosis (affected gene: APOE); cancer, e.g., Familial Adenomatous Polyposis Coli (affected gene: APC gene); auto-immune diseases, e.g., autoimmune polyendocrinopathy-candidosis-ectodermal dysplasia (affected gene: APECED); disorders of the muscle, e.g., Duchenne muscular dystrophyvaccines (affected gene: DMD); diseases of the nervous system, e.g., Alzheimer's Disease (affected genes: PS1 and PS2).

In even other embodiments, the vectors of the invention are used to treat and/or prevent diseases and disorders caused by pathologically high activity of a protein. In these embodiments of the invention, the DNA sequence of interest encodes an antagonist of the overactive protein. Such antagonists include, but are not limited to, antisense RNA molecules, ribozymes, antibodies, and dominant negative proteins. In specific embodiments of the invention, the DNA sequence of interest encodes an inhibitor of an oncogene.

In certain embodiments, the DNA sequence of interest encodes a molecule that antagonizes neoplastic growth. In specific embodiments of the invention, the DNA sequence of interest encodes a tumor suppressor, such as, but not limited to, p53. In other specific embodiments, the DNA sequence of interest encodes an activator of apoptosis, such as but not limited to, a Caspase.

The invention provides methods, whereby a DNA sequence of interest is expressed in a subject. In certain embodiments, a vector containing one or more expression cassettes of a DNA sequence of interest is administered to the subject, wherein the subject does not express the Bovine Papilloma Virus E1 protein.

5.4 Therapeutic Methods for use with the Invention 5.4.1 Recombinant DNA

In various embodiments of the invention, -the vector of the invention comprises one or more expression cassettes comprising a DNA sequence of interest. The DNA sequence of interest can encode a protein and/or a biologically active RNA molecule. In either case, the DNA sequence is inserted into the vector of the invention for expression in recombinant cells or in cells of the host in the case of gene therapy.

An expression cassette, as used herein, refers to a DNA sequence of interest operably linked to one or more regulatory regions or enhancer/promoter sequences which enables expression of the protein of the invention in an appropriate host cell. "Operably-linked" refers to an association in which the regulatory regions and the DNA sequence to be expressed are joined and positioned in such a way as to permit transcription, and in the case of a protein, translation.

The regulatory regions necessary for transcription of the DNA sequence of interest can be provided by the vector of the invention. In a compatible host-construct system, cellular transcriptional factors, such as RNA polymerase, will bind to the regulatory regions of the vector to effect transcription of the DNA sequence of interest in the host organism. The precise nature of the regulatory regions needed for gene expression may vary from host cell to host cell. Generally, a promoter is required which is capable of binding RNA polymerase and promoting the transcription of an operably-associated DNA sequence. Such regulatory regions may include those 5'-non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

Both constitutive and inducible regulatory regions may be used for expression of the DNA sequence of interest. It may be desirable to use inducible promoters when the conditions optimal for growth of the host cells and the conditions for high level expression of the DNA sequence of interest are different. Examples of useful regulatory regions are provided below (section 5.4.4).

In order to attach DNA sequences with regulatory functions, such as promoters, to the DNA sequence of interest or to insert the DNA sequence of interest into the cloning site of a vector; linkers or adapters providing the appropriate compatible restriction sites may be ligated to the ends of the cDNAs by techniques well known in the art [Wu et al., Methods in Enzymol 152 (1987) 343-349]. Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

The vector comprising a DNA sequence of interest operably linked to a regulatory region (enhancer/promoter sequences) can be directly introduced into appropriate host cells for expression of the DNA sequence of interest without further cloning.

For expression of the DNA sequence of interest in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein II gene, mouse mammary tumor virus glucocorticoid responsive long terminal repeats (MMTV-LTR), β-interferon gene, and hsp70 gene [Williams et al., Cancer Res. 49 (1989) 2735-42; Taylor et al., Mol. Cell Biol., 10 (1990) 165-75]. It may be advantageous to use heat shock promoters or stress promoters to drive expression of the DNA sequence of interest in recombinant host cells.

In addition, the expression vector may contain a selectable or screenable marker gene for initially isolating, identifying or tracking host cells that contain the vector. A number of selection systems may be used for mammalian cells, including but not limited to the Herpes simplex virus thymidine kinase [Wigler et al., Cell 11 (1977) 223], hypoxanthine-guanine phosphoribosyltransferase [Szybalski and Szybalski, Proc. Natl. Acad. Sci. USA 48 (1962) 2026], and adenine phosphoribosyltransferase [Lowy et al., Cell 22 (1980) 817] genes can be employed in tk$^-$, hgprt$^-$ or aprt$^-$ cells, respectively. Also, antimetabolite resistance can be used as the basis of selection for dihydrofolate reductase (dhfr), which confers resistance to methotrexate [Wigler et al., Natl. Acad. Sci. USA 77 (1980) 3567; O'Hare et al., Proc. Natl. Acad. Sci. USA 78 (1981) 1527]; gpt, which confers resistance to mycophenolic acid [Mulligan & Berg, Proc. Natl. Acad. Sci. USA 78 (1981) 2072]; neomycin phosphotransferase (neo), which confers resistance to the aminoglycoside G-418 [Colberre-Garapin et al., J. Mol. Biol. 150 (1981) 1]; and hygromycin phosphotransferase (hyg), which confers resistance to hygromycin [Santerre et al., 1984, Gene 30 (1984)147]. Other selectable markers, such as but not limited to histidinol and Zeocin® can also be used.

5.4.2 Expression Systems and Host Cells

For use with the methods of the invention, the host cell and/or the host organism preferably does not express the Bovine Papilloma Virus E1 protein. Furthermore, preferably the vector of the invention does not encode the Bovine Papilloma Virus E1 protein.

Preferred mammalian host cells include but are not limited to those derived from humans, monkeys and rodents, (see, for example, Kriegler M. in "Gene Transfer and Expression: A Laboratory Manual", New York, Freeman & Co. 1990), such as monkey kidney cell line transformed by SV40 (COS-7, ATCC CRL 1651); human embryonic kidney line (293, 293-EBNA, or 293 cells subcloned for growth in suspension culture, Graham et al., J. Gen. Virol., 36 (1977) 59; baby hamster kidney cells (BHK, ATCC CCL 10); chinese hamster ovary-cells-DHFR [CHO, Urlaub and Chasin. Proc. Natl. Acad. Sci. 77 (1980) 4216]; mouse sertoli cells [Mather, Biol. Reprod. 23 (1980) 243-251]; mouse fibroblast cells (NIH-3T3), monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); and mouse mammary tumor cells (MMT 060562, ATCC CCL51).

The vectors of the invention may be synthesized and assembled from known DNA sequences by well-known techniques in the art. The regulatory regions and enhancer elements can be of a variety of origins, both natural and synthetic. Some host cells may be obtained commercially.

The vectors of the invention containing a DNA sequence of interest can be introduced into the host cell by a variety of techniques known in the art, including but not limited to, for prokaryotic cells, bacterial transformation (Hanahan, 1985, in DNA Cloning, A Practical Approach, 1:109-136), and for eukaryotic cells, calcium phosphate mediated transfection [Wigler et al., Cell 11 (1977) 223-232], liposome-mediated transfection [Schaefer-Ridder et al., Science 215 (1982) 166-168], electroporation [Wolff et al., Proc Natl Acad Sci 84 (1987)3344], and micro-injection [Cappechi, Cell 22 (1980) 479-4889].

In a specific embodiment, cell lines that express the DNA sequence of the invention may be engineered by using a vector that contains a selectable marker. By way of example but not limitation, following the introduction of the vector, engineered cells may be allowed to grow for 1-2 days in an enriched media, and then are switched to a selective media. The selectable marker in the vector confers resistance to the selection and optimally allows only cells that contain the vector with the selectable marker to grow in culture.

5.4.3 Vaccine Approaches

In certain embodiments, a vector of the invention comprising an expression cassette of a DNA sequence of interest is administered to a subject to induce an immune response. Specifically, the DNA sequence of interest encodes a protein (for example, a peptide or polypeptide), which induces a specific immune response upon its expression. Examples of such proteins are discussed in section 5.3.

For the delivery of a vector of the invention for use as a vaccine, methods may be selected from among those known in the art and/or described in section 5.4.6.

5.4.4 Gene Therapy Approaches

In a specific embodiment, a vector of the invention comprising an expression cassette comprising DNA sequences of interest is administered to treat, or prevent various diseases. The DNA sequence of interest may encode a protein and/or a biologically active RNA molecule. Gene therapy refers to therapy performed by the administration to a subject of an expressed or expressible DNA sequence. In this embodiment of the invention, the DNA sequences produce their encoded protein or RNA molecule that mediates a therapeutic effect.

Any of the methods for gene therapy available in the art can be used according to the present invention. Exemplary methods are described below.

For general reviews of the method of gene therapy, see, Goldspiel et al., Clinical Pharmacy 12 (1993) 488-505; Wu and Wu, Biotherapy 3 (1991) 87-95; Tolstoshev, Ann. Rev. Pharmacol. Toxicol. 32 (1993) 573-596; Mulligan, Science 260 (1993) 926-932; Morgan and Anderson, Ann. Rev. Biochem. 62 (1993) 191-217; May, TIBTECH 1,I(5) (1993)155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

The following animal regulatory regions, which exhibit tissue specificity and have been utilized in transgenic animals, can be used for expression of the DNA sequence of interest in a particular tissue type: elastase I gene control region which is active in pancreatic acinar cells [Swift et al., Cell 38 (1984) 639-646; Ornitz et al., Cold Spring Harbor Symp. Quant. Biol. 50 (1986) 399-409; MacDonald, Hepatology 7 (1987) 425-515]; insulin gene control region which is active in pancreatic beta cells [Hanahan, Nature 315 (1985) 115-122], immunoglobulin gene control region which is active in lymphoid cells [Grosschedl et al., Cell 38 (1984) 647-658; Adames et al., Nature 318 (1985) 533-538; Alexander et al., Mol. Cell. Biol. 7 (1987) 1436-1444], mouse mammary tumor virus control region which is active in testicular, breast, lymphoid and mast cells [Leder et al., Cell 45 (1986) 485-495], albumin gene control region which is active in the liver [Pinkert et al., Genes and Devel. 1 (1987) 268-276], alpha-fetoprotein gene control region which is active in the liver [Krumlauf et al., Mol. Cell. Biol. 5 (1985)1639-1648; Hammer et al., Science 235 (1987) 53-58; alpha 1-antitrypsin gene control region which is active in the liver [Kelsey et al., Genes and Devel. 1 (1987) 161-171], beta-globin gene control region which is active in myeloid cells [Mogram et al., Nature 315 (1985) 338-340; Kollias et al., Cell 46 (1986) 89-94]; myelin basic protein gene control region which is active in oligodendrocyte cells in the brain [Readhead et al., Cell 48 (1987) 703-712]; myosin light chain-2 gene control region which is active in skeletal muscle [Sani, Nature 314 (1985) 283-286], and gonadotropic releasing hormone gene control region which is active in the hypothalamus [Mason et al., Science 234 (1986)1372-1378].

Methods of delivery fro gene therapy approaches are well known in the art and/or described in section 5.4.6.

5.4.5 Inhibitory Antisense and Ribozyme

In certain embodiments of the invention a vector of the invention contains a DNA sequence of interest that encodes an antisense or ribozyme RNA molecule. Techniques for the production and use of such molecules are well known to those of skill in the art.

Antisense RNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with at least the non-polyA portion of an RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Antisense nucleic acids should be at least six nucleotides in length, and are preferably oligonucleotides ranging-from 6 to about 50 nucleotides in length. In specific aspects the oligonucleotide is at least 10 nucleotides, at least 17 nucleotides, at least 25 nucleotides or at least 50 nucleotides. In other embodiments of the invention, the antisense nucleic acids are at least 100, at least 250, at least 500, and at least 1000 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense DNA sequence are compared with those obtained using a control DNA sequence. It is preferred that the control DNA sequence is of approximately the same length as the test oligonucleotide and that the DNA sequence of the oligonucleotide differs from the antisense sequence no more than is necessary to prevent specific hybridization to the target sequence.

While antisense DNA sequences complementary to the target gene coding region sequence could be used, those complementary to the transcribed, untranslated region are most preferred.

For expression of the biologically active RNA, e.g., an antisense RNA molecule, from the vector of the invention the DNA sequence encoding the biologically active RNA molecule is operatively linked to a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector of the invention can be introduced, e.g., such that it is taken up by a cell and directs the transcription of an antisense RNA. Such vectors can be constructed by recombinant DNA technology methods standard in the art. Expression of the sequence encoding the antisense RNA can be by any promoter known in the art to act in mammalian, preferably human cells. Such promoters can be inducible or constitutive. Such promoters include but are not limited to: the SV40 early promoter region [Bernoist and Chambon, Nature 290 (1981) 304-310], the promoter contained in the 3 long terminal repeat of Rous sarcoma virus [Yamamoto, et al., Cell 22 (1980) 787-797], the herpes thymidine kinase promoter [Wagner, et al., Proc. Natl. Acad. Sci. U.S.A. 78 (1981) 1441-1445], the regulatory sequences of the metallothionein gene [Brinster, et al., 1982, Nature 296 (1982) 39-42], etc.

In certain embodiments of the invention, a vector of the invention contains a DNA sequence, which encodes a ribozyme. Ribozyme molecules designed to catalytically cleave target gene mRNA transcripts can also be used to prevent translation of a target gene mRNA and, therefore, expression of a target gene product [see, e.g., PCT International Publication WO90/11364, published Oct. 4, 1990; Sarver, et al., Science 247 (1990) 1222-1225].

Ribozymes are enzymatic RNA molecules capable of catalyzing the specific cleavage of RNA. [For a review, see Rossi, Current Biology 4 (1994) 469-471]. The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site-specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, Molecular Biology and Biotechnology: A Comprehensive Desk Reference, VCH Publishers, New York, (see especially FIG. 4, page 833) and in Haseloff & Gerlach, Nature, 334 1988) 585-591, which is incorporated herein by reference in its entirety.

Preferably the ribozyme is engineered so that the cleavage recognition site is located near the-5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators [Zaug, et al., Science, 224 (1984) 574-578; Zaug and Cech, Science, 231 (1986) 470-475; Zaug, et al., Nature, 324 (1986) 429-433; published International patent application No. WO 88/04300 by University Patents Inc.; Been & Cech, Cell, 47 (1986) 207-216]. The Cech-type ribozymes have an eight base pair active site, which hybridizes to a target RNA sequence whereafter cleavage of the target RNA takes place. The invention encompasses those Cech-type ribozymes, which target eight base-pair active site sequences that are present in the target gene.

Expression of a ribozyme can be under the control of a strong constitutive pol III or pol II promoter, so that transfected cells will produce sufficient quantities of the ribozyme to destroy endogenous target gene messages and inhibit trans-lation. Because ribozymes unlike antisense molecules, are catalytic, a lower intracellular concentration is required for efficiency.

In instances wherein the antisense and/or ribozyme molecules described herein are utilized to inhibit mutant gene expression, it is possible that the technique may so efficiently reduce or inhibit the translation of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.4.4 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Methods of administering the ribozyme and antisense RNA molecules are well known in the art and/or described in section 5.4.6.

5.4.6 Pharmaceutical Formulations and Modes of Administration

In a preferred aspect, a pharmaceutical of the invention comprises a substantially purified vector of the invention (e.g., substantially free from substances that limit its effect or produce undesired side-effects). The subject to whom the pharmaceutical is administered in the methods of the invention is preferably an animal, including but not limited to animals such as cows, pigs, horses, chickens, cats, dogs, etc., and is preferably a mammal, and most preferably a human.

In certain embodiments, the vector of the invention is directly administered in vivo, where the DNA sequence of interest is expressed to produce the encoded product. This can be accomplished by any of numerous methods known in the art. The vectors of the invention can be administered so that the nucleic acid sequences become intracellular. The vectors of the invention can be administered by direct injection of naked DNA; use of microparticle bombardment (e.g., a gene gun; Biolistic, Dupont); coating with lipids or cell-surface receptors or transfecting agents; encapsulation in microparticles or microcapsules; administration in linkage to a peptide which is known to enter the nucleus; administration in linkage to a ligand subject to receptor-mediated endocytosis [see, e.g., Wu and Wu, J. Biol. Chem. 262 (1987) 4429-4432] (which can be used to target cell types specifically expressing the receptors); etc. In a specific embodiment, the compound or composition can be delivered in a vesicle, in particular a liposome [see Langer, Science 249 (1990) 1527-1533; Treat et al, 1989, in Liposomes in the Therapy of Infectious Disease and Cancer, Lopez-Berestein and Fidler (eds.), Liss, New York, pp. 353-365; Lopez-Berestein, ibid., pp. 317-327].

In certain embodiments, the vector of the invention is coated with lipids or cell-surface receptors or transfecting agents, or linked to a homeobox- like peptide which is known to enter the nucleus [see e.g., Joliot et al, Proc. Natl. Acad. Sci. USA 88 (1991) 1864-1868], etc.

In certain other embodiments, nucleic acid-ligand complexes can be formed in which the ligand comprises a fusogenic viral peptide to disrupt endosomes, allowing the nucleic acid to avoid lysosomal degradation.

In yet other embodiments, the vector of the invention can be targeted in vivo for cell specific uptake and expression, by targeting a specific receptor (see, e.g., PCT Publications WO 92/06 180; WO 92/22635; W092/20316; W093/14188, and WO 93/20221).

Methods for use with the invention include, but are not limited to, intradermal, intramuscular, intraperitoneal, intravenous, subcutaneous, intranasal, epidural, and oral routes. Methods for use with the invention further include administration by any convenient route, for example by infusion or bolus injection, by absorption through epithelial or mucocutaneous linings (e.g., oral mucosa, rectal and intestinal mucosa, etc.). In a specific embodiment, it may be desirable to administer a vector of the invention by injection, by means of a catheter, by means of a suppository, or by means of an implant, said implant being of a porous, non-porous, or gelatinous material, including a membrane, such as a sialastic membrane, or a fiber. Care must be taken to use materials to which the vector does not absorb. Administration can be systemic or local.

In certain embodiments, a vector of the invention is administered together with other biologically active agents such as chemotherapeutic agents or agents that augment the immune system.

In yet another embodiment, methods for use with the invention include delivery via a controlled release system. In one embodiment, a pump may be used [see Langer, supra; Sefton, CRC Crit. Ref. Biomed. Eng. 14 (1989) 201; Buchwald et al., Surgery 88 (1980) 507; Saudek et al., N. Engl. J. Med. 321 (1989) 574]. In another embodiment, polymeric materials can be used [see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, New York; Ranger and Peppas, Macromol. Sci. Rev. Macromol. Chem. 23 (1983) 61; see also Levy et al., Science 228 (1985) 190; During et al., Ann. Neurol. 25 (1989) 351; Howard et al., J. Neurosurg. 71 (1989) 105].

Other controlled release systems are discussed in the review by Langer, Science 249 (1990)1527-1533.

Pharmaceutical compositions of the invention comprise a therapeutically effective amount of a vector of the invention, and a suitable pharmaceutical vehicle. In a specific embodiment, the term "suitable pharmaceutical vehicle" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or vehicle with which the therapeutic is administered. Such suitable pharmaceutical vehicles can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein of the invention, preferably in purified form, together with a suitable amount of carrier so as to provide the form for proper administration to the patient. The formulation should suit the mode of administration.

In a specific embodiment, the pharmaceutical of the invention is formulated in accordance with routine procedures as a pharmaceutical composition adapted for intravenous administration to human beings. Typically, compositions for intravenous administration are solutions in sterile isotonic aqueous buffer. Where necessary, the pharmaceutical of the invention may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical of the invention is to be administered by infusion, it can be dispensed with an infusion bottle containing sterile pharmaceutical grade water or saline. Where the pharmaceutical of the invention is administered by injection, an ampoule of sterile water for injection or saline can be provided so that the ingredients may be mixed prior to administration.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The amount of a vector of the invention, which will be effective in the treatment or prevention of the indicated disease, can be determined by standard clinical techniques. In addition, in vitro assays may optionally be employed to help identify optimal dosage ranges. The precise dose to be employed in the formulation will also depend on the route of administration, and the stage of indicated disease, and should be decided according to the judgment of the practitioner and each patient's circumstances. Effective doses may be extrapolated from dose-response curves derived from in vitro or animal model test systems.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

6. EXAMPLES

6.1. Example 1

Figure 1:
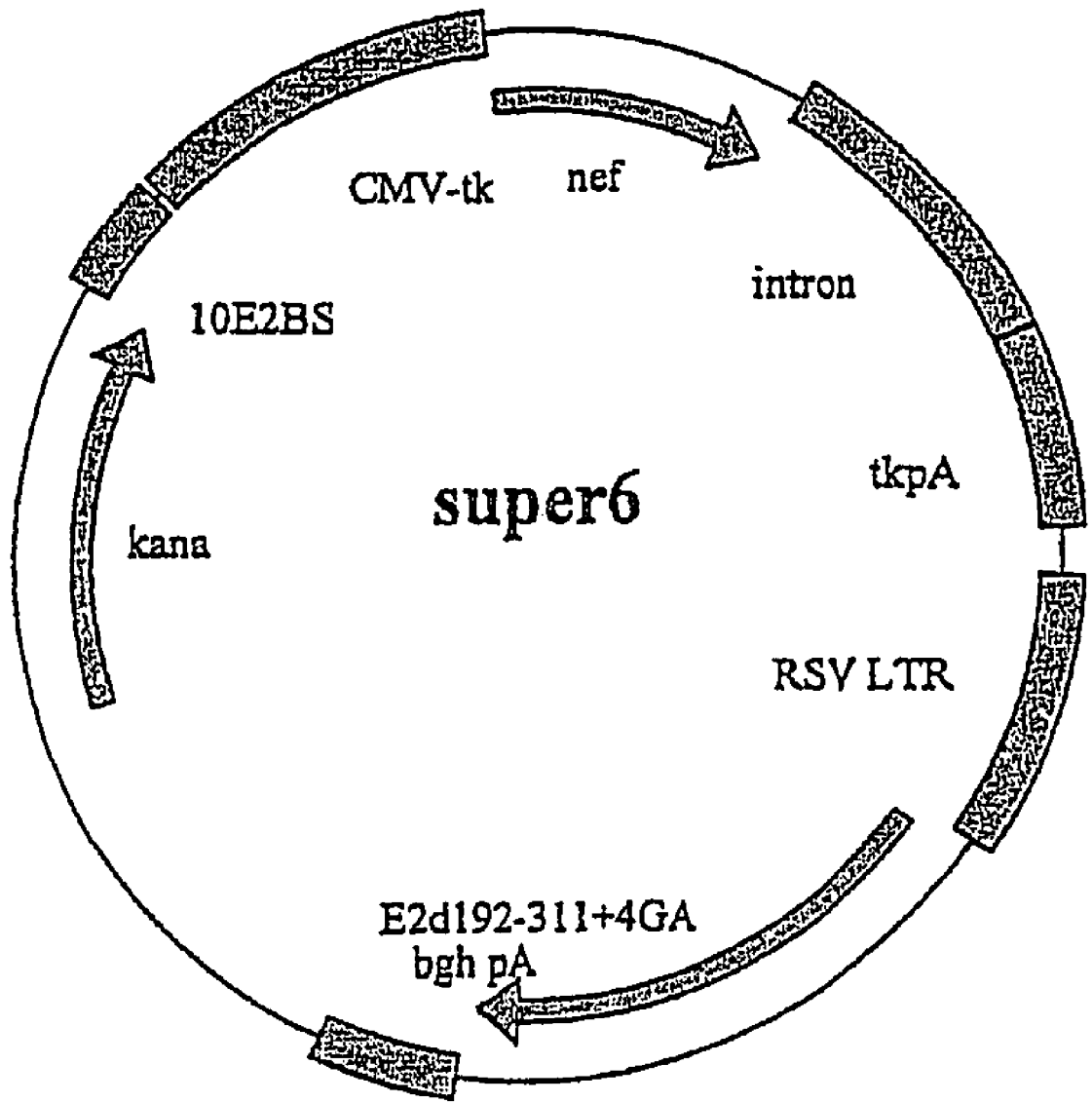
FIG. 1 shows the schematic map of plasmid super6.
Figure 2:
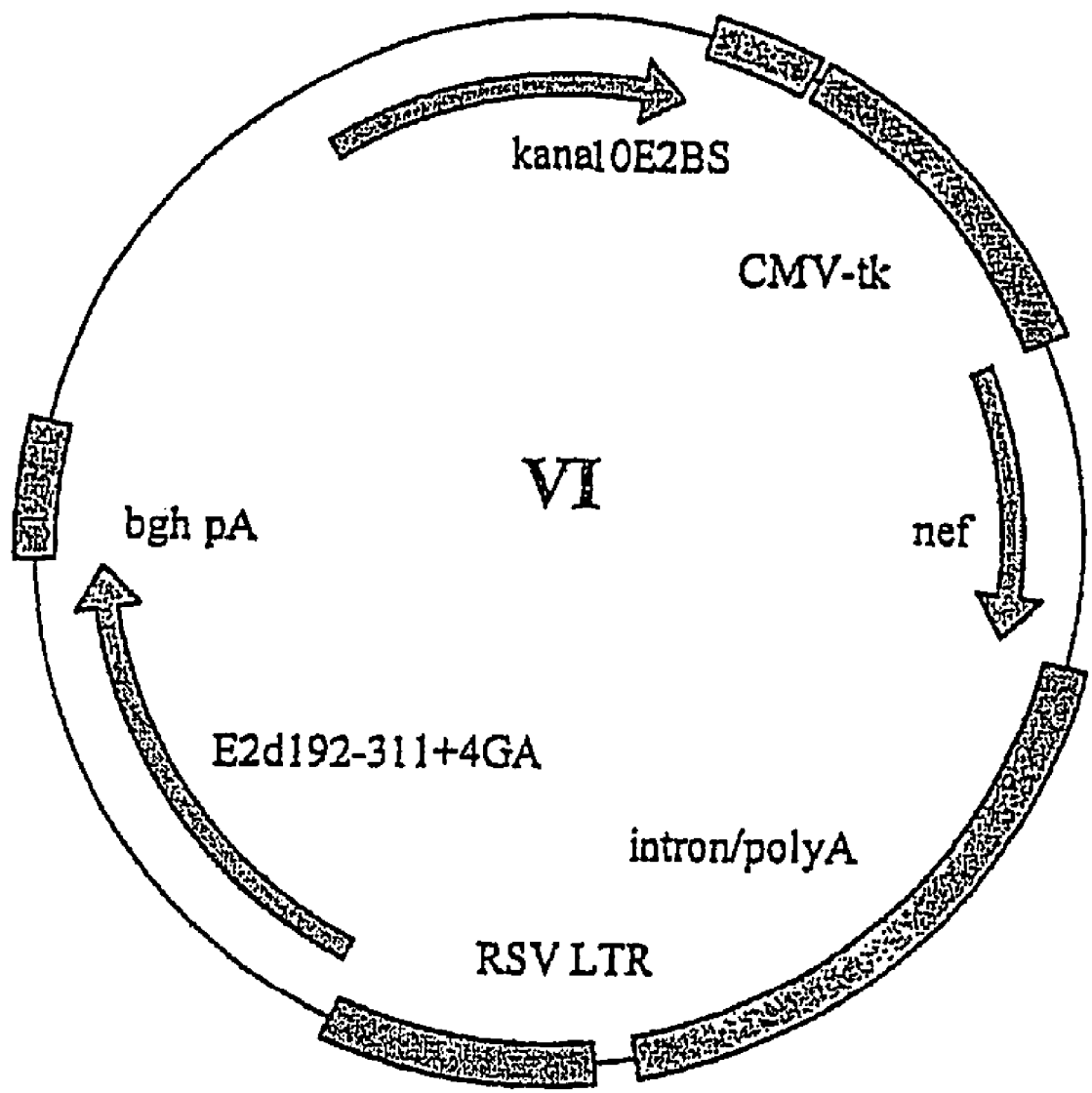
FIG. 2 shows the schematic map of plasmid VI.

Cloning and Analysis of the Expression Properties of the Vectors Super6 and Super6wt The vector plasmids super6 (FIG. 1) and super6wt were prepared from previous generation based gene vaccination vectors VI (FIG. 2) and VIwt, respectively. Vectors VI and VIwt are principally synthetic bacterial plasmids that contain a transposon Tn903 derived kanamycin resistance marker gene [Oka, A., et al., J Mol Biol 147 (1981) 217-226] and a modified form of pMB1 replicon [Yanisch-Perron, C., et al., Gene 33 (1985) 103-119] needed for the propagation in Escherichia coli cells. Vectors VI and VIwt also contain a Cytomegalovirus Immediately Early Promoter combined with a HSV1 TK leader sequence and rabbit β-globin gene sequences, which both are derived from plasmid pCG [Tanaka, M., et al., 60 (1990) Cell 375-386]. The latter elements are needed for expressing from the nef coding sequence derived from a HAN2 isolate of the HIV-1 strain [Sauermann, U., et al., AIDS Research. Hum. Retrov. 6 (1990) 813-823]. The expression vectors for the Nef carry clustered ten high affinity E2 binding sites (derived from plasmid pUC1910BS, unpublished) just upstream of the CMV promoter.

The parent vector VI contains a modified E2 coding sequence: the hinge region of E2 (amino acids 192-311) is replaced with four glycine-alanine repeats from EBNA1 protein of Epstein-Barr Virus [Baer, R. J., et al., Nature 310 (1984) 207-211]. The protein encoded by this sequence was named as E2d192-311+4G. The parent vector VIwt contains an expression cassette for wild type E2 protein of the bovine papilloma virus type 1 with point mutations introduced for the elimination E3 and E4 open reading frame (ORF) coding capacity by two stop codons into both these ORFs. In the vectors the E2 coding sequences are cloned between a Rous sarcoma virus proviral 5' LTR [Long, E. O., et al., Hum. Immunol. 31 (1991) 229-235] and bovine growth hormone polyadenylation region [Chesnut, J. D., et al., J Immunol Methods 193 (1996) 17-27].

Plasmid vectors super6 and super6wt were constructed by deleting from the respective parent vectors VI and VIwt all beta-globin sequences downstream of the nef gene except the second intron of the rabbit beta-globin gene. The beta-globin sequences (especially the fragment of the exon) show some homology with sequences in the human beta-globin gene, whereas the intron lacks any significant homology to human genomic sequences. The intron was amplified by PCR from the plasmid pCG [Tanaka, M. et al., Cell 60 (1990) 375-386] using oligonucleotides with some mismatches for modifying the sequences of splicing donor and acceptor sites of the intron to the perfect match to consensus motifs. The Herpes Simplex Virus type 1 thymidine kinase gene polyadenylation region from pHook [Chesnut, J. D., et al., J Immunol Methods 193 (1996) 17-27] was then cloned just next to the 3'-end of the intron, because in parent plasmids the rabbit β-globin polyadenylation signal were used.

Figure 3:
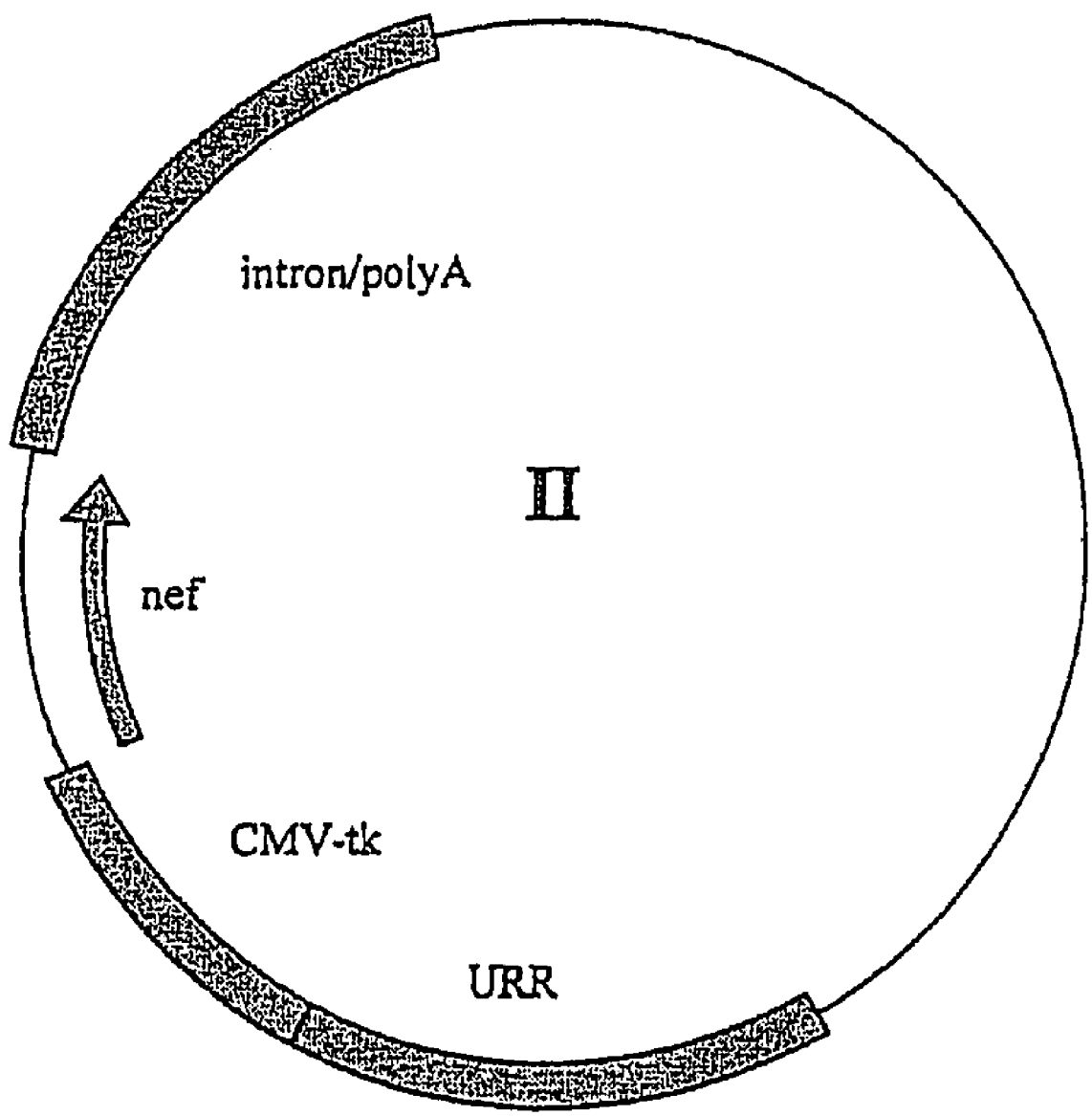
FIG. 3 shows the schematic map of plasmid II.

The expression properties of the Nef and E2 proteins expressed by the plasmid vectors super6 and super6wt were analyzed and compared with the expression properties of the Nef and E2 proteins expressed by VI and VIwt by Western blotting [Towbin et al., Proc Natl Acad Sci USA 76 (1979) 4350-4354] with monoclonal antibodies against Nef and E2. First, Jurkat cells (a human T-cell lymphoblast cell line) were transfected by electroporation [Ustav et al. EMBO J 2 (1991) 449-457] with 1 μg of super6, super6WT or equimolar amounts of the plasmids VI, VIwt. As a control an equimolar amount of vector II (FIG. 3), which contains an identical Nef cassette but no E2 coding sequence, was used. Carrier DNA was used as a negative control. Briefly, the plasmid and carrier DNA were mixed with the cell suspension in a 0.4 cm electroporation cuvette (BioRad Laboratories, Hercules, USA) followed an electric pulse (200V; 1 mF) using Gene Pulser IITM with capacitance extender (BioRad Laboratories, Hercules, USA).

Forty-nine hours post-transfection the cells were lysed by treating with a sample buffer containing 50 mM Tris-HCl pH 6.8; 2% SDS, 0.1% bromophenol blue, 100 mM dithiothreitol, and 10% (v/v) glycerol. The lysates were run on a 10% or 12.5% SDS-polyacrylamide gel and subsequently transferred onto a 0.45 μm PVDF nitrocellulose membrane (Millipore). The membrane was first blocked overnight with a blocking solution containing 5% dry milk (fat-free), 0.1% Tween 20 in 50 mM Tris-HCl pH 7.5; 150 mM NaCl and thereafter incubated for 1 h with diluted monoclonal anti-Nef antisera (1:100) or anti-E2-antisera (1:1000) in the blocking solution. After each incubation step, unbound proteins were removed by washing strips three times with TBS -0.1% Tween-20. The binding of primary immunoglobulins was detected by incubating the strips with horse raddish peroxidase conjugate anti-mouse IgG (Labas, Estonia) followed by visualization using a chemoluminesence detection system (Amersham Pharmacia Biotech, United Kingdom).

Figure 4:
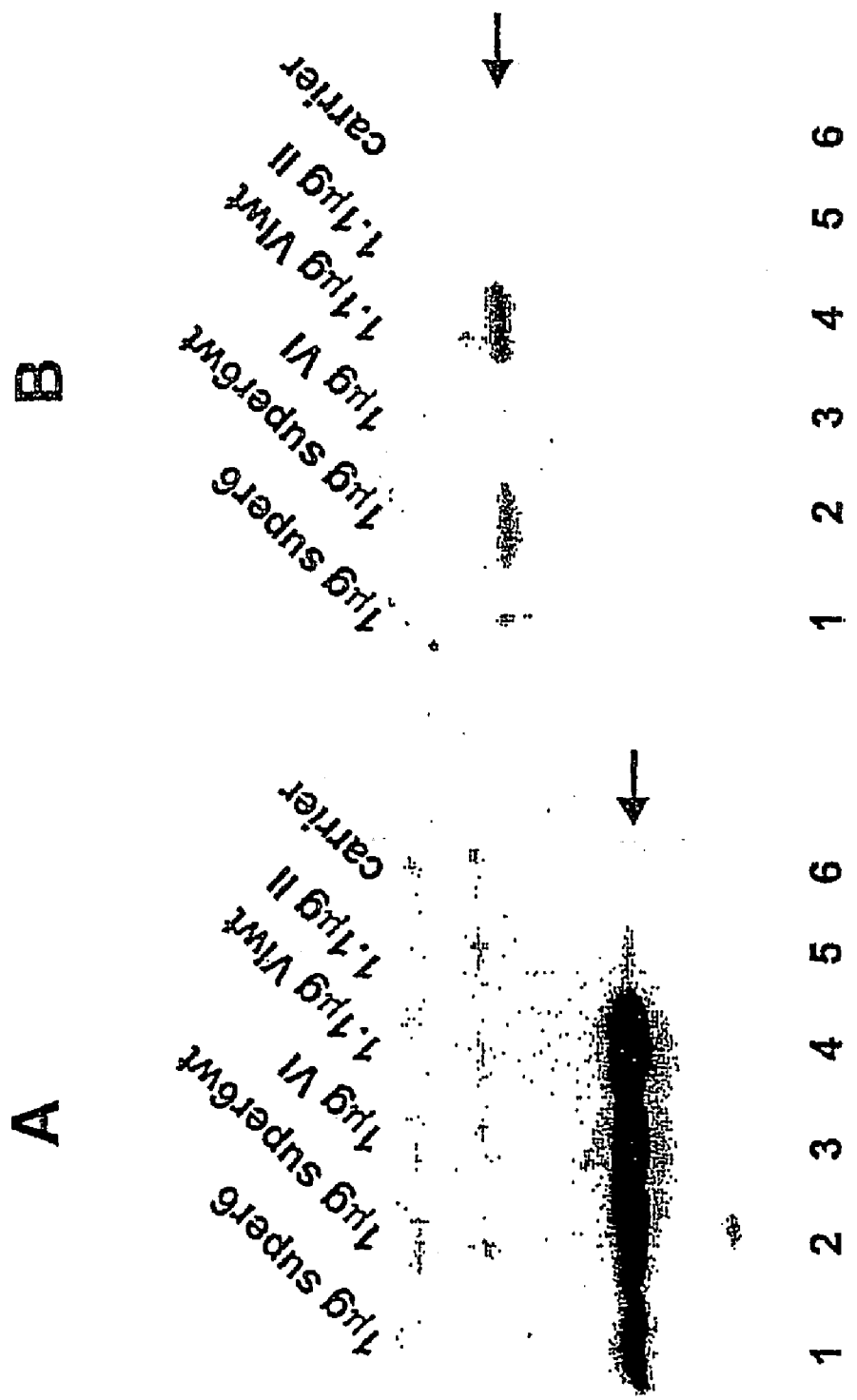
FIG. 4 shows the expression of the Nef and E2 proteins from the vectors super6, super6wt, VI, VIwt, and II in Jurkat cells.

The results are shown in FIG. 4. The expression of the Nef protein is shown on panel A and the expression of E2 protein on panel B. The arrows indicate the right molecular sizes of the Nef and E2 proteins. The expression level of the E2d 192-311+4GA is very low and for this reason cannot be seen on the blot presented in FIG. 4.

The amounts of Nef expressed from the plasmids super6, super6wt, VI and VIwt (lanes 1-4 in FIG. 4A) are quite similar (FIG. 4, panel A, lanes 1 to 4). Much less protein is produced from plasmid II (lane 5). The expression levels of the Nef protein are higher from vectors containing wtE2 (cf. lane 1 compared with lane 2 and lane 3 compared with lane 4). This is in accordance with the expression levels of E2 and E2d192-311+4GA proteins from these plasmids (FIG. 4, panel B).

6.2. Example 2

Figure 5:
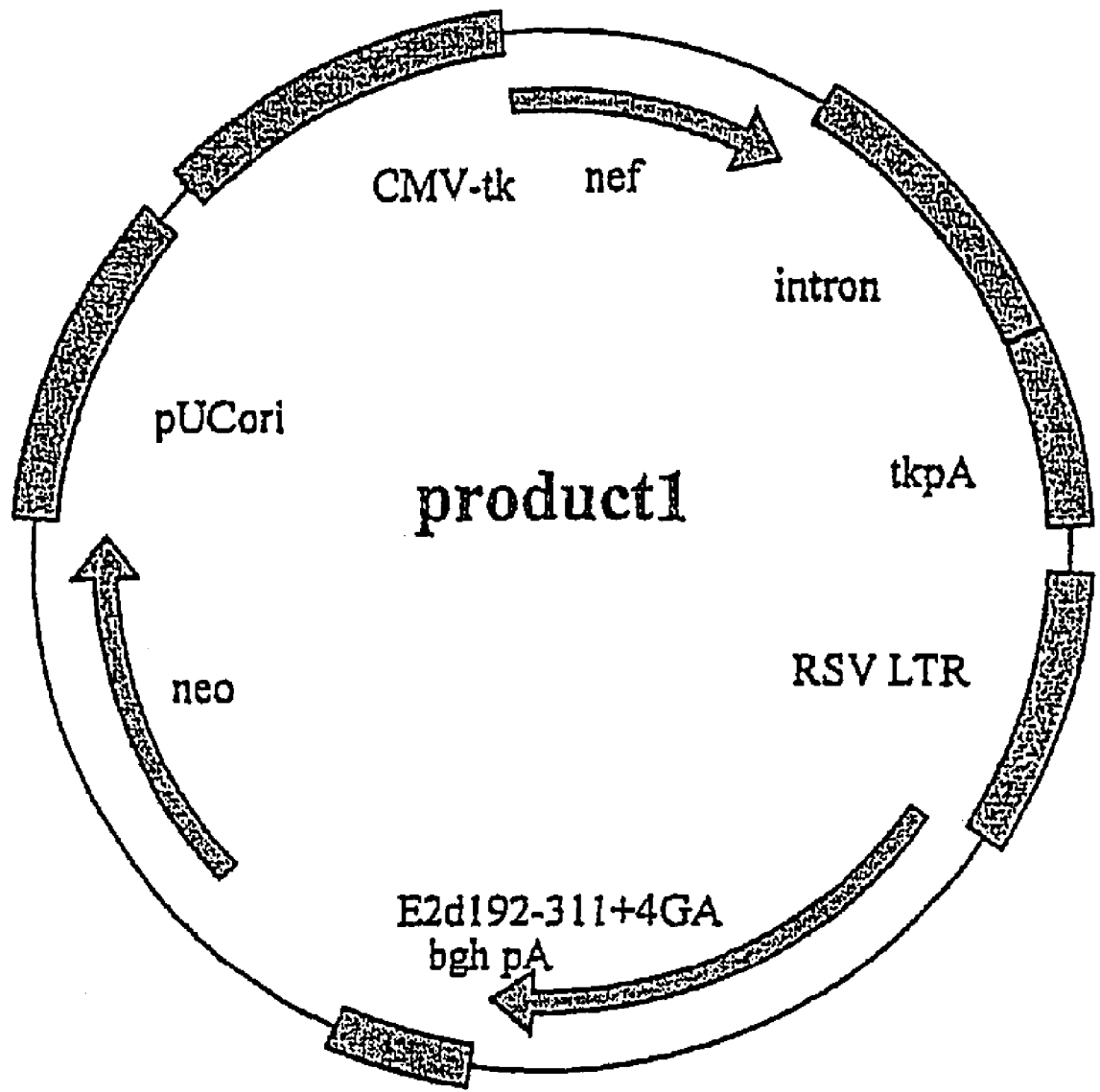
FIG. 5 shows the schematic map of plasmid product1.

Cloning and Analysis of the Expression Properties of Plasmids in Series Product1 and NNV To increase the copy number of the vectors super 6 and super6wt in Escherichia coli further modifications were made in these vectors. The Tn903 kanamycin resistance gene, pMB1 replicon and ten E2 binding sites were removed by HindIII/NheI digestion followed by replacing with the Hind III/NheI fragment from retroviral vector pBabe Neo [Morgenstern, J. P. and Land, H., Nucleic Acids Research 18 (1990) 3587-3596]. This fragment contains a modified pMB1 replicon and the Tn5 kanamycin resistance gene that allow relaxed high copy-number replication of the plasmids in bacteria. The new plasmids were named as the product1 (FIG. 5), and product1wt respectively. An unsuccessful attempt to reinsert the ten E2 binding sites back into the blunted NheI site upstream of the CMV promoter of the product1 resulted in vector New Vector NNV, respectively, with only two binding sites integrated in the plasmid.

Figures 6A, 6B:
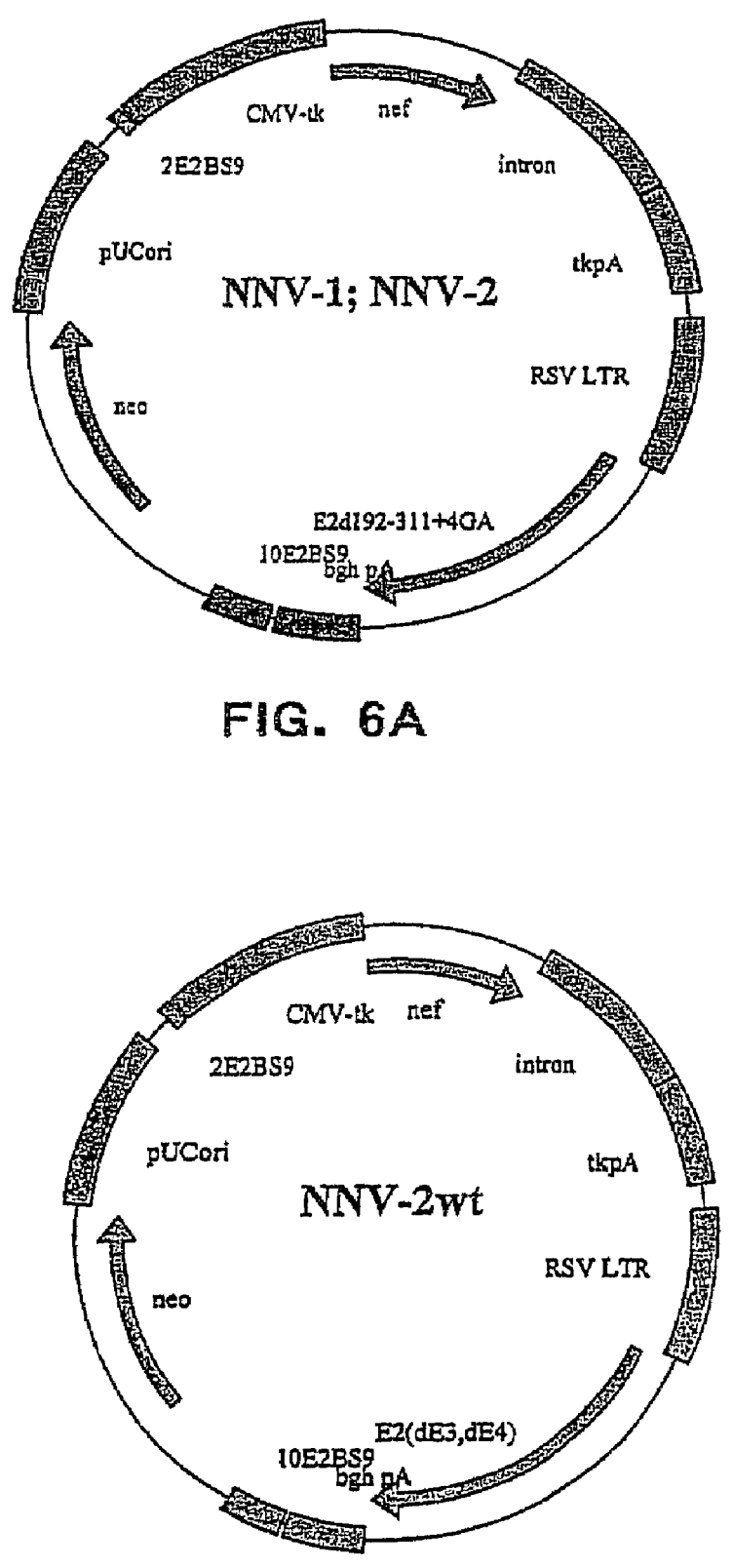

Additional ten E2 binding sites were inserted from plasmid pUC1910BS into the New Vector in just downstream the E2 expression cassette. These new vectors were named NNV-1 and NNV-2 (FIG. 6A). For replacing the E2d192-311+4GA with wt E2 (with deleted E3 and E4 ORFS), the E2d192-311+4GA coding sequence containing Bsp 120I fragment was replaced with wtE2 containing an analogous Bsp 120I fragment from the super6wt. Generated plasmids were named NNV-1wt and NNV-2wt (FIG. 6B), respectively. The numbers 1 or 2 in vectors of the NNV series mark the orientation of the 10 E2 binding sites region relative to the E2 expression cassette.

Figure 7:
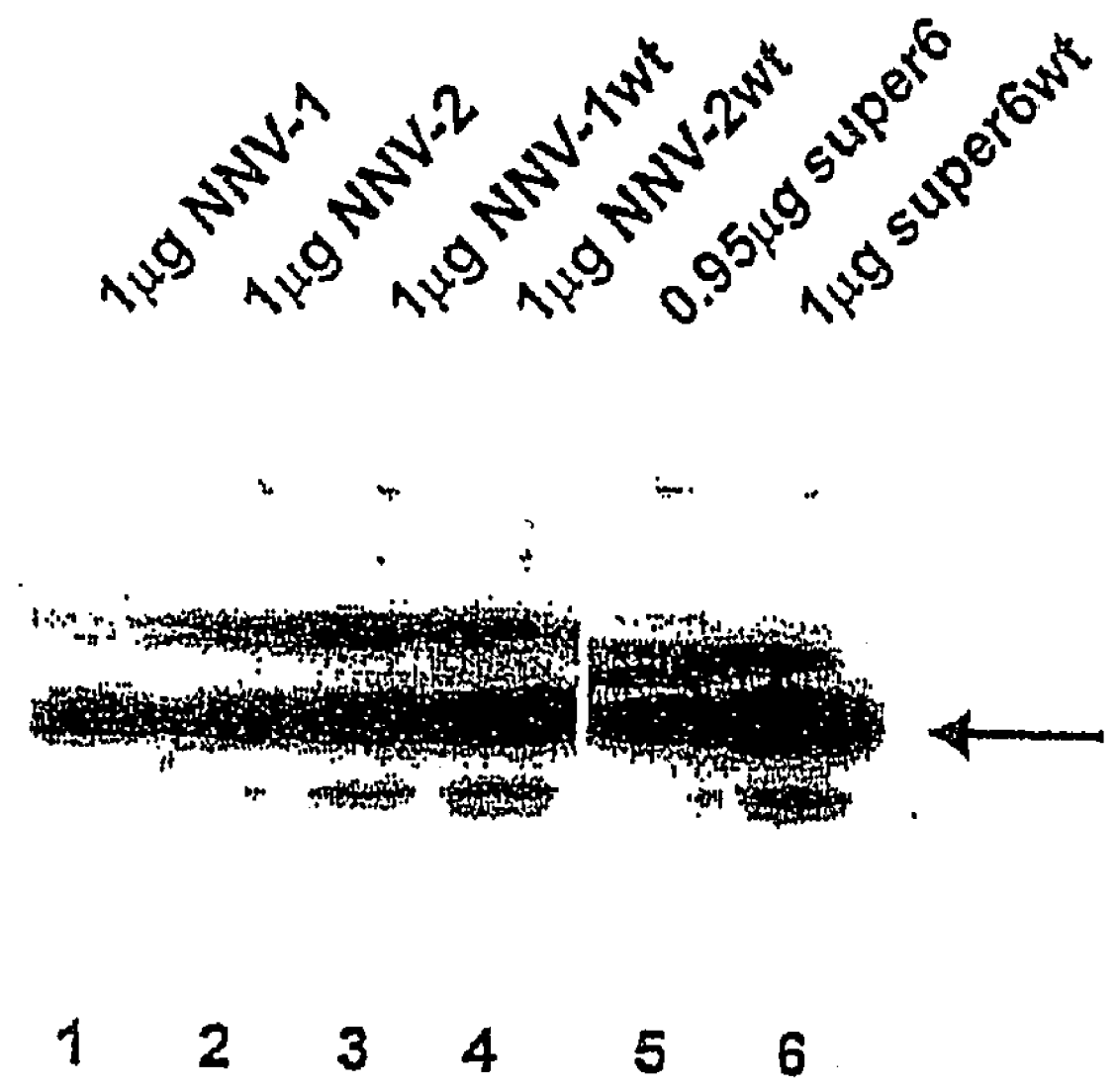

The expression properties of the Nef protein from the NNV plasmids, i.e. NNV-1, NNV-2, NNVwt and NNV-2wt, after the transfection of Jurkat cells by electroporation at a concentration of 1 ig of the plasmid were analyzed and compared with the expression properties of the Nef proteins from super6 and super6wt by Western blotting essentially as described in Example 1. The amounts of super6 and super6wt used for the transfection were 0,95 and 1 ig, respectively. The results are shown in FIG. 7.

Figure 8:
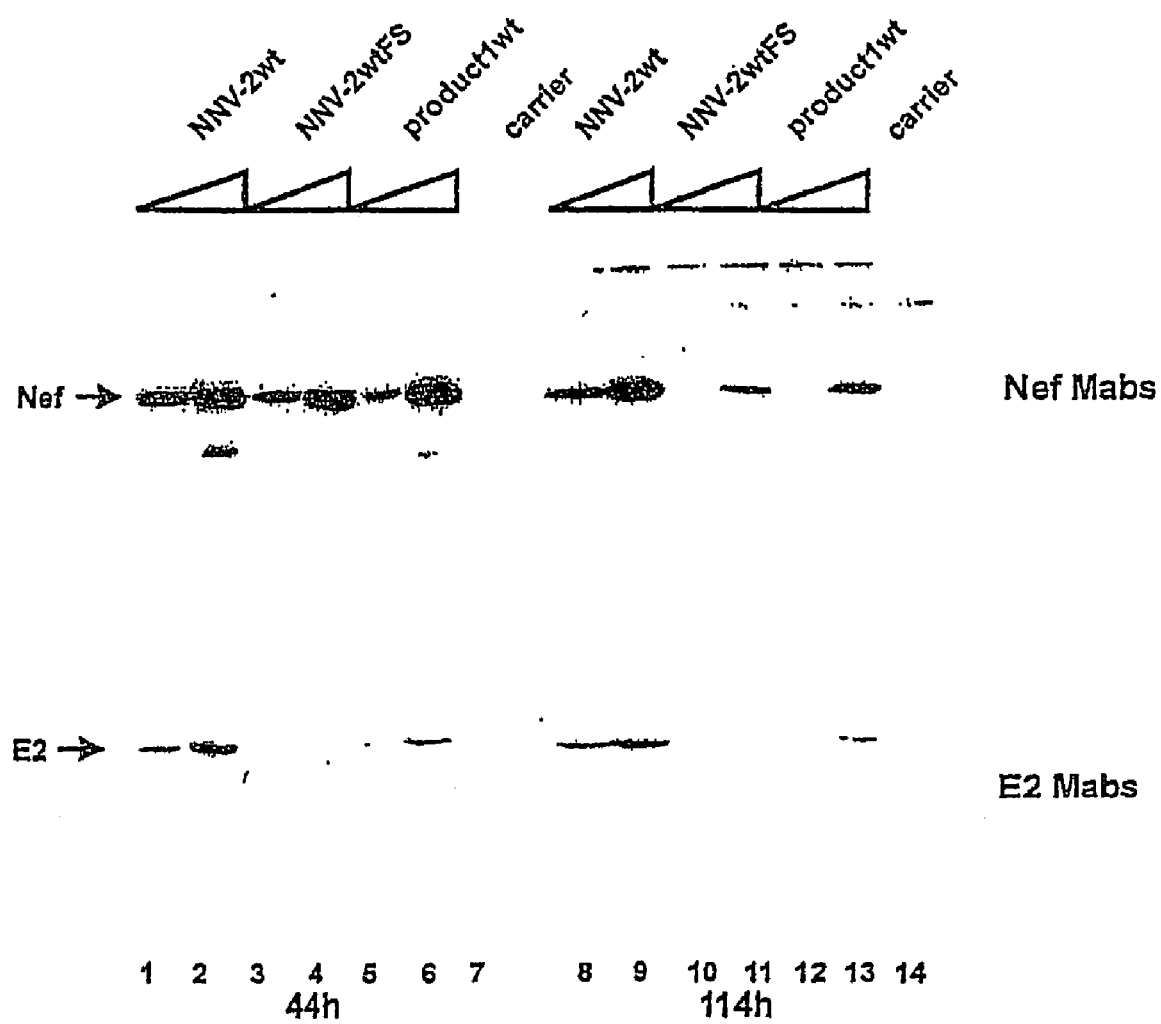
FIG. 8 shows the expression of the Nef and E2 proteins from the plasmids NNV-2-wt, NNV-2-wtFS, and product I in Jurkat cells.

NNV-1 and NNV-2 vectors have expression potential similar to plasmid super6 as evident from the comparison of lanes 1 and 2 on FIG. 8 with lane 5. The same applies to vectors NNV-1wt, NNV-2wt and super6wt (compare lanes 3 and 4 with lane 6 on FIG. 7). In accordance with the previous results the plasmids expressing wt E2 produce more Nef protein than E2d192-311+4GA vectors do (compare lane 1 with lane 3 and lane 2 with lane 4 in FIG. 7). In view of this and since the Nef expression from NNV-2wt was slightly higher than that from NNV-1wt, vector NNV-2wt was selected for further tests.

6.3 Example 3

Analysis of the Expression Properties of NNV-2wt

To analyse the expression properties of NNV-2wt, four different cell lines, i.e. the Jurkat (human T-cell lymphoblasts), P815 (mouse mastocytoma cells), CHO (Chinese Hamster Ovary cells) lines and RD (human embryo rhabdomyosarcoma cells), were transfected by electroporation and analyzed for their expression of Nef of and E2. To reveal the transcription activation and maintenance properties mediated by E2 protein and E2 oligomerized binding sites product1wt, which lacks the E2 binding sites (FIG. 5), was used as a control. An additional control plasmid was plasmid NNV-2wtFS, which differs from NNV-2wt by containing a frameshift introduced into E2 coding sequence, whereby it does not express functional E2 protein.

Each cell line was transfected with different amounts of the vector DNA by electroporation essentially as described in Example 1. Time-points were taken approximately two and five days after transfection. The results of analyses are presented in FIGS. 8 to 10.

The Jurkat cells were transfected with 0.5 µg or 2 µg of the NNV-2wt (lanes 1,2, 8, and 9 in FIG. 8) and equal amounts of the plasmids NNV-2wtFS (lanes 3, 4, 10, and 11 in FIG. 8) and product1wt (lanes 5, 6, 12, and 13 in FIG. 8) or carrier only (lanes 7 and 14 in FIG. 8). Time-points were taken 44 hours (lanes 1-7) and 114 hours (lanes 8-14) after transfection: The expression of the Nef and E2 proteins was analyzed by Western blotting essentially as described in Example 1.

Figure 9:
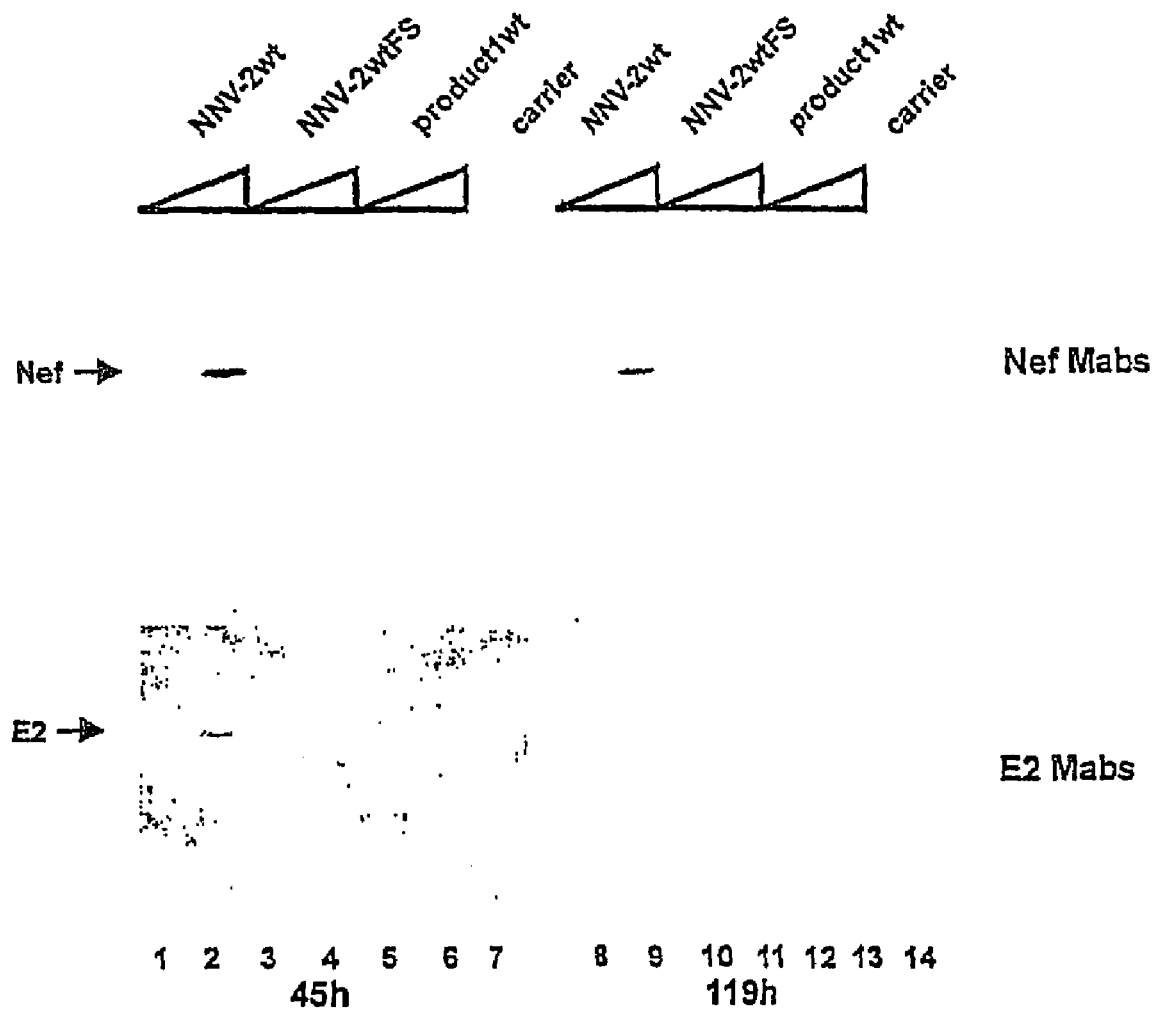
FIG. 9 shows the expression of the Nef and E2 proteins from the plasmids NNV-2-wt, NNV-2-wtFS, and product I in P815 cells.

The P815 cells were transfected with 0.5 µg or 2 µg of the NNV-2wt (lanes 1,2, 8, and 9 in FIG. 9) and equal amounts of the plasmids NNV-2wtFS (lanes 3, 4, 10, and 11 in FIG. 9) and product 1wt (lanes 5, 6, 12, and 13 in FIG. 9) or carrier only (lanes 7 and 14 in FIG. 9). Time-points were taken 45 hours (lanes 1-7) and 119 hours (lanes 8-14) after transfection: The expression of the Nef proteins was analyzed by Western blotting essentially as described in Example 1. The blot with anti-E2 antibodies 119h post-transfection is not shown, because no special signal could be detected. Generally, the expression level of the Nef protein correlated with the expression level of E2 protein in these cells, which confirms the fact that the function of the E2 protein is to activate the transcription and to help the plasmid to be maintained for a longer time in the proliferating cells.

Figure 10:
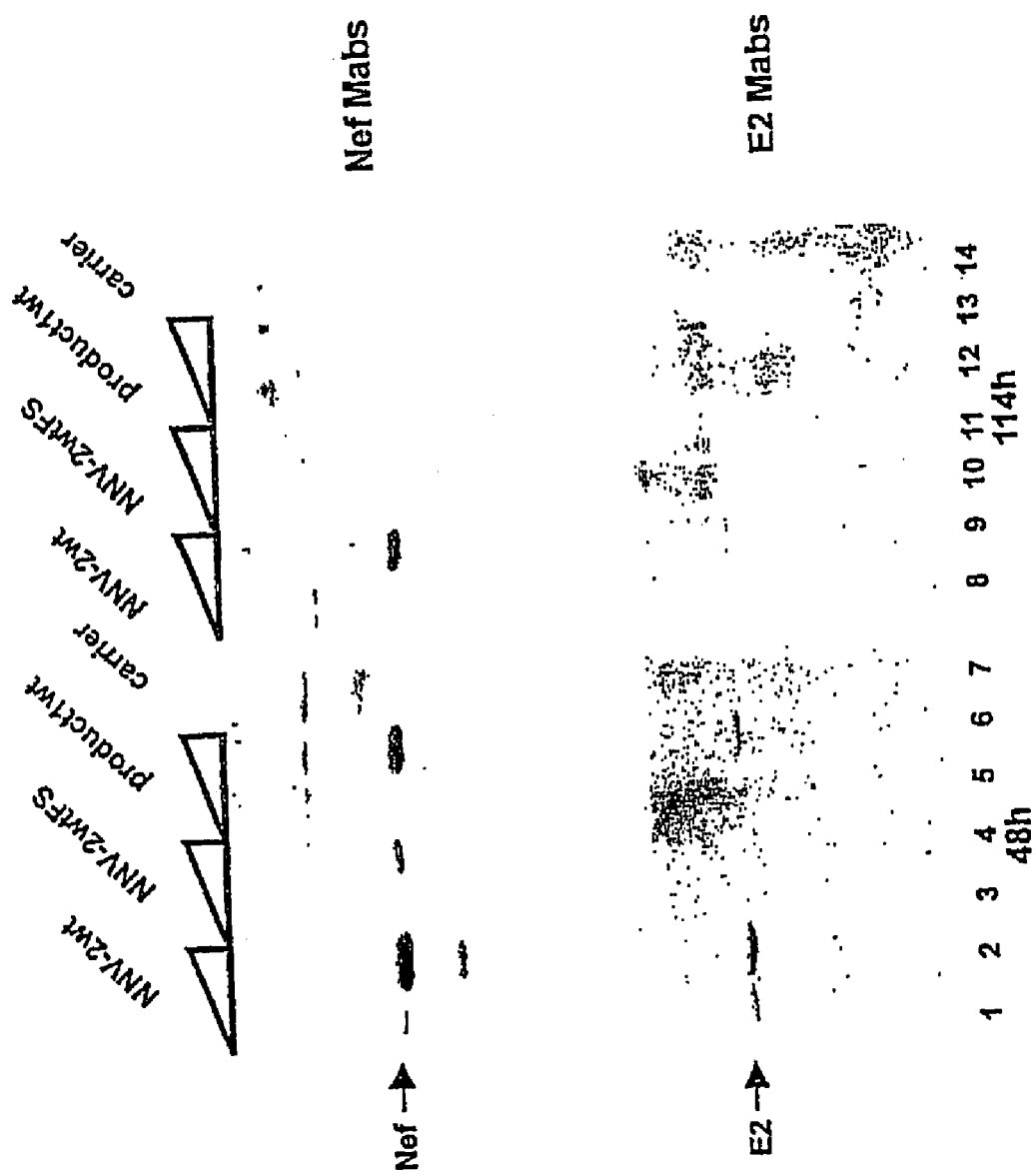
FIG. 10 shows the expression of the Nef and E2 proteins from the plasmids NNV-2-wt, NNV-2-wtFS, and product I in CHO cells.

The CHO cells were transfected with 0.5 µg or 2 µg of the NNV-2wt (lanes 1,2, 8, and 9 in FIG. 10) and equal amounts of the plasmids NNV-2wtFS (lanes 3, 4, 10, and 11 in FIG. 10) and product1wt (lanes 5, 6, 12, and 13 in FIG. 10) or carrier only (lanes 7 and 14 in FIG. 10). Time-points were taken 48 hours (lanes 1-7) and 114 hours (lanes 8-14) after transfection. The expression of the Nef and E2 proteins was analyzed by Western blotting essentially as described in Example 1.

Figure 11:
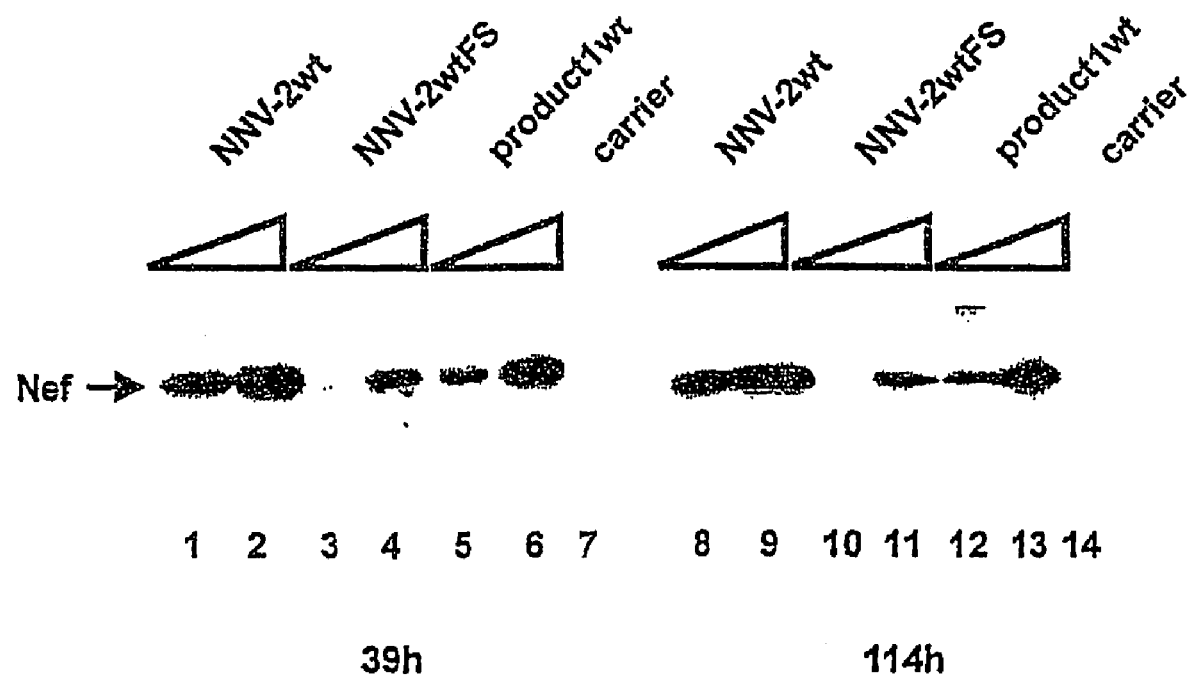

The RD cells were transfected with 0.5 µg or 2 µg of the NNV-2wt (lanes 1,2, 8, and 9 in FIG. 11) and equal amounts of the plasmids NNV-2wtFS (lanes 3, 4, 10, and 11 in FIG. 11) and product1wt (lanes 5, 6, 12, and 13 in FIG. 11) or carrier only (lanes 7 and 14 in FIG. 11). Time-points were taken 39 hours (lanes 1-7) and 110 hours (lanes 8-14) after transfection. The expression of the Nef protein was analyzed by Western blotting essentially as described in Example 1.

In all four cell lines the expression level of the Nef protein, taken at earlier time points (lanes 1-7 in FIGS. 8-11) and at later time points (lanes 8-14 in FIGS. 8-11) hours, from the NNV-2wt was higher than from control vectors. The superiority of the NNV-2wt was more obvious at later time-points as evident from the comparision of lane 8 with lanes 10 and 12 in FIG. 8, and also from the comparision of lane 9 with lanes 11 and 13 in FIGS. 8, 9 and 10.

The expression pattern of RNA from these plasmids was also analyzed using the Northern analysis [Alwine, J. C, et al., Proc Natl Acad Sci USA 74 (1977) 5350-5354] for the NNV-2wt vector. For this purpose, Jurkat and CHO cells were transfected with 2 µg of the NNV-2wt. For the transfection of P815 cells 10 µg of NNV-2wt were used. The transfections were made essentially as described in Example 1. Forty-eight hours post-transfection total RNA was extracted using RNAeasy kit (Qiagen) and samples containing 21 µg (P815), 15 µg (CHO) or 10 µg (Jurkat) of the RNA were analysed by electrophoresis under the denaturing conditions (1.3% agarose gel containing 20 mM MOPS pH 7.0; 2 mM NaOAc; 1 mM EDTA pH 8.0; 2.2M formaldehyde). The running buffer contained the same components except formaldehyde. The samples were loaded in a buffer containing formamide and formaldehyde. After the electrophoresis the separated RNAs were blotted onto the HybondN+ membrane (Amersham Pharmacia Biotech, United Kingtom) and hybridization with a radio-labeled nef coding sequence, E2 coding sequence or whole vector probes was carried out. The RNA from cells transfected with the carrier was used as a control. The results of the Northern blot analyses are shown in FIG. 12.

Figure 12:
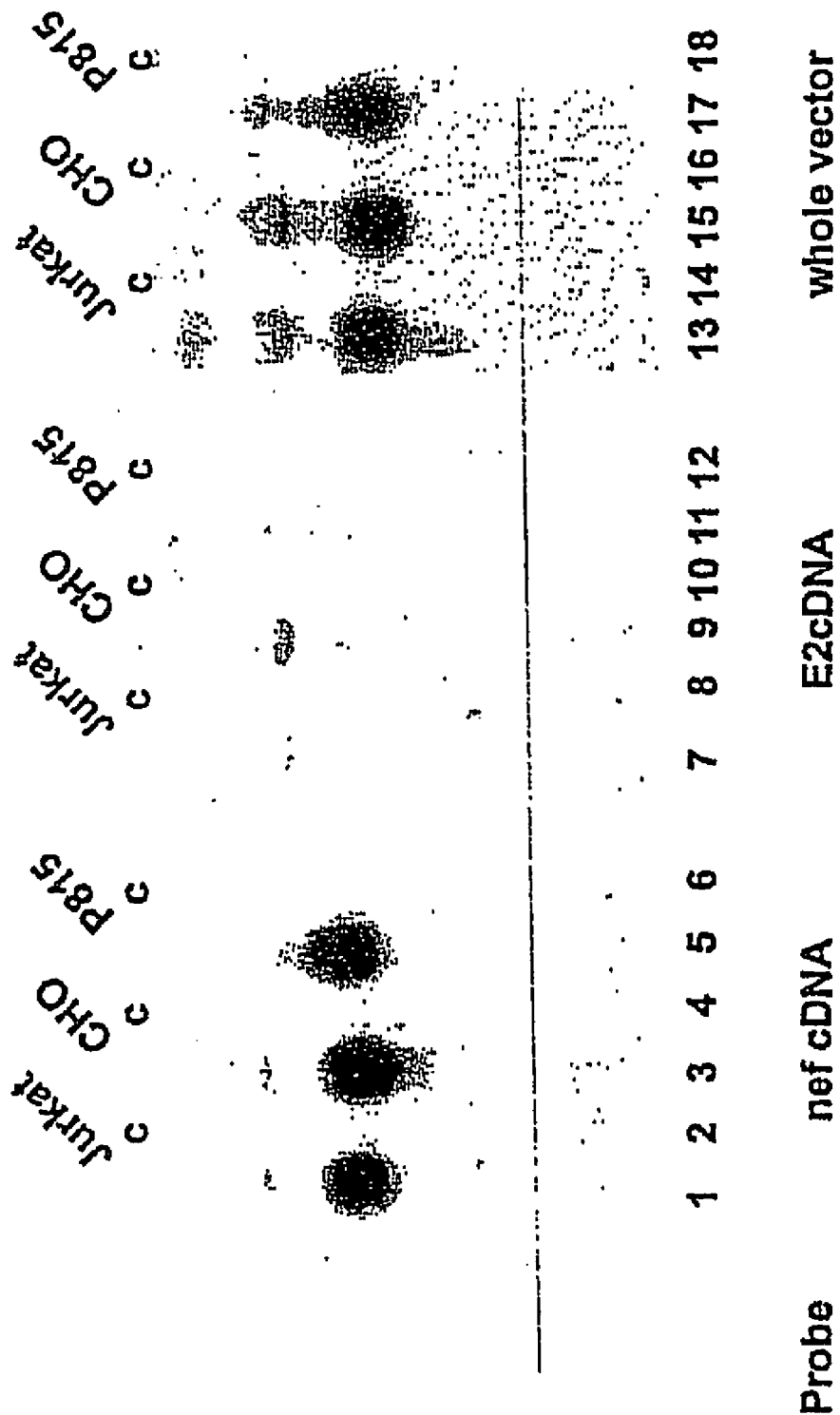
FIG. 12 shows the expression of the RNA molecules NNV-2wt in CHO, Jurkat cells, and P815 cells.

The results indicate that no other RNA species than complementary mRNAs for E2 and nef are expressed from the vector, since no additional signals can be detected with the whole vector probe compared with nef and E2 specific hybridizations (compare lanes 1-12 with lanes 13-18 in FIG. 12).

6.4 Example 4

Analysis of the Attachment of the NNV-2wt to Mitotic Chromosomes

The attachment of the NNV-2wt to mitotic chromosomes in CHO cells was analyzed by fluoresence in situ hybridisation (FISH) [Tucker J. D., et al., In: J. E. Celis (ed.), Cell Biology: A Laboratory Handbook, vol 2, p. 450-458. Academic Press, Inc. New York, N.Y. 1994.].

Thirty-six hours post-transfection the CHO cells by electroporation with 1 μg of NNV-2wt or with equimolar amounts of the control plasmids NNV-2wtFS and product1wt (performed essentially as described in Example 1) the cultures were treated with colchicin (Gibco) for arresting the cells in metaphase of the mitosis. Briefly, cells were exposed to colchicine added to medium at final concentration of 0.1 μg/ml for 1-4 h to block the cell cycle at mitosis. Blocked cells were harvested by a trypsin treatment and suspended in a 0.075M KCl solution, incubated at room temperature for 15 min, and fixed in ice-cold methanol-glacial acetic acid (3:1, vol/vol). The spread-out chromosomes at metaphase and nuclei at interphase for fluorescence in situ hybridization analyses were prepared by dropping the cell suspension on wet slides. Several slides from one culture were prepared.

Hybridization probes were generated by nick-translation, using biotin-16-dUTP as a label and plasmid Product1wt as template. A typical nick-translation reaction mixture contained a nick-translation buffer, unlabeled dNTPs, biotin-16-dUTP, and $E.\ coli$ DNA polymerase.

Chromosome preparations were denatured at 70° C. in 70% formamide (pH 7.0-7.3) for 5 min, then immediately dehydrated in a series of washes (70%, 80%, and 96% ice-cold ethanol washes for 3 min each), and air-dried. The hybridization mixture (18 μl per slide) was composed of 50% formamide in 2×SSC (1×SSC is 0.15 M NaCl plus 0.015 M sodium citrate), 10% dextran sulfate, 150 ng of biotinylated plasmid probe DNA and 10 μg of herring sperm carrier DNA. After 5 min of denaturation at 70° C., probe DNA was applied to each slide, sealed under a coverslip, and hybridized for overnight at 37° C. in a moist chamber. The slides were washed with three changes of 2×SSC, nd 2×SSC containing 0.1% IGEPAL CA-630 (Sigma Chemical Co.) at 45° C. Prior to the immunofluorescence detection, slides were preincubated for 5 min in PNM a buffer [PN buffer (25.2 g $Na_2HPO_4.7\ H_2O$, 083 g $NaH_2PO_4.\_\square\ H_2O$ and 0.6 ml of IGEPAL CA-630 in 1 liter of $H_2O$] with 5% nonfat dried milk and 0.02% sodium azide).

Subsequently, the probe was detected with fluorescein isothiocyanate (FITC)-conjugated extravidin. The signal was amplified with biotinylated antiavidin antibody and a second round of extravidin-FITC tretment. Between each of the steps, the slides were washed in PN buffer containing 0.05% IGEPAL CA-630 at room temperature for 2×5 min. Chromosomes were counterstained with propidium iodide and mounted in p-phenylenediamine antifade mounting medium.

Slides were analyzed with a Olympus VANOX-S fluorescence microscope equipped with appropriate filter set.

The results are shown in Table 1.

TABLE 1

| Chromosomal attachment of the NNV-2 wt. | | | |
|---|---|---|---|
| Culture | Metaphases with episomal signal on chromosomes | Analyzed metaphases | % |
| 0.5 μg NNV-2wt | 11 | 158 | 7 |
| 0.5 μg NNV-2wtFS | 0 | 100 | 0 |
| 0.48 μg product1wt | 0 | 100 | 0 |
| carrier | 0 | 100 | 0 |

The data indicate clearly that the E2 protein and its binding sites are needed for the chromosomal attachment because only the NNV-2wt but not two other vectors have this ability.

6.5 Example 5

Stability of NNV-2wt During Propagation in Bacterial Cells

The stability of NNV-2wt during propagation in bacterial cells was tested. The plasmid NNV-2wt was mixed with competent $Escherichia\ coli$ cells of the DH5alpha strain [prepared as described in Inoue, H., et al., Gene 96 (1990) 23-28] and incubated on ice for 30 minutes. Subsequently, the cell suspension was subjected to a heat-shock for 3 minutes at 37° C. followed by a rapid cooling on ice. One milliliter of LB medium was added to the sample and the mixture was incubated for 45 minutes at 37° C. with vigorous shaking. Finally, a portion of the cells was plated onto dishes containing LB medium with 50 μg/ml of kanamycin. On the next day, the cells from a single colony were transferred onto the new dishes containing the same medium. This procedure was repeated until four generations of bacteria had been grown, and the plasmid DNA from the colonies of each generation was analyzed.

One colony from each generation was used for an inoculation of 2 ml LB medium containing 50 μg/ml of kanamycin followed by an overnight incubation at 37° C. with vigorous shaking. The cells were harvested and the plasmid DNA was extracted from the cell using classical lysis by boiling. [Sambrook, S., et al., Molecular Cloning A Laboratory Manual. Second ed. Cold Spring Harbor Laboratory Press, Cold Spring Harbor, N.Y.]. The samples were digested with restriction endonuclease XbaI (Fermentas, Lithuania) and analyzed by agarose gel electrophoresis in comparison with the original DNA used for transformation. The results are shown in FIG. 13.

Figure 13:
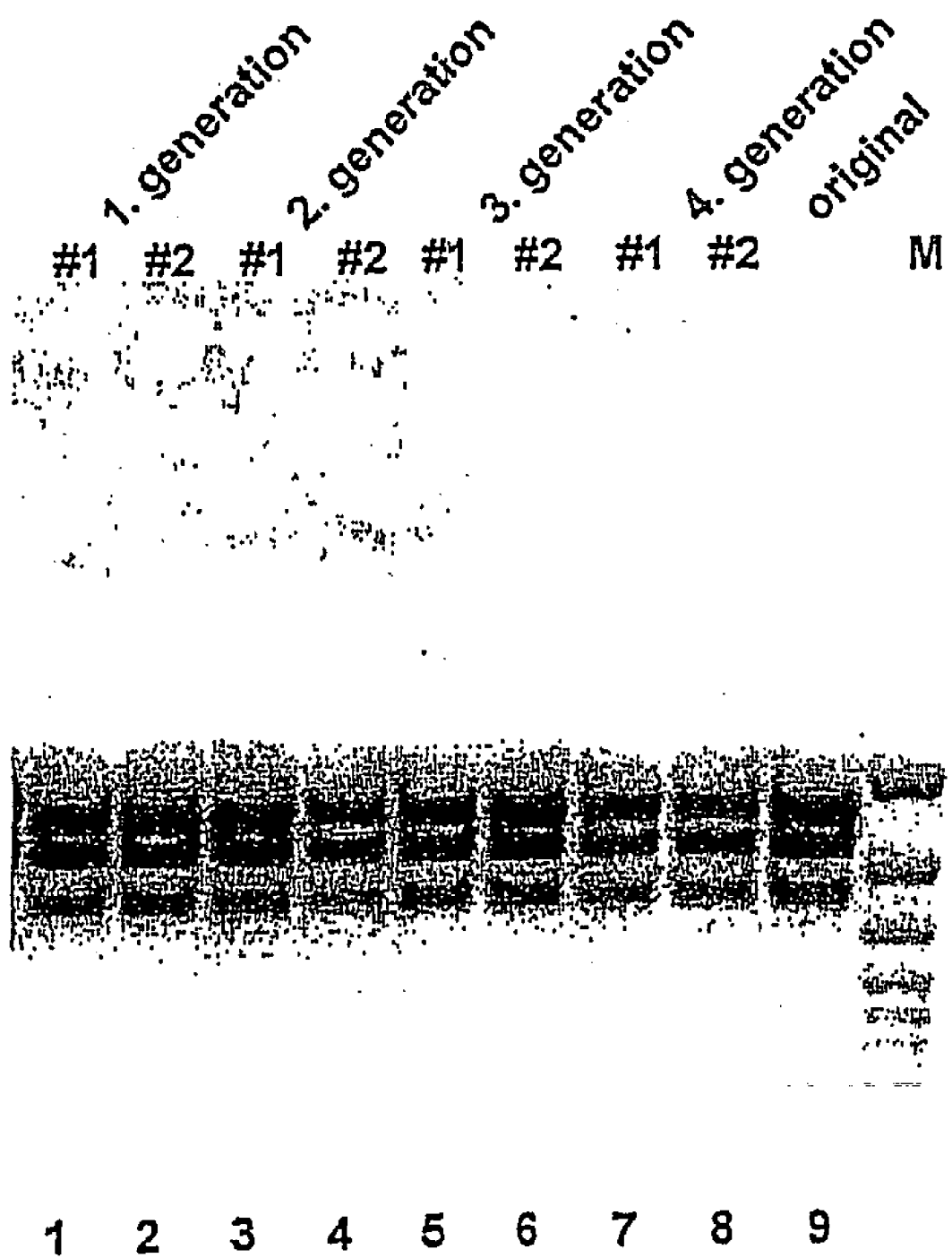
FIG. 13 shows the stability of NNV-2wt in bacterial cells.

As can be seen in FIG. 13, the vector is stable during the passage in $Escherichia\ coli$ cells: no colonies with re-arrangements were observed when compared with the DNA used for transformation (lane 9).

6.6 Example 6

Stability of NNV-2wt in Eukaryotic Cells

Figure 14:
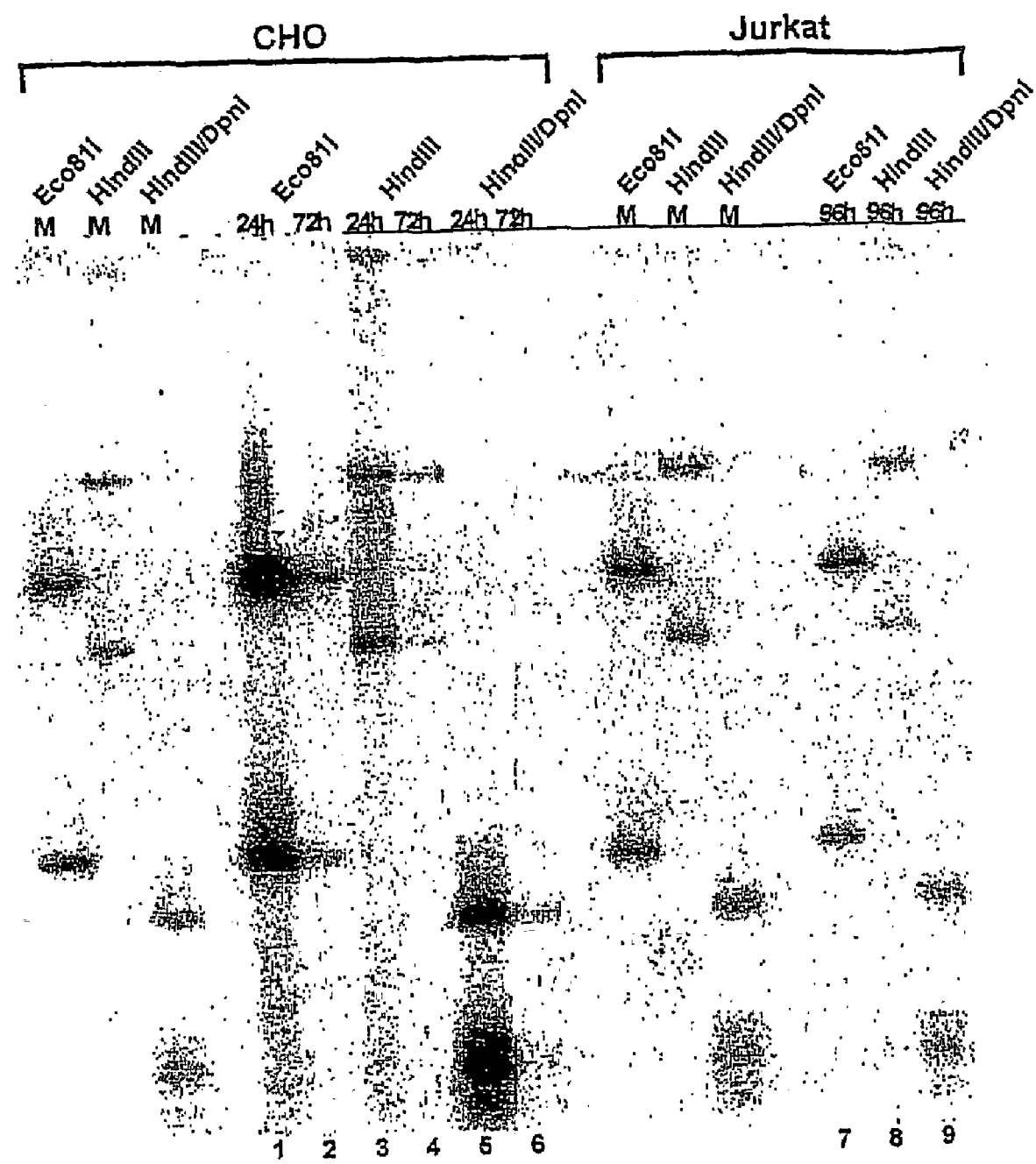
FIG. 14 shows the Southern blot analysis of stability of the NNV-2wt as non-replicating episomal element in CHO and Jurkat cell lines.

The stability of the plasmid NNV-2wt as a non-replicating episomal element was also analyzed in eukaryotic cells. For this purpose the CHO and Jurkat cells were transfected with 2 μg of NNV-2wt. Total DNAs of the cells were extracted at 24, 72 or 96 hours post-transfection. Briefly, the cells were lyzed in 20 mM Tris-HCl pH 8.0; 10 mM EDTA pH 8.0; 100 mM NaCl; 0.2% SDS; in presence of 200 μg/ml of proteinase K (Fermentas, Lithuania). Next, the samples were extracted sequentially with phenol and with chloroform and precipitated with ethanol. The nucleic acids were resuspended in 10 mM Tris-HCl pH 8.0; 1 mM EDTA pH 8.0; 20 μg/ml of RNase A (Fermentas, Lithuania) and incubated for 1 hour at 37° C. Finally the DNA was re-precipitated with ammonium acetate and ethanol, washed with 70% ethanol and resuspended in 10 mM Tris-HCl pH 8.0; 1 mM EDTA pH 8.0. The samples were digested with different restriction endonucleases: with Eco81I (Fermentas, Lithuania) that has two recognition sites on the plasmid, with HindIII (Fermentas, Lithuania) that does not cut the NNV-2wt DNA and with DpnI (New England Biolabs, USA) that digest only DNA synthesized in *Escherichia coli* cells. Restricted DNAs were separated on TAE agarose electrophoresis and analyzed by Southern blotting [Southern, E.M. J. Mol. Biol. 98 (1975) 503-517] with a vector specific radiolabeled probe. The results are illustrated on FIG. 14. As obvious from comparison of the fragment sizes of Eco81I digestion (lanes 1, 2 and 7 in FIG. 14) with respective marker lanes no arrangements of the vector were detected in the assay. Neither were signals observed at a position different from the marker lanes in cases of the Hind III (lanes 3, 4 and 8 in FIG. 14) or HindIII/DpnI (lanes 5, 6 and 9 in FIG. 14) digestion indicating that integration and/or replication events were not observed.

6.7 Example 7

Figure 15:
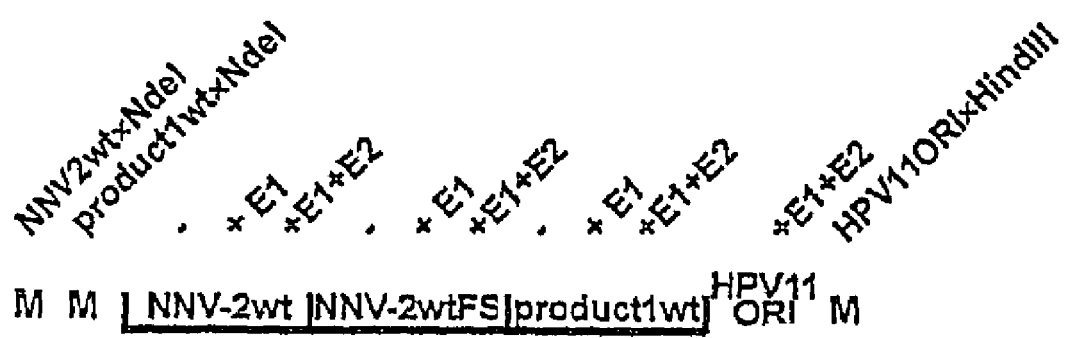
FIG. 15 shows that the vectors NNV2wt, NNV2wtFS and product1 are unable to HPV-11 replication factor-dependent replication.
Figure 15:
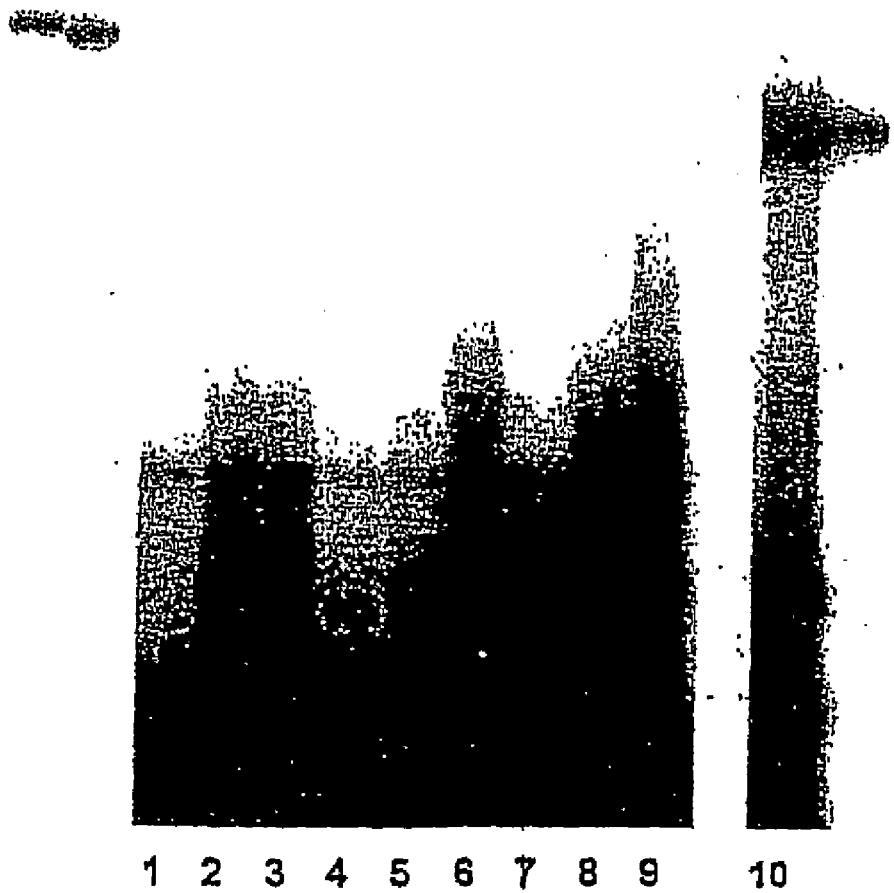

Analysis of Replication of the NNV-2wt in the Presence of Human Papillomaviral Replication Factors It has been demonstrated previously that papillomaviral proteins are able to initiate the replication of heterologous ori-containing plasmids from many other human and animal papillomaviruses [Chiang, C. M., et al., Proc Natl Acad Sci U S A 89 (1992) 5799-5803]. Although NNV-2wt does not contain an intact viral origin of replication, it was tested how the replication is initiated in the presence of human papillomavirus type 1 E1 and E2 proteins. CHO cells were transfected with one microgram of either plasmids NNV-2wt, NNV-2wtFS or product 1 alone or with 4.5 μg of the HPV-11 E1 expression vector pMT/E1 HPV11 or with same amount of pMT/E1 HPV11 and 4.5 μg HPV-11 E2 protein expression vector pMT/E2 HPV 11 as indicated on the top of the FIG. 15. Transfections were done essentially as described in Example 1. E1 and E2 expression vectors are described previously (Chiang, C. M. et al., supra). An equimolar amount of HPV-11 replication origin containing plasmid HPV11ORI was transfected with the same expression vectors as a positive control.

Low-molecular weight DNA was extracted by modified Hirt lysis [Ustav, et al., EMBO J 2 (1991) 449-457] at 67 hours post-transfection. Briefly, the cells washed with PBS were lyzed on ice at 5 minutes by adding alkaline lysis solutions I (50 mM glucose; 25 mM Tris-HCl, pH 8.0; 10 mM EDTA, pH 8.0) arid II (0.2M NaOH; 1% SDS) in a ratio of 1:2 onto the dishes. The lysates were neutralized by 0.5 vol solution III (a mixture of potassium acetate and acetic acid, 3M with respect to potassium and 5M with respect to acetate). After centrifugation the supernatant was precipitated with isopropanol, resuspended and incubated at 55° C. in 20 mM Tris-HCl pH 8.0; 10 mM EDTA pH 8.0; 100 mM NaCl; 0:2% SDS; in presence of 200 μg/ml of proteinase K (Fermentas, Lithuania). Next, the samples were extracted sequentially with phenol and with chloroform followed by precipitation with ethanol. The nucleic acids were resuspended in 10 mM Tris-HCl pH 8.0; 1 mM EDTA pH 8.0; 20 μg/ml RNase A (Fermentas, Lithuania) and incubated for 30 min at 65° C. The samples were digested with linearizing endonuclease (NdeI; Fermentas, Lithuania) in case of the vectors or HindIII (Fermentas, Lithuania) in case of the HPV11ORI) and DpnI (New England Biolabs, USA) (breaks nonreplicated DNA), followed by Southern blotting performed essentially as described earlier using a vector specific radiolabeled probe. For positive control of hybridization appropriate markers of the linearized vectors and HPV11ORI were used (lanes marked as M on FIG. 15). As seen from the results set forth in FIG. 15, no replication signal was detected in case of any vector plasmids.

6.8 Example 8

Analysis of the E2 and its Binding Sites Dependent Segregation Function of the Vectors in Dividing Cells As has been described previously, bovine papillomavirus type 1 E2 protein in trans and its multiple binding sites in cis are both necessary and sufficient for the chromatin attachment of the episomal genetic elements. The phenomenon is suggested to provide a mechanism for partitioning viral genome during viral infection in the dividing cells [Ilves, I., et al., J Virol. 73 (1999) 4404-4412]. Because both functional elements are also included into our vector system, the aim of this study was analyze the importance of the E2 protein and oligomerized binding sites for maintenance of the transcriptionally active vector element in population of dividing cells.

For this purpose the Nef coding sequence of the vectors NNV-2wt and super6wt was replaced with coding sequence of the destabilized form of green fluorescent protein (d1EGFP) derived from vector pd1EGFP-N1 (Clontech Laboratories). Because the half-life of this protein is as short as 1 hour, it does not accumulate in the cells and the d1EGFP expression detected by flow cytometer correlates with the presence of transcriptionally active vector in these cells.

Figure 16:
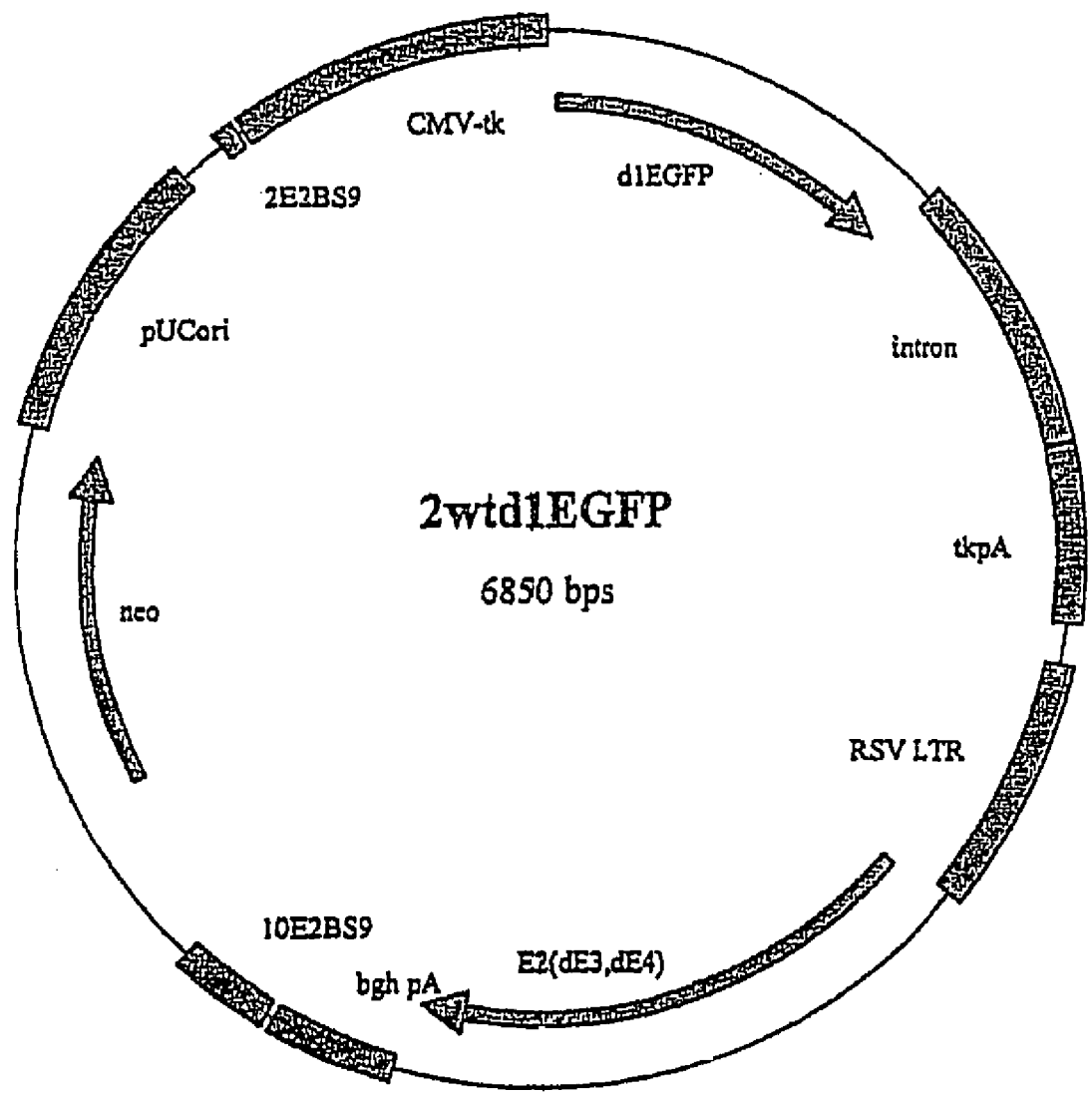
FIG. 16 shows the schematic map of the plasmid 2wtd1EGFP.

From NNV-2wt the nef coding sequence was removed and SmaI-NotI fragment from the pd1EGFP-N1 was inserted instead of it. New vector was named as 2wtd 1 EGFP (FIG. 16). Similar replacement was made in case of super6wt for generation gf10bse2 (FIG. 17), respectively. The recognition sequence for restrictional endonuclease SpeI was introduced into the EcoRI site in the super6wt just upstrem the ten E2BS. The vector gf10bse2 is derived from this plasmid by replacing the Nef coding sequence containing NdeI-Bst1107I fragment with d1EGFP coding sequence containing fragment from 2wtd1EGFP, cut out with same enzymes.

Figure 18:
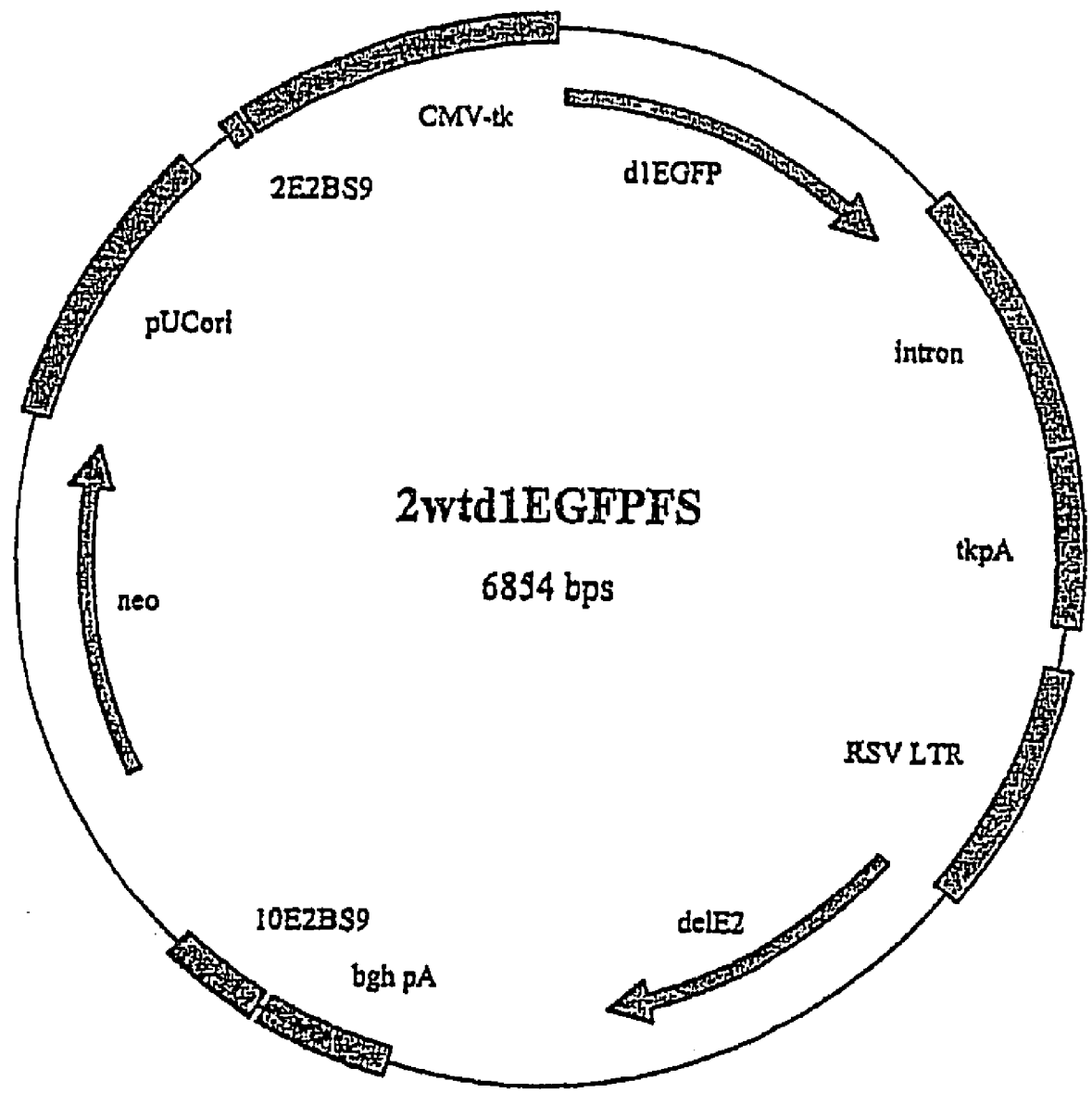
FIG. 18 shows the schematic map of the plasmid 2wtd1EGFPFS.
Figure 19:
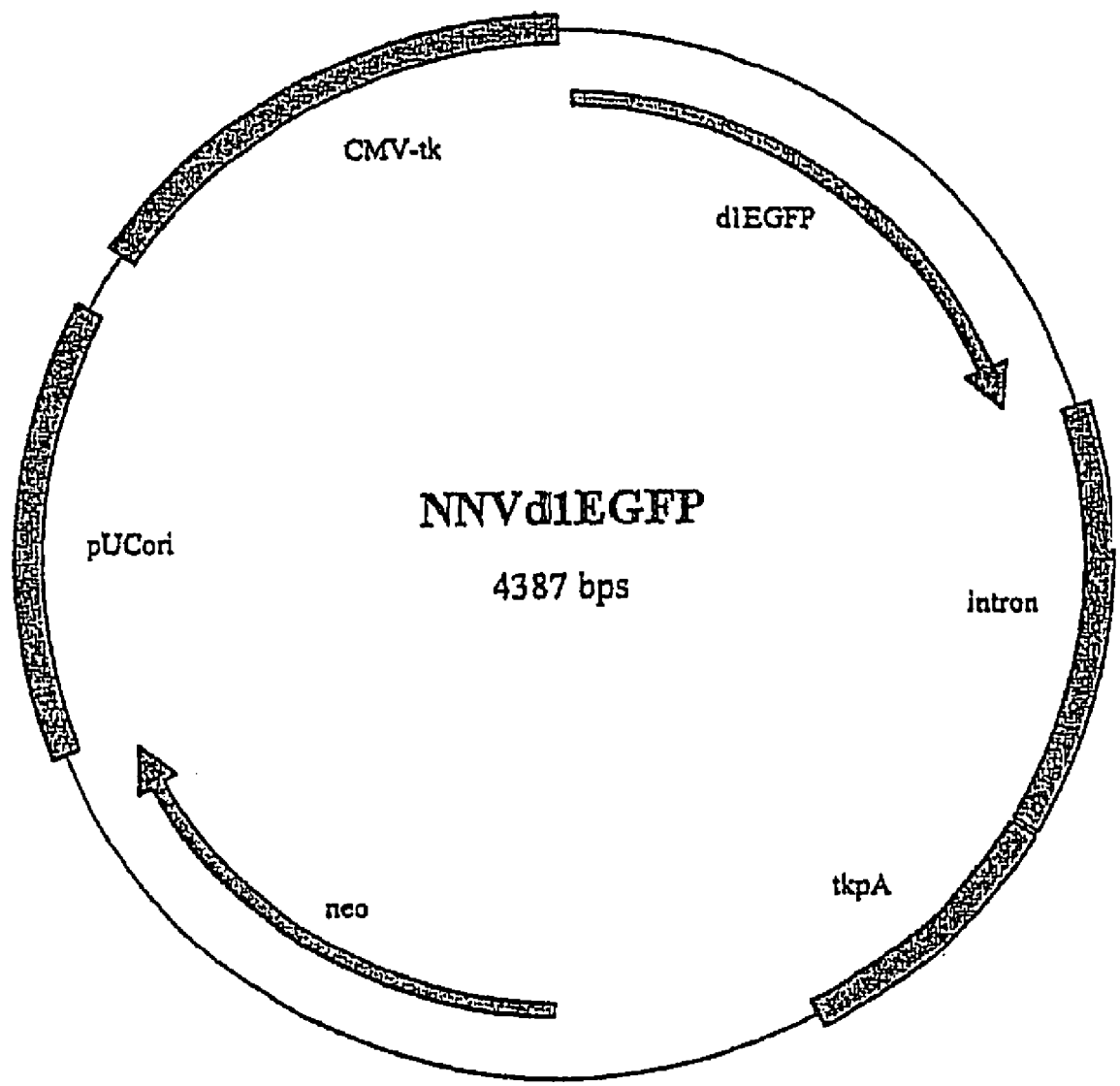
FIG. 19 shows the schematic map of the plasmid NNVd1EGFP.

Negative control plasmids lacking either functional E2 coding sequence or its binding sites were also made: The frameshift was introduced into the E2 coding sequence in context of the 2wtd1EGFP by replacing E2 coding sequence containing Bsp 120I-Bsp 120I with similar fragment from plasmid NNV-2wtFS. The resulting vector was named as 2wtd1EGFPFS (FIG. 18). For the construction the control plasmid NNVd1EGFP (FIG. 19) the whole E2 expression cartridge (as well bacterial replicon) from the 2wtd1EGFP was removed by Bst1107 and NheI digestion. The replicon was reconstituted from plasmid product1 as HindIII (filled in)-NheI fragment.

Jurkat cells were transfected by electroporation with 1 µg of the vector 2wtd1EGFP or with equimolar amounts of the plasmids 2wtd1EGFPFS, NNVd1EGFP, gf10bse2 or with carrier DNA only as described in Example 1. At different time-points post-transfection the equal aliquots of the cell suspension were collected for analysis and the samples were diluted thereafter with the fresh medium. At every time-point total number of the cells as well the number of the d1EGFP expressing cells were counted by flow cytometer (Becton-Dickinson FACSCalibur System). With these data, the percentages of d1EGFP expressing cells, alterations of total numbers of cells and numbers of d1EGFP expressing cells in samples were calculated using the carrier-only transfected cells as a negative control for background fluorescence. The calculations of cell numbers were done in consideration of the dilutions made. Finally, the error values were calculated based on technical data of the cytometer about fluctuations of speed of the flow.

Two independent experiments were done. First, the maintenance of d1EGFP expressed from the plasmids 2wtd1EGFP, 2wtd1EGFPFS and NNVd1EGFP were analyzed during the eight days post-transfection. In the second experiment the maintenance of d1EGFP expressed from the plasmids 2wtd1EGFP, 2wtd1EGFPFS and gf10bse2 were analyzed during the thirteen days post-transfection.

Figure 20:
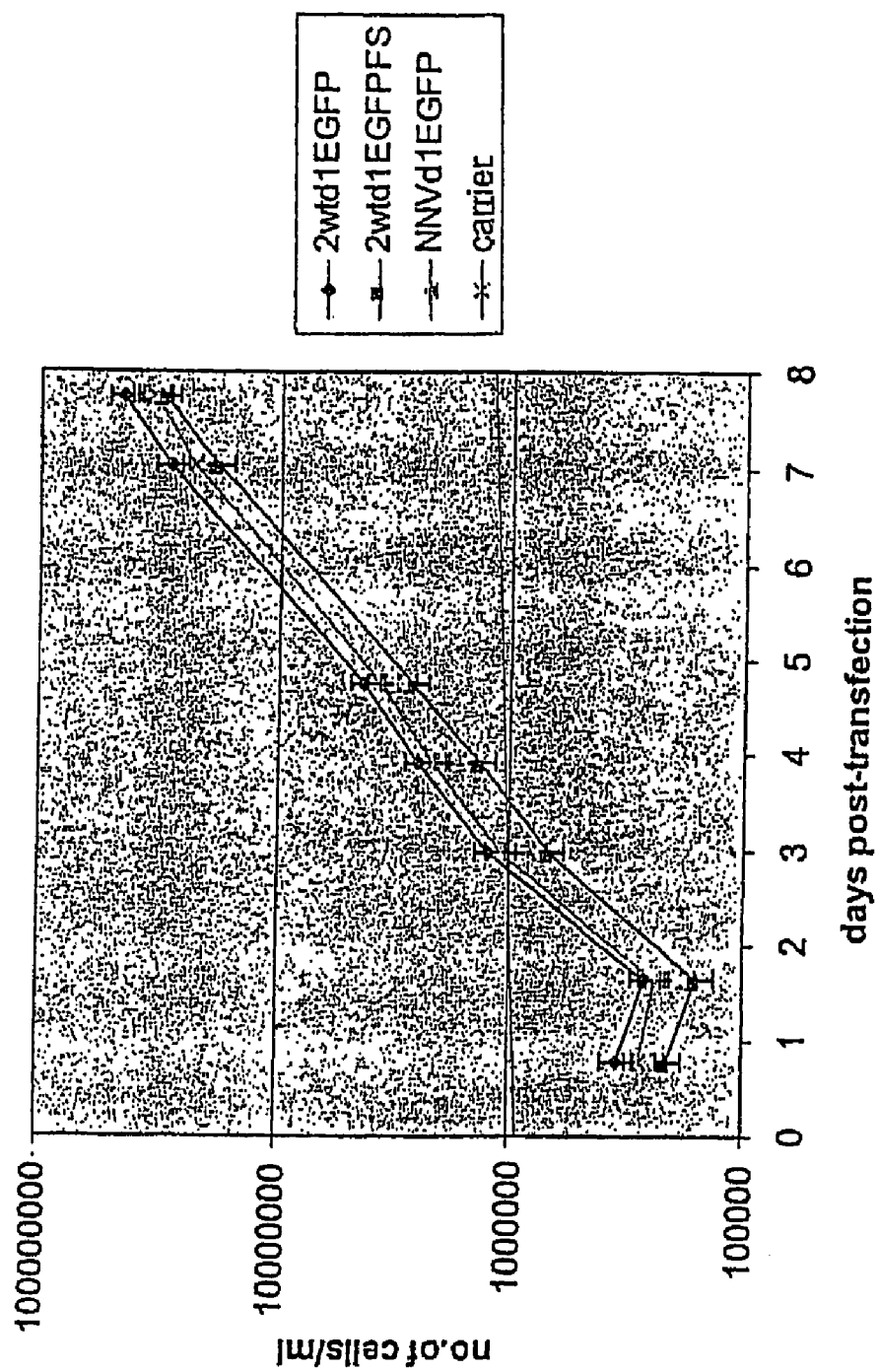
FIG. 20 shows the growth curves of the Jurkat cells transfected with the plasmids 2wtd1EGFP, 2wtd1EGFPFS, NNVd1EGFP or with carrier DNA only.
Figure 21:
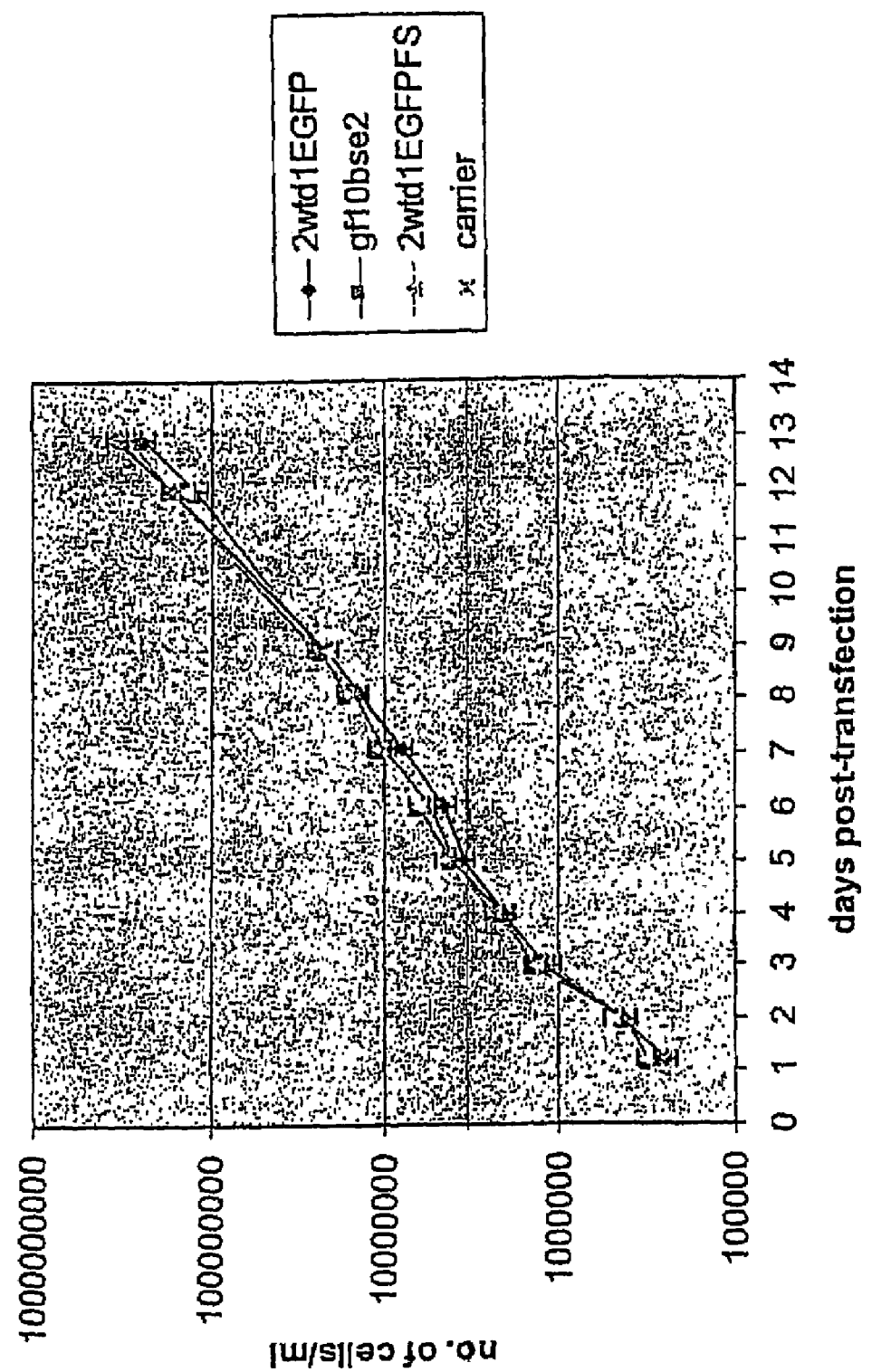
FIG. 21 shows the growth curves of the Jurkat cells transfected with the plasmids 2wtd1EGFP, 2wtd1EGFPFS, gf10bse2 or with carrier DNA only.

As is obvious from FIGS. 20 and 21, there was no difference of the growth speed of the cells transfected with any vector or carrier only. It means that differences in the d1EGFP expression maintenance are not caused by influences of transfected vectors themselves on the dividing of the cells. Also, during the assay the logarithmic growth of the cells were detected, except the period until second time-point in the experiment represented in FIG. 20. This lag period of the growth is probably caused by the electroporation shock of the cells, because the first time-point was taken already 19 hours after the transfection.

Figure 22:
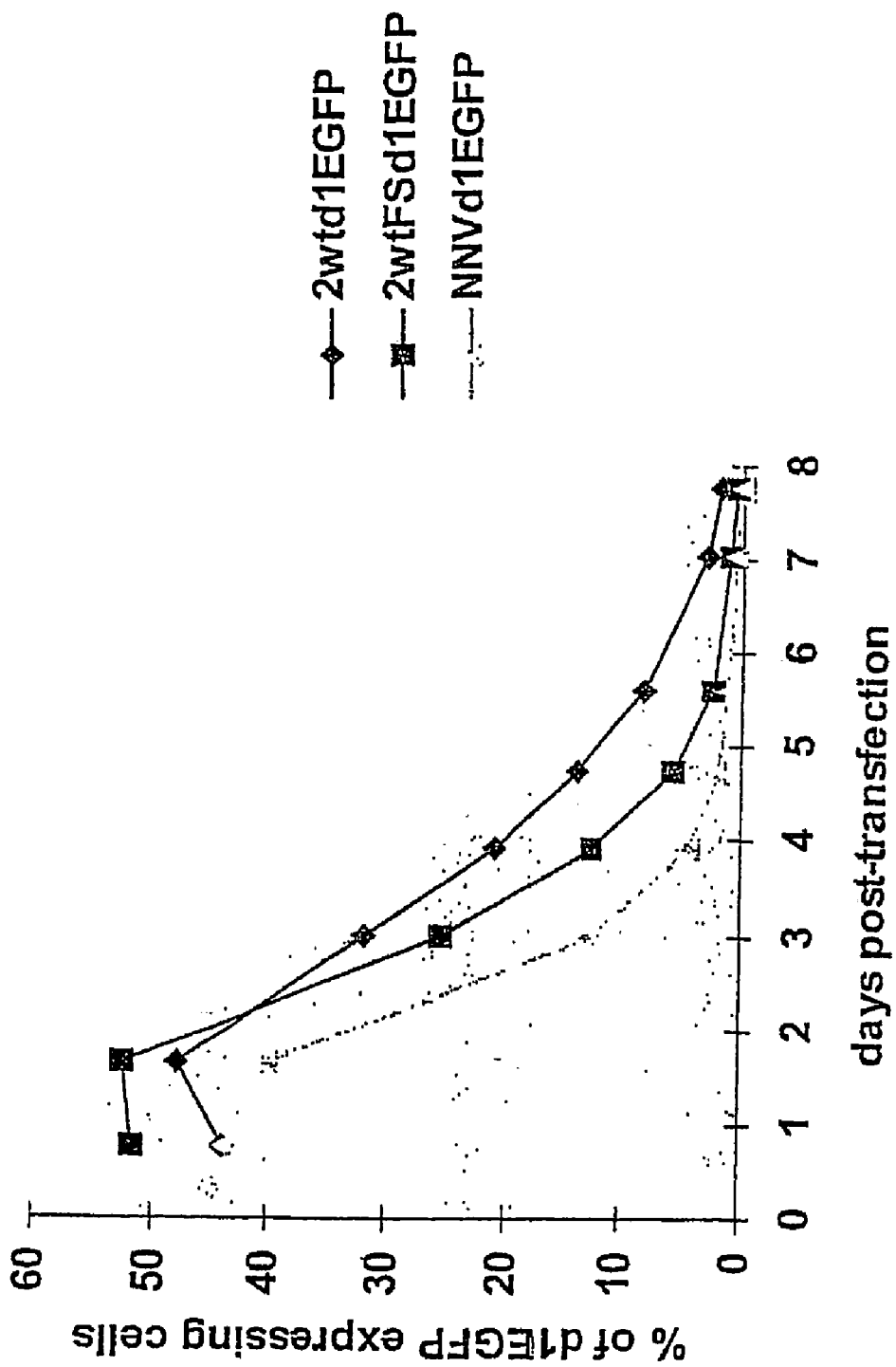
FIG. 22 shows the change in the percentage of d1EGFP positive cells in a population of Jurkat cells transfected with the vectors 2wtd1EGFP, 2wtd1EGFPFS or NNVd1EGFP.
Figure 23:
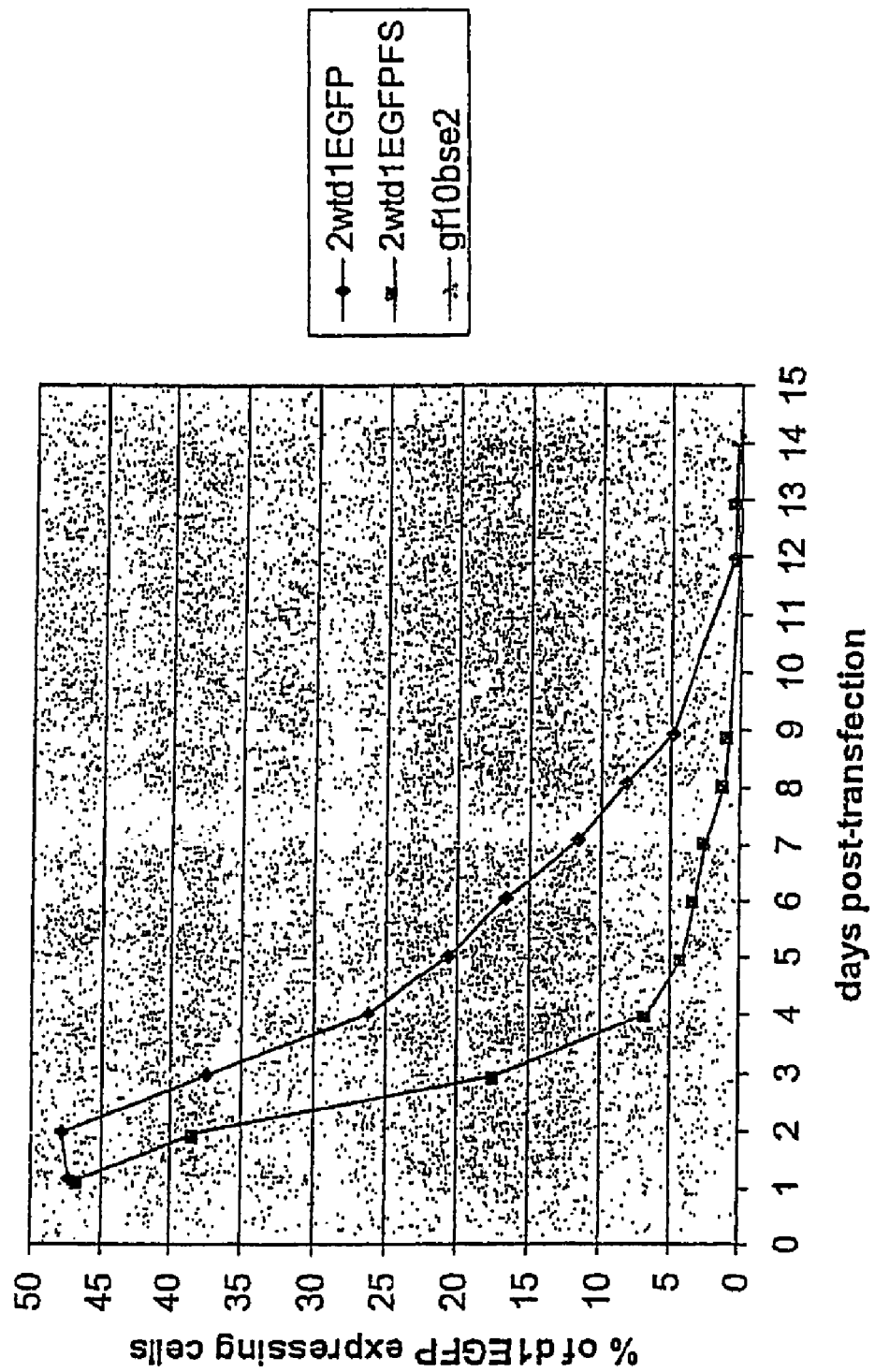
FIG. 23 shows the change in percentage of the d1EGFP positive cells in a population of Jurkat cells transfected with the vectors 2wtd1EGFP, 2wtd 1EGFPFS or gf10bse2.

As illustrated in FIGS. 22 and 23, the percentages of green fluorescent protein expressing cells decrease in all populations transfected with either plasmid, because the vectors do not replicate in the cells. However, as is seen on the charts, the fraction of positive cells declines more rapidly in cases of control vectors, if compared with the 2wtd1EGFP or gf10bse2. If compared with each other, the gf10bse2 have clear benefit to 2wtd1EGFP (FIG. 23.). There is also a notable difference of maintenance between control plasmids 2wtFSd1EGFP and NNVd1EGFP (FIG. 22).

Figure 24:
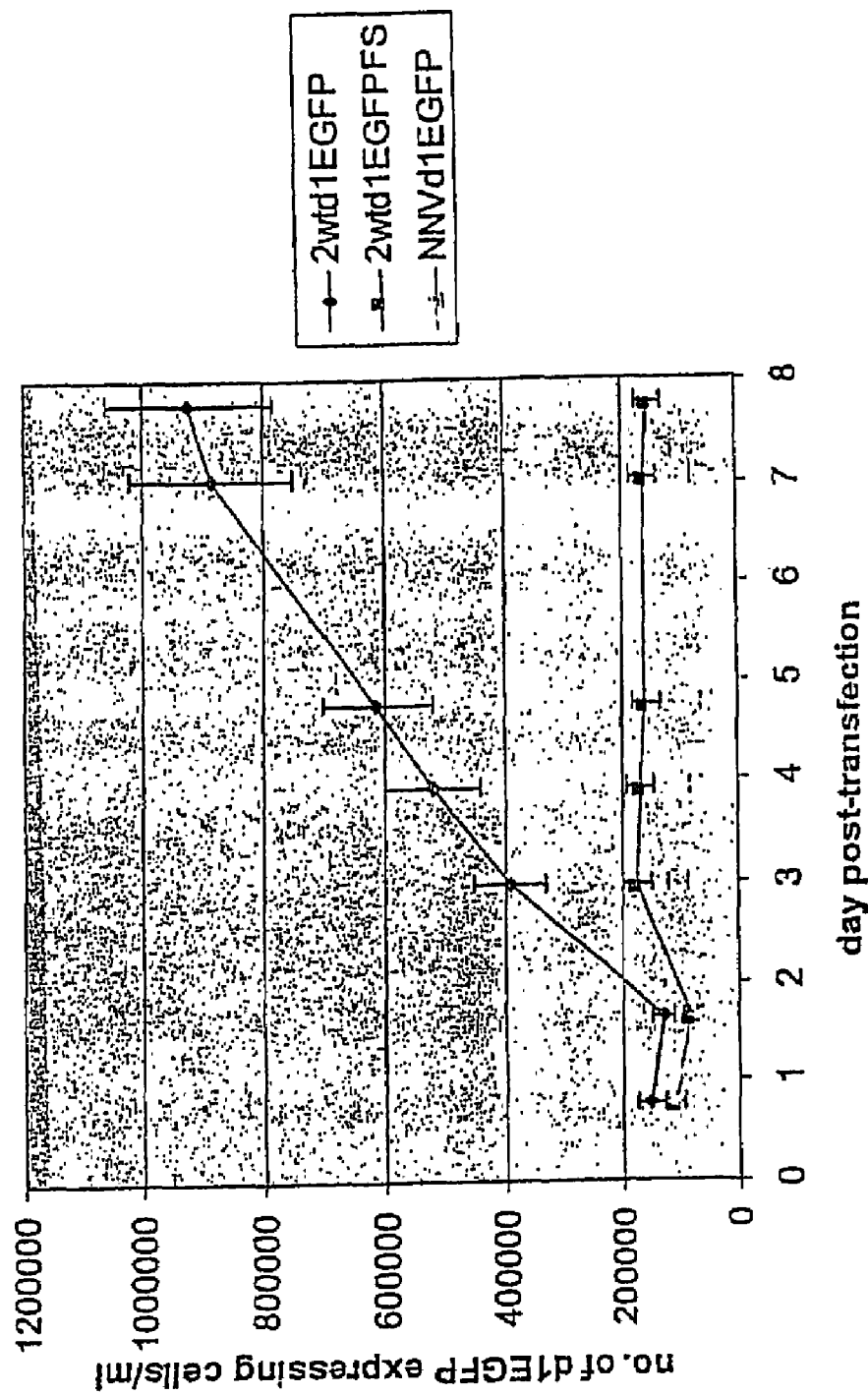
FIG. 24 shows the change in the number of d1EGFP expressing cells in a population of Jurkat cells transfected with the vectors 2wtd1EGFP, 2wtd1EGFPFS or NNVd1EGFP.
Figure 25:
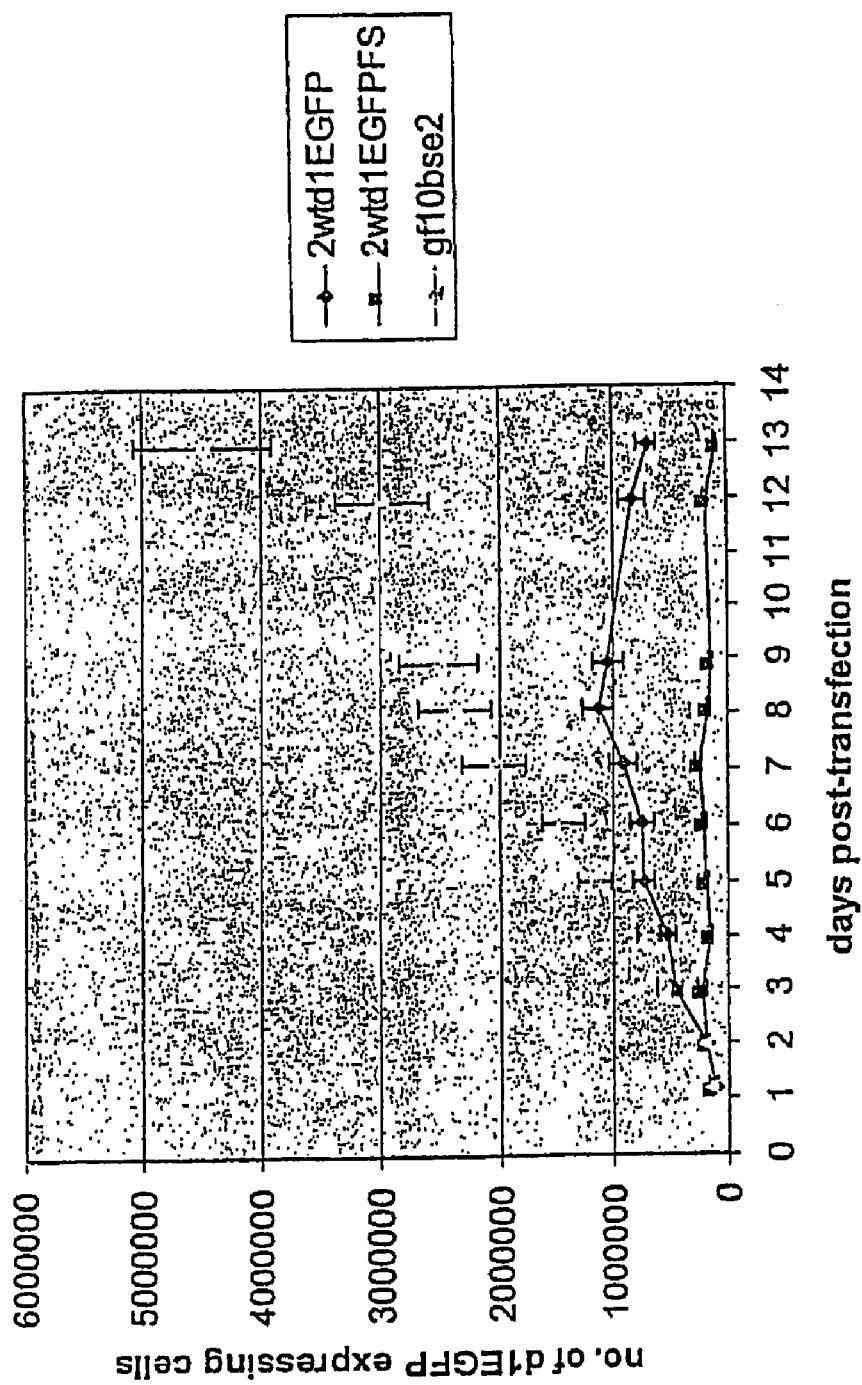
FIG. 25 shows the change in the number of d1EGFP expressing cells in a population of Jurkat cells transfected with the vectors 2wtd1EGFP, 2wtd1EGFPFS or gf10bse2.

These differences between the vectors become much more obvious, if the data are represented as alterations of the numbers of the d1EGFP expressing cells in the populations (FIGS. 24 and 25). The numbers of the positive cells in cases of the control plasmids are not notable changed during the assay. In contrast, in case of the 2wtd1EGFP the number of d1EGFP expressing cells increases during the first week after the transfection becoming approximately five to ten times higher than in control samples (FIG. 24). After this time-point the number start to decrease (FIG. 25). The difference of maintenance is strongest in the case of the gf10bse2 vector. The number of positive cells increases continuously during the analyses period. After two weeks it is 6 times higher than in the sample transfected with 2wtd1EGFP and 45 times higher than in the population transfected with frameshift mutant (FIG. 25).

The data demonstrate clearly that the vector system of the present invention has active mechanism of segregation based on a nuclear-anchoring protein, i.e. bovine papillomavirus type 1 E2 protein and its binding sites that promotes its maintenance in a population of proliferating cells as a transcriptionally active element.

6.9 Example 9

Cloning of the Aire Gene into Super6wt and Expression in an Epithelial Cell Line The AIRE gene coding for the AIRE protein (AIRE=autoimmune regulator) is mutated in an autosomally heredited syndrome APECED (Autoimmune polyendocrinopathy candidiasis ectodermal dystrophy). AIRE is expressed in rare epithelial cells in the medulla of thymus and in the dendritic cells in peripheral blood and in peripheral lymphoid organs. APECED could thus be treated by transferring the non-mutated AIRE gene ex vivo to peripheral blood dendritic cells, followed by the introduction of the corrected dendritic cells back to the patient. To test this possibility human AIRE gene and the homologous murine AIRE gene were transferred to COS-1 cells.

For cloning of the AIRE gene into Super6wt a maxi-preparation of the vector was prepared. First a transfection with Super6wt was done to TOP10-cells (chemically competent *Escherichia coli* by Invitrogen) according to manufacturer's protocol. Briefly, the cells were incubated on ice for 30 minutes, after which a heat shock was performed in a water bath at +42° C. for 30 seconds. The cells were then transferred directly on ice for 2 minutes and grown in 250 µl of SOC-medium (2% tryptone, 0.5% yeast extract, 10 mM NaCl, 2.5 mM KCl, 10 mM MgCl2, 10 mM MgSO4, 20 mM glucose) at +37° C. with shaking for 1 hour.

Plating was done on LB-plates using kanamycin (50 µg/ml) for selection. For maxiprep, colonies were transferred to 150 ml of LB-solution containing kanamycin (50 µg/ml) and grown overnight at +37° C. with shaking. Preparation of maxiprep was done using Qiagen's Plasmid Maxi Kit according to manufacturer's protocol.

A digestion with BamHI and SalI restriction enzymes was used to check the vector. The reaction mixture contained 500 ng of Super6w, 5 U of BamHI, 5 U of SalI, 2 µl of 2XTANGO buffer (both the restriction enzymes and buffer from Fermentas) and sterile water in total volume of 10 µl. The digestion was carried out at +37° C. for one hour.

The digested vector was checked with 1% agarose gel containing ethidium bromide 1 µg/ml in 1X TAE-buffer.

For cloning of the PCR amplified AIRE gene and Aire fragments into the Super6wt, 4 µg of Super6wt was digested with 10 U NotI restriction enzyme (MBI Fermentas, in 2 µl enzyme buffer and sterile water added to a final volume of 20 µl. The digestion was carried at +37° C. for 1.5 hours, after which 1U of ZIP-enzyme (alkaline phosphatase) was added to the reaction mixture and incubated further for 30 minutes. The ZIP-enzyme treatment was done to facilitate the insertion of the AIRE gene into the vector by preventing the self-ligation of the vector back to a circular mode. After the digestion the vector was purified using GFXTM PCR DNA and Gel Band Purification Kit (Amersham Pharmacia Biotech) and dissolved in to a concentration of 0.2 micrograms/microliter.

Human and mouse AIRE-gene PCR-products were also digested with NotI restriction enzyme. To the digestion, 26 µl of PCR product, 3 µl of an appropriate enzyme buffer and 10U of NotI restriction enzyme (the buffer and enzyme from MBI Fermentas) was used. The digestion was carried out at +37° C. for 2 hours, after which digested PCR-products were purified and dissolved in sterile water to a volume of 10 µl.

The PCR amplified and digested human and mouse AIRE genes were ligated to Super6wt by a T4 DNA ligase (MBI Fermentas). The digested insert DNA was taken (a total volume of 10 μl), 1.5 μl of ligase buffer (MBI Fermentas), 5U of T4 DNA ligase and sterile water was added to a final concentration of 15 μl. The ligation was carried out at +17° C. overnight.

After the ligation 10 μl of ligation reaction mixture was taken for transfection into TOP10 cells according to manufacturer's protocol. The cells were incubated on ice for 30 minutes, after which a heat shock was performed in a water bath at +42° C. for 30 seconds. The cells were then transferred directly on ice for 2 minutes and grown in 250 μl of SOC-medium (2% tryptone, 0.5% yeast extract, 10 mM NaCl, 2.5 mM KCl, 10 mM $MgCl_2$, 10 mM $MgSO_4$, 20 mM glucose) at +37° C. with shaking for 1 hour.

The transfected bacterial cells were plated onto LB-kanamycin plates and colonies were picked on the following day to 2 ml of LB-medium (1% tryptone, 0.5% yeast extract, 170 mM NaCl) with kanamycin and grown overnight at +37° C.

Miniprep DNA preparations from selected colonies were purified using Qiagen's Plasmid Midi Kit and dissolved to a volume of 50 μl, of sterile water. The presence and size of the insert was checked with NotI and BamHI digestion. 10 μl, of miniprep DNA was taken for digestion, 5U of NotI and 5U of BamHI enzymes, 2 ml of R+ enzyme buffer and sterile water was added to a final volume of 20 μl. The digestion was carried out at +37° C. for 1 hour.

The orientation of the insert was analysed with BamHI restriction enzyme. Ten μl of minprep DNA was taken, 5 U of BamHI, 2 μl of BamHI buffer (MBI Fermentas) and sterile water was added to a final volume of 20 μl. The digestion was carried out for 1 hour at +37° C. and the products were checked on a 1% agarose gel with EtBr in 1XTAE.

On the basis on these results, a plasmid containing a mouse AIRE-gene and a plasmid containing a human AIRE-gene were picked and maxipreps were prepared. Briefly, 0.5 ml of *E. coli* cell suspension containing the plasmid of interest or a miniprep culture was added to a 150 ml LB-medium containing kanamycin (50 μg/ml) and grown overnight at +37° C. Maxiprep DNAs were prepared using Qiagen's Plasmid Maxi Kit.

The plasmid containing the mouse AIRE-gene was designated as pS6wtmAIRE and plasmid containing the human AIRE-gene as pS6wthAIRE.

The generated vectors were sequenced for approximately 500 bp from both ends to verify the orientation and correctedness of the insert. The sequencing was performed using the dideoxy method with PE Biosystem's Big Dye Terminator RR-mix, which contains the four different terminating dideoxynucleotide triphosphates labeled with different fluorescent labels.

Plasmids containing the AIRE gene and AIRE gene fragments were inserted into selected cell lines to check the expression of the protein with Western blot after the transfection.

Cos-1 cells were harvested with trypsin-EDTA (Bio Whittaker Europe) solution and suspended 10×106 cells/ml into Dulbecco's MEM (Life Technologies) medium and 250 μl of cell suspension was taken for transfection. The transfection of Cos-1 cells was performed using electroporation with 2.5× 106 cells, 50 μg of salmon sperm DNA as a carrier and 5 μg of appropriate vector. The transfections were made with pS6wthAIRE, pS6wtmAIRE, Super6wt, pCAIRE, psiAIRE and pCAIRE S1-4. pCAIRE and psiAIRE are positive human AIRE controls, pCAIRE S1-4 is a positive mouse AIRE control and Super6wt is a negative control.

The electroporation was done using Biorad's Gene Pulser with capacitance 960 μFd, 240 V and 1 pulse. After the pulse the cells were kept at room temperature for 10 minutes and 400 μl of medium was added. The cells were transferred to 5 ml of medium and centrifuged for 5 minutes with 1000 rpm. Cells were plated and grown for 3 days at +37° C., 5% $CO_2$.

The cells were harvested with trypsin-EDTA and centrifuged. Then Cells were then washed once with 500 ml of 1XPBS (0.14 mM NaCl, 2.7 mM KCl, 7.9 μM Na2HPO4, 1.5 μM KH2PO4). 50 μl of PBS and 100 μl of SDS loading buffer (5% mercaptoethanol, 16 μM Bromphenolblue, 20 μM Xylene Cyanol, 1.6 mM Ficoll 400) was added and cells were heated at +95° C. for 10 minutes.

For the western blot analysis SDS-PAGE was prepared with 10% separation and 5% stacking gels in a SDS running buffer (25 mM Tris, 250 mM glysin, 0.1% SDS). Cell samples and biotinylated molecular weigh marker were loaded on the gel and electrophoresis was performed with 150 V for 1 h 50 minutes. The transfer of proteins to a nitrocellulose membrane was performed at 100 V for 1.5 hours at room temperature with a cooler in transfer buffer.

The membrane was blocked in 5% milk in TBS (0.05 M Tris-Cl, 0.15 M NaCl, pH 7.5) for 30 minutes at room temperature. A primary antibody mixture, anti-AIRE6.1 (human) and anti-AIRE8.1 (mouse) antibodies at a dilution of 1:100 in 5% milk in TBS, was added onto membrane and incubated overnight at +4° C. The membrane was washed two times with 0.1% Tween in TBS for 5 minutes and once with TBS for 5 minutes. The secondary antibody, biotinylated anti-mouse IgG at a dilution of 1:500 in 5% milk in TBS was incubated for 1 hour at room temperature. The membrane was washed and horseradish peroxidase avidin D at a dilution of 1:1000 in 5% milk in TBS was added. The membrane was incubated at room temperature for 1 hour and washed. A substrate for the peroxidase was prepared of 5 ml chloronaphtol, 20 ml TBS and 10 μl, hydrogen peroxide and added onto membrane. After the development of the color the membrane was washed with TBS and dried.

The antibody detecting with human AIRE (anti-AIRE6.1) detected the AIRE protein expression in the preparates transfected with pS6wthAIRE, pCAIRE and psiAIRE. The antibody detecting murine AIRE detected likewise the murine AIRE in cells transfected with pS6wtmAIRE and pCAIRE S1-4. The negative control (Super6wt) showed no AIRE/aire proteins.

6.10 Example 10

Detection of Cellular and Humoral Immune Response Toward HIV.1 NEF in Mice Immunized with the NNV-NEF Construct DNA Immunizations To further study the induction of humoral immunity by the vectors of the inventions, 5-8 weeks old both male and female BALB/c (H-2d) mice were used. For the DNA immunizations, the mice were anaesthetized with 1,2 mg of pentobarbital (i.p) and DNA was inoculated on shaved abdominal skin using plasmid DNA coated gold particles. The inoculation was made with Helios Gene Gun (Bio-Rad) using the pressure of 300 psi. The gold particles were 1 μm in diameter, ~1 μg of DNA/cartridge. The mice were immunized twice (on day 0 and day 7) with a total amount of DNA of 0,4 or 8 μg/mouse. The control mice were immunized with 8 μg of the plain vector without the nef-gene, i.e. NNV-deltanef.

A blood sample was taken from the tail of the mice two weeks after the last immunization. The mice were sacrificed four weeks after the last immunization and blood samples (100 μl) were collected to Eppendorf tubes containing 10 μl of 0,5 M blotting (++ vs. +) and in ELISA (higher OD, more mice in higher-dose above cut-off EDTA. The absolute number of leukocytes/ml of blood was calculated from these samples for each mouse. The sera were collected for antibody assays and stored at −20° C. The spleens were removed aseptically, weighted and then homogenized to single cell suspensions for use in T, B and NK cell assays and staining.

Detection of the Humoral Immunogenicity of the Vectors of the Invention

For the detection of Nef-specific antibodies by Western blotting, serum samples from mice immunized with the vector constructs of the invention were diluted 1:100 to 5% milk in TBS and applied on nitrocellulose strips made with recombinant HIV-1 Nef protein. For the preparation of the nitrocellulose strips, the purified recombinant protein was boiled in a sample buffer containing 1% SDS and 1% 2-mercaptoethanol, then run on a 10 or 12.5% polyacrylamide gel and subsequently transferred onto a 0.45 μm nitrocellulose paper. The strips were first blocked with 2% BSA in 5% defatted milk-TBS and thereafter incubated with diluted sera (1:100) overnight. After incubation, unbound proteins were removed by washing the strips three times with TBS-0.05% Tween-20 and twice with water. After washings, the strips were probed with a 1:500 dilution of biotinylated anti-mouse IgG (Vector Laboratories, USA) for 2 hour. After further washings, horseradish peroxidase-avidin in a dilution of 1:1000 (Vector Laboratories, USA) was added for 1 h, the strips were washed again and the bound antibodies were detected with a hydrogen peroxidase substrate, 4-chloro-1-naphtol (Sigma, USA).

The sera were also tested in ELISA to determine the exact antibody titers induced by each construct. Nef antibody ELISA was performed as previously described (Tähtinen et al., 2001). Briefly, Nunc Maxi Sorp plates were coated with 50 ng of Nef (isolate HAN), blocked with 2% BSA in phosphate buffered saline (PBS), and the sera in a dilution of 1:100 to 1:25000 were added in duplicate wells for an overnight incubation. After extensive washings, the secondary antibody, peroxidase conjugated anti-mouse IgG or IgM (DAKO), was added, and the plates were incubated for two hours and then washed. Color intensity produced from the substrate (2,2'-azino-bis(3-ethylbenzthiazoline-6-sulfonic acid, ABTS, Sigma) in a phosphate-citrate buffer was measured at 405 nm using a Labsystems Multiscan Plus ELISA-plate reader: The optical density cut-off value for positive antibody reactions was determined as follows:

cut-off=$OD$ ($xI$ control mice sera)+3$SD$.

Detection of the Cellular Immunogenicity of the Vectors of the Invention

To analyze the capacity of the vectors of the invention to induce cellular immunity, T-cell and B-cell assays as well as cell surface staining were performed.

T cell proliferation assay. The spleen cells were suspended to a final concentration of 1×106/ml RPMI-1640 (Gibco-BRL) supplemented with 10% FCS (GibcoBRL), 1% penicillin-streptomycin (GibcoBRL) and 50 μM beta-mercaptoethanol (Sigma). Cells were incubated in microtitre plates at 200 μl/well with media only or with different stimuli. The final concentrations of stimuli were: Con A 5 μg/ml, HIV-Nef-protein at a concentration of 1 and 10 μg/ml, and a negative control antigen HIV-gag at a concentration of 1 and 10 μg/ml. All reactions were made in quadruplicates. On the sixth day of the incubation 100 μl of supernatant from each well was collected and stored at −80° C. for cytokine assays. Six hours before harvesting 1 μCi of 3H-thymidine (Amersham Pharmacia Biotech) was added to each well. The cells were harvested and radioactivity incorporated (cpm) was measured in a scintillation counter. The stimulation indexes (SI) were calculated as follows $SI$=mean experimental $cpm$/mean media $cpm$.

Lymphocyte activation. T and B cell activation was detected by double surface staining of fresh splenocytes with anti-CD3-FITC plus anti-CD69-PE (early activation marker) and anti-CD19-FITC plus anti-CD69-PE antibodies (all from Pharmingen). Stainings were analyzed with flow cytometer (FACScan, Becton Dickinson).

CTL assays. Mouse splenocytes were co-cultured with fixed antigen presenting cells (P-815 cells infected with MVA-HIV-nef or control MVA-F6) for five days after which they were tested in a standard 4 hour 51 chromium release assay [Hiserodt, J., et al., J Immunol 135 (1995) 53-59; Lagranderie, M., et al., J Virol 71 (1997) 2303-2309) against MVA-HIV-nef infected or control target cells. In CTL assays the specific lysis of 10% or more was considered positive.

Cytokine assay. IFN-gamma and IL-10 were measured from antigen-stimulated cell culture supernatants in order to analyze, whether immunized mice develop a Th1 type or Th2 response. The supernatants were collected from antigen-stimulated cells as described above. Pro-inflammatory cytokines TNF-alfa and IL-10 were measured in the sera of the immunized mice. All cytokines were measured with commercial ELISA kits (Quantikine, R&D Systems).

Spontaneous proliferation. Spontaneous splenocyte proliferation was detected by 3H-thymidine uptake of the cells cultured in the medium only for 6 days.

Anti-double strand (ds) DNA antibodies. dsDNA antibodies were measured in the sera of immunized mice, positive control mice (mrI/Ipr, a generous gift from Dr. Gene Shearer, NIH, USA) and normal mice. The antibodies were assayed with ELISA on poly-L-Lysine bounded lambda phage dsDNA. The results are shown in Tables 2 and 3.

Table 2 shows complete immunological results of the mice immunized with HIV-Nef plasmid DNA. Although HIV-1 Nef recombinant protein, which was used for in vitro T cell stimulation, induced some non-HIV-specific proliferation of the cells in each immunized group, there was a significant increase in the mean SI of mice immunized with 0,4 μg of the plasmid (mean SI=72,2) compared to others. Furthermore, negative control protein HIV-gag did not induce any T cell response. Only the T cells of the mice in the group that had nef-specific proliferation also produced nef-specific IFN-gamma. None of the immunized mice had cells producing IL-10, which shows that the T cell response in the immunized mice was of Th1 type and not of Th2 type. In contrast to the T cell response, mice immunized with the higher concentration of nef plasmid DNA (8 μg) had a stronger B cell response compared to mice immunized with 0,4 μg: the humoral response in mice immunized with the higher dose was detectable already three weeks after the last immunization and the response detected was stronger both in Western-). The antibodies detected belonged to IgG-class, no IgM response was detected. None of the mice developed E2 specific antibody.

The mice immunized with 0.4 μg of HIV-nef plasmid DNA had an increased number of leukocytes (6.38×10⁶/ml) in the peripheral blood compared to other groups of immunized mice and normal mice (3.8×10⁶/ml) (Table 3). The same mice had twice as much activated T cells (21%, CD3+CD69+) compared to other mice (9% and 10%). This finding is in correlation with the positive T cell response to HIV-Nef (Table 2), since the mice with a positive T cell response to Nef also had an increased number of activated T cells in their spleens. The results of Table 3 also show that none of the immunized mice developed anti-dsDNA antibodies as compared to positive control sera (OD=1,208) indicating that there is no adverse effect of the immunization.

TABLE 2

| Mice | HIV-1 nef SI* | HIV-1 gag SI | IFN-g Th1 | IL-10 Th2 | HIV-1 nef Ab | E2 Ab |
|---|---|---|---|---|---|---|
| NNV-Nef 8 | | | | | | |
| 1 | 6 | 1 | – | – | ++ | – |
| 2 | 8 | 1 | – | – | ++ | – |
| 3 | 13 | 2 | – | – | ++ | – |
| 4 | 15 | 1 | – | – | ++ | – |

TABLE 2-continued

| Mice | HIV-1 nef SI* | HIV-1 gag SI | IFN-g Th1 | IL-10 Th2 | HIV-1 nef Ab | E2 Ab |
|---|---|---|---|---|---|---|
| 5 | 7 | 1 | – | – | ++ | – |
| Mean | 9.8 | 1.2 | | | | |
| NNV-NEF 0.4 | | | | | | |
| 1 | 24 | 1 | + | – | + | – |
| 2 | 112 | 1 | + | – | + | – |
| 3 | 83 | 1 | + | – | + | – |
| 4 | 73 | 1 | + | – | + | – |
| 5 | 69 | 1 | + | – | + | – |
| Mean | 72.2 | 1 | | | | |
| NNV-ΔNef 8 | | | | | | |
| 1 | 6 | 1 | – | – | – | – |
| 2 | nt | nt | – | – | – | – |
| 3 | 11 | 1 | – | – | – | – |
| 4 | 23 | 2 | – | – | – | – |
| 5 | 12 | 1 | – | – | – | – |
| Mean | 13 | 1.25 | | | | |

SI* = stimulation index
nt = not tested
'–', negative
'+', positive
'++', strong positive

TABLE 3

| Mice | WBC ×10⁶/ml | CD3 % spleen | CD3+CD69+ % spleen | CD19 % spleen | CD19+CD69+ % spleen | anti-dsDNA ab OD(1:10 dil) |
|---|---|---|---|---|---|---|
| NM | | | | | | |
| 1 | | | | | | 0.355 |
| 2 | | | | | | 0.255 |
| 3 | | | | | | 0.231 |
| Mean | | | | | | 0.280 |
| NNV-Nef 8 | | | | | | |
| 1 | 5 | nt | nt | nt | nt | 0.387 |
| 2 | 4.3 | 50 | 4 | 11 | 3 | 0.457 |
| 3 | 4.9 | 57 | 4 | 15 | 4 | 0.514 |
| 4 | 4.3 | 55 | 6 | 15 | 4 | 0.367 |
| 5 | 5.1 | 54 | 5 | 7 | 0 | 0.478 |
| mean | 4.72 | 54 | 4.75 (9%) | 12 | 2.75 | 0.441 |
| NNV-Nef 0.4 | | | | | | |
| 1 | 3.9 | nt | nt | nt | nt | 0.418 |
| 2 | 8 | 41 | 9 | 18 | 5 | 0.263 |
| 3 | 7.5 | 39 | 8 | 25 | 9 | 0.375 |
| 4 | 5 | 46 | 9 | 16 | 6 | 0.285 |
| 5 | 7.5 | 43 | 10 | 13 | 7 | 0.396 |
| mean | 6.38 | 42.25 | 9 (21%) | 18 | 6.75 | 0.347 |
| NNV-ΔNef 8 | | | | | | |
| 1 | 4.5 | 61 | 4 | 9 | 2 | 0.413 |
| 2 | 4.6 | 59 | 4 | 15 | 1 | 0.353 |
| 3 | 3.8 | 50 | 6 | 17 | 5 | 0.382 |
| 4 | 3.1 | 46 | 7 | 25 | 8 | 0.448 |
| 5 | 3.5 | nt | nt | nt | nt | 0.501 |
| mean | 3.9 | 54 | 5.25 (10%) | 16.5 | 4 | 0.419 |

Normal mouse mean WBC = 3.8 × 10⁶/ml
nt, not tested
a-dsDNA positive control sera OD was 1.208 (1:10 dil)

6.11. Example 11

Safety and Immunogenicity of a Prototype HIV Vaccine GTU-NEF in HIV Infected Patients Production of the NNV-2-Nef Vaccine (CHECK whether NNV-2 or NNVwt-2 was used)

The investigational vaccine NNV-2-Nef was prepared according to Example 2 with the Manufacturing License No. LLDnro 756/30/2000 (issued by the Finnish National Agency for Medicines on 21.12.2000).

The manufacturing processes performed fulfilled the current Good Manufacturing Practices (cGMP) requirements and provided plasmid DNA preparations suitable for use in clinical phase I and II studies. The manufacturing process consisted of four steps:

a) Establishment of Master Cell Banks and Working Cell Banks
b) Fermentation
c) Purification
d) Aseptic filling of the vaccine In detail, NNV-2-Nef was produced in E. coli bacteria. The Master Cell Banks (MCBs) and Working Cell Banks (WCBs) containing E. coli DH5 alpha T1 phage resistant cell strain were established in accordance with the specific Standard Operating Procedure from pure cultured and released Research Cell Banks.

a) Establishment of Master Cell Banks and Working Cell Banks

The schematic procedure for establishing the cell bank system is illustrated below:

Thaw of one vial of Research Cell Bank [E. coli DH5 alpha T1 phage resistant cell strain (Gibco RBL) transformed with the NNV-2-Nef plasmid.

Inoculate of the culture on modified Luria Bertani medium plate (containing 25 μg/ml of kanamycin)

Incubate overnight (14-16 h) at 37° C.

Select of a single colony from the plate and inoculation into 50 ml of modified Luria Bertani medium (containing 25 μg/ml of kanamycin)

Incubate overnight (14-16 h) at 37° C.

Measure optical density of the bacterial culture ($OD_{600}$=2.0-6.0)

Add glycerol to bacterial culture

Divide the culture-glycerol mix to aliquots

Label and store the Master Cell Banks

Following the same diagram, the Working Cell Bank was established using one vial of the Master Cell Bank as the starting material. The routine tests performed on the MCB and WCB were: microbiological characterization, absence of contamination, assessment of the plasmid stability by replica plating and the plasmid identity (restriction enzyme digestion and sequencing).

b) Fermentation. In the fermentation the DH5 alpha T1 phage resistant E. coli strain (Gibco RBL, UK) transformed with NNV-2-Nef (WCB) was first cultured on plate. From the plate a single colony was inoculated to a 100 ml liquid preculture before the actual fermentation in the fermentation reactor. The fermentation was carried out in a 5 l fermentor (B. Braun Medical) on a fed-batch system basis, after which cells were harvested. The culture medium composition for one liter contained 7 g of yeast extract, 8 g of peptone from soy meal, 10 g of NaCl, 800 ml of water for injection (WFI), 1N NaOH, pH 7.0, kanamycin 50 mg/ml (Sigma), silicon anti-foaming agent (Merck), 1M $K_2PO_4$ (BioWhittaker).

In the beginning of the fermentation run, a 1 ml sample was taken through the harvesting tube to determine the initial cell density ($OD_{600}$). The preculture was used to inoculate the fermentation medium. During the fermentation, fresh culture medium and 1 M potassium phosphate buffer, pH 6.5-7.3, were fed to the reactor with the pumps. Addition of the medium allows replenishment of essential nutrients before they run out and phosphate buffer maintains the pH constant. When the fermentation process had continued for approximately 5 hours and at the end of the fermentation run (after approximately 10 hours of fermentation), samples of 1 ml were taken as above and the cell density was measured. After the fermentation, the culture medium was centrifuged (10,000 rpm, 30 minutes, +4° C.) and the bacterial pellet (50-60 g) was recovered.

c) Purification. The methodology used for the purification of DNA was based on the QIAGEN process scale technology (Qiagen Plasmid Purification Handbook 11/98). The NN2-Nef was purified using the following steps:

Resuspend the bacterial pellet in the resuspension buffer (100-150 ml, RT)

Lyse with the lysis buffer (100-150 ml, 5 minutes, RT)

Neutralize with the neutralization buffers (100-150 ml, +4° C.)

Incubate (30 minutes, +4° C.)

Centrifugate (10,000 rpm, 30 minutes, +4° C.)

Filtrate supernatant (0.22 micrometers)

Remove endotoxins with Endotoxin removal buffer (60-90 ml)

Equilibrate Ultrapure column with Equilibration buffer (350 ml, flow rate 10 ml/min)

Load lysate to the column (flow rate 4-6 ml/min)

Wash the column with Wash buffer (3 l, overnight, flow rate 4-6 ml/min)

Elute the plasmid DNA with Elution buffer (400 ml, flow rate 3.1 ml/min)

Filtrate the eluate (0.22 micrometer)

Precipitate DNA with isopropanol

Centrifuge (20000 g, 30 minutes, 4° C.)

Purified plasmid DNA

Buffers used within the purification were as follows. The resuspension buffer contained 50 mM Tris-Cl, pH 8.0, plus RNase A (50 mg); the lysis buffer was 200 mM NaOH; the neutralization buffer was 3M potassium acetate, pH 5.5; the endotoxin removal buffer contained 750 mM NaCl, 10% Triton X-100; 50 mM MOPS, pH7.0; the equilibration buffer contained 750 mM NaCl, 50 mM MOPS, pH 7.0; the wash buffer contained 1 M NaCl, 50 mM MOPS, pH 7.0, 15% isopropanol; and elution buffer contained 1.6 M NaCl, 50 mM MOPS, pH 7.0, 15% isopropanol.

d) Aseptic Filling

The purified DNA representing the final bulk was dissolved in 0.9% sterile physiological saline to a final concentration of 1 mg/ml and sterile filtered (0.22 micrometer) during the same day. The purified bulk was filled manually (filling volume 0.5 ml) in Schott Type 1 plus glass vials using a steam sterilized Finnpipette® and sterile endotoxin-free tips. The vials filled with the NN2-Nef vaccine were closed immediately, labelled and packed in accordance to the specific Standard Operating Procedure (SOP).

2. Administration of the Test Vaccine to the Patients

Ten HIV-1 infected patients undergoing Highly Active Anti-Retroviral therapy (HAART) were immunized with the experimental DNA vaccine NN2-Nef, expressing the HIV-1 Nef gene (Clade B). For immunizations, two intramuscular injections in the gluteal muscle were given two weeks apart. The doses were 1 and 20 micrograms/injection. Blood samples were drawn at −4, 0, 1, 2, 4, 8 and 12 weeks. The samples were analyzed for humoral (ELISA, Western blot)

and cell mediated immune response (T-cell subsets, T-cell proliferation, ELISPOT, cytokine expression, intracellular cytokines).

A clinical examination was performed to each patient participating the study. The clinical examination included a patient interview (anamnesis) and weight determination. Cardiac and pulmonar functions were checked by auscultation and percussion, the blood pressure and heart rate were recorded. Enlargement of lymph nodes, liver and thyroid gland were determined by palpation.

Laboratory tests to evaluate the safety of the vaccine were performed at each visit. These tests included:

Hematology: red blood cell count, haemoglobin, total and differential WBC, platelet count, prothrombin time and activated partial thromboplastin time at baseline; mean erythrocyte corpuscular volume and hemoglobin content has been calculated.

Immunology: nuclear and ds-DNA antibodies.

Serum chemistries: total bilirubin, alkaline phosphatase, SGOT/SLT or SGPT/ALT, serum creatinine, protein electrophoresis, total serum cholesterol, triglycerides, glucose (at baseline), sodium, potassium, and calcium.

Urine analysis: dipstick protein, glucose, ketones, occult blood, bile pigments, pH, specific gravity and microscopic examination of urinary sediment (RBC, WBC, epithelial cells, bacteria, casts), when dipstick determination showed one or more abnormal values.

Viral load: Increases of more than one log 10 should be followed by a confirmatory viral load estimate after two weeks.

None of the patients experienced subjective or objective adverse reactions to the vaccination. No adverse laboratory abnormalities were observed in the panel of clinical chemistry tests (see material and methods for details) performed repeatedly during the vaccination period.

The following immunological studies were performed:

Lymphocyte Proliferation Assay (LPA)

Peripheral blood mononuclear cells (PBMC) were isolated from heparinized venous blood by FicoII-Hypaque density-gradient (Pharmacia) centrifugation and resuspended at $1 \times 10^6$ cells/ml in RPMI 1640 medium (Gibco) supplemented with 5% pooled, heat-inactivated $AB^+$ serum (Sigma), antibiotics (100 U/ml penicillin and 100 µg/ml streptomycin; Gibco) and L-glutamine (complete medium, CM). Quadruplicate cultures were then set up in flat-bottomed micro titer plates ($1 \times 10^5$ PBMC/well) and the cells were incubated for 6 days in the presence or absence of the following stimuli: rNef (0.2, 1 and 5 µg/ml), GST (0.2, 1 and 5 µg/ml), purified protein derivative of tuberculin (PPD, 12.5 µg/ml; Statens Seruminstitut), *Candida albicans* antigen (20 µg/ml; Greer Laboratories) and Phytohaemagglutinin (PHA; 5 µg/ml; Life Technologies). For the last 6 h of the incubation period $^3$H-thymidine (1 µCi/well; Amersham) was added to the cultures and the cells were harvested onto glass fiber filters and incorporated radioactivity was measured in a γ-counter. Results are expresses as delta cpm (cpm in the presence of antigen-cpm without antigen) or as stimulation index (cpm in the presence of antigen/cpm without antigen).

The results are shown in FIGS. 26 and 27. None of the vaccinees showed significant T-cell proliferative response to the test antigen, HIV-1 Nef before the vaccination. In contrast, 2 out of 5 vaccinees in the group that had received 1 microgram dose of the test vaccine (patients 1 and 3) (FIG. 26) and 2 out of 5 in the group receiving 20 micrograms of the test vaccine (patients 9 and 10) (FIG. 27) showed a strong T-cell proliferative response after the first vaccination. After the second vaccination, one (patient 2) vaccinee responded in the 1-microgram group.

IFN-γ Assays

The type of immune response (Th1/Th2) induced by the vaccine was evaluated by measuring interferon-gamma (IFN-γ) released in 6 days old culture supernatant after antigen (rNef, rGST, PPD) or mitogen (PHA) stimulation of PBMC. For determinations, commercial ELISA kits (R&D Quantikine) were used. The assay employ the quantitative sandwich enzyme immunoassay technique where a monoclonal antibody specific for IFN-γ has been coated onto a microplate. Standards and samples are pipetted into the wells and any IFN-γ present is bound by the immobilized antibody. After washing away any unbound substances, an enzyme-linked polyclonal antibody specific for IFN-γ is added to the wells. Following a wash to remove any unbound antibody-enzyme reagent, a substrate solution is added to the wells and color develops in proportion to the amount of the cytokine bound in the initial step. The color development is stopped and the intensity of the color is measured.

IFN-γ response data from patient #1 is shown in FIG. 28. As can be seen, the vaccinee responded to the rNef antigen by marked IFN-γ response correlated with the T-cell proliferation, indicating that the response seen in the vaccinee is in fact of the Th1 type.

HIV-1 infection is characterized by low or totally lacking cell-mediated immune response towards all HIV proteins. The results show that it is possible to induce a robust CMI in such patients with exceptionally low doses of the DNA vaccine NN2-Nef. The doses used were minimal to what has generally been required with DNA vaccines. Thus, for instance, Merch announced recently good results with their experimental HIV vaccine but the doses required were from 1000 to 5000 micrograms (IAVI report, 2002).

6.12 Example 12

Construction of the Plasmid Expressing Epstein-Barr Virus (EBV) EBNA-1 Protein and Containing 20 Binding Sites for EBNA-1 (FR Element)

To construct a plasmid expressing Epstein-Barr virus (EBV) EBNA-1 protein and containing 20 binding sites for EBNA-1 (FR element), BPV-1 E2 binding sites were first replaced by EBV EBNA-1 binding sites (oriP without DS element). Plasmid FRE2d1EGFP (FIG. 29) was constructed by isolating the XmiI(AccI)/Eco32I(EcoRV) DNA fragment (blunt-ended with Klenow enzyme) of pEBO LPP plasmid (FIG. 29A) (the fragment contains 20 binding sites for EBNA-1) and inserting it by blunt end ligation into the SpeI/NheI site of s6E2d1EGFP (FIG. 29B) (blunt-ended with Klenow enzyme). The constructed plasmid FRE2d1EGFP (FIG. 29) was used as a negative control in further experiments. It contains binding sites for EBNA-1 protein instead of the BPV1 E2 10 binding sites, expressing E2, but not EBNA-1.

Next, the sequence encoding BPV-1 E2 protein in FRE2d1EGFP plasmid was replaced by a sequence encoding EBV EBNA-1 protein as follows. The XmiI(AccI)/EcoRI fragment of pEBO LPP plasmid was isolated and bluntended with Klenow enzyme and inserted into the XbaI/XbaI site of FRE2d1EGFP plasmid (blunted with Klenow enzyme). The vector FRE2d1EGFP was previously grown in *Escherichia coli* strain DH5α lacking Dam$^-$ methylation, because one XbaI site is sensitive for methylation. The constructed plasmid FREBNAd1EGFP (FIG. 30) expresses EBNA-1 protein and contains 20 binding sites for EBNA-1.

For expression, Jurkat, human embryonic kidney cell line 293 (ATCC CRL 1573) and mouse fibroblast cell line 3T6 cells (ATCC CCL 96) were maintained in Iscove's modified Dulbecco's medium (IMDM) supplemented with 10% fetal calf serum (FCS). Four million cells (Jurkat), 75% confluent dishes (293) or ¼ of 75% confluent dishes (3T6) were used for each transfection, which were carried out by electroporation as follows. Cells were harvested by centrifugation (1000 rpm, 5 min, at 20° C., Jouan CR 422), and resuspended in a complete medium containing 5 mM Na-BES buffer (pH 7.5). 250 µl cell of the cell suspension was mixed with 50 µg of carrier DNA (salmon sperm DNA) and 1 µg (in the case of Jurkat and 3T6) or 5 µg (in the case of 293) of plasmid DNA and electroporated at 200 V and 1000 µF for Jurkat cells, 170 V and 950 µF for 293 cells and 230 V and 975 µF for 3T6 cells. The transfected Jurkat cells were plated on 6-cm dishes with 5 ml of medium; ⅓ of transfected 293 and 3T6 cells were plated on a 6-cm dishes with 5 ml of medium and ⅔ of the cells were plated on a 10-cm dishes with 10 ml of medium.

The transfected cells were analysed for the expression of d1EGFP protein (modified enhanced green fluorescent protein). All of the constructed plasmids expressed d1EGFP protein, which was detected by measuring the fluorescence using a flow cytometer. Because of the short half-life of the d1EGFP protein, it does not accumulate, and the expression of this protein reflects the presence of transcriptionally active plasmids in the cells. Becton-Dickinson FACSCalibur system was used. The volume of the Jurkat cell suspension was measured before each time-point (approximately after every 24 hour) and if the volume was less than 5 ml, the missing volume of medium was added. Depending on the cell suspension density the appropriate volume was taken for measuring (1 or 2 ml) and replaced with the same amount of medium. This was later taken into consideration when the dilution was calculated.

For the first time-point, 293 cells from the 6-cm dish were suspended in 5 ml of medium for measuring. In every following time-point half of the cells were taken from the 10-cm dish, suspended in 5 ml of medium and then measured. An appropriate volume was added to the rest of the cell suspension. For the first time-point, 3T6 cells from the 6-cm dish were suspended in 1 ml of trypsin, which was then inactivated with 100 µl of FCS. For every following time-point, cells from the 10-cm dish were suspended in 2 ml of trypsin. 1 ml of this suspension was treated as described previously. 9 ml of medium was added to the rest of the suspension. The analyzed cells were taken out of the incubator immediately before the measurement. The appropriate flow speed (500-1000 cells/sec) was determined before each time-point using cells transfected only with carrier DNA as a control. Three different parameters were used to measure size, surface structure and fluorescence of the cells.

The results are presented as graphs in FIG. 31. Cells transfected only with carrier DNA were used to measure the auto-fluorescence of the cell-line. 1% of this auto-fluorescence was considered as background fluorescence and was subtracted later from the d1EGFP fluorescence. The received data was analyzed using Microsoft Excel program.

Percentages of the d1EGFP expressing cells were calculated using cells transfected with the carrier only as a negative control for background fluorescence. As shown in FIG. 33, the two vectors were maintained in the cells with different kinetics.

The number of the d1EGFP expressing cells was calculated taking the dilutions into consideration using cells transfected with the carrier only as a negative control for background fluorescence. As seen from FIG. 53, the plasmids expressing EBNA-1 and carrying EBNA-1 specific multimeric binding sites are maintained very efficiently in the transfected cells. At day 1 after transfection approximately $8 \times 10^4$ cells expressed EGFP. At day 8, in the case of maintenance vector (FREBNAd1EGFP), the number of the plasmid positive d1EGFP expressing cells had increased ten times to $8 \times 10^5$. With the plasmid lacking EBNA-1 expression (FRE2d1EGFP) or having no EBNA-1 binding sites, the number of plasmid positive cells was retained or in many cases decreased. This fact reflects the mechanism for segregation/partitioning Epstein-Barr virus. Maintenance and segregation function by EBNA1 and EBNA-1 binding sites provides maintenance function to the plasmid if EBNA-1 is expressed and plasmid carries EBNA-1 binding sites. The same mechanism and the same components actually provide the segregation function to Epstein-Barr Virus in the latent phase of life-cycle.

Figure 34A:
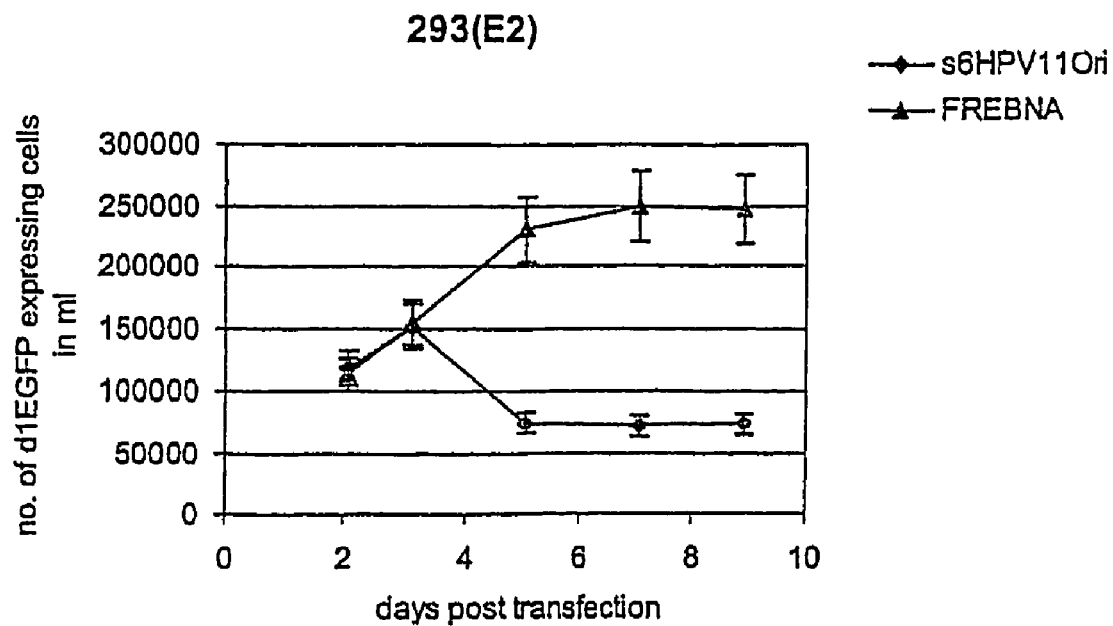
Figure 34B:
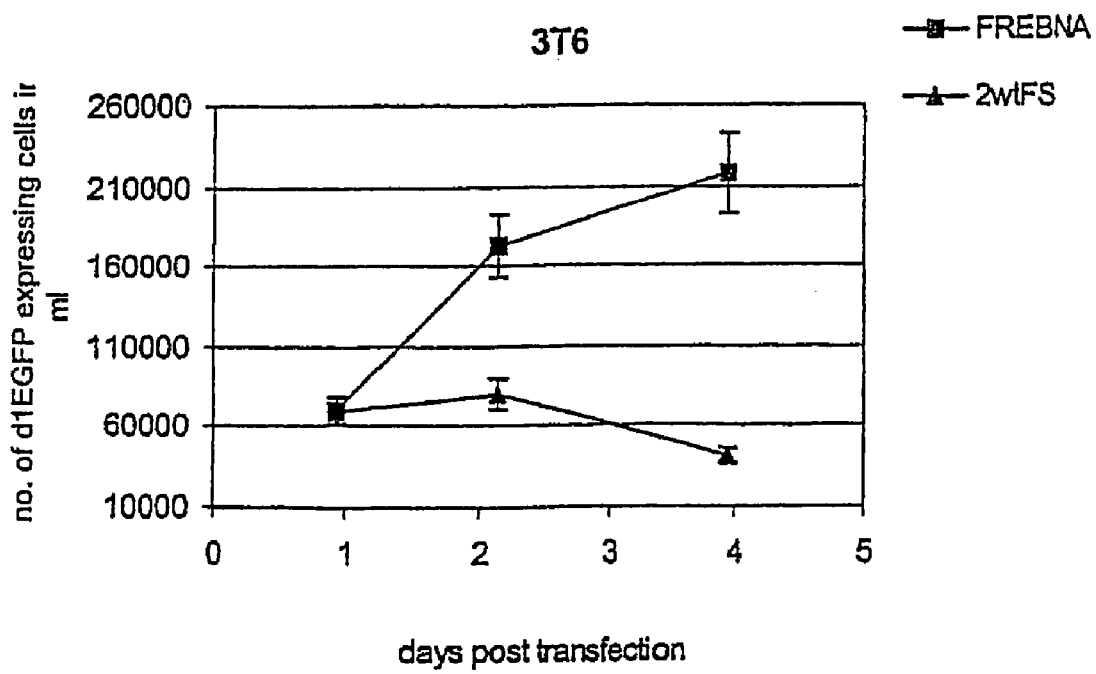

Similar results were obtained also in human embryonic cell line 293 and mouse cell line 3T6 (FIG. 34). As a control for the maintenance for 293 and 3T6 cells, s6HPV11 and 2wtFS, respectively, were used. 6.53 Example 13

The Immunogenicity of GTU-Multigene Vectors

The Immunogenicity of GTU-1-Multigene Vectors

The immunogenicity of six different multi-gene vaccine constructs prepared in Example 12, i.e. GTU-1-RNT, GTU-1-TRN, GTU-1-RNT-CTL, GTU-1-TRN-CTL, GTU-1-TRN-optgag-CTL, and GTU-1-TRN-CTL-optgag vectors were tested in mice. The vectors were transformed into TOP10 or DH5alpha cells, and the MegaPreps were prepared using commercial Qiagen columns. Endotoxins were removed with Pierce Endotoxin Removal Gel.

The test articles were coated on 1 µm gold particles according to the instructions given by the manufacturer (Bio-Rad) with slight modifications. Balb/c mice were immunized with a Helios Gene Gun using a pressure of 400 psi and 0.5 mg gold/cartridge. Mice were immunized three times at weeks 0, 1, and 3. Mice were sacrificed two weeks after the last immunization.

Mice were divided into six test groups (5 mice/group), which received 3×1 µg DNA as follows:

Group 1. GTU-1-RNT
Group 2. GTU-1-TRN
Group 3. GTU-1-RNT-CTL
Group 4. GTU-1-TRN-CTL
Group 5. GTU-1-TRN-optgag-CTL
Group 6. GTU-1-TRN-CTL-optgag
Group 7. Control mice immunized with empty gold particles not loaded with DNA.

The humoral response was followed from tail-blood samples from each mouse. First pre-immunization sample was taken from anesthetized mice before the first immunization was given. Second sample was taken from anesthetized mice before the third immunization. At sacrifice, whole blood sample was used for white blood cell counting, and serum was collected for humoral immunity tests.

The blood samples were tested for antibodies with ELISA using a standard procedure. Nunc Maxi Sorp plates were coated with 100 ng of Nef, Rev, Tat, Gag, CTL or E2 proteins, blocked and sera at a dilution of 1:100 were added in duplicate wells for an overnight incubation. After washing, the plates were incubated for 2 hours with a diluted (1:500) secondary antibody, peroxidase conjugated anti-mouse IgG (DAKO). Color intensity produced from the substrate (2,2'- azino-bis(3-ethylbenzthiazoline-6-sulfonic acid) (ABTS) in phosphate-citrate buffer was measured at 405 nm using Labsystems ELISA-plate reader.

All vectors induced Nef antibodies in all mice, whereas none of the mice showed E2, CTL or Rev antibodies (FIGS. 35, 36, and Table 4). Some of the mice immunized with GTU-1-RNT or GTU-1-RNT-CTL also developed Tat antibodies (FIG. 36 and Table 4). Furthermore, mice immunized with vectors containing the optgag sequence developed also Gag antibodies, but the construct GTU1-TRN-optgag-CTL was a better antibody inducer that the construct GTU-1-TRN-CTL-optgag (FIG. 37 and Table 4). The antibodies induced were mainly of the IgG1 class indicating a Th2 type of response usually seen with gene gun immunization. The antibody assays shown below were done from the sera collected when mice were sacrificed.

The results show that a multigene construct, expressing several HIV genes as a fusion protein, can induce an immune response to most of the gene products. The orientation and order of the genes in the multigene and corresponding proteins in the fusion proteins affects the results, however, dramatically. Thus, a response against Tat was seen only when the Tat gene was placed inside the fusion protein (vectors with RNT motif and not when Tat was the amino terminal protein (vectors with the TRN motif). Response to the Gag proteins was seen only with the vector, where Gag was placed before the CTL containing a stretch of Th and CTL epitopes.

attached to each other in various orders to multi-regulatory (multireg) antigen coding reading frames (Nef-Tat-Rev, Tat-Rev-Nef, Rev-Tat-Nef, Tat-Nef-Rev and Rev-Nef-Tat; Sequences Id. No. 1 to 5, respectively). These sequences were cloned to the Bsp119I and NotI sites of the GTU-1 vector.

Figure 17:
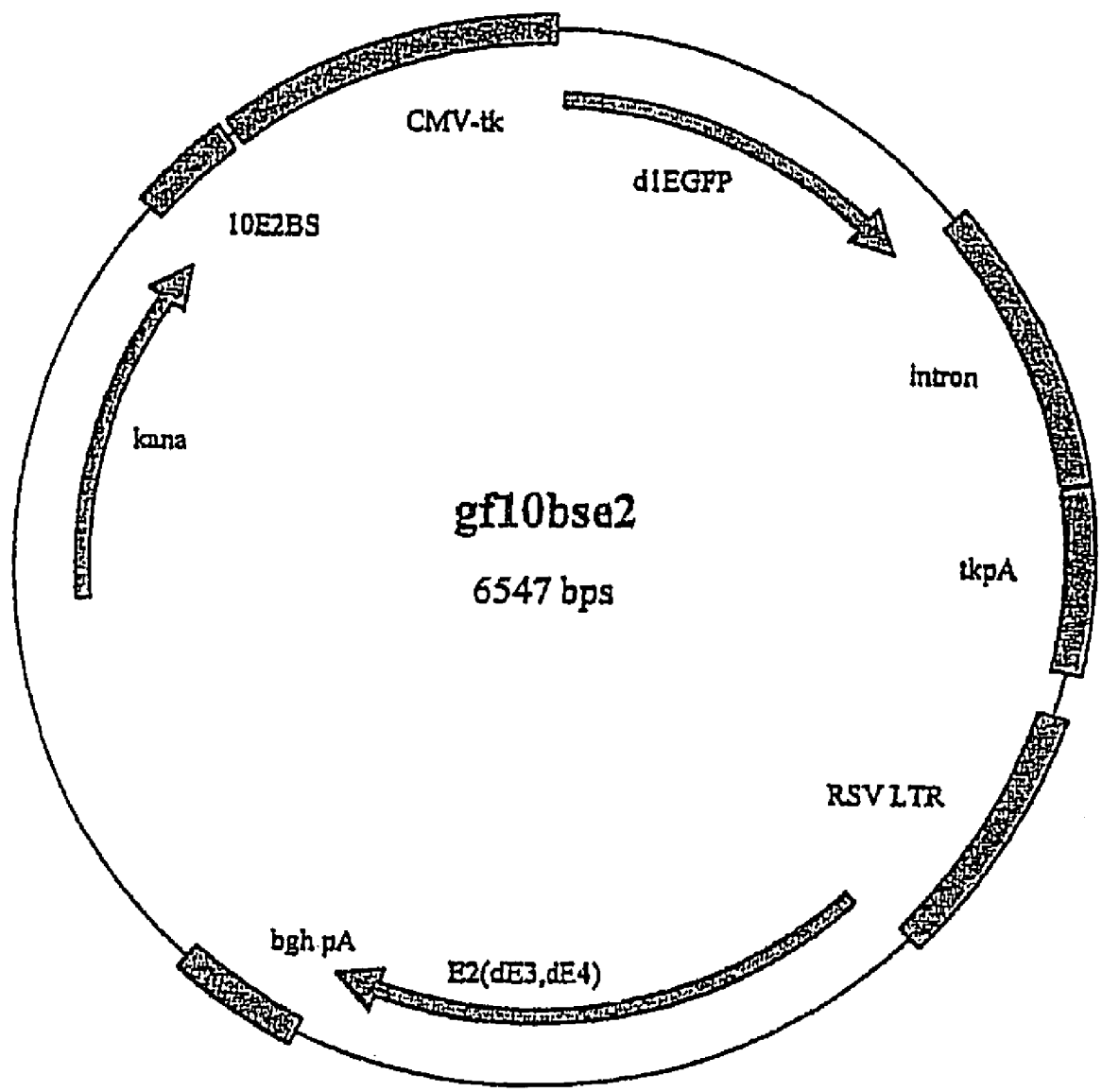
FIG. 17 shows the schematic map of the plasmid gf10bse2
Figure 38A:
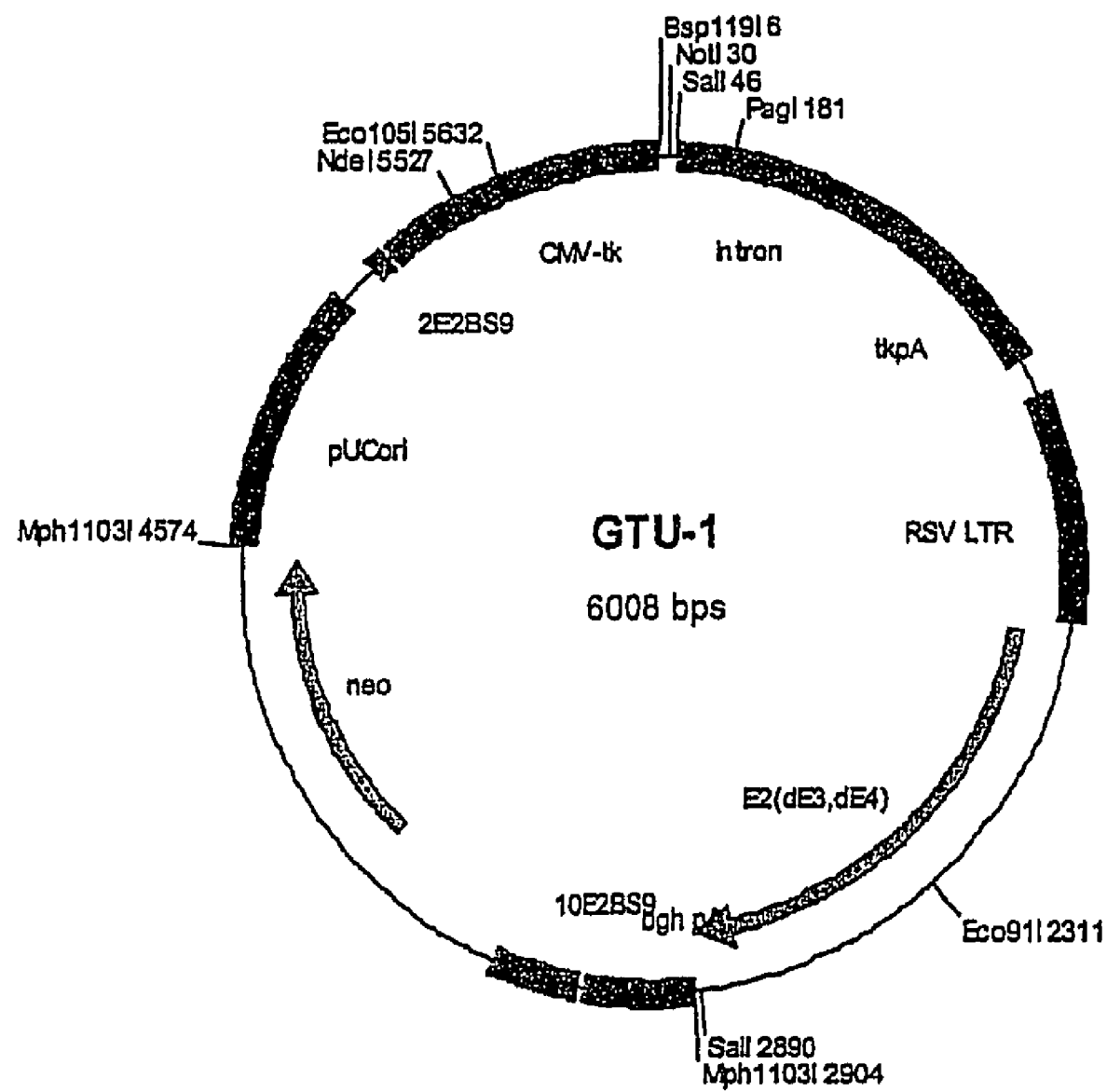
Figure 38B:
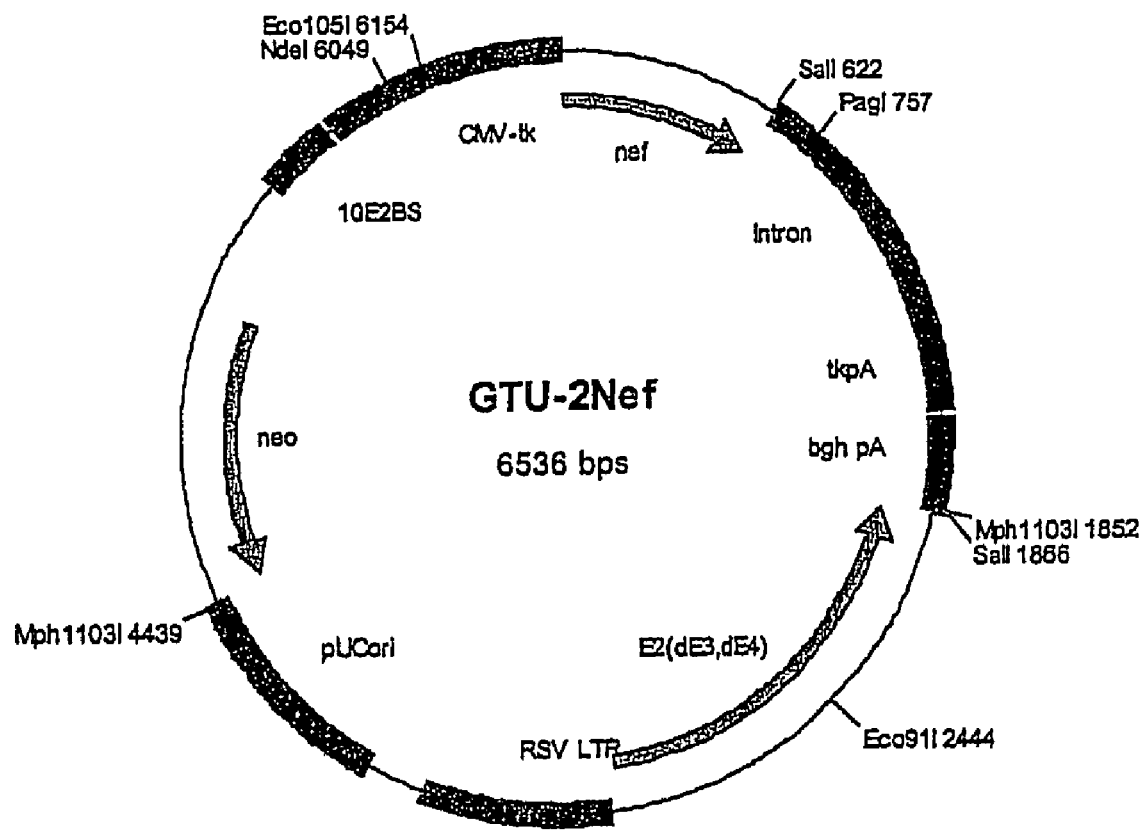
Figure 38C:
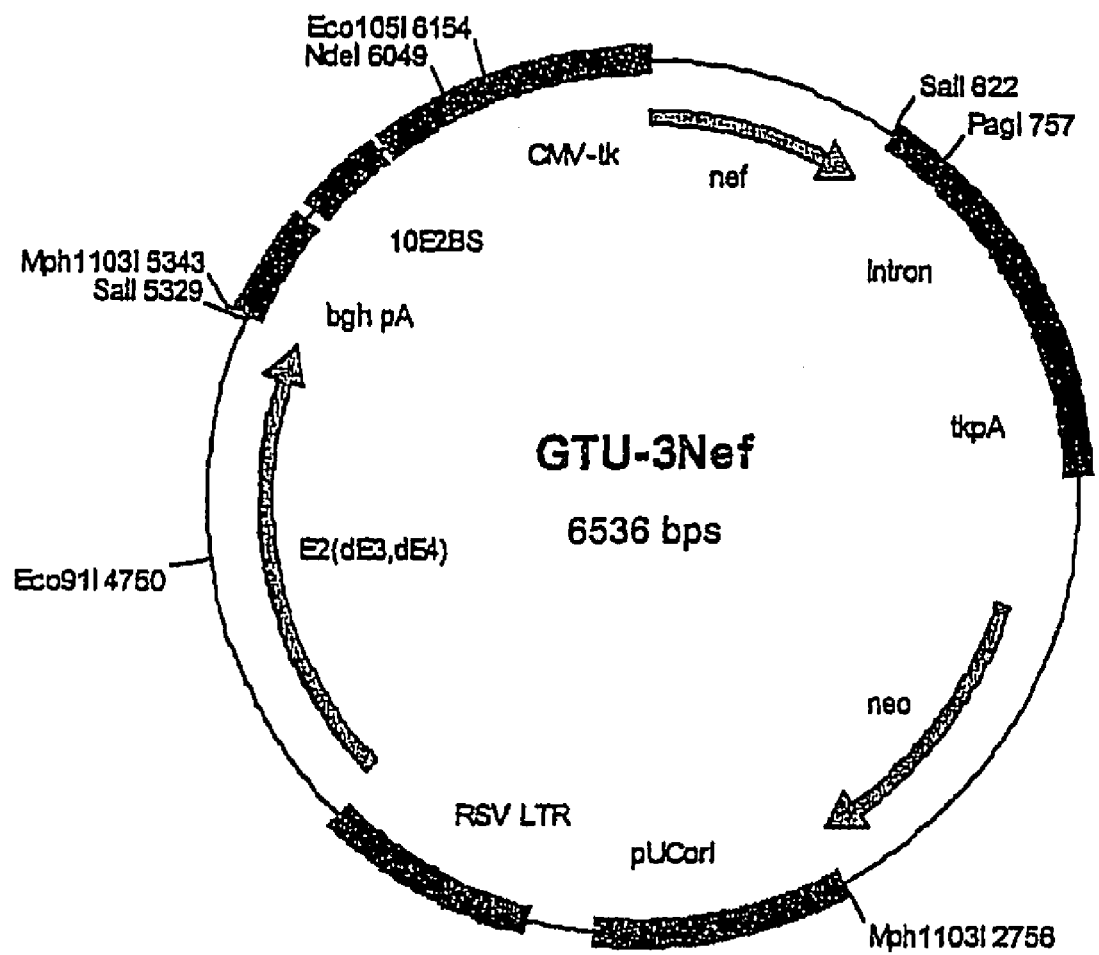
Figure 38D:
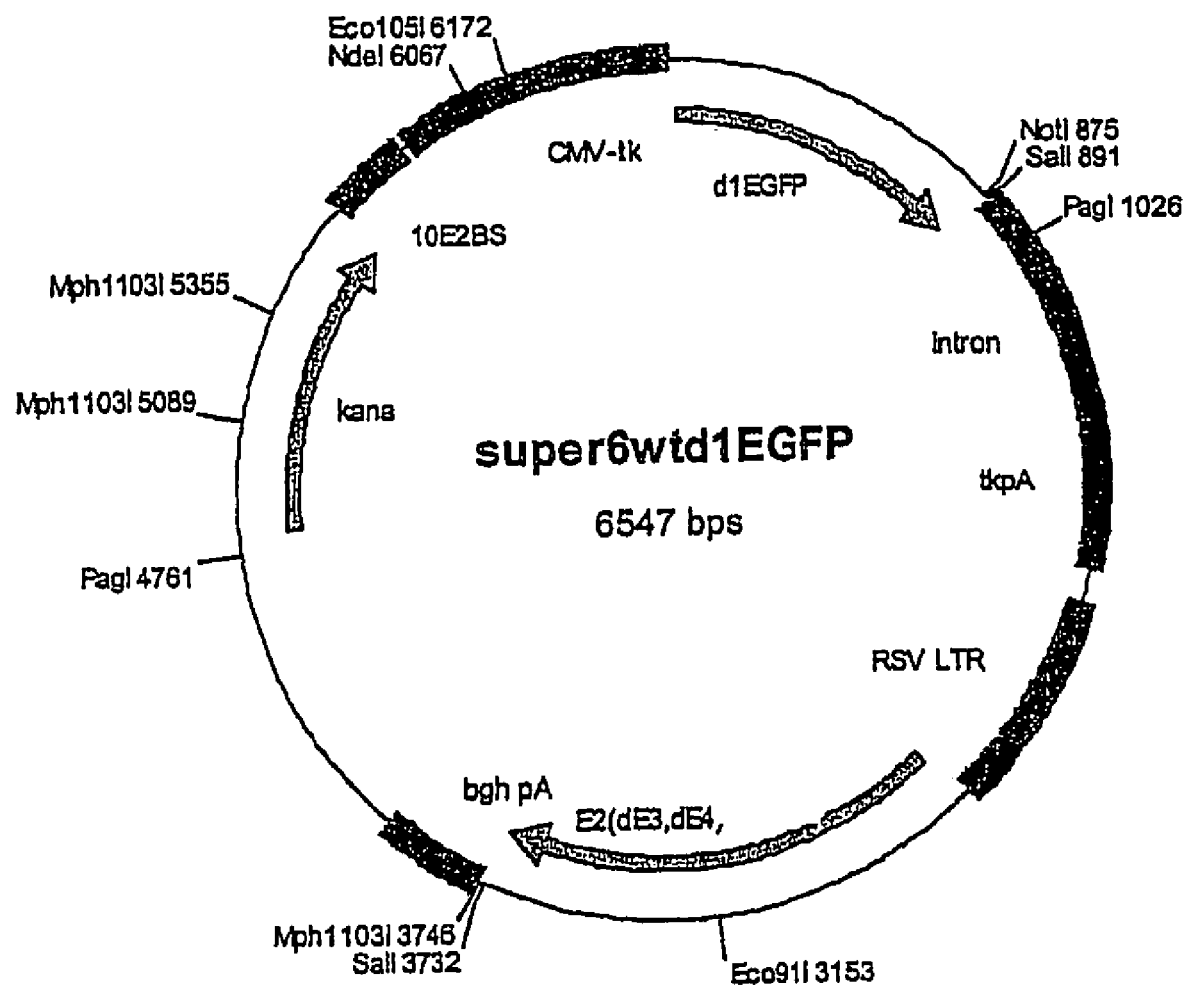
Figure 38E:
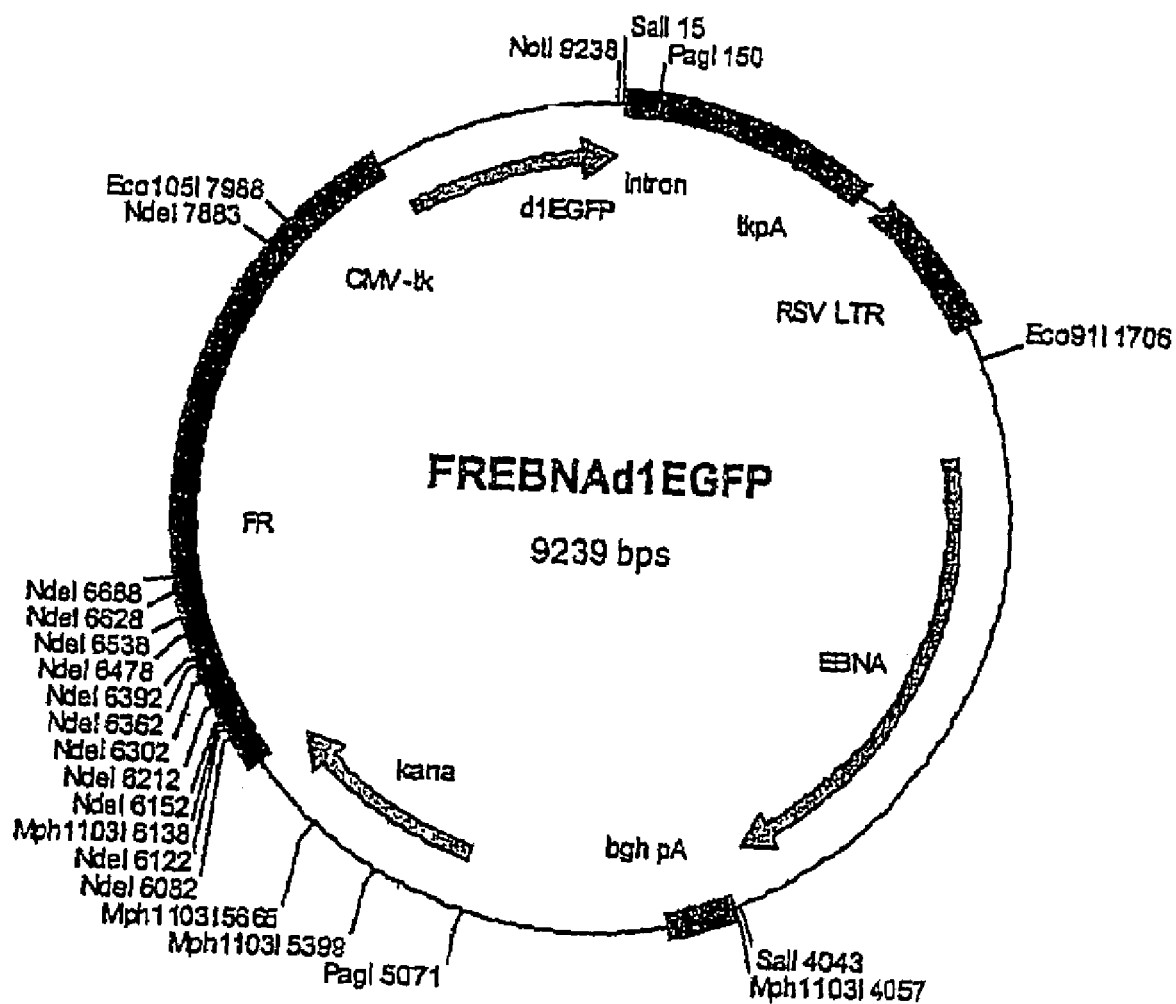
Figure 38F:
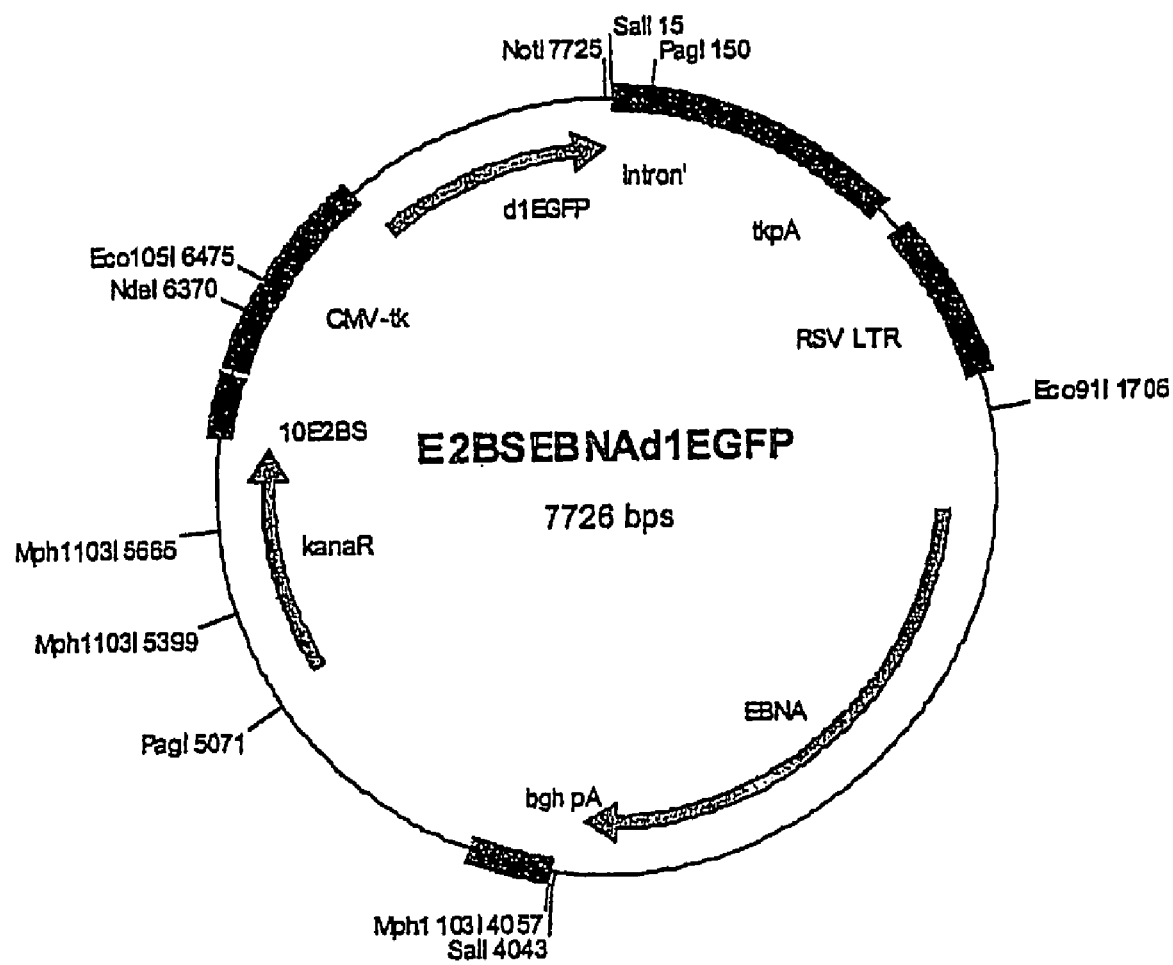
Figure 38G:
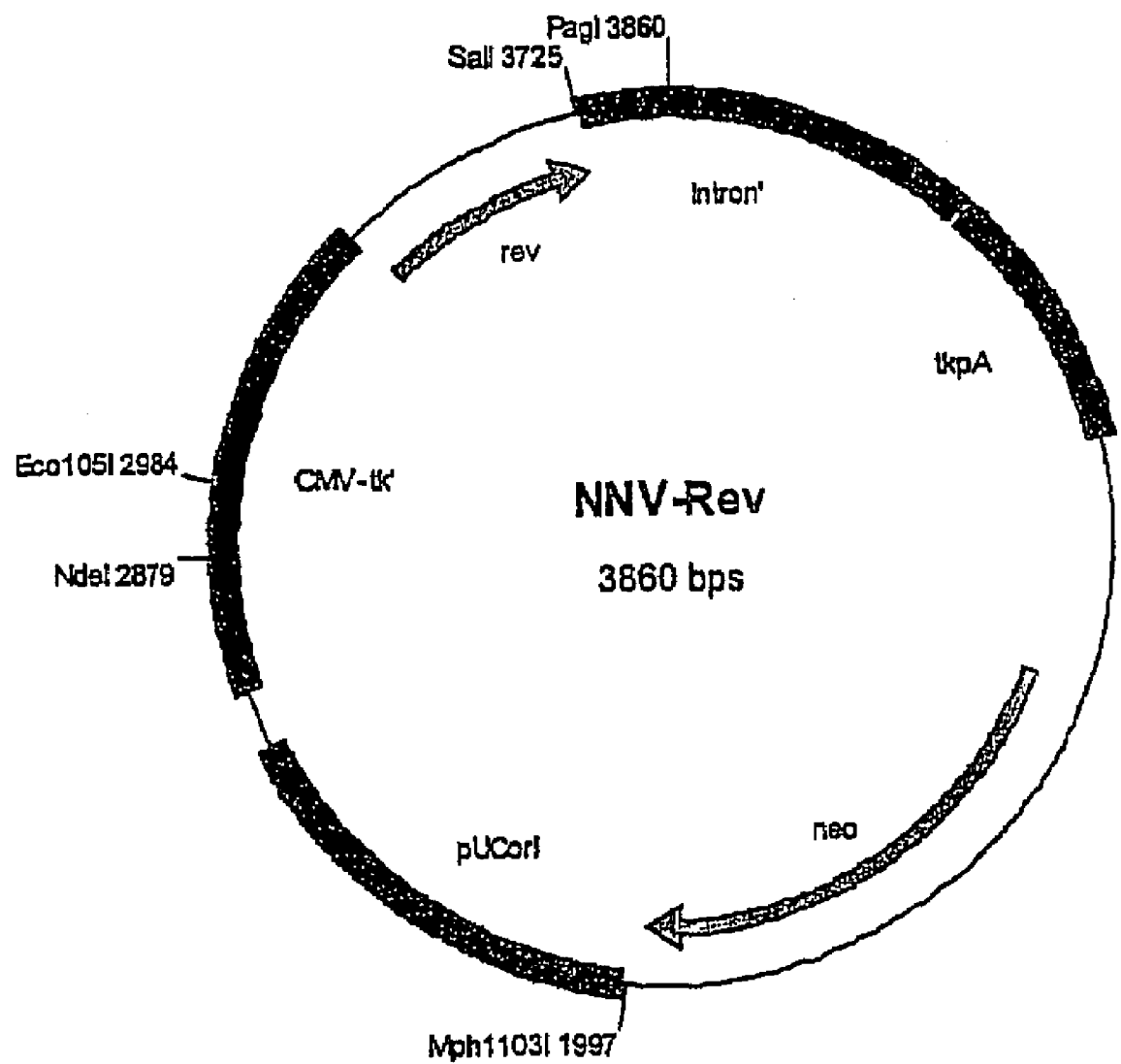
Figure 39A:
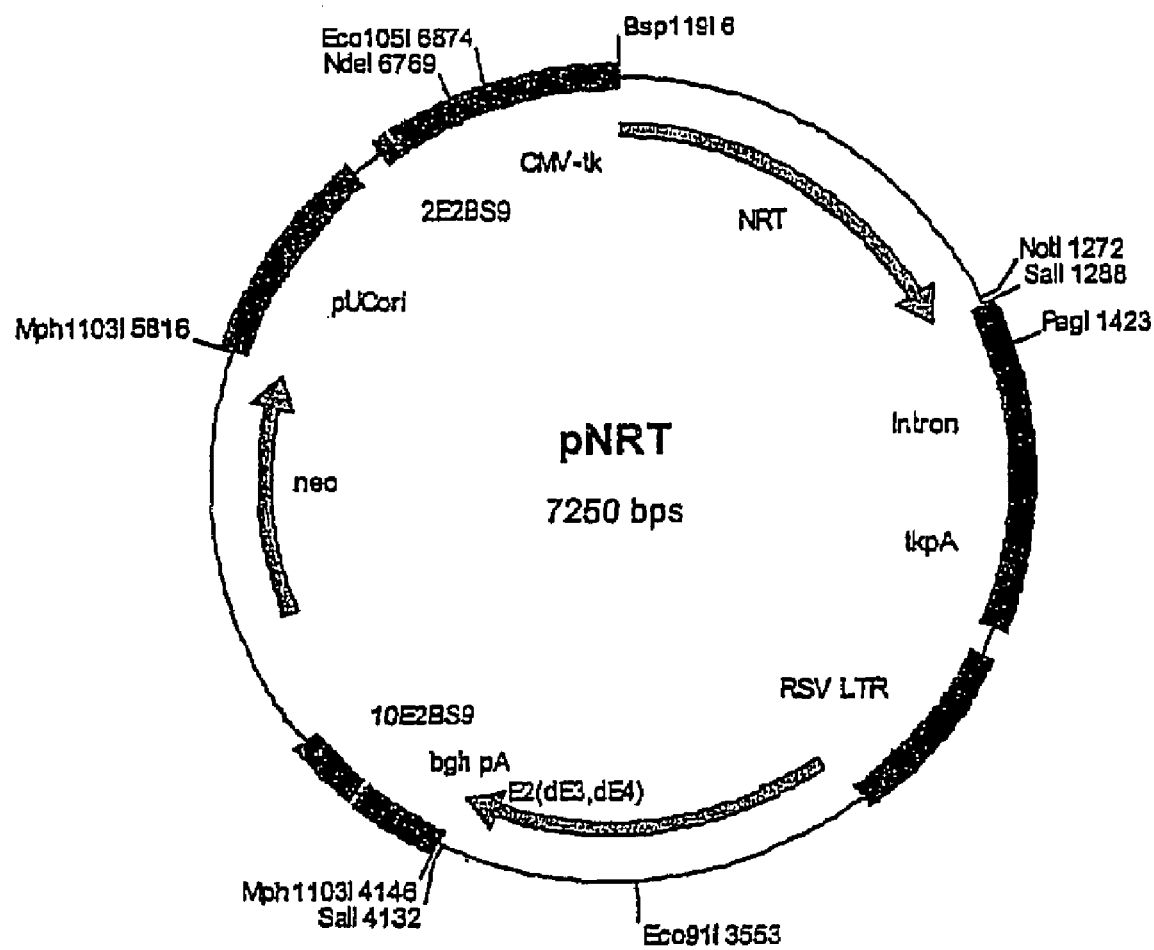
Figure 39B:
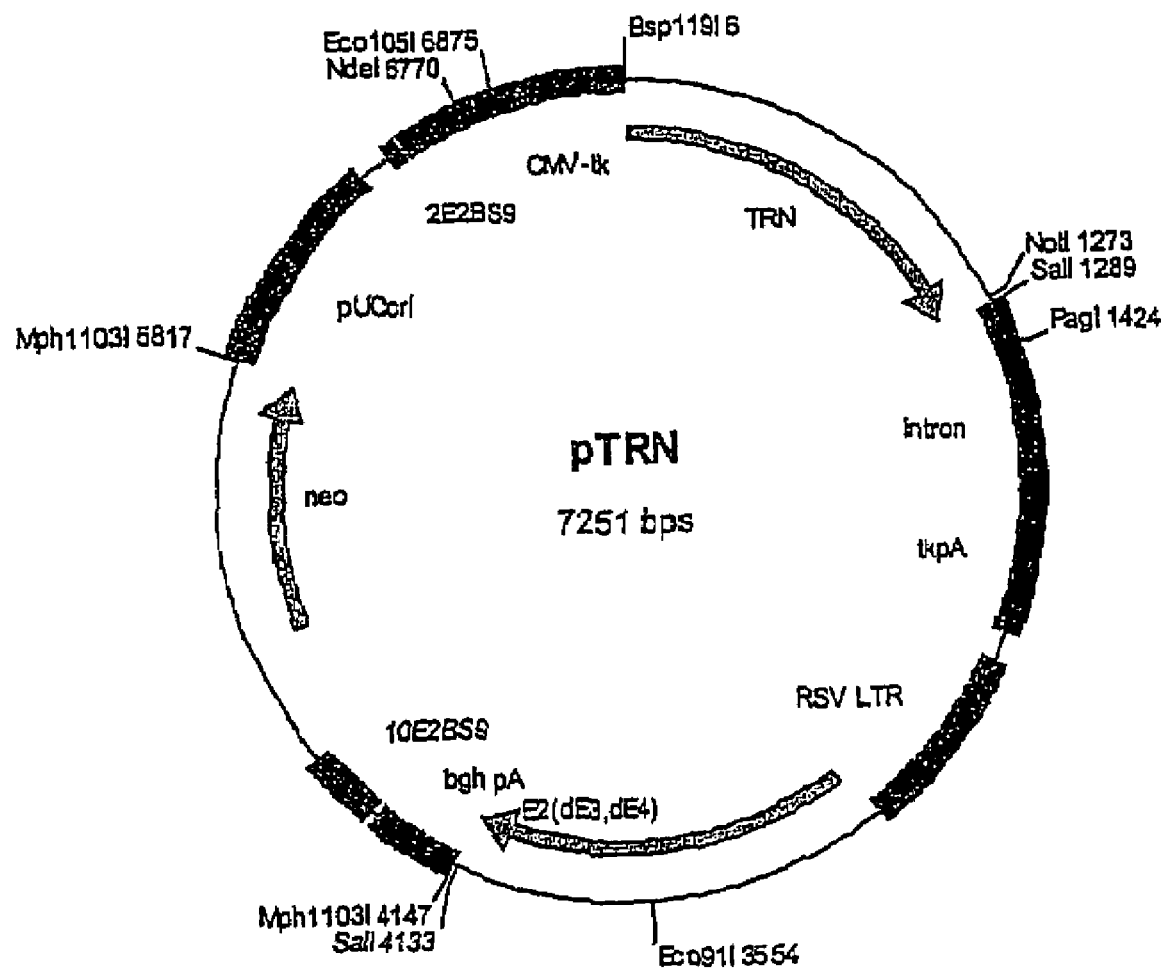
Figure 39C:
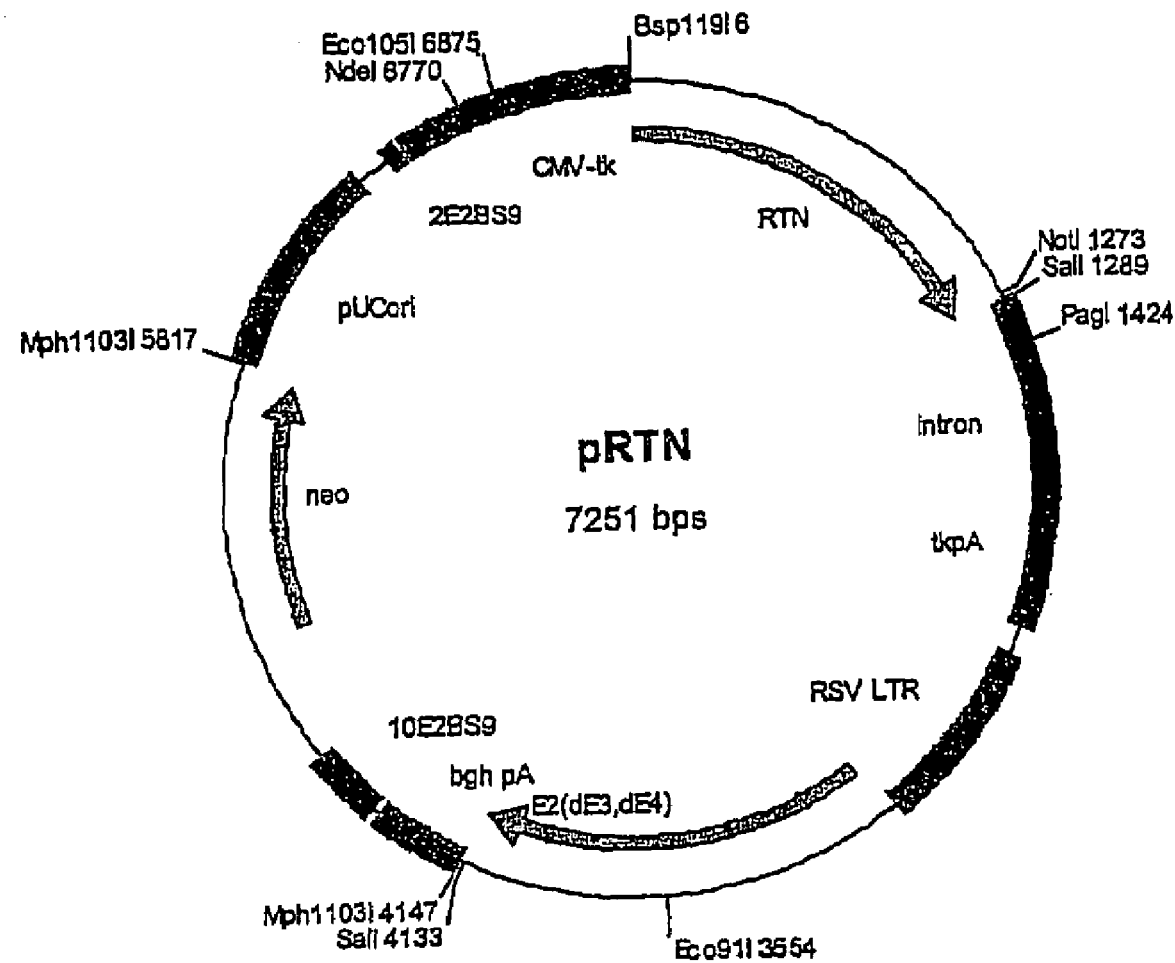
Figure 39D:
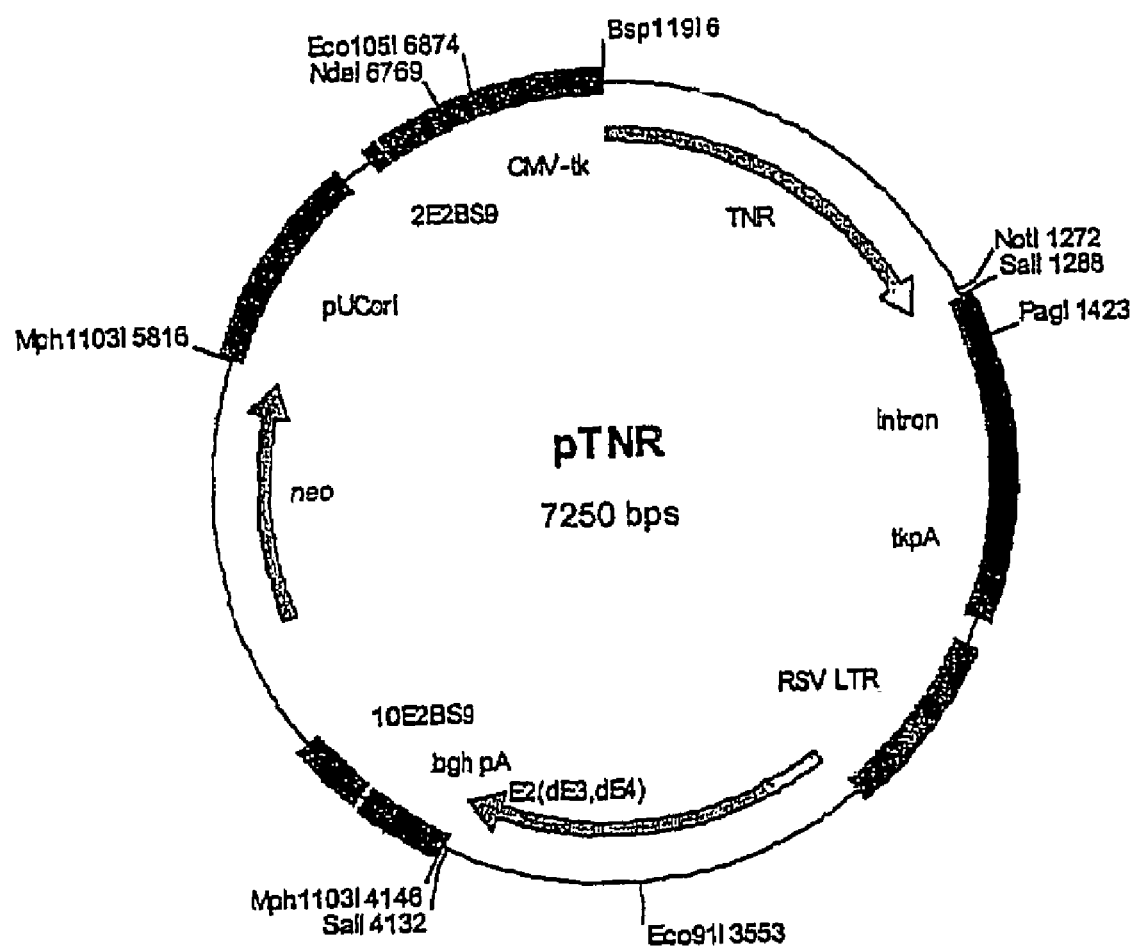
Figure 39E:
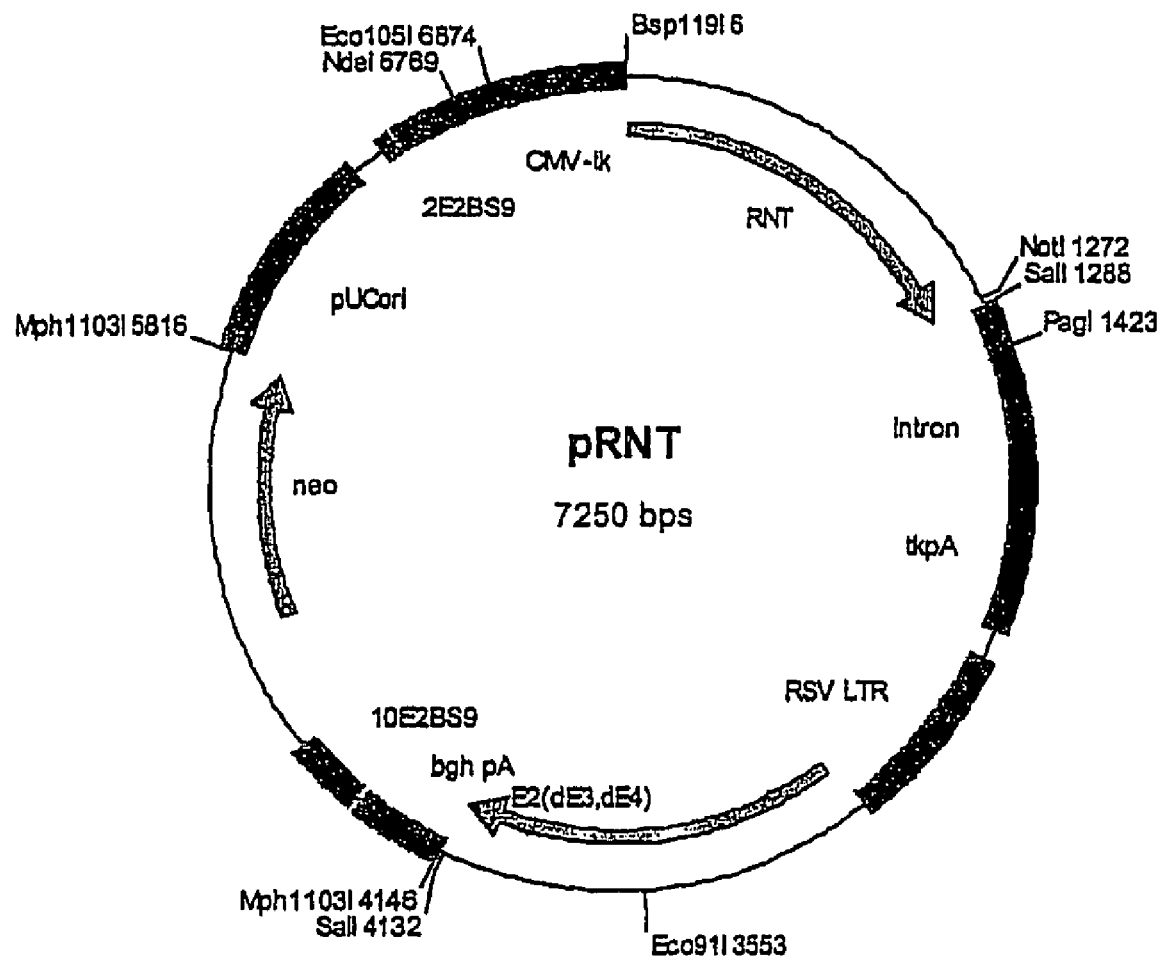
Figure 39F:
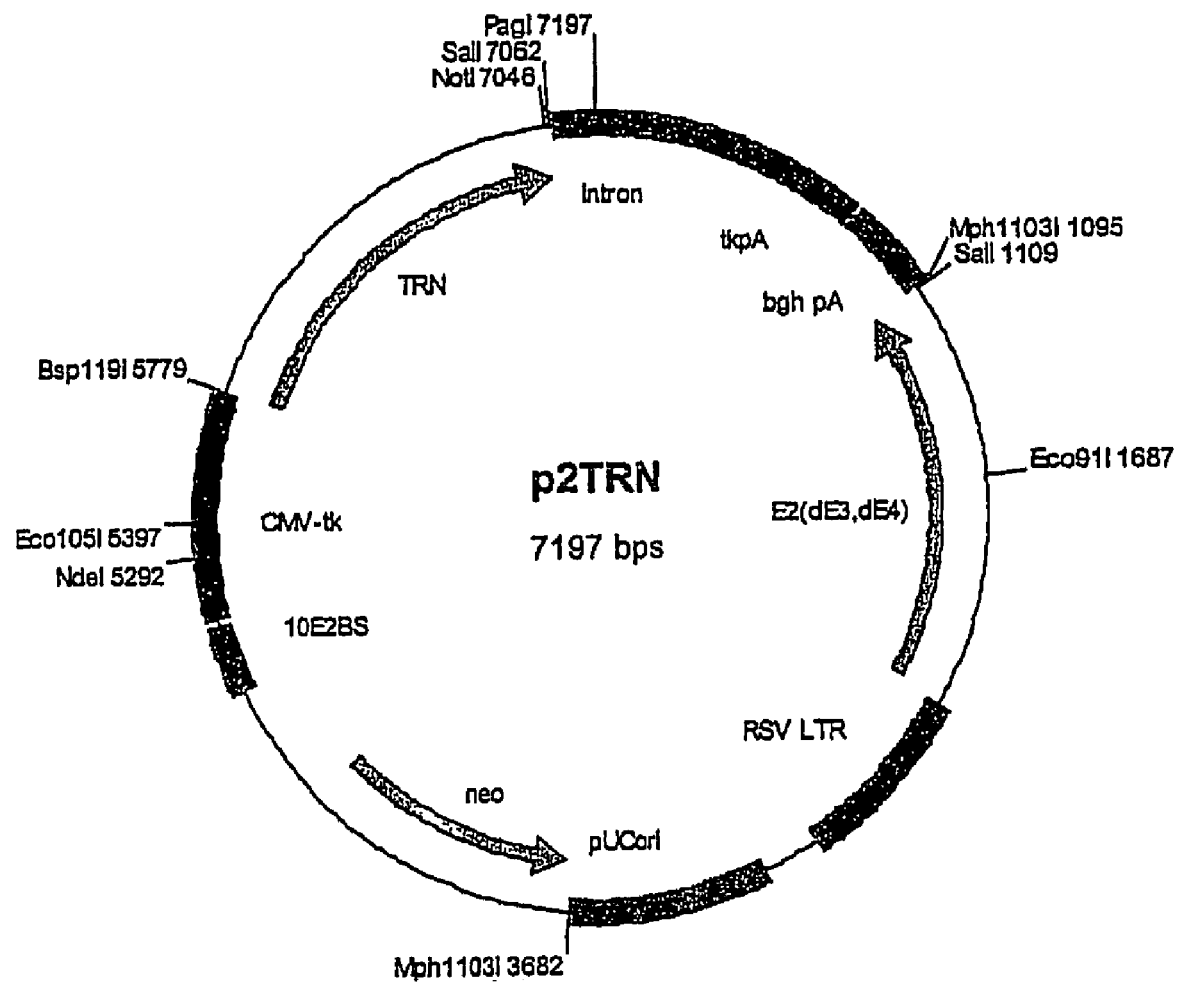
Figure 39G:
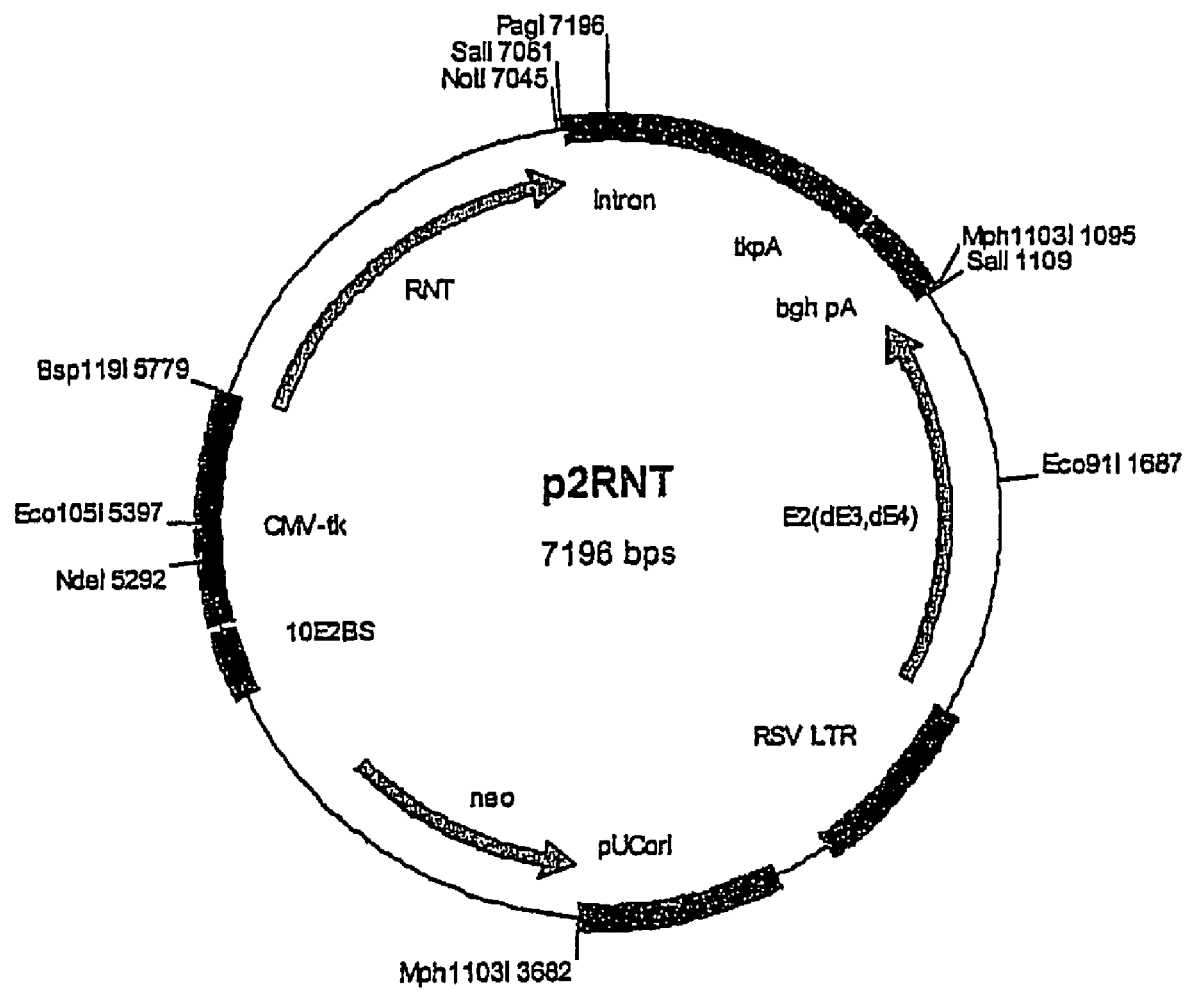
Figure 39H:
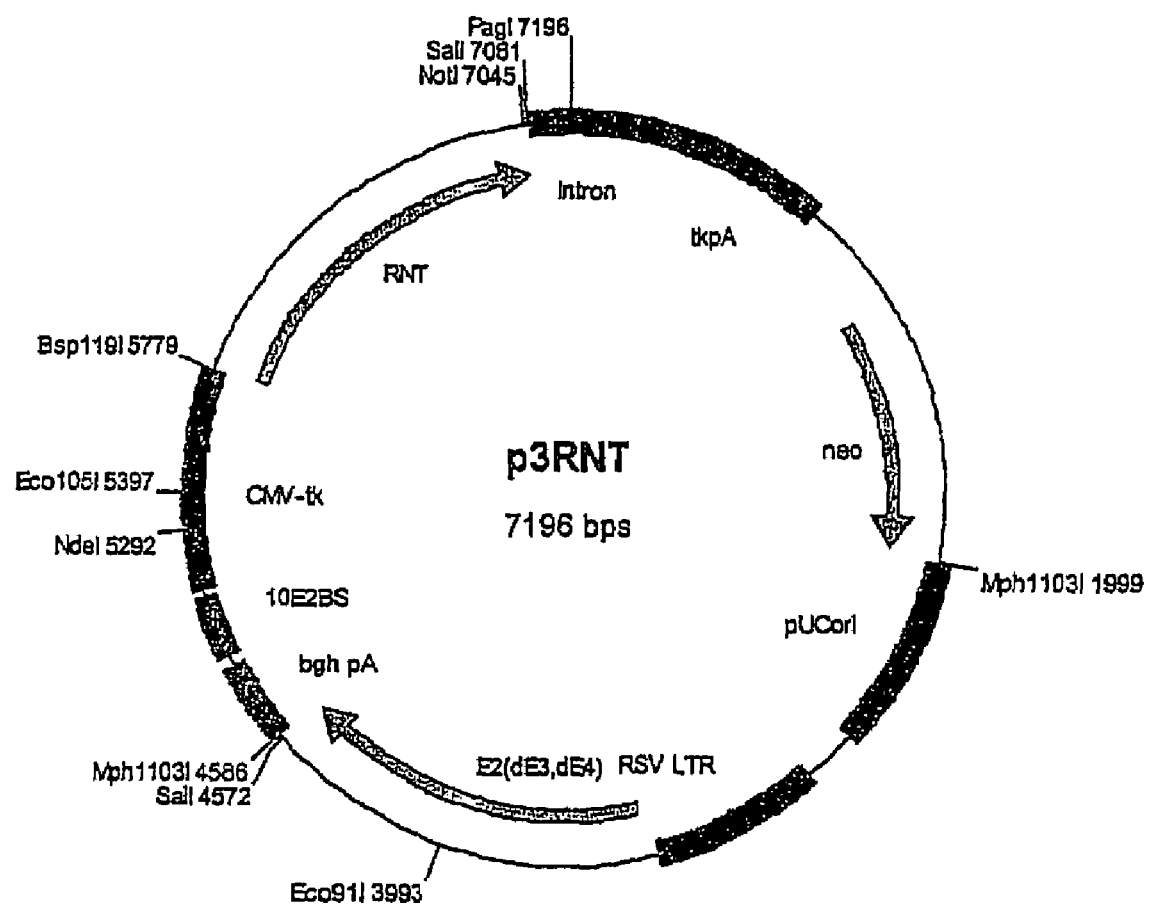
Figure 39:
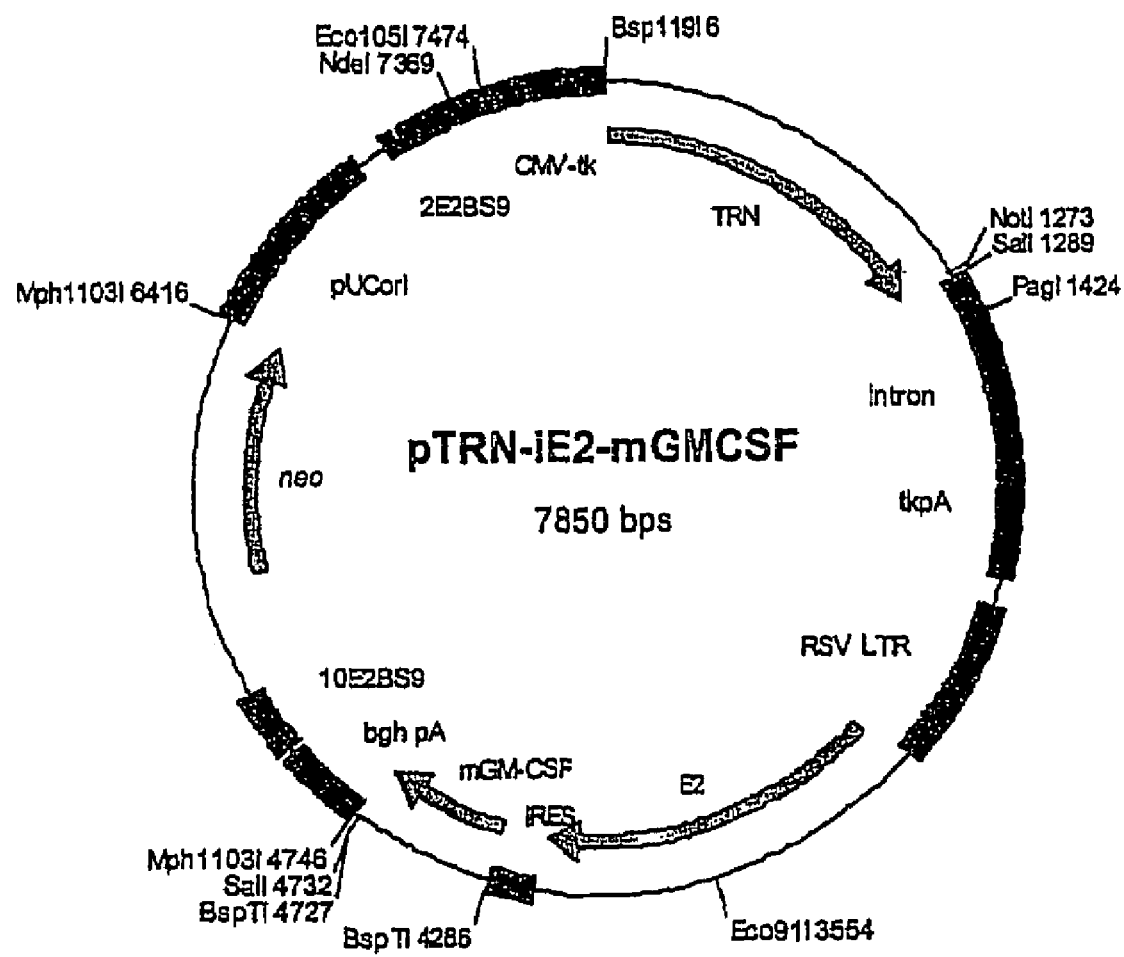
Figure 39J:
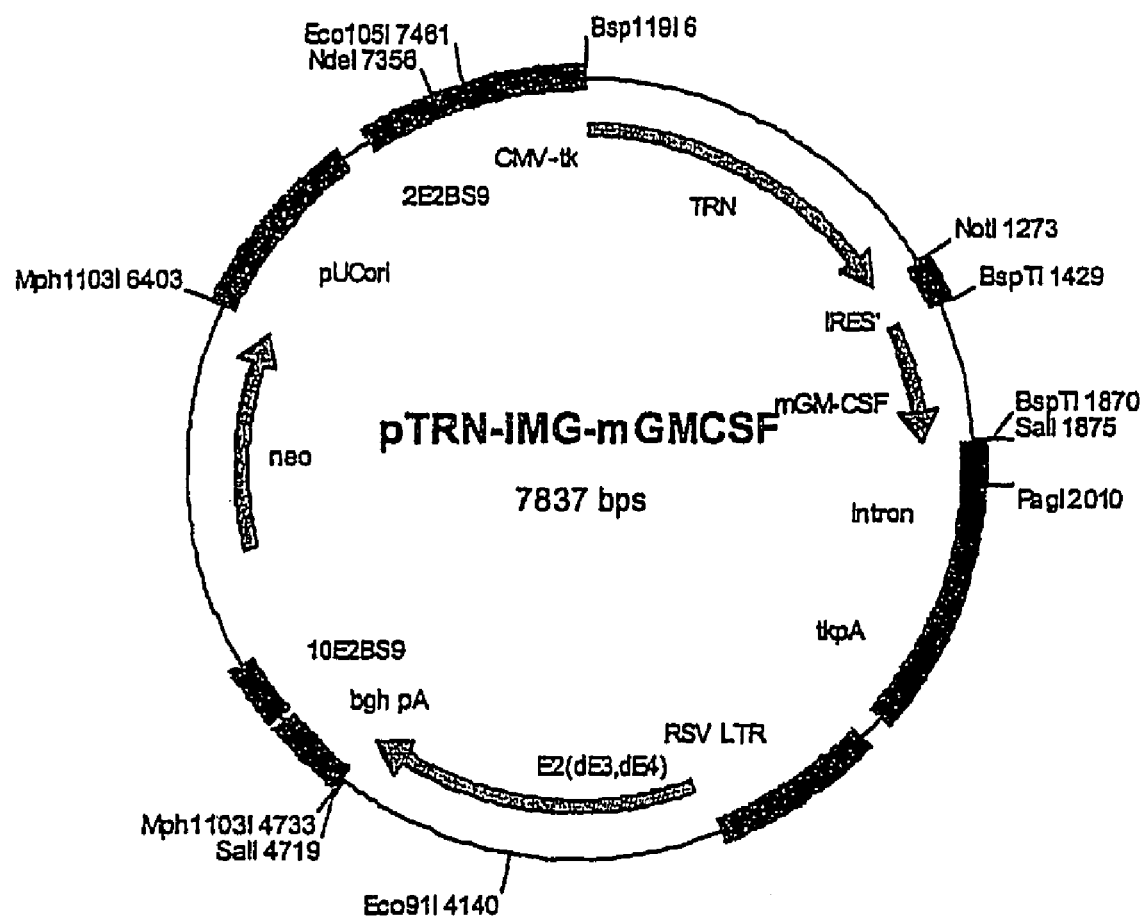
Figure 40A:
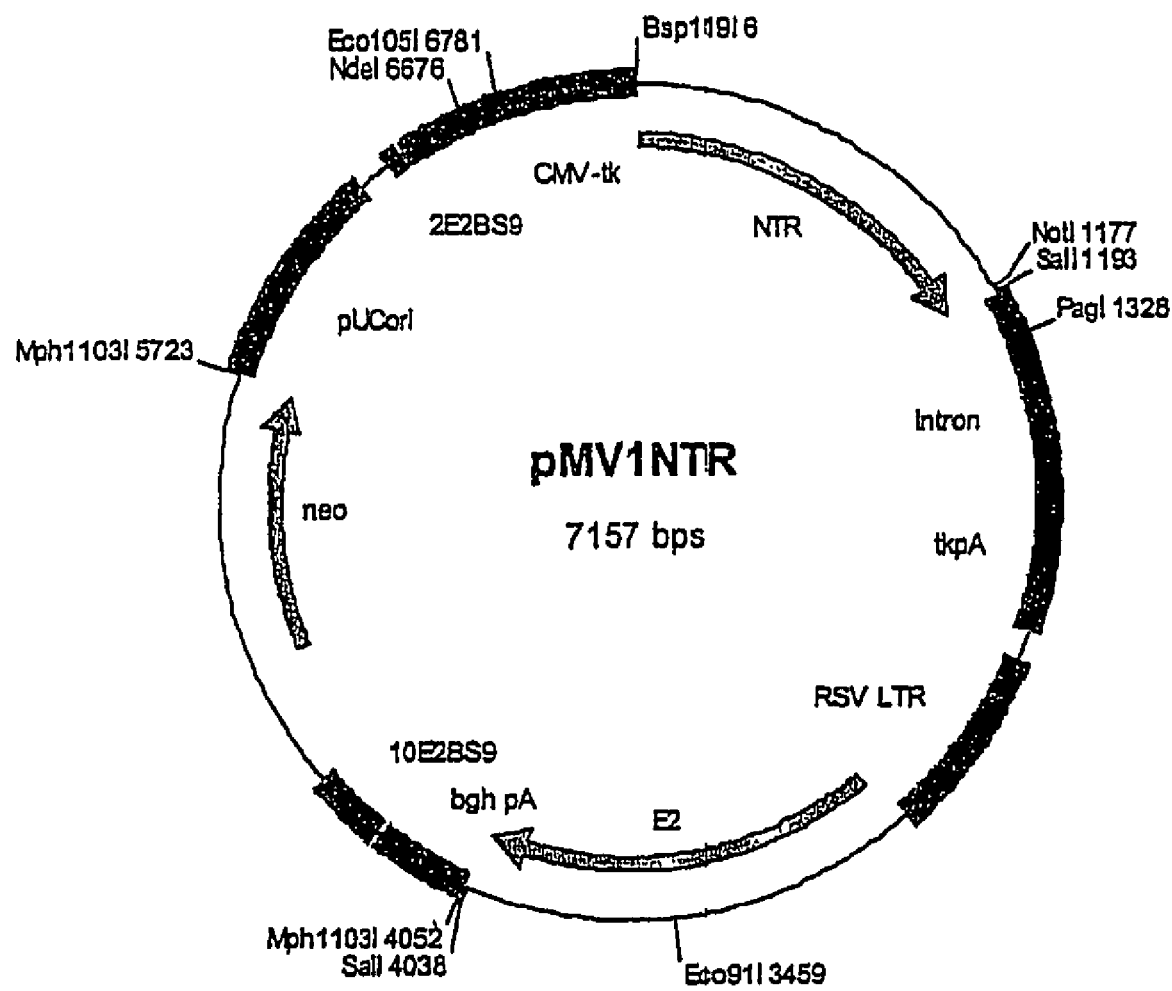
Figure 40B:
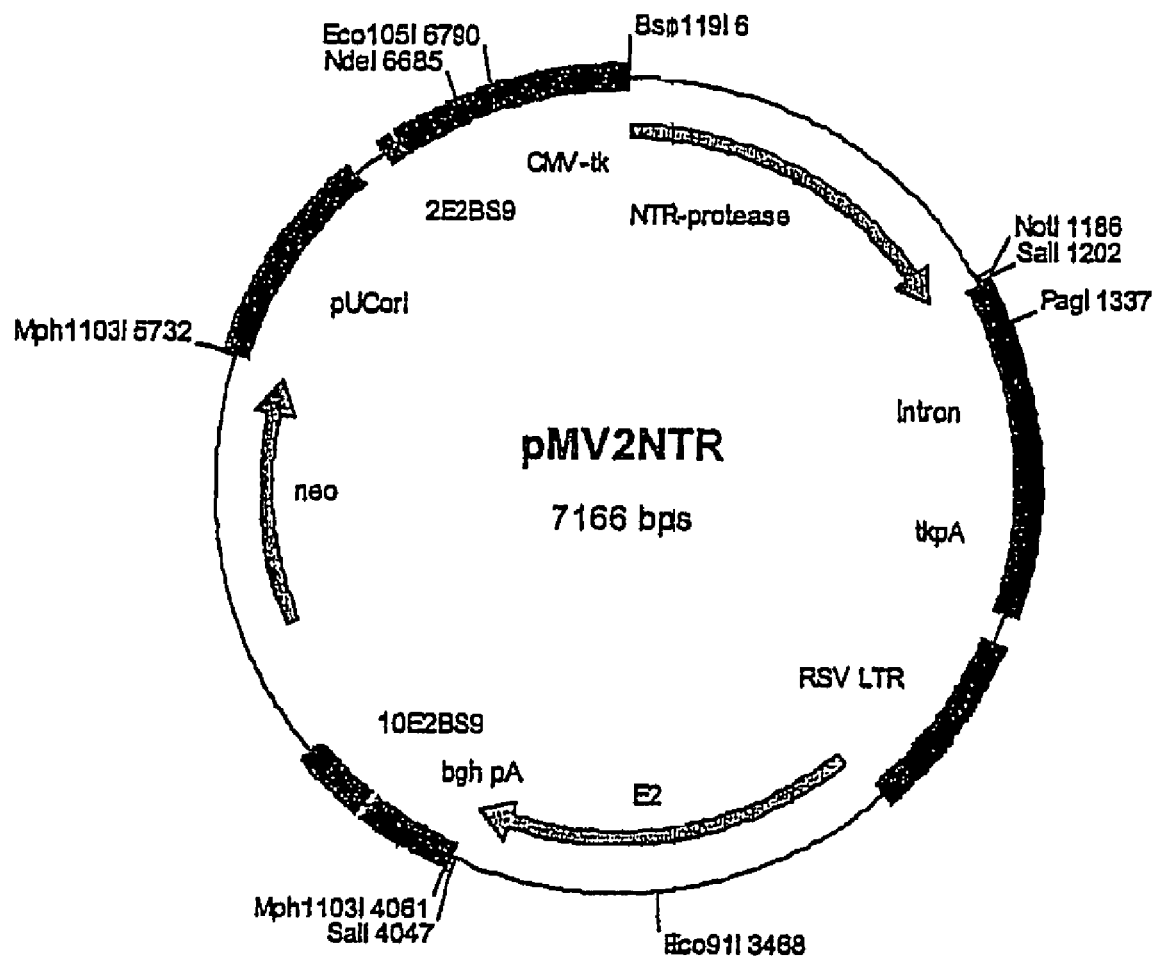
Figure 40C:
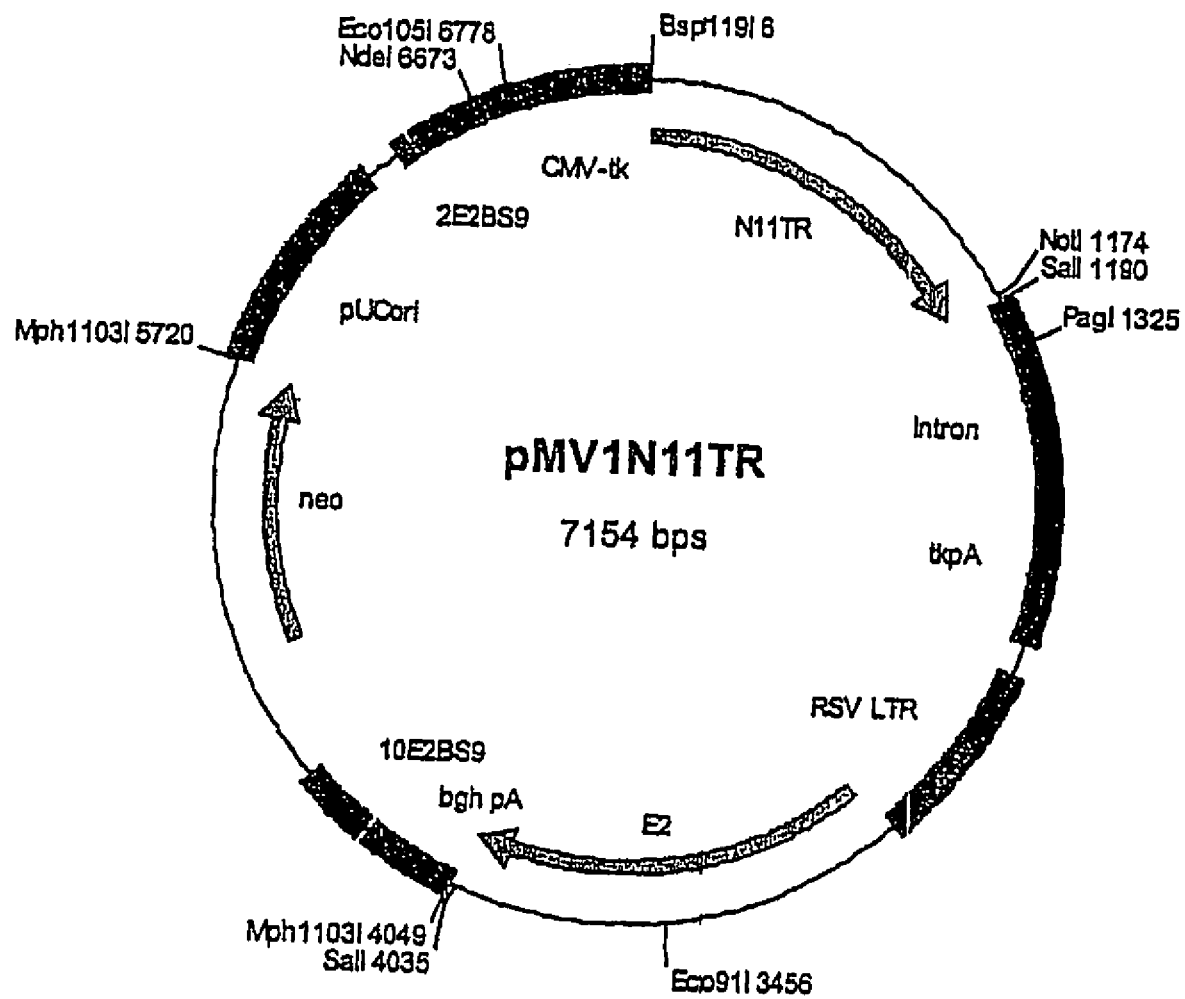
Figure 40D:
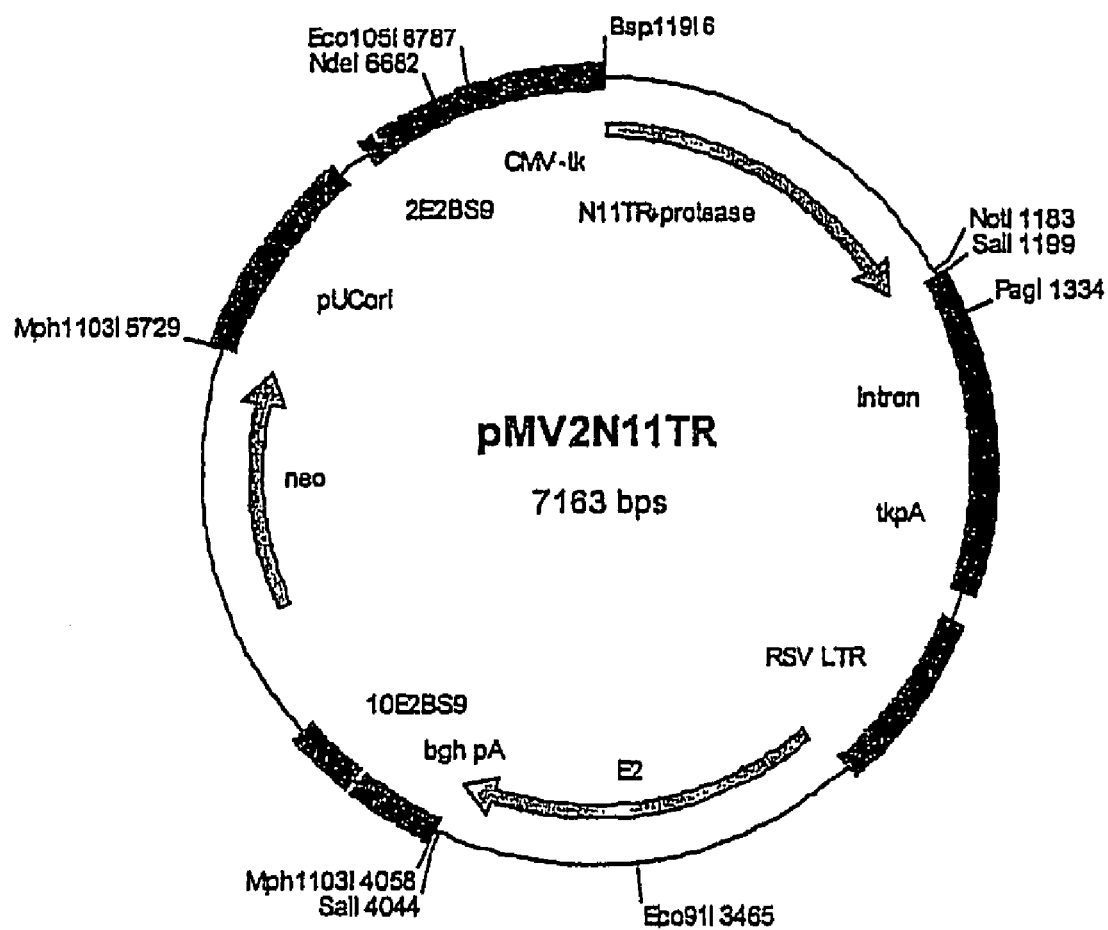

Similarly, Nef protein expressing GTU-2 and GTU-3 vectors (FIGS. 38B and 38C; see also FIG. 6B for NNV-2wt)) were also used as backbones for the production of HIV multigene vectors. Additionally, the vector super6wt expressing destabilized enhanced green fluorescent protein or d1EGFP (super6wtd1EGFP; FIG. 17 and FIG. 38D) and plasmid utilizing the EBNA-1 protein and its binding sites (FREBNAd1EGFP; FIG. 38E) were used as a Gene Transfer Unit (GTU) platform. For control "non-GTU"vectors, a regular cytomegalovirus (CMV) vector NNV-Rev expressing Rev and a plasmid EBNA-1 and E2BS containing d1EGFP plasmid (NNV-Rev and E2BSEBNAd1EGFP, respectively; FIGS. 38G and F) were used as backbones.

For the preparation of different GTU-2 and GTU-3 vectors (PNRT, pTRN, pRTN, pTNR and pRNT; and p2TRN and p2RNT; and p3RNT, FIGS. 39A-E, 39F-G and 39H, respectively), the Nef gene in vectors GTU-2Nef and GTU-3Nef was substituted by the respective multireg antigen using NdeI and Pag I sites. The sequence of the letters N(ef), R(ev) and T(at) in the name shows the position of respective coding sequences of the protein in the multi-gene. Also two vectors, which contain the IRES element placed into the SalI sites

TABLE 4

| Immuno III A mice ELISA results (OD mean of five mice) | | | | | | |
|---|---|---|---|---|---|---|
| Immunogen | Group number | Nef (own prot) | Tat | Rev | Gag | CTL |
| GTU-1-RNT | 1 | 2.194 | 1.391 | 0.31 | 0.155 | 0.36 |
| GTU-1-TRN | 2 | 1.849 | 0.197 | 0.252 | 0.302 | 0.38 |
| GTU-1-RNT-CTL | 3 | 1.922 | 0.555 | 0.295 | 0.154 | 0.439 |
| GTU-1-TRN-CTL | 4 | 1.677 | 0.211 | 0.298 | 0.14 | 0.425 |
| GTU-1-TRN-optgag-CTL | 5 | 1.722 | 0.182 | 0.24 | 0.667 | 0.381 |
| GTU-1-TRN-CTL-optgag | 6 | 0.547 | 0.225 | 0.322 | 0.228 | 0.43 |
| Controls | 7 | 0.316 | 0.226 | 0.282 | 0.16 | 0.405 |

| Immunogen | Group | Percent of Nef response | Tat response | Rev response | Gag response | CTL response |
|---|---|---|---|---|---|---|
| GTU-1-RNT | 1 | 100 | 80 | 0 | 0 | 0 |
| GTU-1-TRN | 2 | 100 | 0 | 0 | 20 | 0 |
| GTU-1-RNT-CTL | 3 | 100 | 40 | 0 | 0 | 0 |
| GTU-1-TRN-CTL | 4 | 100 | 0 | 0 | 0 | 0 |
| GTU-1-TRN-optgag-CTL | 5 | 80 | 0 | 0 | 60 | 0 |
| GTU-1-TRN-CTL-optgag | 6 | 100 | 0 | 0 | 20 | 0 |

6.14. Example 14

Expression of Hybrid Protein Expressing NEF, REV and TAT in Different Combinations (Multireg)

For the production of HIV multi-gene vectors, GTU-1 vector with a multi-cloning site (FIG. 38A) was used as a backbone. Intact Nef, Rev and Tat coding sequences were amplified by the polymerase chain reaction (PCR) and following either the multi-antigen or E2 coding sequences, were prepared (pTRN-iE2-GMCSF and pTRN-iMG-GMCSF, respectively; FIGS. 39I and J). The latter sequence, which controls the translation of the coding sequence of the mouse granulocyte-magrophage colony stimulating factor (GM-CSF), was cloned into the single BspTI site introduced with IRES.

Additionally, a set of the vectors, in which only immunodominant parts of the regulatory proteins were used for building up the polyproteins, were cloned into the Bsp119I and NotI sites of the GTU-1 (pMV1NTR, pMV2NTR, pMV1N11TR and pMV2N11TR; FIGS. 40A-D). In case of the pMV2 constructs, linkers that could be digested by intracellular proteases separate the regions of the multi-antigene derived from different regulatory proteins.

Figure 41A:
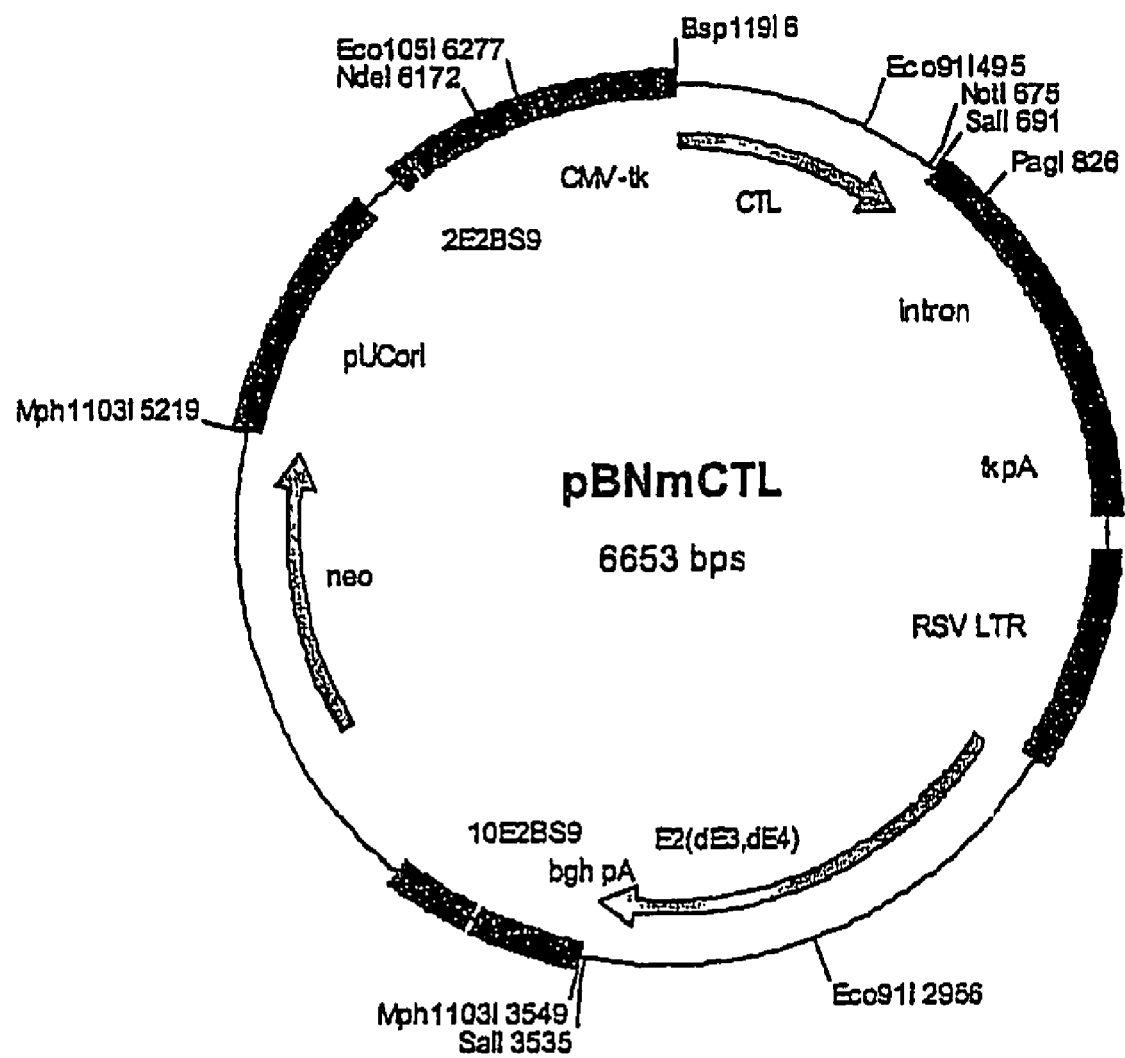
Figure 41B:
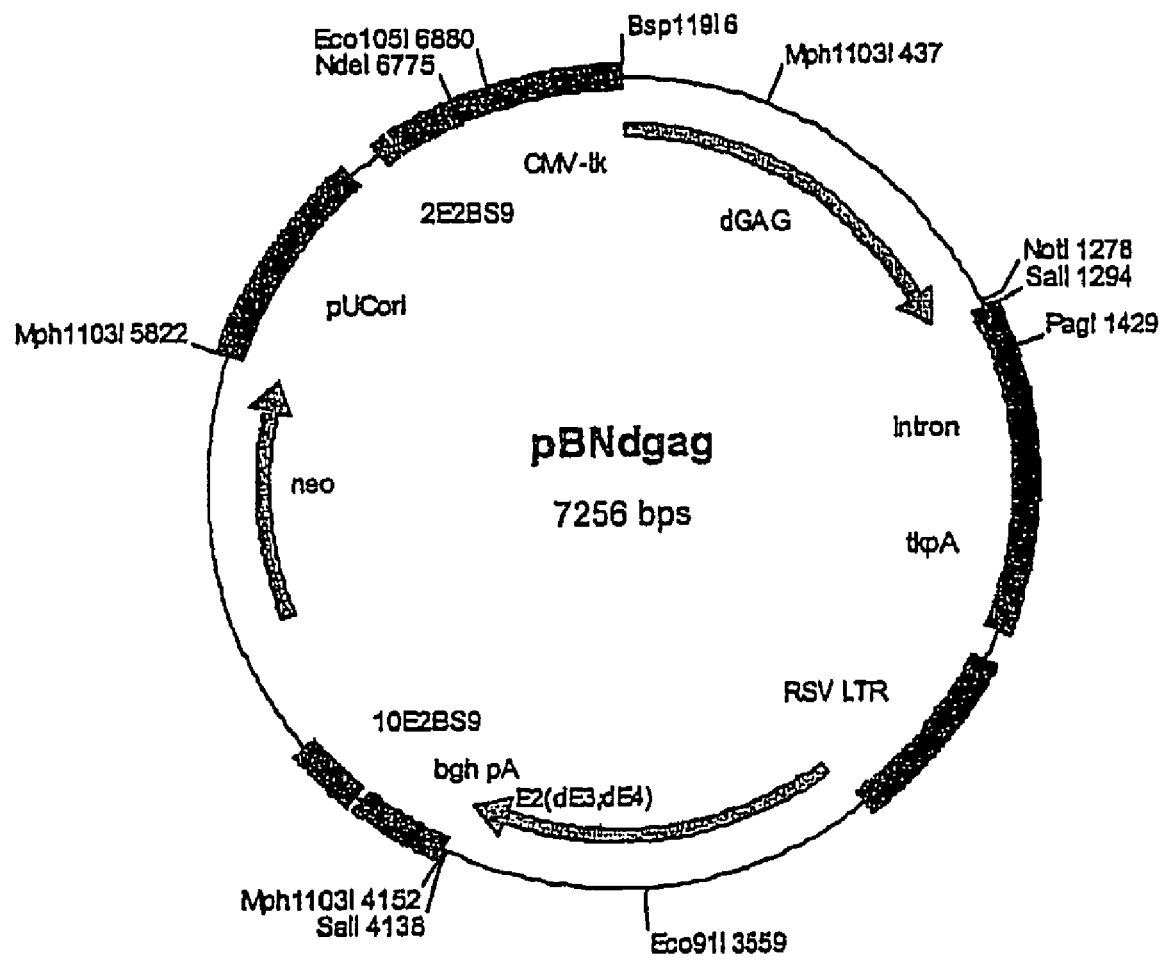
Figure 41C:
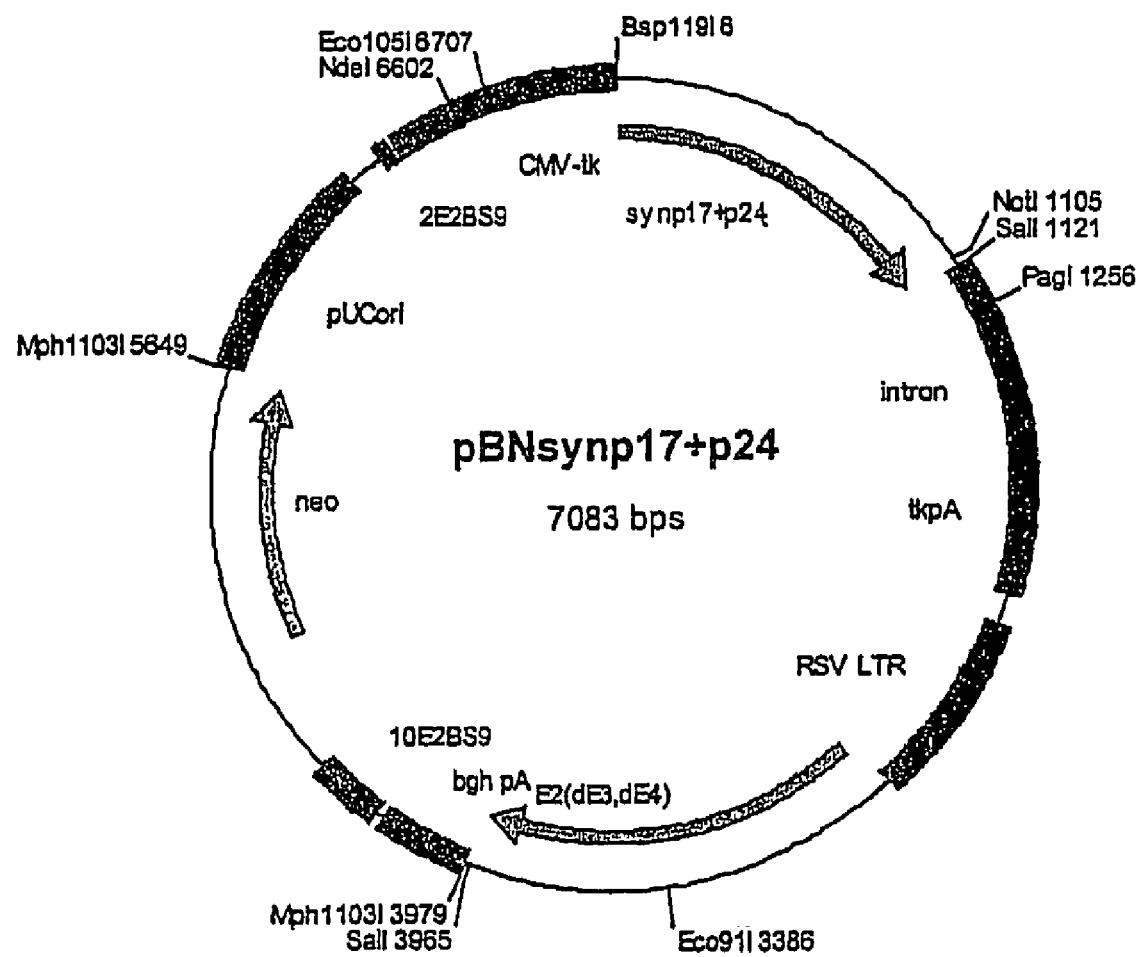
Figure 41D:
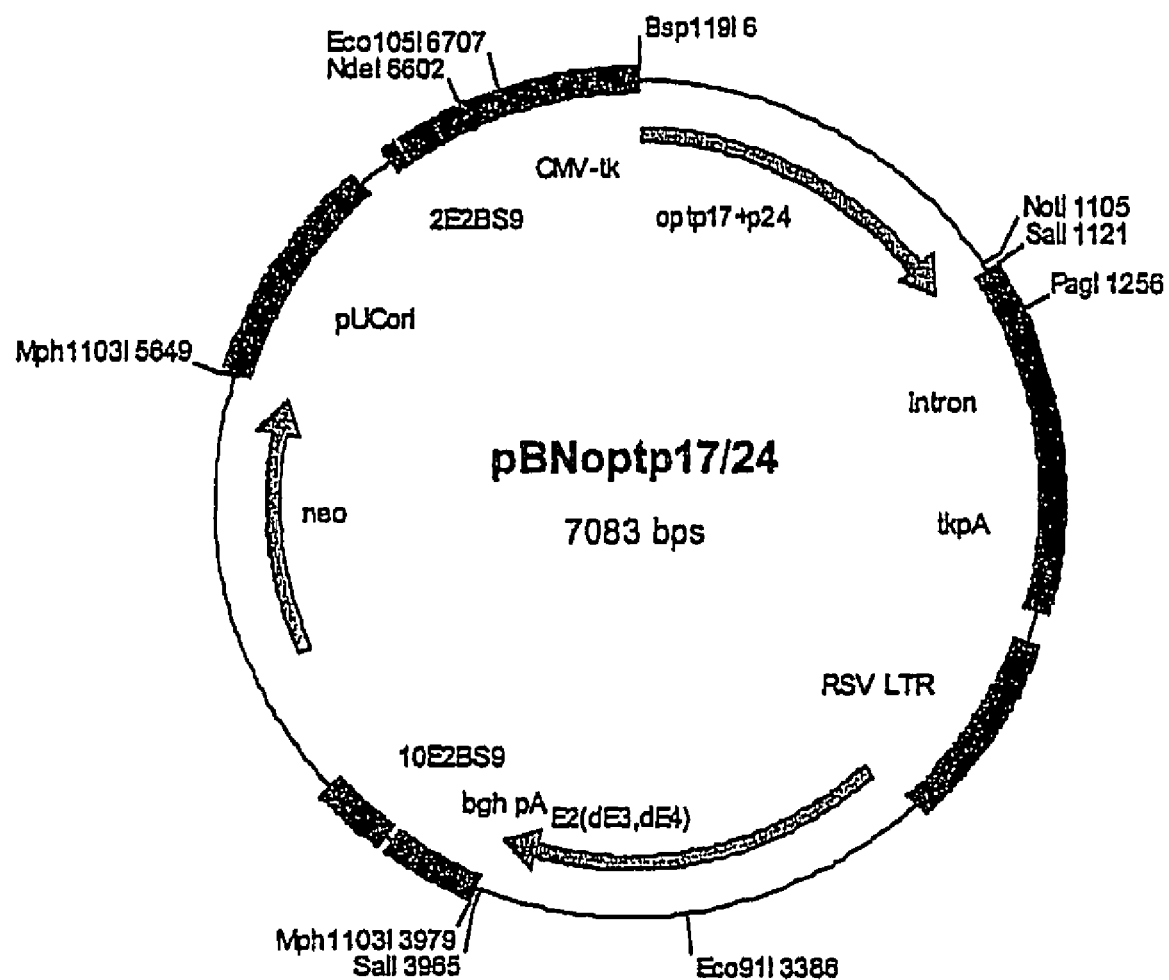
Figure 41E:
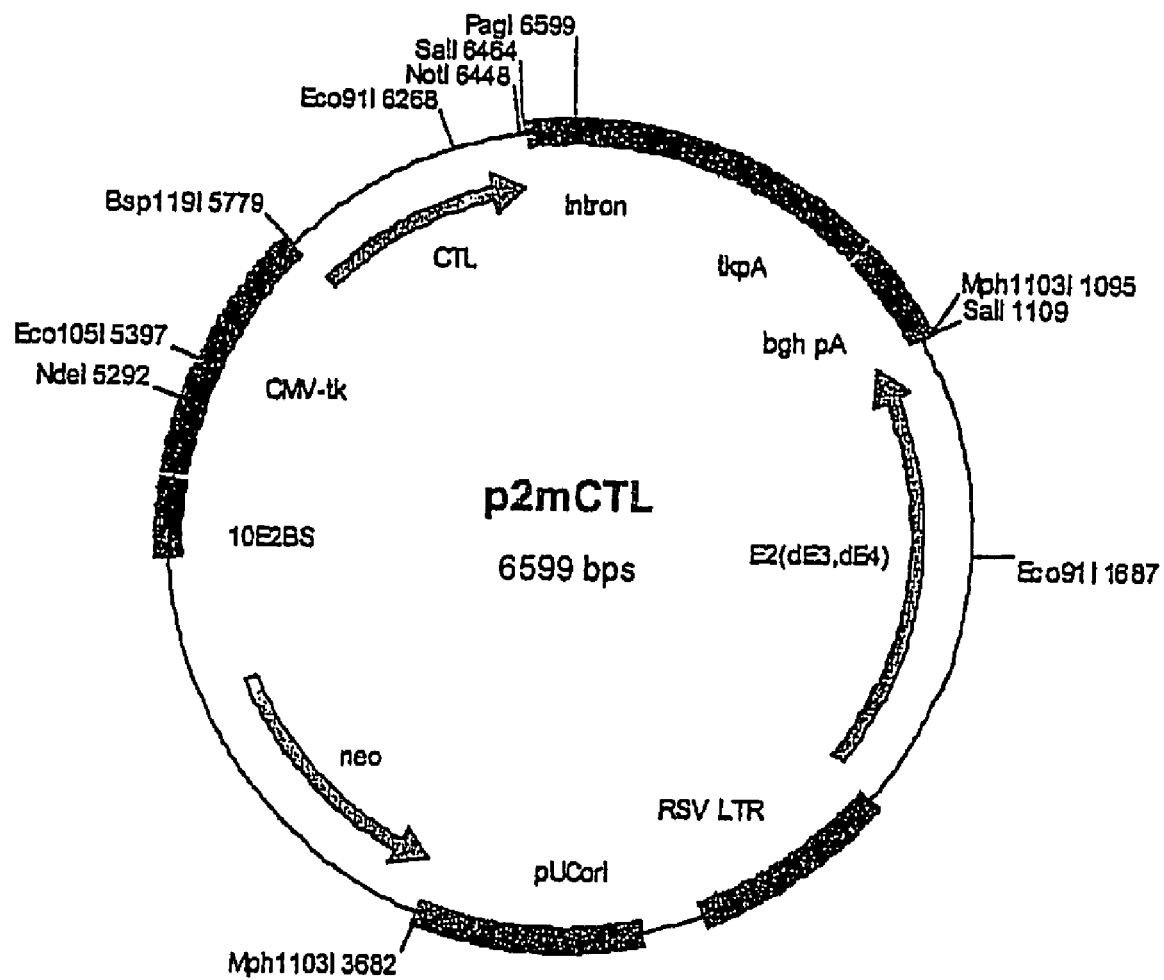
Figure 41F:
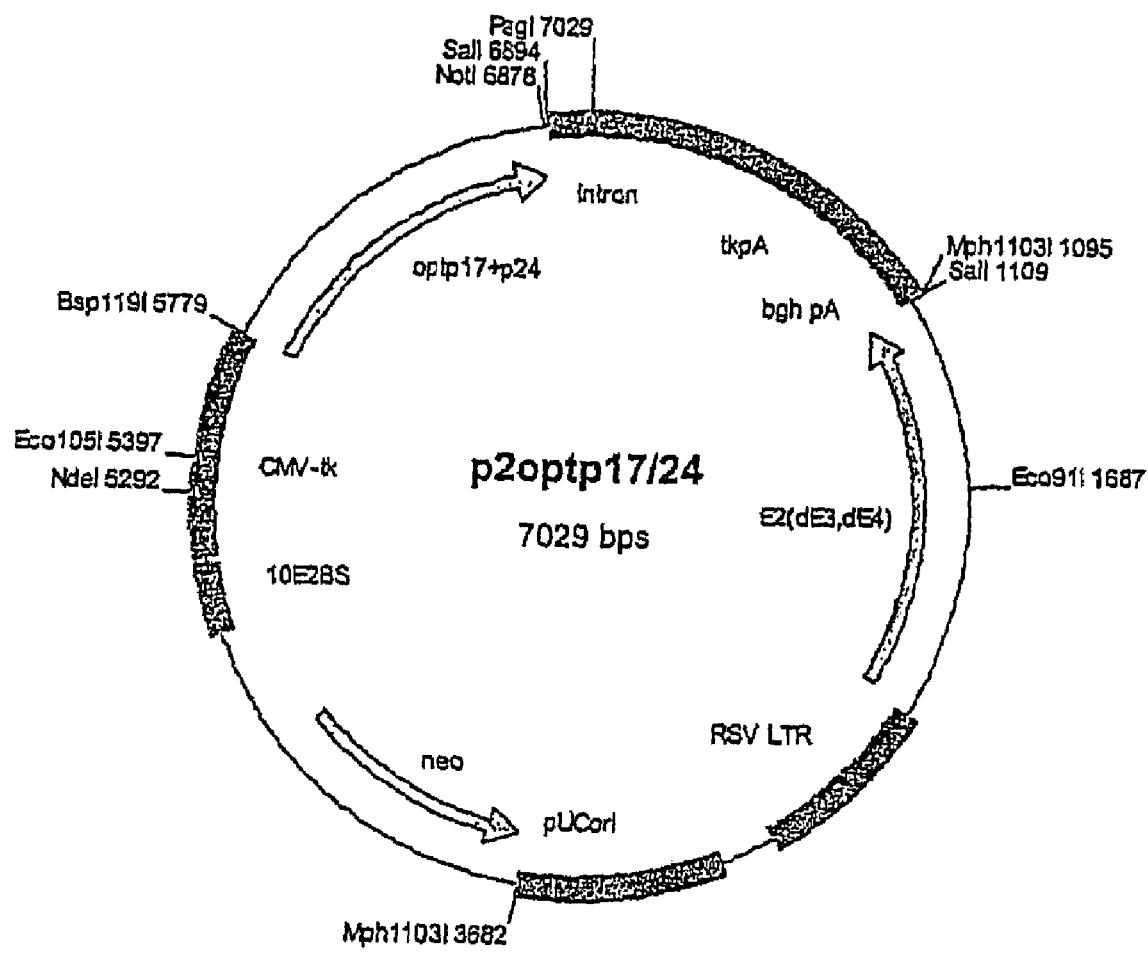
Figure 41G:
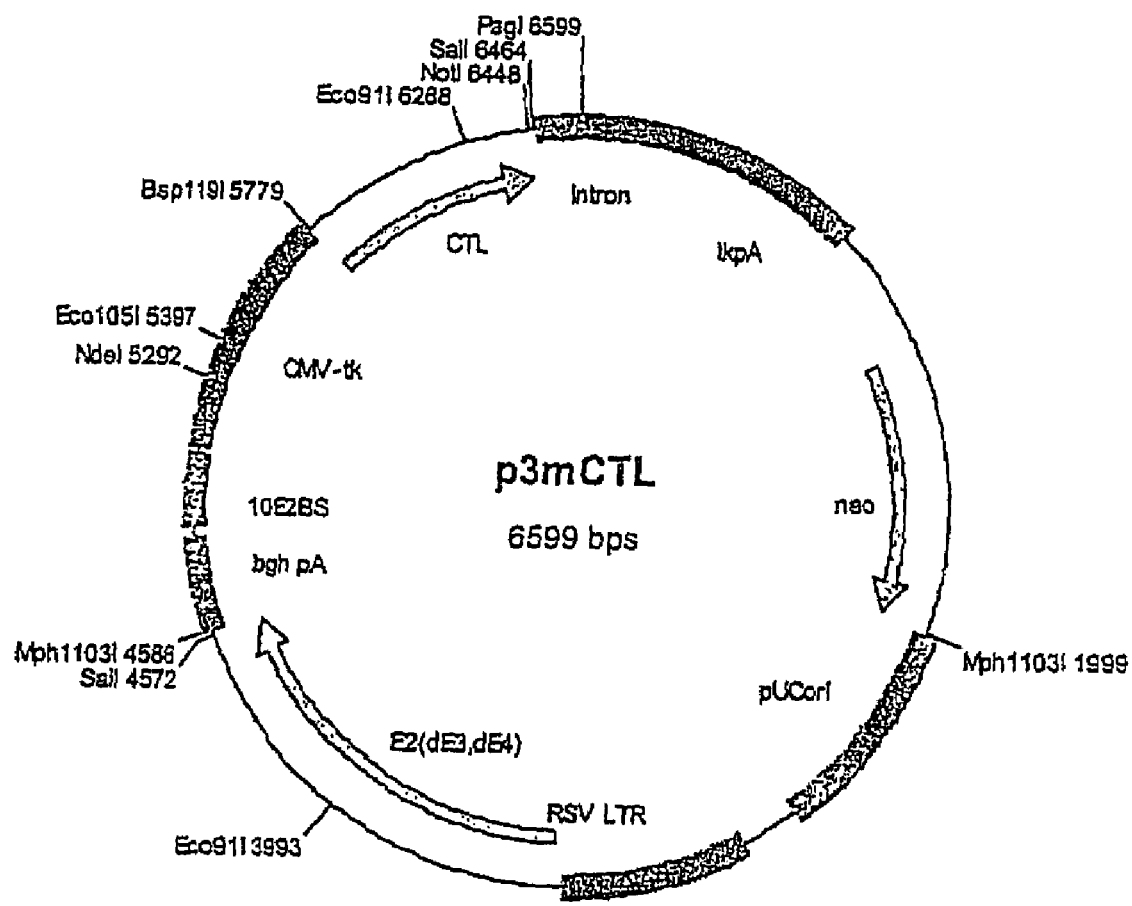
Figure 41H:
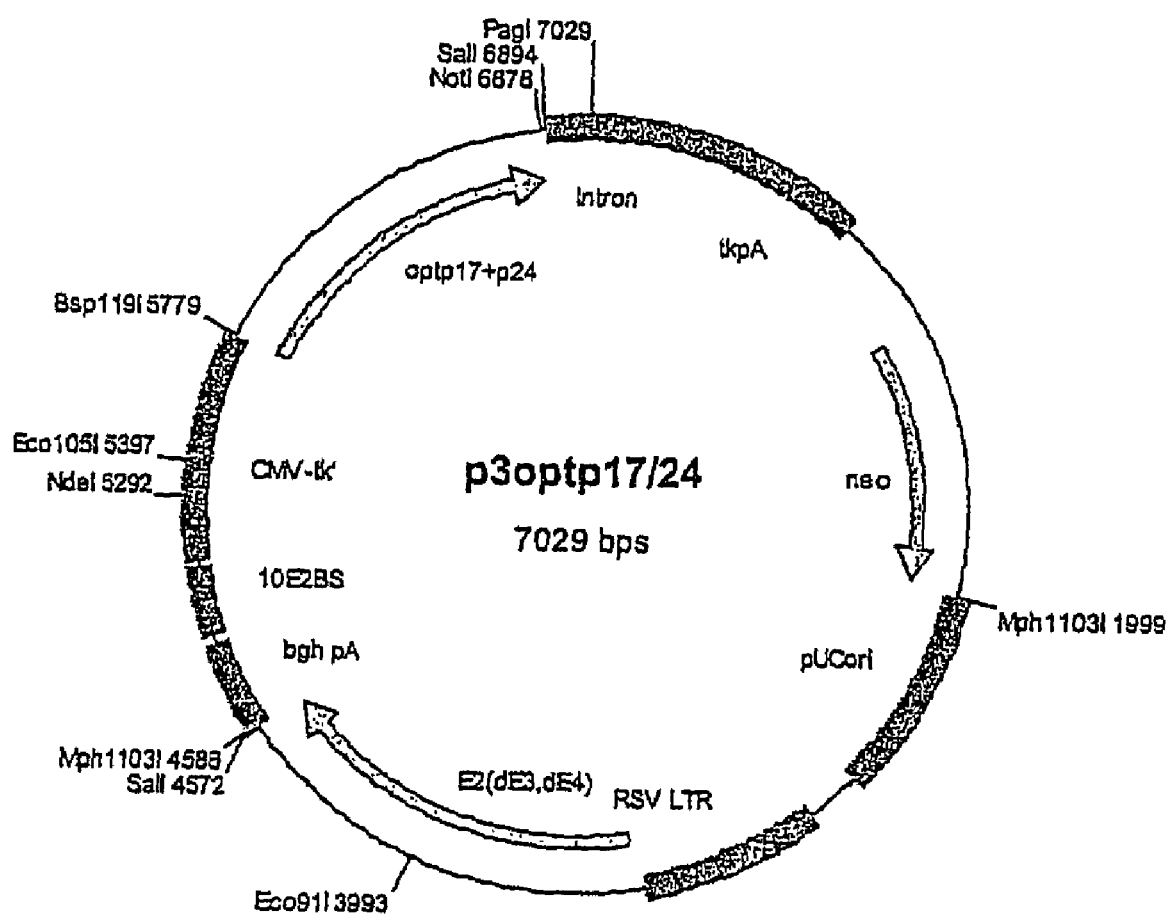

Further, GTU-1, GTU-2 and GTU-3 vectors, which express the structural proteins encoded by the gag gene or an artificial polyprotein composed by previously described CTL epitopes, were prepared. The coding sequences were cloned as Bsp119I and Not I digested PCR fragments into the GTU-1 vector (pCTL=BNmCTL, pdgag=pBNdgag, psynp17/24=pBNsynp17+24, poptp17/24=pBNoptp17/24; FIGS. 41A-D), and transferred in a Nde I-Pac I fragment to the GTU-2 (p2mCTL and p2optp17/24; FIGS. 41E and F) and GTU-3 (p3mCTL and p3optp17/24; FIGS. 41G and H).

The coding segment designated as CTL (Sequence Id. No. 10) contains fragments from pol and env regions involving many previously identified CTL epitopes. The codon usage is optimized so that only codons used frequently in human cells are involved. This coding sequence also contains a well-characterized mouse CTL epitope used in potency assay and an epitope for recognition by anti-mouse CD43 antibody. Also, a dominant SIV p27 epitope was included for use in potency studies in macaques.

The dgag contains truncated p17 (start at 13 aa) +p24+p2+p7 (p1 and p6 are excluded) (Sequence Id. No. 11) of gag region of the Han2 isolate. The synp17/24 (Sequence Id. No. 12) codes for the p17+p24 polypeptide of the Han2 HIV-1. The codon usage is modified to be optimal in human cells. Also, previously identified AU rich RNA instability elements were removed by this way. The optp17/24 coding (Sequence Id. No. 13) region is very similar to the synp17/24 with the exception that the two synonymous mutations made therein do not change the protein composition but remove a potential splicing donor site.

Figure 42T:
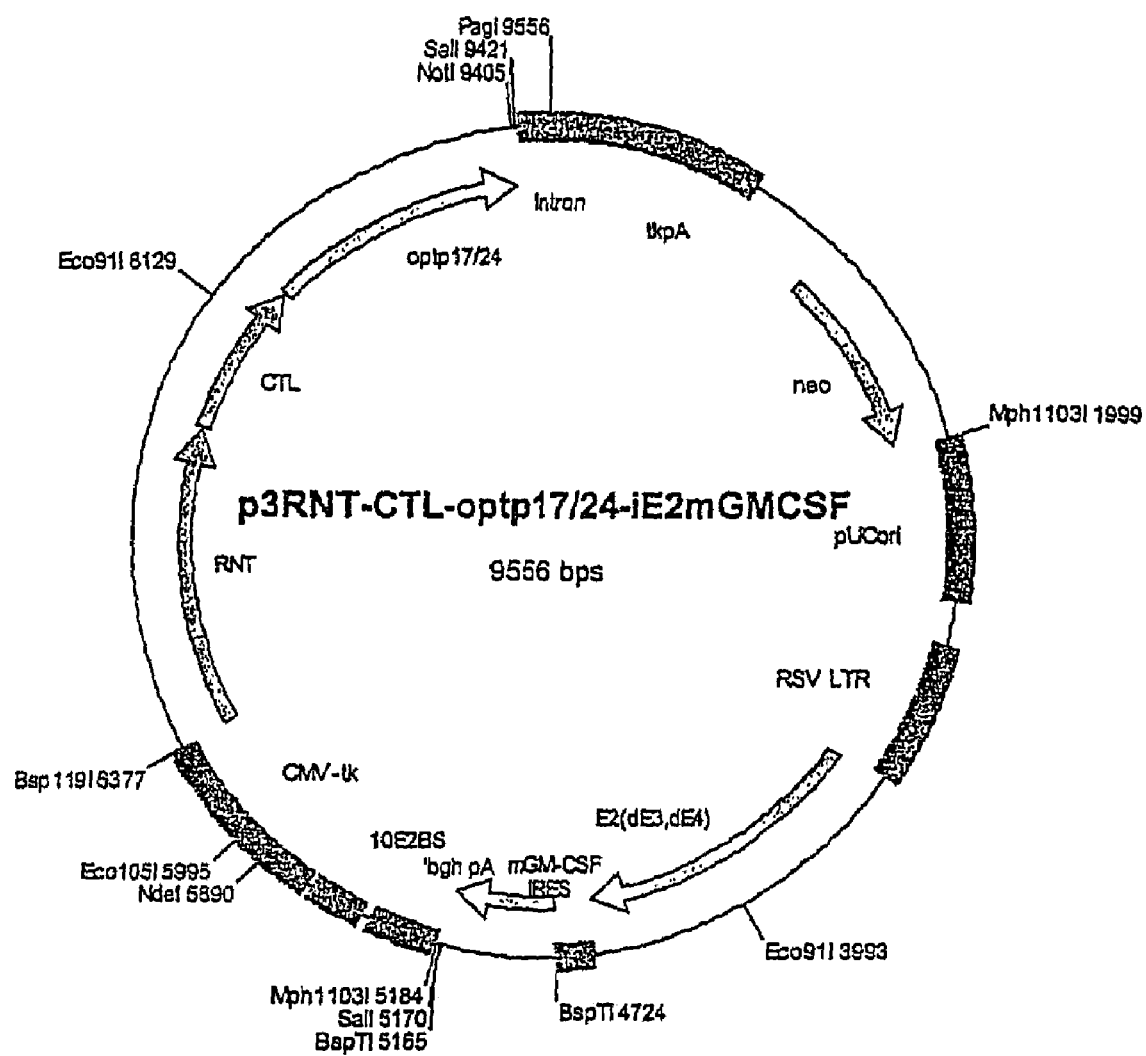

Further, a set of the multi-HIV vectors, which contain both a multireg antigen and structural antigens as a single polyprotein, were created: pTRN-CTL, pRNT-CTL, pTRN-dgag, pTRN-CTL-dgag, pRNT-CTL-dgag, pTRN-dgag-CTL, pRNT-dgag-CTL, pTRN-optp17/24-CTL, pTRN-CTL-optp17/24, and pRNT-CTL-optp17/24; p2TRN-optp17/24-CTL, p2RNT-optp17/24-CTL, p2TRN-CTL-optp17/24, p2RNT-CTL-optp17/24, p2TRN-CTL-optp17/24-iE2-mGMCSF, and p2RNT-CTL-optp17/24-iE2-mGMCSF; and p3TRN-CTL-optp17/24, p3RNT-CTL-optp17/24, p3TRN-CTL-optp17/24-iE2-mGMCSF, and p3RNT-CTL-optp17/24-iE2-mGMCSF, FIGS. 42A-T.

For cloning, as a first step the STOP codon was removed from the regulatory multi-antigen coding sequences. Then the structural antigen coding sequences were added by cloning into the NotI site at the end of the frame so that a NotI site was reconstituted. If both CTL and gag were added, the first antigen coding sequence was without the STOP codon. Generally, the clonings were made in context of GTU-1 and for making the respective GTU-2 (p2 . . . ) and GTU-3 (p3 . . . ) vectors, the Nef gene in the plasmids GTU-2Nef and GTU-2Nef was replaced using sites for NdeI and Pag I. However, the RNT-optp17/24-CTL antigen was built up directly in GTU-2 vector.

Figure 42U:
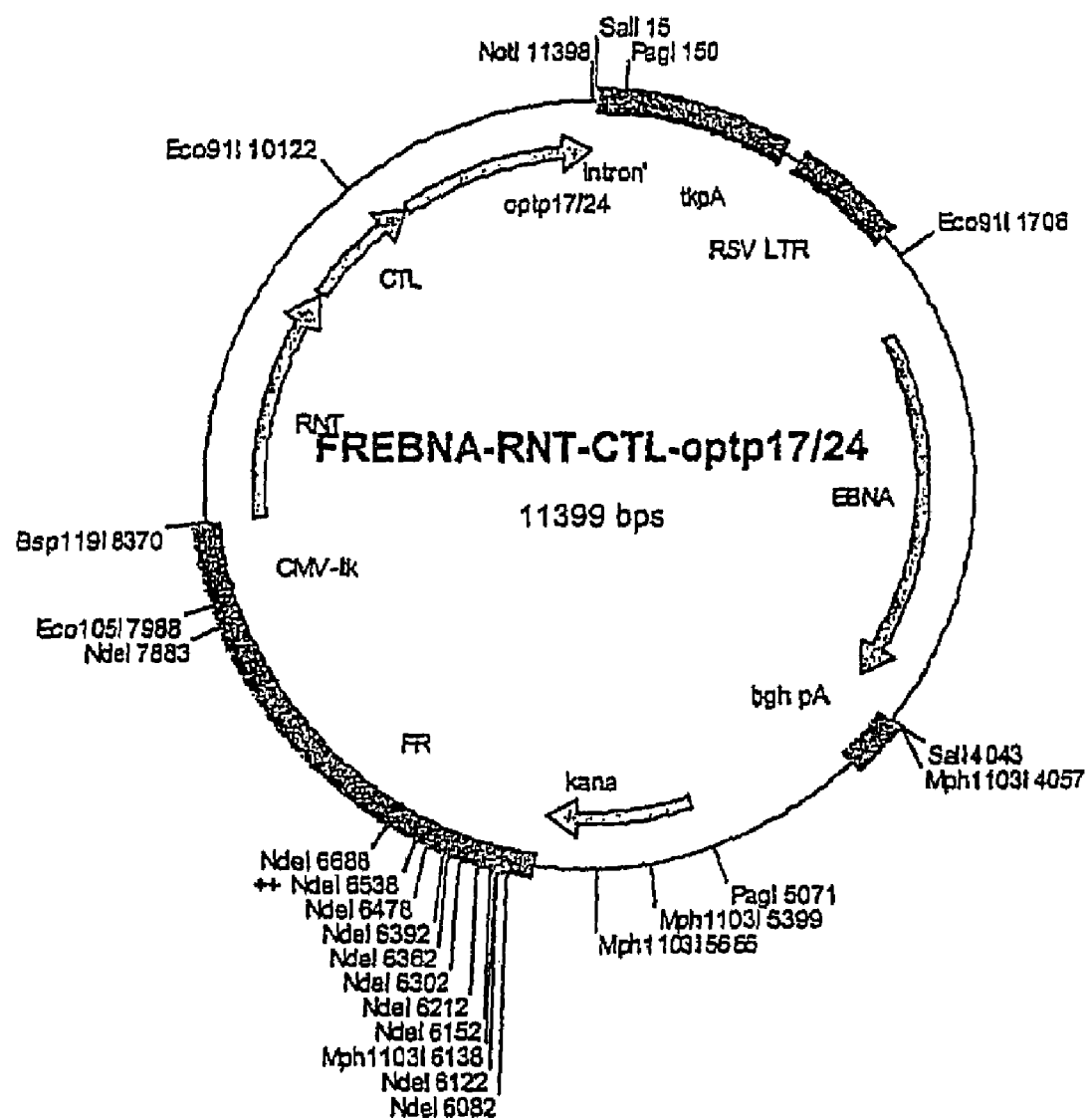
Figure 42V:
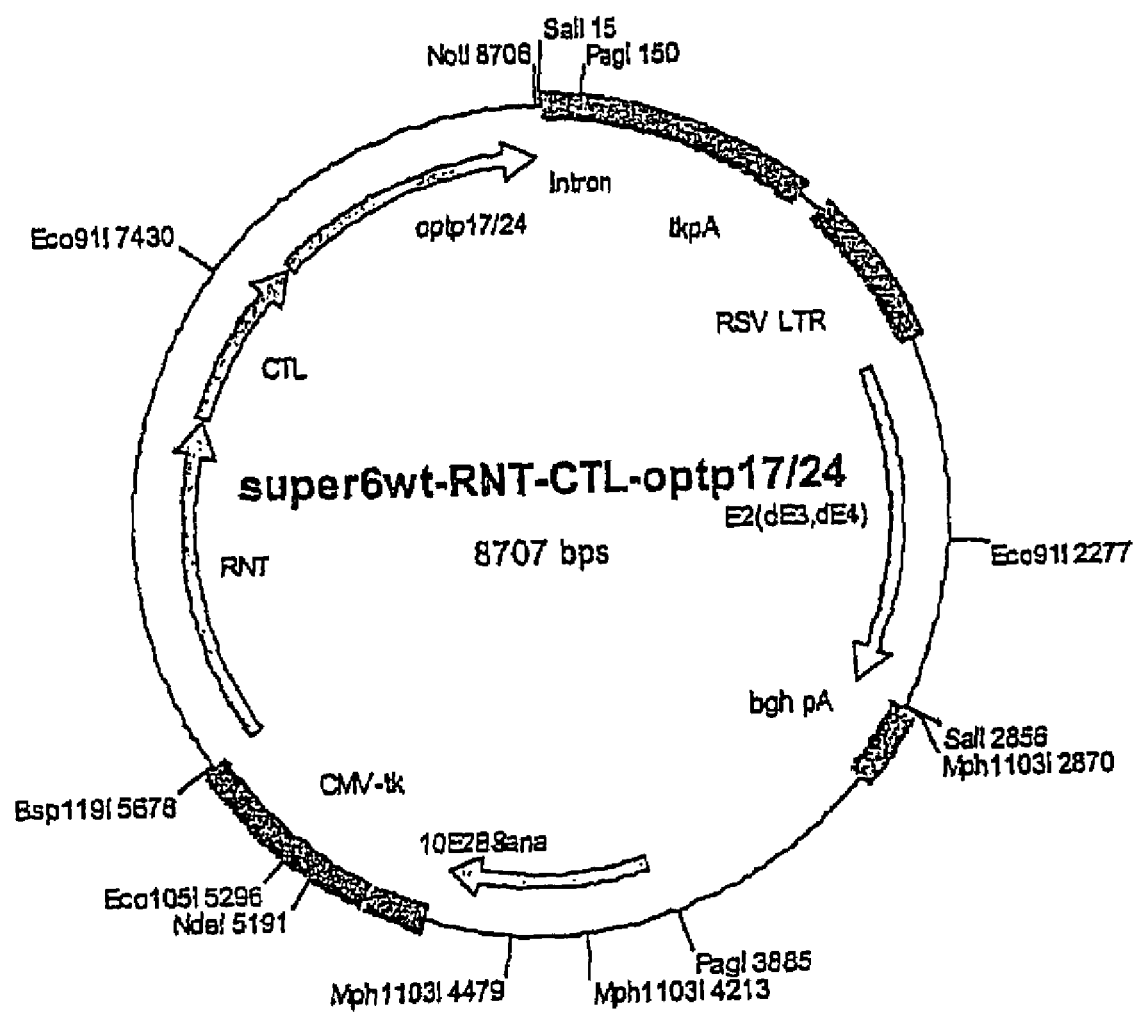

The HIV multi-antigen was cloned to the vectors super6wtd1EGFP and FREBNAd1EGFP instead of the d1EGFP using sites for Eco105I and NotI (super6wt-RNT-CTL-optp17/24 and FREBNA-RNT-CTL-optp17/24; FIGS. 43V and 42U, respectively). If indicated, the IRES and mouse mGM-CSF were cloned into the GTU-2 and GTU-3 vectors behind the E2 coding sequence into the sites Mph1103I and Eco91I from pTRN-iE2-mGMCSF (cut out using same restrictases).

Figure 42W:
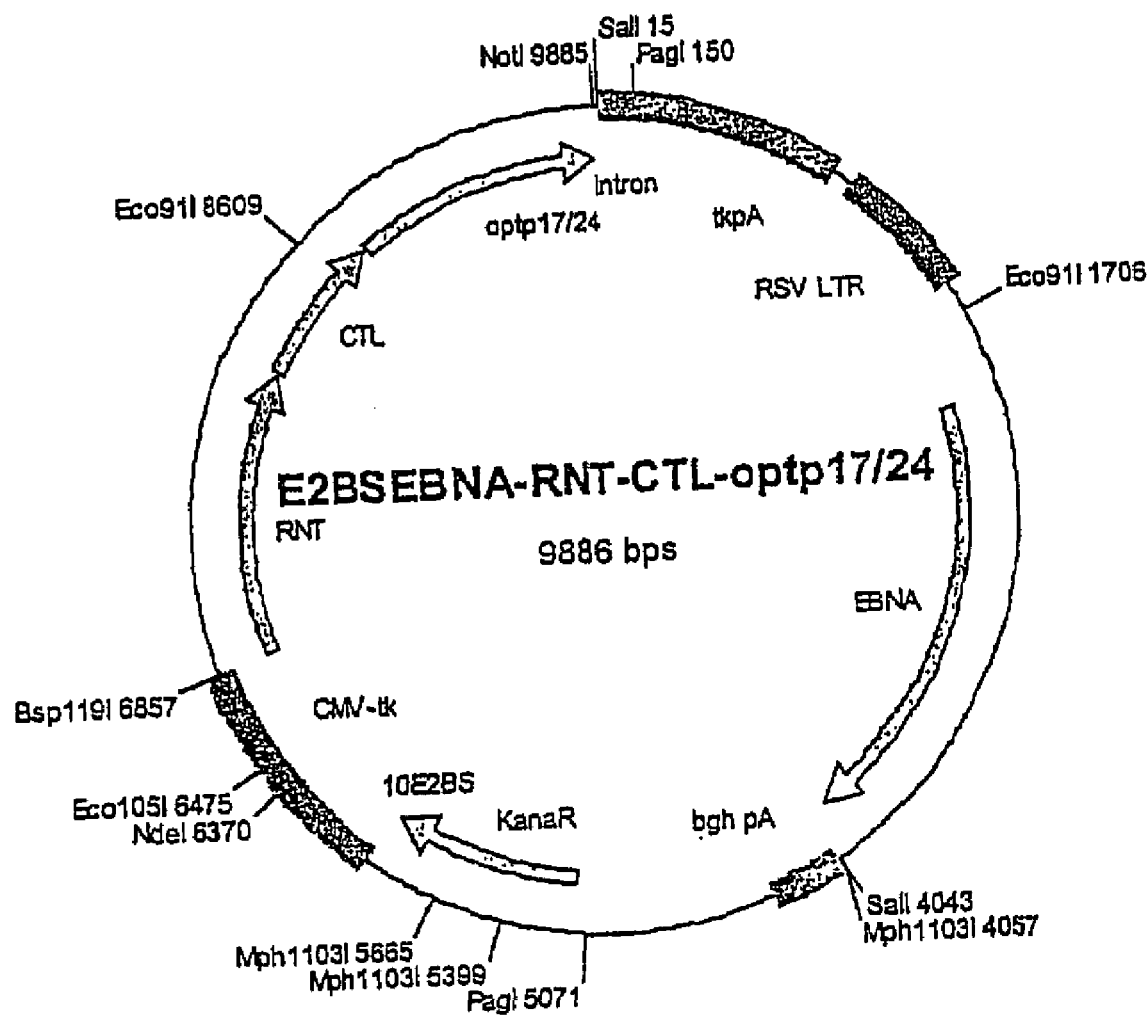
Figure 42X:
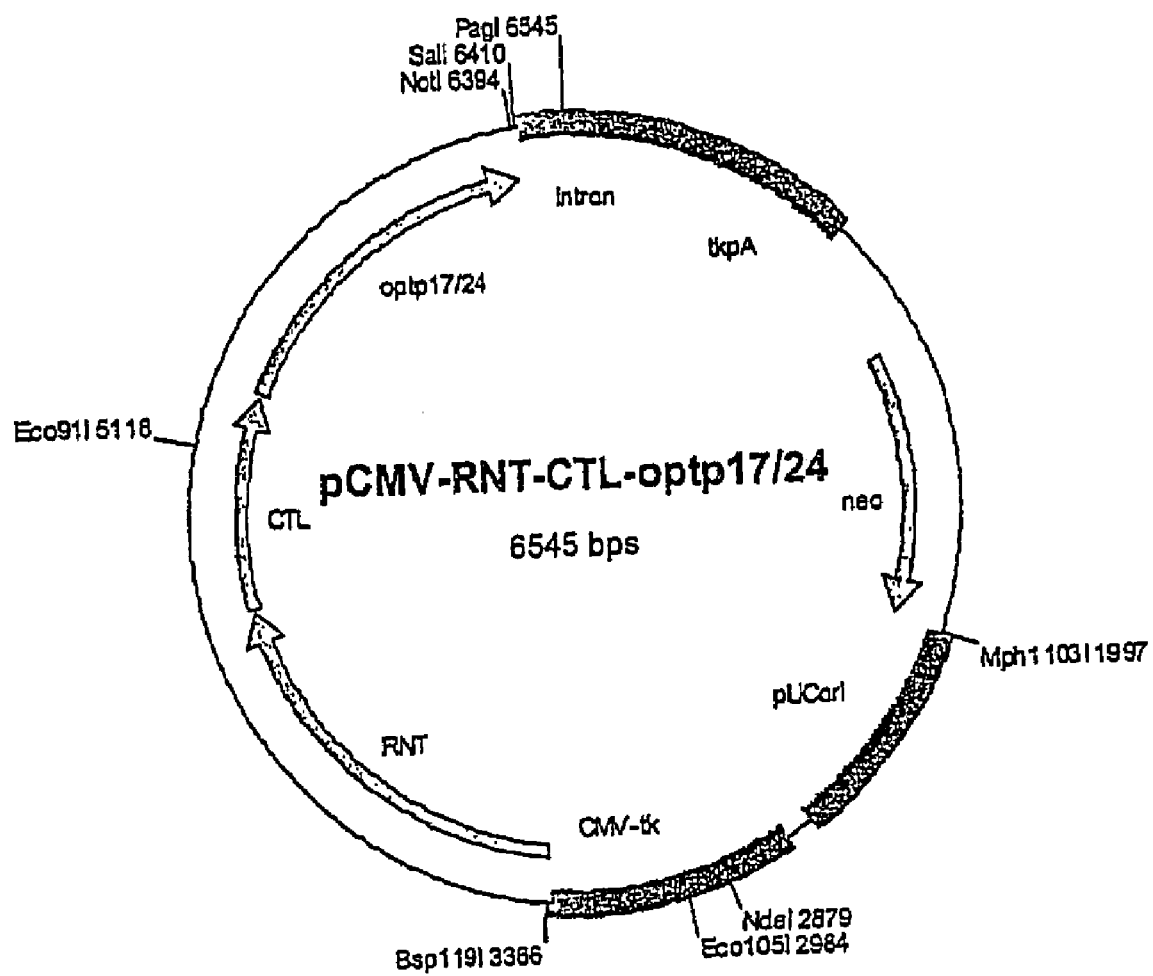

Finally, "non-GTU" control vector E2BSEBNA-RNT-CTL-optp17/24 (FIG. 42W) for the system utilizing EBNA-1 (contains EBNA-1 expression cassette with E2 binding sites) was made in a similar way as the FREBNA-RNT-CTL-optp17/24. The regular CMV vector pCMV-RNT-CTL-optp17/24 expressing the multi HIV antigen (FIG. 42D) was made by cloning the multi-HIV coding fragment from respective GTU-1 vector using sites for NdeI and Pag I.

6.5.2 Expression Properties of the Multireg Antigens Carrying Only Immunodominant Regions of the Regulatory Proteins.

1. Intracellular Localization of the MultiREG Antigens

The intracellular localization of MultiREG antigens expressed by the vectors of the invention was studied by in situ immunofluorescence in RD cells using monoclonal antibodies against Nef, Rev and Tat proteins essentially as described in Example 4. The results are summarized in Table 5 and illustrated in FIG. 45. All antigens that are comprised of intact Nef, Rev and Tat proteins showed exclusive localization in cytoplasm. The aberrant protein initially designed as N(ef)T(at)R(ev), which has a frame-shift before the Rev sequence, showed only the nuclear localization. MultiREG antigens carrying truncated sequences of the regulatory proteins were localized in cytoplasm. In this cases distinct structures like "inclusion bodies" were frequently observed. The same was true for antigens, which carried the protease sites expressed from pMV2 vectors. However in these cases the proteins in nucleus were also detected (FIG. 45).

TABLE 5

Intracellular localization in multireg antigenes

| Construct | anti-Nef | anti-Rev | anti-Tat |
|---|---|---|---|
| empty GTU-1 | negative | negative | negative |
| pTRN | strong staining in cytoplasm | good staining in cytoplasm | positive staining in cytoplasm |
| pNTR | strong staining in nucleus, nucleolus | negative | positive staining in nucleus |
| pRNT | strong staining in cytoplasm | good staining in cytoplasm | good staining in cytoplasm |
| pNRT | strong, cytoplasmic | good staining in cytoplasm | good staining in cytoplasm |

TABLE 5-continued

Intracellular localization in multireg antigenes

| Construct | anti-Nef | anti-Rev | anti-Tat |
|---|---|---|---|
| pRTN | strong, cytoplasmic | good staining in cytoplasm | positive staining in cytoplasm |
| pTNR | strong, cytoplasmic | good staining in cytoplasm | good staining in cytoplasm |
| pMV1NTR | strong, cytoplasmic | cytoplasmic + inclusions | cytoplasmic + inclusions |
| pMV1N11TR | strong cytoplasmic + inclusions | cytoplasmic + inclusions | cytoplasmic + inclusions |
| pMV2NTR | inclusions in nuclei and in cytopi. | inclusions in nuclei and cytoplasm | inclusions in nuclei and cytoplasm |
| pMV2N11TR | only inclusions, in nuclei and in cytopi | only inclusions in nuclei and in cytopi | only inclusions in nuclei and in cytopi. |

The intracellular localization of dgag and p17+p24 proteins was also analyzed in RD cells by immunofluorescence with monoclonal anti p24 antibodies. In accordance with the Western blot results in Jurkat cells, the dgag could not be detected. However, the p17/24 protein showed localization in plasma membranes (FIG. 45). The localization of CTL protein was not analyzed, because no suitable antibody was available.

6.6 Example 15

Analysis of Vectors Encoding Recombinant GAG Antigens and Cytotoxic T-Cell Epitopes (CTL) from POL

6.6.1. Expression

Analysis of expression of the vectors expressing CTL cds or proteins from the gag region were performed by western blot. As seen on FIGS. 46A and 46B, the CTL and dgag expression was clearly demonstrated in Cos-7 cells as predicted size proteins (25 kD and 47 kD, respectively). The co-transfection of the Nef, Rev and Tat significantly enhanced the expression of the dgag protein. We interpret this as a result of REV protein action on the GAG mRNA expression We also tried to express the dgag protein from GTU-1 vector in Jurkat cells, but we failed to detect any signal (FIG. 46C). The analysis of the codon usage showed that wt GAG sequence had not optimal codon usage for human cells. When the codon usage was optimized (constructs psynp17/24 and poptp17/24), strong p17+p24 (40 kD) protein expression was detected in Jurkat cells (FIGS. 46C and 46D).

6.6.2. Intracellular Localization

For dgag and p17+p24 proteins, the intracellular localization was also analyzed in RD cells by immunofluorescence with anti p24 Mab. Similar to the western blot results in Jurkat cells, the dgag could not be detected. The p17/24 protein showed localization in plasma membranes (FIG. 47). The localization of CTL protein was not analyzed caused by lacking of suitable antibody

6.7 Example 16

Multireg+Structural Proteins as Multi-HIV Antigen Expression

As next step, the expression of the MultiHIV antigenes consisting of both, regular multigene together with gag encoded protein and/or CTL multiepitope as single polypeptide was analysed. On FIG. 48, the Western blot shows the expression of several multiHIV-antigenes expressing vectors transfected to the Cos-7 cells. It is clearly seen that the expression levels of all regulatory+structural multi-antigenes are significantly lower than of the RNT or TRN proteins. All tested MultiHIV antigenes migrate in the gel as distinct bands near the position of predicted size (73 kD for multireg+CTL; 95 kD for multireg+dgag and 120 kD for multireg+CTL+dgag). Similar to the RNT and TRN, the RNT-CTL migrates more slowly than TRN-CTL. Also, in cases of both TRN and RNT constructs, the MultiREG–CTL–dgag combination showed higher expression level than MultiREG–dgag–CTL.

More detailed analysis of the multiHIV antigenes was performed in Jurkat cells. For this reason, most of the constructed MultiHIV antigenes (multireg+structural), included the MultiREG+CTL+optp17/24 (with predicted size 113 kD) were analyzed by Western blotting using antibodies against different parts of the antigene. The results are presented on FIG. 49 are principially similar to those were reported in previous section in case of Cos-7 cells. As it was seen in the previous experiments, the dgag containing multi-antigenes express very low levels of the hybrid protein in Jurkat cells. The expression from the vector pTRNdgag was undetectable on all blots. In lanes loaded material from cells transfected with other dgag containing antigene expression vectors, very faint signals only on the Nef Mab hybridized blot were detected at positions of predicted sizes. In contrast, if the dgag part is replaced with the codon optimized p17/24, the expression level increase was observed. Because the TRN-CTL-optp17/24 and RNT-optp17/24 were initially chosen for further analysis, the expression of the antigenes was analyzed from all GTU vectors containing these expression cassettes. Also, the E2 protein expression from these plasmids was analyzed. The results are illustrated on FIG. 50. There are no big differences between the vectors in expression levels of both multi-antigene and the E2 protein. The E2 expression level is not significantly influenced by presence of IRES element followed mouse GM-CSF gene in the plasmid, translated from the same mRNA as the E2.

6.7.1. Example 17

Maintenance of Expression of Antigen

The maintenance of the plasmid in a population of dividing cells was proved using the green fluorescent protein and Nef protein as markers. The maintenance of the expression of the RNT-CTL-optp17/24 antigen produced from different GTU or non-GTU vectors was also analyzed. Specifically, GTU-1

(p RNT-CTL-optp17/24), GTU-2 (p2 RNT-CTL-optp17/24), GTU-3 (p3 RNT-CTL-optp17/24), super6wt (super6wt-RNT-CTL-optp17/24) vectors each utilize the E2 protein and its binding sites for the plasmid maintenance activity. In this experiment, also EBNA-1 and its binding site utilizing GTU vector FREBNA-RNT-CTL-optp17/24 was included. As negative controls, "non-GTU" plasmid containing a mixed pair of the EBNA-1 expression cassette together with E2 binding sites (E2BSEBNA-RNT-CTL-optp17/24) was used. Also, regular CMV expression vector pCMV-RNT-CTL-optp17/24 was used.

Jurkat cells were transfected with equimolar amounts of the plasmids and the antigen expression was studied at 2 and 5 days post-transfection using a monoclonal anti-Nef antibodies. Transfection with carrier DNA only was used as a negative control. The results are presented in FIG. 51.

As it seen from FIG. 51, the expression is detectable only from GTU vectors at the second time-point. The antigen expression from the FREBNA-RNT-CTL-optp17/24 was lower at both time-points, because, unlike E2, the EBNA-1 does not have transcription activation ability.

Also the intracellular localization of the multireg+structural polyproteins was studied by in situ immunofluorescence analysis in RD cells essentially as described in Example 4. The results are presented in FIG. 52.

In all cases localization only in cytoplasm was detected using either monoclonal anti-Nef or anti-p24 antibodies. In accordance with Western blot data, the expression level of optp17/24 containing proteins was much stronger than dgag fragment containing antigens.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A vaccine comprising an expression vector and a pharmaceutically acceptable excipient, wherein said expression vector comprises:
   (a) a heterologous promoter operatively linked to a DNA sequence encoding a nuclear-anchoring protein, wherein said nuclear-anchoring protein comprises:
      (i) a DNA binding domain which binds to a specific DNA binding sequence, and
      (ii) a functional domain of the Bovine Papilloma Virus (BPV) type 1 E2 protein, wherein said functional domain binds to a nuclear component;
   (b) a multimerized DNA sequence that forms a binding site for said nuclear anchoring protein; and
   (c) at least one expression cassette comprising a DNA sequence encoding a protein or peptide that stimulates an immune response specific to the protein or peptide;
   wherein said expression vector lacks an origin of replication functional in mammalian cells.

2. The vaccine of claim 1, wherein said nuclear component is selected from the group consisting of mitotic chromatin, the nuclear matrix, nuclear domain 10 (ND10), and nuclear domain PML oncogenic domain (POD).

3. The vaccine of claim 1, wherein said nuclear-anchoring protein is a chromatin-anchoring protein, and said functional domain binds mitotic chromatin.

4. The vaccine of claim 1, wherein said nuclear-anchoring protein comprises a hinge or linker region.

5. The vaccine of claim 1, wherein said nuclear-anchoring protein is a natural protein of viral origin.

6. The vaccine of claim 1, wherein said nuclear-anchoring protein is an artificial protein.

7. The vaccine of claim 1, wherein said expression cassette comprises a gene obtained from an infectious pathogen.

8. The vaccine of claim 1, wherein said expression cassette comprises a gene obtained from a fungal pathogen.

9. The vaccine of claim 1, wherein said expression cassette comprises a DNA sequence of HIV origin.

10. The vaccine of claim 1, wherein said vector comprises:
    (a) a first expression cassette comprising a DNA sequence encoding Nef, Tat or Rev; and
    (b) a second expression cassette comprising a DNA sequence encoding Nef, Tat or Rev.

11. The vaccine of claim 1, wherein said vector comprises:
    (a) a first expression cassette comprising a DNA sequence encoding Nef, Tat or Rev; and
    (b) a second expression cassette comprising a DNA sequence encoding a structural protein of HIV.

12. The vaccine of claim 1, wherein said expression cassette comprises a DNA sequence encoding a protein or peptide associated with cancer, or an immunogenic fragment thereof.

13. The vaccine of claim 1, wherein:
    said DNA binding domain comprises the DNA binding domain of the BPV Type 1 E2 protein; and
    said multimerized DNA sequence comprises multimerized E2 binding sites.

14. The vaccine of claim 1, wherein:
    said nuclear-anchoring protein comprises the Bovine Papilloma Virus (BPV) type 1 E2 protein, and
    said multimerized DNA sequence comprises multimerized E2 binding sites.

15. The vaccine of claim 6, wherein said nuclear-anchoring protein is selected from the group consisting of a recombinant protein, a fusion protein, and a protein obtained by molecular modeling techniques.

16. The vaccine of claim 7, wherein said infectious pathogen is a virus.

17. The vaccine of claim 7, wherein said infectious pathogen is a bacterium.

18. The vaccine of claim 16, wherein said virus is selected from the group consisting of Human Immunodeficiency Virus (HIV), Herpex Simplex Virus (HSV), Hepatitis C Virus, Influenzae Virus, and Enterovirus.

19. The vaccine of claim 17, wherein said bacterium is selected from the group consisting of *Chiamydia trachomatis*, *Mycobacterium tuberculosis*, and *Mycoplasma pneumonia*.

20. The vaccine of claim 17, wherein said bacterium is *Salmonella*.

21. The vaccine of claim 8, wherein said fungal pathogen is *Candida albicans*.

22. The vaccine of claim 9, wherein said DNA sequence of HIV origin encodes a non-structural regulatory protein of HIV, or an immunogenic fragment thereof.

23. The vaccine of claim 9, wherein said DNA sequence of HIV origin encodes a structural protein of HIV, or an immunogenic fragment thereof.

24. The vaccine of claim 22, wherein said nonstructural regulatory protein of HIV is selected from the group consisting of Nef, Tat and Rev.

25. The vaccine of claim 24, wherein said nonstructural regulatory protein of HIV is Nef.

26. The vaccine of claim 23, wherein said DNA sequence of HIV origin is HIV gp120/gp160.

* * * * *

SEQUENCE LISTING

<160> NUMBER OF SEQ ID NOS: 52

<210> SEQ ID NO 1
<211> LENGTH: 1260
<212> TYPE: DNA
<213> ORGANISM: Artificial Sequence
<220> FEATURE:
<223> OTHER INFORMATION: Hybrid protein comprised of Nef-Tat-Rev (NTR)

<400> SEQUENCE: 1

```
atggtgggca agtggtcaaa atgtagtgga tggcctactg taagggaaag aatgaaacaa      60
gctgagcctg agccagcagc agatggggtg ggagcagcat ctcgagacct ggaaaaacat     120
ggagcaatca caagtagcaa tacagcaact aataacgctg cttgtgcctg gctagaagca     180
caagaggaag aggaagtggg ttttccagtc agacctcagg tacctttaag accaatgact     240
tacaagggag ctttagatct tagccacttt ttaaaagaaa aggggggact ggaagggtta     300
atttactccc caaaaagaca agagatcctt gatctgtggg tctaccacac acaaggctac     360
ttccctgatt ggcagaacta cacaccaggg ccaggggtca gatatccact gacctttgga     420
tggtgcttca agttagtacc agttgaacca gatgaagaag agaacagcag cctgttacac     480
cctgcgagcc tgcatgggac agaggacacg gagagagaag tgttaaagtg gaagtttgac     540
agccatctag catttcatca caaggcccga gagctgcatc cggagtacta caaagactgc     600
actagtgcag gaagaagcgg agacagcgac gaagagctcc tcaagacagt cagactcatc     660
aagtttctct accaaagcaa ccctcctccc agcaacgagg ggacccgaca ggcccgaaga     720
aatcgaagaa gaaggtggag agagacag aggcagatcc gttcgattag tgagcggatt     780
cttagcactt ttctgggacg acctgcggag cctgtgcctc ttcagctacc gccgcttgag     840
agacttactc ttgattgtag cgaagattgt ggaaactctg ggacgcaggg ggtgggaagt     900
cctcaagtat tggtggaatc tcctgcagta ttggagccag aactaaaga aaagcttgag     960 ccagtagatc ctagactaga gccctggaag catccaggaa gtcagcctag gacccccttgt    1020 accaattgct attgtaaaaa gtgttgcctt cattgccaag tttgtttcac aagaaaaggc    1080
ttaggcatct cctatggcag gaagaagcgg agacagcgac gaagagctcc tcaagacagt    1140
```

```
cagactcatc aagtttctct accaaagcaa ccctcctccc agcaacgagg ggacccgaca    1200
ggcccgaaga atcgaagaa gaaggtggag agagagacag aggcagatcc gttcgattag    1260

<210> SEQ ID NO 2
<211> LENGTH: 1260
<212> TYPE: DNA
<213> ORGANISM: Artificial Sequence
<220> FEATURE:
<223> OTHER INFORMATION: Hybrid protein comprised of Tat-Rev-Nef (TRN)

<400> SEQUENCE: 2
atggagccag tagatcctag actagagccc tggaagcatc caggaagtca gcctaggacc      60
ccttgtacca attgctattg taaaaagtgt tgccttcatt gccaagtttg tttcacaaga     120
aaaggcttag gcatctccta tggcaggaag aagcggagac agcgacgaag agctcctcaa     180
gacagtcaga ctcatcaagt ttctctacca agcaaccct cctcccagca cgaggggac      240 ccgacaggcc cgaagaaatc gaagaagaag gtggagagag agacagaggc agatccgttc     300
gatactagtg caggaagaag cggagacagc gacgaagagc tcctcaagac agtcagactc     360
atcaagtttc tctaccaaag caaccctcct cccagcaacg aggggacccg acaggcccga     420
agaaatcgaa gaaggtg gagagagaga cagaggcaga tccgttcgat tagtgagcgg       480
attcttagca cttttctggg acgacctgcg agcctgtgc ctcttcagct accgccgctt      540
gagagactta ctcttgattg tagcgaagat tgtggaaact ctgggacgca ggggtggga     600 agtcctcaag tattggtgga atctcctgca gtattggagc caggaactaa agaaaagctt     660
gtgggcaagt ggtcaaaatg tagtggatgg cctactgtaa gggaaagaat gaaacaagct     720
gagcctgagc cagcagcaga tggggtggga gcagcatctc gagacctgga aaaacatgga     780
gcaatcacaa gtagcaatac agcaactaat aacgctgctt gtgcctggct agaagcacaa     840
gaggaagagg aagtgggttt tccagtcaga cctcaggtac cttta agacc aatgacttac     900 aagggagctt tagatcttag ccacttttta aaagaaaagg ggggactgga agggttaatt     960
tactccccaa aaagacaaga gatccttgat ctgtgggtct accacacaca aggctacttc    1020
cctgattggc agaactacac accagggcca ggggtcagat atccactgac ctttggatgg    1080
tgcttcaagt tagtaccagt tgaaccagat gaagaagaga acagcagcct gttacaccct    1140
gcgagcctgc atgggacaga ggacgcgag agagaagtgt taaagtggaa gtttgacagc    1200
catctagcat ttcatcacaa ggcccgagag ctgcatccgg agtactacaa agactgctga    1260

<210> SEQ ID NO 3
<211> LENGTH: 1260
<212> TYPE: DNA
<213> ORGANISM: Artificial Sequence
<220> FEATURE:
<223> OTHER INFORMATION: Hybrid protein comprised of Rev-Tat-Nef (RTN)

<400> SEQUENCE: 3
atggcaggaa gaagcggaga cagcgacgaa gagctcctca agacagtcag actcatcaag      60
tttctctacc aaagcaaccc tcctcccagc aacgagggga cccgacaggc ccgaagaaat     120
cgaagaagaa ggtggagaga gagacagagg cagatccgtt cgattagtga gcggattctt     180 agcactttc tgggacgacc tgcggagcct gtgcctcttc agctaccgcc gcttgagaga     240
cttactcttg attgtagcga agattgtgga aactctggga cgcaggggggt gggaagtcct     300 caagtattg tggaatctcc tgcagtattg gagccaggaa ctaaagaaac tagtgagcca     360
gtagatccta gactagagcc ctggaagcat ccaggaagtc agcctaggac cccttgtacc     420
```

```
aattgctatt gtaaaaagtg ttgccttcat tgccaagttt gtttcacaag aaaaggctta      480
ggcatctcct atggcaggaa gaagcggaga cagcgacgaa gagctcctca agacagtcag      540
actcatcaag tttctctacc aaagcaaccc tcctcccagc aacgagggga cccgacaggc      600
ccgaagaaat cgaagaagaa ggtggagaga gagacagagg cagatccgtt cgataagctt      660
gtgggcaagt ggtcaaaatg tagtggatgg cctactgtaa gggaaagaat gaaacaagct      720
gagcctgagc cagcagcaga tggggtggga gcagcatctc gagacctgga aaaacatgga      780
gcaatcacaa gtagcaatac agcaactaat aacgctgctt gtgcctggct agaagcacaa      840
gaggaagagg aagtgggttt tccagtcaga cctcaggtac ctttaagacc aatgacttac      900
aagggagctt tagatcttag ccacttttta aagaaaagg ggggactgga agggttaatt      960
tactccccaa aagacaaga gatccttgat ctgtgggtct accacacaca aggctacttc     1020
cctgattggc agaactacac accagggcca ggggtcagat atccactgac ctttggatgg     1080
tgcttcaagt tagtaccagt tgaaccagat gaagaagaga acagcagcct gttacaccct     1140
gcgagcctgc atgggacaga ggacacggag agagaagtgt taaagtggaa gtttgacagc     1200
catctagcat ttcatcacaa ggcccgagag ctgcatccgg agtactacaa agactgctga     1260
```

<210> SEQ ID NO 4
<211> LENGTH: 1260
<212> TYPE: DNA
<213> ORGANISM: Artificial Sequence
<220> FEATURE:
<223> OTHER INFORMATION: Hybrid protein comprised of Tat-Nef-Rev (TNR)

<400> SEQUENCE: 4

```
atggagccag tagatcctag actagagccc tggaagcatc caggaagtca gcctaggacc       60
ccttgtacca attgctattg taaaaagtgt tgccttcatt gccaagtttg tttcacaaga      120
aaaggcttag gcatctccta tggcaggaag aagcggagac agcgacgaag agctcctcaa      180
gacagtcaga ctcatcaagt ttctctacca aagcaaccct cctcccagca acgaggggac      240
ccgacaggcc cgaagaaatc gaagaagaag gtggagagag agacagaggc agatccgttc      300
gatactagtg tgggcaagtg gtcaaaatgt agtggatggc ctactgtaag ggaaagaatg      360
aaacaagctg agcctgagcc agcagcagat ggggtgggag cagcatctcg agacctggaa      420
aaacatggag caatcacaag tagcaataca gcaactaata acgctgcttg tgcctggcta      480
gaagcacaag aggaagagga agtgggtttt ccagtcagac ctcaggtacc tttaagacca      540
atgacttaca agggagcttt agatcttagc cacttttta aagaaaaggg gggactggaa       600
gggttaattt actccccaaa aagacaagag atccttgatc tgtgggtcta ccacacacaa      660
ggctacttcc ctgattggca gaactacaca ccagggccag gggtcagata tccactgacc      720
tttggatggt gcttcaagtt agtaccagtt gaaccagatg aagaagagaa cagcagcctg      780
ttacaccctg cgagcctgca tgggacagag gacacggaga gagaagtgtt aaagtggaag      840
tttgacagcc atctagcatt tcatcacaag gcccgagagc tgcatccgga gtactacaaa      900
gactgcaagc ttgcaggaag aagcggagac agcgacgaag agctcctcaa gacagtcaga      960
ctcatcaagt ttctctacca aagcaaccct cctcccagca acgaggggac ccgacaggcc     1020
cgaagaaatc gaagaagaag gtggagagag agacagaggc agatccgttc gattagtgag     1080
cggattctta gcacttttct ggacgacct gcggagcctg tgcctcttca gctaccgccg     1140
cttgagagac ttactcttga ttgtagcgaa gattgtggaa actctgggac gcaggggtg     1200
```

```
ggaagtcctc aagtattggt ggaatctcct gcagtattgg agccaggaac taaagaatag    1260
```

<210> SEQ ID NO 5
<211> LENGTH: 1260
<212> TYPE: DNA
<213> ORGANISM: Artificial Sequence
<220> FEATURE:
<223> OTHER INFORMATION: Hybrid protein comprised of Rev-Nef-Tat (RNT)

<400> SEQUENCE: 5

```
atggcaggaa gaagcggaga cagcgacgaa gagctcctca agacagtcag actcatcaag      60
tttctctacc aaagcaaccc tcctcccagc aacgagggga cccgacaggc ccgaagaaat     120
cgaagaagaa ggtggagaga gagacagagg cagatccgtt cgattagtga gcggattctt     180
agcactttc tgggacgacc tgcggagcct gtgcctcttc agctaccgcc gcttgagaga      240
cttactcttg attgtagcga agattgtgga aactctggga cgcaggggt gggaagtcct      300
caagtattgg tggaatctcc tgcagtattg agccaggaac taaagaaac tagtgtgggc      360
aagtggtcaa atgtagtgg atggcctact gtaagggaaa gaatgaaaca agctgagcct      420
gagccagcag cagatggggt gggagcagca tctcgagacc tggaaaaaca tggagcaatc      480
acaagtagca atacagcaac taataacgct gcttgtgcct ggctagaagc acaagaggaa      540
gaggaagtgg gttttccagt cagacctcag gtacctttaa gaccaatgac ttacaaggga      600
gctttagatc ttagccactt ttttaaagaa aaggggggac tggaagggtt aatttactcc      660
ccaaaaagac aagagatcct tgatctgtgg gtctaccaca cacaaggcta cttccctgat      720
tggcagaact acacaccagg gccaggggtc agatatccac tgacctttgg atggtgcttc      780
aagttagtac cagttgaacc agatgaagaa gagaacagca gcctgttaca ccctgcgagc      840
ctgcatggga cagaggacac ggagagagaa gtgttaaagt ggaagtttga cagccatcta      900
gcatttcatc acaaggcccg agagctgcat ccggagtact acaaagactg caagcttgag      960
ccagtagatc ctagactaga gccctggaag catccaggaa gtcagcctag acccccttgt     1020
accaattgct attgtaaaaa gtgttgcctt cattgccaag tttgtttcac aagaaaaggc     1080
ttaggcatct cctatggcag gaagaagcgg agacagcgac gaagagctcc tcaagacagt     1140
cagactcatc aagtttctct accaaagcaa ccctcctccc agcaacgagg ggacccgaca     1200
ggcccgaaga atcgaagaa gaaggtggag agagagacag aggcagatcc gttcgattag     1260
```

<210> SEQ ID NO 6
<211> LENGTH: 1164
<212> TYPE: DNA
<213> ORGANISM: Artificial Sequence
<220> FEATURE:
<223> OTHER INFORMATION: Protein comprised of Immunodominant parts of
      the Nef-Tat-Rev(NTR)

<400> SEQUENCE: 6

```
atgggatggc ctactgtaag ggaaagaatg aaacaagctg agcctgagcc agcagcagat      60
ggggtgggag cagcatctcg agacctggaa aaacatggag caatcacaag tagcaataca     120
gcaactaata acgctgcttg tcctggcta gaagcacaag aggaagagga agtgggtttt     180
ccagtcagac tcaggtacc tttaagacca atgacttaca agggagcttt agatcttagc     240
cacttttta aagaaaaggg gggactggaa gggttaattt actccccaaa aagacaagag     300
atccttgatc tgtgggtcta ccacacacaa ggctacttcc ctgattggca gaactacaca     360
ccagggccag gggtcagata tccactgacc tttggatggt gcttcaagtt agtaccagtt     420
```

```
gaaccagatg aagaagagaa cagcagcctg ttacaccctg cgagcctgca tgggacagag    480
gacacggaga gagaagtgtt aaagtggaag tttgacagcc atctagcatt tcatcacaag    540
gcccgagagc tgcatccgga gtactacaaa gactgcgctc tggccgccgt tgagccagta    600
gatcctagac tagagccctg gaagcatcca ggaagtcagc ctaggacccc ttgtaccaat    660
tgctattgta aaaagtgttg ccttcattgc caagtttgtt tcacaagaaa aggcttaggc    720
atctcctatg gcaggaagaa gcggagacag cgacgaagag ctcctcaaga cagtcagact    780
catcaagttt ctctaccaaa gcaaccctcc tcccagcaac gaggggaccc gacaggcccg    840
aagaaatccg gactggccat cctgctgagc gacgaagagc tcctcaagac agtcagactc    900
atcaagtttc tctaccaaag caaccctcct cccagcaacg aggggacccg acaggcccga    960
agaaatcgaa gaagaaggtg gagagagaga cagaggcaga tccgttcgat tagtgagcgg   1020
attcttagca ctttttctggg acgacctgcg gagcctgtgc ctcttcagct accgccgctt   1080
gagagactta ctcttgattg tagcgaagat tgtggaaact ctgggacgca gggggtggga   1140
agtcctcaag tattggtgga atga                                          1164
```

<210> SEQ ID NO 7
<211> LENGTH: 1173
<212> TYPE: DNA
<213> ORGANISM: Artificial Sequence
<220> FEATURE:
<223> OTHER INFORMATION: Protein comprised of Immunodominant parts of
      the Nef-Tat-Rev separated by protease sites(NTR)

<400> SEQUENCE: 7

```
atgggatggc ctactgtaag ggaaagaatg aaacaagctg agcctgagcc agcagcagat     60
ggggtgggag cagcatctcg agacctggaa aaacatggag caatcacaag tagcaataca    120
gcaactaata acgctgcttg tgcctggcta gaagcacaag aggaagagga agtgggtttt    180
ccagtcagac ctcaggtacc tttaagacca atgacttaca agggagcttt agatcttagc    240
cactttttaa agaaaagggg ggactggaa gggttaattt actccccaaa aagacaagag    300
atccttgatc tgtgggtcta ccacacacaa ggctacttcc ctgattggca gaactacaca    360
ccagggccag ggtcagata tccactgacc tttggatggt gcttcaagtt agtaccagtt    420
gaaccagatg aagaagagaa cagcagcctg ttacaccctg cgagcctgca tgggacagag    480
gacacggaga gagaagtgtt aaagtggaag tttgacagcc atctagcatt tcatcacaag    540
gcccgagagc tgcatccgga gtactacaaa gactgcgctc tggccttcaa gcgggttgag    600
ccagtagatc ctagactaga gccctggaag catccaggaa gtcagcctag gaccccttgt    660
accaattgct attgtaaaaa gtgttgcctt cattgccaag tttgtttcac aagaaaaggc    720
ttaggcatct cctatggcag gaagaagcgg agacagcgac gaagagctcc tcaagacagt    780
cagactcatc aagtttctct accaaagcaa ccctcctccc agcaacgagg ggacccgaca    840
ggcccgaaga aatccgtacg ggagaagcgg ctgctgagcg acgaagagct cctcaagaca    900
gtcagactca tcaagtttct ctaccaaagc aaccctcctc cagcaacga ggggacccga    960 caggcccgaa gaaatcgaag aagaaggtgg agagagagac agaggcagat ccgttcgatt   1020
agtgagcgga ttcttagcac ttttctggga cgacctgcgg agcctgtgcc tcttcagcta   1080
ccgccgcttg agagacttac tcttgattgt agcgaagatt gtggaaactc tgggacgcag   1140
ggggtgggaa gtcctcaagt attggtggaa tga                                1173
```

<210> SEQ ID NO 8

<211> LENGTH: 1161
<212> TYPE: DNA
<213> ORGANISM: Artificial Sequence
<220> FEATURE:
<223> OTHER INFORMATION: Protein comprised of Immunodominant parts of
      the regulatory proteins Nef-Tat-Rev started from aa1 of Nef
      (N11TR)

<400> SEQUENCE: 8

| | | | | | |
|---|---|---|---|---|---|
| atgtggccta | ctgtaaggga | agaatgaaa | caagctgagc | ctgagccagc | agcagatggg | 60 |
| gtgggagcag | catctcgaga | cctggaaaaa | catggagcaa | tcacaagtag | caatacagca | 120 |
| actaataacg | ctgcttgtgc | ctggctagaa | gcacaagagg | aagaggaagt | gggttttcca | 180 |
| gtcagacctc | aggtaccttt | aagaccaatg | acttacaagg | gagctttaga | tcttagccac | 240 |
| tttttaaaag | aaaaggggggg | actggaaggg | ttaattact | ccccaaaaag | acaagagatc | 300 |
| cttgatctgt | gggtctacca | cacacaaggc | tacttccctg | attggcagaa | ctacacacca | 360 |
| gggccagggg | tcagatatcc | actgaccttt | ggatggtgct | tcaagttagt | accagttgaa | 420 |
| ccagatgaag | aagagaacag | cagcctgtta | caccctgcga | gcctgcatgg | gacagaggac | 480 |
| acggagagag | aagtgttaaa | gtggaagttt | gacagccatc | tagcatttca | tcacaaggcc | 540 |
| cgagagctgc | atccggagta | ctacaaagac | tgcgctctgg | ccgccgttga | gccagtagat | 600 |
| cctagactag | agccctggaa | gcatccagga | agtcagccta | ggaccccttg | taccaattgc | 660 |
| tattgtaaaa | agtgttgcct | tcattgccaa | gtttgtttca | agaaaaagg | cttaggcatc | 720 |
| tcctatggca | ggaagaagcg | gagacagcga | cgaagagctc | ctcaagacag | tcagactcat | 780 |
| caagtttctc | taccaaagca | accctcctcc | agcaacgag | gggacccgac | aggcccgaag | 840 |
| aaatccggac | tggccatcct | gctgagcgac | gaagagctcc | tcaagacagt | cagactcatc | 900 |
| aagtttctct | accaaagcaa | ccctcctccc | agcaacgagg | ggacccgaca | ggcccgaaga | 960 |
| aatcgaagaa | gaaggtggag | agagagacag | aggcagatcc | gttcgattag | tgagcggatt | 1020 |
| cttagcactt | ttctgggacg | acctgcggag | cctgtgcctc | ttcagctacc | gccgcttgag | 1080 |
| agacttactc | ttgattgtag | cgaagattgt | ggaaactctg | ggacgcaggg | ggtgggaagt | 1140 |
| cctcaagtat | tggtggaatg | a | | | | 1161 |

<210> SEQ ID NO 9
<211> LENGTH: 1170
<212> TYPE: DNA
<213> ORGANISM: Artificial Sequence
<220> FEATURE:
<223> OTHER INFORMATION: Protein comprised of Immunodominant parts of
      the regulatory proteins Nef-Tat-Rev started from aa1 of Nef
      separated by protease sites (N11TR)

<400> SEQUENCE: 9

| | | | | | |
|---|---|---|---|---|---|
| atgtggccta | ctgtaaggga | agaatgaaa | caagctgagc | ctgagccagc | agcagatggg | 60 |
| gtgggagcag | catctcgaga | cctggaaaaa | catggagcaa | tcacaagtag | caatacagca | 120 |
| actaataacg | ctgcttgtgc | ctggctagaa | gcacaagagg | aagaggaagt | gggttttcca | 180 |
| gtcagacctc | aggtaccttt | aagaccaatg | acttacaagg | gagctttaga | tcttagccac | 240 |
| tttttaaaag | aaaaggggggg | actggaaggg | ttaatttact | ccccaaaaag | acaagagatc | 300 |
| cttgatctgt | gggtctacca | cacacaaggc | tacttccctg | attggcagaa | ctacacacca | 360 |
| gggccagggg | tcagatatcc | actgaccttt | ggatggtgct | tcaagttagt | accagttgaa | 420 |
| ccagatgaag | aagagaacag | cagcctgtta | caccctgcga | gcctgcatgg | gacagaggac | 480 |
| acggagagag | aagtgttaaa | gtggaagttt | gacagccatc | tagcatttca | tcacaaggcc | 540 |

```
cgagagctgc atccggagta ctacaaagac tgcgctctgg ccttcaagcg ggttgagcca      600
gtagatccta gactagagcc ctggaagcat ccaggaagtc agcctaggac cccttgtacc      660
aattgctatt gtaaaaagtg ttgccttcat tgccaagttt gtttcacaag aaaaggctta      720
ggcatctcct atggcaggaa gaagcggaga cagcgacgaa gagctcctca agacagtcag      780
actcatcaag tttctctacc aaagcaaccc tcctcccagc aacgagggga cccgacaggc      840
ccgaagaaat ccgtacggga agcggctg ctgagcgacg aagagctcct caagacagtc      900
agactcatca gtttctcta ccaaagcaac cctcctccca gcaacgaggg gacccgacag      960
gcccgaagaa atcgaagaag aaggtggaga gagacagag gcagatccg ttcgattagt     1020 gagcggattc ttagcacttt tctgggacga cctgcggagc ctgtgcctct tcagctaccg     1080
ccgcttgaga gacttactct tgattgtagc gaagattgtg gaaactctgg gacgcagggg     1140
gtgggaagtc ctcaagtatt ggtggaatga                                     1170
```

<210> SEQ ID NO 10
<211> LENGTH: 663
<212> TYPE: DNA
<213> ORGANISM: Artificial Sequence
<220> FEATURE:
<223> OTHER INFORMATION: Protein comprised of Cytotoxic T-cell epitopes of Pol and Env genes (CTL)

<400> SEQUENCE: 10

```
atgatcaccc tgtggcagcg ccccctggtg gccctgatcg agatctgcac cgagatggag       60
aaggagggca agatcagcaa gatcggcccc gccggcctga agaagaagaa gagcgtgacc      120
gtgctggacg tgggcgacgc ctacttcagc gtgcccctgg ataaggactt ccgcaagtac      180
accgccttca ccatccccag catctggaag ggcagccccg ccatcttcca gagcagcatg      240
accaagaagc agaaccccga catcgtgatc taccagtaca tggacgacct gtacgtgccc      300
atcgtgctgc ccgagaagga cagctggctg gtgggcaagc tgaactgggc cagccagatc      360
tacgccggca tcaaggtgaa gcagctgatc ctgaaggagc ccgtgcacgg cgtgtacgag      420
cccatcgtgg gcgccgagac cttctacgtg gacggcgccg ccaaccgcgc cggcaacctg      480
tgggtgaccg tgtactacgg cgtgcccgtg tggaaggagg ccaccaccac cctggtggag      540
cgctacctgc gcgaccagca gctgctgggc atctggggct gcgcctgcac ccctacgac      600 atcaaccaga tgctgcgcgg ccctggccgc gccttcgtga ccatccgcca gggcagcctg      660
tag                                                                   663
```

<210> SEQ ID NO 11
<211> LENGTH: 1266
<212> TYPE: DNA
<213> ORGANISM: Artificial Sequence
<220> FEATURE:
<223> OTHER INFORMATION: Truncated Gag protein sequence (dgag)

<400> SEQUENCE: 11

```
atgttagaca atgggaaaa aattcggtta aggccagggg gaaagaaaaa atatcaatta       60
aaacatatag tatgggcaag cagggagcta gaacgattcg cagttaatcc tggcctgtta      120
gaaacatcag aaggctgtag acagataatg ggacagctac aaccgtccct tcagacagga      180
tcagaagaac ttagatcatt atataataca gtagcaaccc tctattgtgt gcatcaaaag      240
atagaggtaa aagacaccaa ggaagcttta gacaaggtag aggaagagca aaacaacagt      300
aagaaaaagg cacagcaaga agcagctgac gcaggaaaca gaaaccaggt cagccaaaat      360
```

```
taccctatag tgcaaaacct acagggacaa atggtacatc aggccatatc acctagaact    420
ttaaatgcat gggtaaaagt agtggaagag aaggctttca gcccagaagt aatacccatg    480
ttttcagcat tatcagaagg agccaccccca caagatttaa acaccatgct aaacacagtg   540
gggggacatc aagcagccat gcaaatgtta aaagaaacca tcaatgagga agctgcagaa    600
tgggatagat tgcacccagt gcatgcaggg cctattgcac caggccagat gagagaacca    660
aggggaagtg acatagcagg aactactagt acccttcagg aacaaatagg atggatgaca    720 ataatccac ctatcccagt aggagaaata tataagagat ggataatcct gggattaaat     780
aaaatagtaa gaatgtatag ccctaccagc attctggata aaaacaagg accaaaagaa     840 ccctttagag attatgtaga ccggttctat aaaaccctaa gagccgagca agctacacag    900
gaagtaaaaa attggatgac agaaaccttg ttggtccaaa atgcgaatcc agattgtaag    960 actatttaa aagcattagg accagcagct acactagaag aaatgatgac agcatgtcag     1020
ggagtggggg gacccggcca taaagcaaga gttttggctg aagcaatgag ccaagtaaca    1080
ggttcagctg ccataatgat gcagagaggc aattttagga accaaagaaa gactgttaag   1140
tgtttcaatt gtggcaaaga agggcacata gccagaaatt gcagggcccc taggaaaaag   1200
ggctgttgga aatgtggaaa ggaaggacat caaatgaagg attgcacaga agacaggct    1260 aattag                                                              1266

<210> SEQ ID NO 12
<211> LENGTH: 1092
<212> TYPE: DNA
<213> ORGANISM: Artificial Sequence
<220> FEATURE:
<223> OTHER INFORMATION: Synthetic coding sequence for p17/24 protein of
      Gag gene (syn 17/24)

<400> SEQUENCE: 12
atgggcgcaa gagcctccgt gctgagcggc ggagagctgg acaagtggga gaagatccgc    60 ctgcgcccg gcggcaagaa gaagtaccag ctgaagcaca cgtgtgggc cagccgcgag     120 ctggagcgct tcgccgtgaa ccccggcctg ctcgagacca gcgaaggctg ccgccagatc    180
atgggccagc tccagcccag cctccagacc ggcagcgagg agctgcgcag cctgtacaac    240
accgtggcca ccctgtactg cgtgcaccag aagatcgagt gaaggacac caaggaggcc    300 ctggacaagg tggaggagga gcagaacaac agcaagaaga ggcccagca ggaggccgcc    360 gacgccggca accgcaacca ggtgagccag aactacccca tcgtgcagaa cctgcagggc    420
cagatggtgc accaggccat cagccccgc accctgaacg cctgggtgaa ggtggtggag    480
gagaaggcct tcagccccga ggtgatcccc atgttcagcg ccctgagcga gggcgctacc    540
ccccaggacc tgaacaccat gctgaacacc gtgggcggcc accaggccgc catgcagatg    600
ctgaaggaga ccatcaacga ggaggccgcc gagtgggacc gcctgcaccc cgtgcacgcc    660
gggcccatcg cccccggcca gatgcgcgag cccgcggca gcgacatcgc cggcaccacc    720
agcaccctcc aggagcagat cggctggatg accaacaacc cccccatccc cgtgggcgag    780
atctacaagc gctggatcat cctgggcctg aacaagatcg tccgcatgta cagccccacc    840
agcatcctgg acatcaagca gggccccaag gagcccttcc gcgactacgt ggaccgcttc    900
tacaagaccc tgcgcgccga gcaggccacc caggaggtga gaactggat gaccgagacc    960 ctgctggtgc agaacgccaa ccccgactgc aagaccatcc tcaaggccct gggacccgcc   1020
gccaccctgg aggagatgat gaccgcctgc caaggcgtgg gcggccccgg ccacaaggcc   1080
```

```
cgcgtgctgt ga                                                    1092

<210> SEQ ID NO 13
<211> LENGTH: 1092
<212> TYPE: DNA
<213> ORGANISM: Artificial Sequence
<220> FEATURE:
<223> OTHER INFORMATION: Synthetic coding sequence for p17/24 protein of
      Gag gene optimized for expression in eukaryotic cells (optp17/24)

<400> SEQUENCE: 13
atgggcgcaa gagcctccgt gctgagcggc ggagagctgg acaagtggga gaagatccgc      60
ctgcgccccg gcggcaagaa gaagtaccag ctgaagcaca tcgtgtgggc cagccgcgag     120
ctggagcgct tcgccgtgaa ccccggcctg ctcgagacca gcgaaggctg ccgccagatc     180
atgggccagc tccagcccag cctccagacc ggcagcgagg agctgcgcag cctgtacaac     240
accgtggcca ccctgtactg cgtgcaccag aagatcgagg tgaaggacac caaggaggcc     300
ctggacaagg tggaggagga gcagaacaac agcaagaaga ggcccagca ggaggccgcc      360 gacgccggca accgcaacca agtcagccag aactacccca tcgtgcagaa cctgcagggc     420
cagatggtgc accaggccat cagccccgc accctgaacg cctgggtgaa ggtggtggag      480
gagaaggcct tcagcccga ggtgatcccc atgttcagcg ccctgagcga gggcgctacc      540
ccccaggacc tgaacaccat gctgaacacc gtgggcggcc accaggccgc catgcagatg     600
ctgaaggaga ccatcaacga ggaggccgcc gagtgggacc gcctgcaccc cgtgcacgcc     660
gggcccatcg cccccggcca gatgcgcgag ccccgcggca gcgacatcgc cggcaccacc     720
agcaccctcc aggagcagat cggctggatg accaacaacc cccccatccc cgtgggcgag     780
atctacaagc gctggatcat cctgggcctg aacaagatcg tccgcatgta cagccccacc     840
agcatcctgg acatcaagca gggccccaag gagcccttcc gcgactacgt ggaccgcttc     900
tacaagaccc tgcgcgccga gcaggccacc caggaggtga agaactggat gaccgagacc     960
ctgctggtgc agaacgccaa ccccgactgc aagaccatcc tcaaggccct gggacccgcc    1020
gccaccctgg aggagatgat gaccgccgc caaggcgtgg gcggcccgg ccacaaggcc      1080 cgcgtgctgt ga                                                        1092

<210> SEQ ID NO 14
<211> LENGTH: 1926
<212> TYPE: DNA
<213> ORGANISM: Artificial Sequence
<220> FEATURE:
<223> OTHER INFORMATION: Hybrid protein cds comprised of Tat-Rev-Nef and
      CTL (TRN-CTL)

<400> SEQUENCE: 14
atggagccag tagatcctag actagagccc tggaagcatc caggaagtca gcctaggacc      60
ccttgtacca attgctattg taaaaagtgt tgccttcatt gccaagtttg tttcacaaga    120
aaaggcttag gcatctccta tggcaggaag aagcggagac agcgacgaag agctcctcaa    180
gacagtcaga ctcatcaagt ttctctacca aagcaaccct cctcccagca acgaggggac    240
ccgacaggcc cgaagaaatc gaagaagaag gtggagagag agacagaggc agatccgttc    300
gatactagtg caggaagaag cggagacagc gacgaagagc tcctcaagac agtcagactc    360
atcaagtttc tctaccaaag caaccctcct cccagcaacg agggaccccg acaggcccga    420
agaaatcgaa gaagaaggtg gagagagaga cagaggcaga tccgttcgat tagtgagcgg    480
```

```
attcttagca cttttctggg acgacctgcg gagcctgtgc ctcttcagct accgccgctt    540
gagagactta ctcttgattg tagcgaagat tgtggaaact ctgggacgca ggggtggga    600
agtcctcaag tattggtgga atctcctgca gtattggagc caggaactaa agaaaagctt    660
gtgggcaagt ggtcaaaatg tagtggatgg cctactgtaa gggaagaat gaaacaagct    720
gagcctgagc cagcagcaga tggggtggga gcagcatctc gagacctgga aaaacatgga    780
gcaatcacaa gtagcaatac agcaactaat aacgctgctt gtgcctggct agaagcacaa    840
gaggaagagg aagtgggttt tccagtcaga cctcaggtac ctttaagacc aatgacttac    900
aagggagctt tagatcttag ccacttttta aagaaaagg ggggactgga agggttaatt    960
tactccccaa aaagacaaga gatccttgat ctgtgggtct accacacaca aggctacttc   1020
cctgattggc agaactacac accagggcca ggggtcagat atccactgac ctttggatgg   1080
tgcttcaagt tagtaccagt tgaaccagat gaagaagaga acagcagcct gttacaccct   1140
gcgagcctgc atgggacaga ggacacggag agagaagtgt taaagtggaa gtttgacagc   1200
catctagcat ttcatcacaa ggcccgagag ctgcatccgg agtactacaa agactgcgcg   1260
gccgtcatca ccctgtggca gcgccccctg gtggccctga tcgagatctg caccgagatg   1320
gagaaggagg gcaagatcag caagatcggc cccgccggcc tgaagaagaa gaagagcgtg   1380
accgtgctgg acgtgggcga cgcctacttc agcgtgcccc tggataagga cttccgcaag   1440
tacaccgcct tcaccatccc cagcatctgg aagggcagcc ccgccatctt ccagagcagc   1500
atgaccaaga gcagaaccc cgacatcgtg atctaccagt acatggacga cctgtacgtg   1560
cccatcgtgc tgcccgagaa ggacagctgg ctggtgggca gctgaactg gccagccag    1620
atctacgccg gcatcaaggt gaagcagctg atcctgaagg agcccgtgca cggcgtgtac   1680
gagcccatcg tgggcgccga ccttctac gtggacggcg ccgccaaccg cgccggcaac   1740
ctgtgggtga ccgtgtacta cggcgtgccc gtgtggaagg aggccaccac caccctggtg   1800
gagcgctacc tgcgcgacca gcagctgctg ggcatctggg gctgcgcctg cacccctac   1860
gacatcaacc agatgctgcg cggccctggc cgcgccttcg tgaccatccg ccagggcagc   1920
ctgtag                                                             1926
```

<210> SEQ ID NO 15
<211> LENGTH: 1926
<212> TYPE: DNA
<213> ORGANISM: Artificial Sequence
<220> FEATURE:
<223> OTHER INFORMATION: Hybrid protein cds comprised of Rev-Nef-Tat and CTL (RNT-CTL)

<400> SEQUENCE: 15

```
atggcaggaa gaagcggaga cagcgacgaa gagctcctca agacagtcag actcatcaag     60
tttctctacc aaagcaaccc tcctcccagc aacgagggga cccgacaggc ccgaagaaat    120
cgaagaagaa ggtggagaga gagacagagg cagatccgtt cgattagtga gcggattctt    180
agcacttttc tgggacgacc tcggagcct gtgcctcttc agctaccgcc gcttgagaga    240
cttactcttg attgtagcga agattgtgga aactctggga cgcaggggt gggaagtcct    300
caagtattgg tggaatctcc tgcagtattg gagccaggaa ctaaagaaac tagtgtgggc    360
aagtggtcaa aatgtagtgg atggcctact gtaagggaaa gaatgaaaca agctgagcct    420
gagccagcag cagatgggt gggagcagca tctcgagacc tggaaaaaca tggagcaatc    480
acaagtagca atacagcaac taataacgct gcttgtgcct ggctagaagc acaagaggaa    540
```

-continued

```
gaggaagtgg gttttccagt cagacctcag gtacctttaa gaccaatgac ttacaaggga    600
gctttagatc ttagccactt tttaaaagaa aaggggggac tggaagggtt aatttactcc    660
ccaaaaagac aagagatcct tgatctgtgg gtctaccaca cacaaggcta cttccctgat    720
tggcagaact acacaccagg gccagggggtc agatatccac tgacctttgg atggtgcttc    780
aagttagtac cagttgaacc agatgaagaa gagaacagca gcctgttaca ccctgcgagc    840
ctgcatggga cagaggacac ggagagagaa gtgttaaagt ggaagtttga cagccatcta    900
gcatttcatc acaaggcccg agagctgcat ccggagtact acaaagactg caagcttgag    960
ccagtagatc ctagactaga gccctggaag catccaggaa gtcagcctag acccccttgt   1020
accaattgct attgtaaaaa gtgttgcctt cattgccaag tttgtttcac aagaaaaggc   1080
ttaggcatct cctatggcag gaagaagcgg agacagcgac gaagagctcc tcaagacagt   1140
cagactcatc aagtttctct accaaagcaa ccctcctccc agcaacgagg ggacccgaca   1200
ggcccgaaga atcgaagaa gaaggtggag agagagacag aggcagatcc gttcgatgcg   1260
gccgtcatca ccctgtggca gcgccccctg gtggccctga tcgagatctg caccgagatg   1320
gagaaggagg gcaagatcag caagatcggc ccgccggcc tgaagaagaa gaagagcgtg   1380
accgtgctgg acgtgggcga cgcctacttc agcgtgcccc tggataagga cttccgcaag   1440
tacaccgcct tcaccatccc cagcatctgg aagggcagcc ccgccatctt ccagagcagc   1500
atgaccaaga agcagaaccc cgacatcgtg atctaccagt acatggacga cctgtacgtg   1560
cccatcgtgc tgcccgagaa ggacagctgg ctggtgggca agctgaactg gccagccag   1620
atctacgccg gcatcaaggt gaagcagctg atcctgaagg agcccgtgca cggcgtgtac   1680
gagcccatcg tgggcgccga gaccttctac gtggacggcg ccgccaaccg cgccggcaac   1740
ctgtgggtga ccgtgtacta cggcgtgccc gtgtggaagg aggccaccac cacctggtg   1800
gagcgctacc tgcgcgacca gcagctgctg ggcatctggg gctgcgcctg cacccctac   1860
gacatcaacc agatgctgcg cggccctggc cgcgccttcg tgaccatccg ccagggcagc   1920
ctgtag                                                              1926

<210> SEQ ID NO 16
<211> LENGTH: 2529
<212> TYPE: DNA
<213> ORGANISM: Artificial Sequence
<220> FEATURE:
<223> OTHER INFORMATION: Hybrid protein cds comprised of Tat-Rev-Nef and
      truncated Gag protein (TRN-dgag)

<400> SEQUENCE: 16
atggagccag tagatcctag actagagccc tggaagcatc caggaagtca gcctaggacc     60
ccttgtacca attgctattg taaaaagtgt tgccttcatt gccaagtttg tttcacaaga    120
aaaggcttag gcatctccta tggcaggaag aagcggagac agcgacgaag agctcctcaa    180
gacagtcaga ctcatcaagt ttctctacca aagcaaccct cctcccagca acgaggggac    240
ccgacaggcc cgaagaaatc gaagaagaag gtggagagag agacagaggc agatccgttc    300
gatactagtg caggaagaag cggagacagc gacgaagagc tcctcaagac agtcagactc    360
atcaagtttc tctaccaaag caaccctcct cccagcaacg aggggacccg acaggcccga    420
agaaatcgaa gaagaaggtg gagagagaga cagaggcaga tccgttcgat tagtgagcgg    480
attcttagca ctttttctggg acgacctgcg gagcctgtgc ctcttcagct accgccgctt    540
gagagactta ctcttgattg tagcgaagat tgtggaaact ctgggacgca ggggtggga    600
```

```
agtcctcaag tattggtgga atctcctgca gtattggagc caggaactaa agaaaagctt      660
gtgggcaagt ggtcaaaatg tagtggatgg cctactgtaa gggaaagaat gaaacaagct      720
gagcctgagc cagcagcaga tggggtggga gcagcatctc gagacctgga aaacatgga       780 gcaatcacaa gtagcaatac agcaactaat aacgctgctt gtgcctggct agaagcacaa      840
gaggaagagg aagtgggttt tccagtcaga cctcaggtac ctttaagacc aatgacttac      900
aagggagctt tagatcttag ccactttta aaagaaaagg ggggactgga agggttaatt       960
tactccccaa aaagacaaga gatccttgat ctgtgggtct accacacaca aggctacttc     1020
cctgattggc agaactacac accagggcca ggggtcagat atccactgac ctttggatgg     1080
tgcttcaagt tagtaccagt tgaaccagat gaagaagaga acagcagcct gttacaccct     1140
gcgagcctgc atgggacaga ggacacggag agagaagtgt taaagtggaa gtttgacagc     1200
catctagcat ttcatcacaa ggcccgagag ctgcatccgg agtactacaa agactgcgcg     1260
gccgtgttag acaatgggga aaaaattcgg ttaaggccag ggggaaagaa aaatatcaa      1320 ttaaaacata tagtatgggc aagcagggag ctagaacgat tcgcagttaa tcctggcctg     1380
ttagaaacat cagaaggctg tagacagata atgggacagc tacaaccgtc ccttcagaca     1440
ggatcagaag aacttagatc attatataat acagtagcaa ccctctattg tgtgcatcaa     1500
aagatagagg taaaagacac caaggaagct ttagacaagg tagaggaaga gcaaaacaac     1560
agtaagaaaa aggcacagca agaagcagct gacgcaggaa acagaaacca ggtcagccaa     1620
aattacccta tagtgcaaaa cctacaggga caaatggtac atcaggccat atcacctaga     1680
actttaaatg catgggtaaa agtagtggaa gagaaggctt tcagcccaga gtaatacccc     1740
atgttttcag cattatcaga aggagccacc ccacaagatt taaacaccat gctaaacaca     1800
gtggggggac atcaagcagc catgcaaatg ttaaaagaaa ccatcaatga ggaagctgca     1860
gaatgggata gattgcaccc agtgcatgca gggcctattg caccaggcca gatgagagaa     1920
ccaaggggaa gtgacatagc aggaactact agtacccttc aggaacaaat aggatggatg     1980
acaaataatc cacctatccc agtaggagaa atatataaga gatggataat cctgggatta     2040
aataaaatag taagaatgta tagccctacc agcattctgg atataaaaca aggaccaaaa     2100 gaaccctta gagattatgt agaccggttc tataaaaccc taagagccga gcaagctaca     2160
caggaagtaa aaaattggat gacagaaacc ttgttggtcc aaaatgcgaa tccagattgt     2220
aagactattt taaaagcatt aggaccagca gctacactag aagaaatgat gacagcatgt     2280
cagggagtgg ggggacccgg ccataaagca agagttttgg ctgaagcaat gagccaagta     2340
acaggttcag ctgccataat gatgcagaga ggcaattta ggaaccaaag aaagactgtt      2400
aagtgtttca attgtggcaa agaagggcac atagccagaa attgcagggc ccctaggaaa     2460
aagggctgtt ggaaatgtgg aaaggaagga catcaaatga aggattgcac agaaagacag     2520
gctaattag                                                             2529

<210> SEQ ID NO 17
<211> LENGTH: 3195
<212> TYPE: DNA
<213> ORGANISM: Artificial Sequence
<220> FEATURE:
<223> OTHER INFORMATION: Hybrid protein cds comprised of Tat-Rev-Nef,
      CTL and truncated Gag protein (TRN-CTL-dgag)

<400> SEQUENCE: 17
atggagccag tagatcctag actagagccc tggaagcatc caggaagtca gcctaggacc       60
```

-continued

| | |
|---|---|
| ccttgtacca attgctattg taaaaagtgt tgccttcatt gccaagtttg tttcacaaga | 120 |
| aaaggcttag gcatctccta tggcaggaag aagcggagac agcgacgaag agctcctcaa | 180 |
| gacagtcaga ctcatcaagt ttctctacca aagcaaccct cctcccagca acgaggggac | 240 |
| ccgacaggcc cgaagaaatc gaagaagaag gtggagagag agacagaggc agatccgttc | 300 |
| gatactagtg caggaagaag cggagacagc gacgaagagc tcctcaagac agtcagactc | 360 |
| atcaagtttc tctaccaaag caaccctcct cccagcaacg ggggacccg acaggcccga | 420 |
| agaaatcgaa gaagaaggtg gagagagaga caggagcaga tccgttcgat tagtgagcgg | 480 |
| attcttagca cttttctggg acgacctgcg gagcctgtgc ctcttcagct accgccgctt | 540 |
| gagagactta ctcttgattg tagcgaagat tgtggaaact ctgggacgca ggggtggga | 600 |
| agtcctcaag tattggtgga atctcctgca gtattggagc caggaactaa agaaaagctt | 660 |
| gtgggcaagt ggtcaaaatg tagtggatgg cctactgtaa gggaagaat gaaacaagct | 720 |
| gagcctgagc cagcagcaga tggggtggga gcagcatctc gagacctgga aaaacatgga | 780 |
| gcaatcacaa gtagcaatac agcaactaat aacgctgctt gtgcctggct agaagcacaa | 840 |
| gaggaagagg aagtgggttt tccagtcaga cctcaggtac cttttaagacc aatgacttac | 900 |
| aagggagctt tagatcttag ccactttta aaagaaaagg ggggactgga agggttaatt | 960 |
| tactccccaa aaagacaaga gatccttgat ctgtgggtct accacacaca aggctacttc | 1020 |
| cctgattggc agaactacac accagggcca ggggtcagat atccactgac ctttggatgg | 1080 |
| tgcttcaagt tagtaccagt tgaaccagat gaagaagaga acagcagcct gttacacct | 1140 |
| gcgagcctgc atgggacaga ggacacggag agagaagtgt taaagtggaa gtttgacagc | 1200 |
| catctagcat ttcatcacaa ggcccgagag ctgcatccgg agtactacaa agactgcgcg | 1260 |
| gccgtcatca ccctgtggca gcgcccctg gtggccctga tcgagatctg caccgagatg | 1320 |
| gagaaggagg gcaagatcag caagatcggc ccgccggcc tgaagaagaa gaagagcgtg | 1380 |
| accgtgctgg acgtgggcga cgcctacttc agcgtgcccc tggataagga cttccgcaag | 1440 |
| tacaccgcct tcaccatccc cagcatctgg aagggcagcc ccgccatctt ccagagcagc | 1500 |
| atgaccaaga agcagaaccc cgacatcgtg atctaccagt acatggacga cctgtacgtg | 1560 |
| cccatcgtgc tgcccgagaa ggacagctgg ctggtgggca agctgaactg gccagccag | 1620 |
| atctacgccg gcatcaaggt gaagcagctg atcctgaagg agcccgtgca cggcgtgtac | 1680 |
| gagcccatcg tgggcgccga gaccttctac gtggacggcg ccgccaaccg cgccggcaac | 1740 |
| ctgtgggtga ccgtgtacta cggcgtgccc gtgtggaagg aggccaccac caccctggtg | 1800 |
| gagcgctacc tgcgcgacca gcagctgctg ggcatctggg gctgcgcctg cacccctac | 1860 |
| gacatcaacc agatgctgcg cggccctggc cgcgccttcg tgaccatccc ccagggcagc | 1920 |
| ctggcggccg tgttagacaa atgggaaaaa attcggttaa ggccaggggg aaagaaaaaa | 1980 |
| tatcaattaa aacatatagt atgggcaagc agggagctag aacgattcgc agttaatcct | 2040 |
| ggcctgttag aaacatcaga aggctgtaga cagataatgg gacagctaca accgtccctt | 2100 |
| cagacaggat cagaagaact tagatcatta tataatacag tagcaaccct ctattgtgtg | 2160 |
| catcaaaaga tagaggtaaa agacaccaag gaagctttag acaaggtaga ggaagagcaa | 2220 |
| aacaacagta agaaaaaggc acagcaagaa gcagctgacg caggaaacag aaaccaggtc | 2280 |
| agccaaaatt accctatagt gcaaaaccta cagggacaaa tggtacatca ggccatatca | 2340 |
| cctagaactt taaatgcatg ggtaaaagta gtggaagaga aggctttcag cccagaagta | 2400 |
| atacccatgt tttcagcatt atcagaagga gccaccccac aagatttaaa caccatgcta | 2460 |

```
aacacagtgg ggggacatca agcagccatg caaatgttaa aagaaaccat caatgaggaa    2520
gctgcagaat gggatagatt gcacccagtg catgcagggc ctattgcacc aggccagatg    2580
agagaaccaa ggggaagtga catagcagga actactagta cccttcagga acaaatagga    2640
tggatgacaa ataatccacc tatcccagta ggagaaatat ataagagatg gataatcctg    2700
ggattaaata aaatagtaag aatgtatagc cctaccagca ttctggatat aaaacaagga    2760
ccaaaagaac cctttagaga ttatgtagac cggttctata aaaccctaag agccgagcaa    2820
gctacacagg aagtaaaaaa ttggatgaca gaaaccttgt tggtccaaaa tgcgaatcca    2880
gattgtaaga ctatttttaaa agcattagga ccagcagcta cactagaaga aatgatgaca    2940
gcatgtcagg gagtggggggg acccggccat aaagcaagag ttttggctga agcaatgagc    3000
caagtaacag gttcagctgc cataatgatg cagagaggca attttaggaa ccaaagaaag    3060
actgttaagt gtttcaattg tggcaaagaa gggcacatag ccagaaattg cagggccct   3120 aggaaaaagg gctgttggaa atgtggaaag gaaggacatc aaatgaagga ttgcacagaa    3180
agacaggcta attag                                                    3195
```

```
<210> SEQ ID NO 18
<211> LENGTH: 3195
<212> TYPE: DNA
<213> ORGANISM: Artificial Sequence
<220> FEATURE:
<223> OTHER INFORMATION: Hybrid protein  cds comprised of Rev-Nef-Tat,
      CTL and truncated Gag protein (RNT-CTL-dgag)

<400> SEQUENCE: 18
```

```
atggcaggaa gaagcggaga cagcgacgaa gagctcctca agacagtcag actcatcaag      60
tttctctacc aaagcaaccc tcctcccagc aacgagggga cccgacaggc ccgaagaaat     120
cgaagaagaa ggtggagaga gagacagagg cagatccgtt cgattagtga gcggattctt     180 agcactttttc tgggacgacc tgcggagcct gtgcctcttc agctaccgcc gcttgagaga     240
cttactcttg attgtagcga agattgtgga aactctggga cgcagggggt gggaagtcct     300
caagtattgg tggaatctcc tgcagtattg gagccaggaa ctaaagaaac tagtgtgggc     360
aagtggtcaa atgtagtgg atggcctact gtaagggaaa gaatgaaaca agctgagcct     420
gagccagcag cagatggggt gggagcagca tctcgagacc tggaaaaaca tggagcaatc     480
acaagtagca atacagcaac taataacgct gcttgtgcct ggctagaagc acaagaggaa     540
gaggaagtgg gttttccagt cagacctcag gtaccttaa gaccaatgac ttacaaggga     600
gctttagatc ttagccactt ttttaaaagaa aagggggggac tggaagggtt aatttactcc    660
ccaaaaagac aagagatcct tgatctgtgg gtctaccaca caaggcta cttccctgat      720 tggcagaact acacaccagg gccagggtgtc agatatccac tgacctttgg atggtgcttc    780
aagttagtac cagttgaacc agatgaagaa gagaacagca gcctgttaca ccctgcgagc    840
ctgcatggga cagaggacac ggagagagaa gtgttaaagt ggaagtttga cagccatcta    900
gcatttcatc acaaggcccg agagctgcat ccggagtact acaaagactg caagcttgag    960
ccagtagatc ctagactaga gccctggaag catccaggaa gtcagcctag gacccctttgt   1020 accaattgct attgtaaaaa gtgttgcctt cattgccaag tttgtttcac aagaaaaggc    1080
ttaggcatct cctatggcag gaagaagcgg agacagcgac gaagagctcc tcaagacagt    1140
cagactcatc aagtttctct accaaagcaa ccctcctccc agcaacgagg ggacccgaca    1200
ggcccgaaga aatcgaagaa gaaggtggag agagagacag aggcagatcc gttcgatgcg    1260
```

```
gccgtcatca ccctgtggca gcgcccctg gtggccctga tcgagatctg caccgagatg    1320
gagaaggagg gcaagatcag caagatcggc cccgccggcc tgaagaagaa gaagagcgtg    1380
accgtgctgg acgtgggcga cgcctacttc agcgtgcccc tggataagga cttccgcaag    1440
tacaccgcct tcaccatccc cagcatctgg aagggcagcc ccgccatctt ccagagcagc    1500
atgaccaaga agcagaaccc cgacatcgtg atctaccagt acatggacga cctgtacgtg    1560
cccatcgtgc tgcccgagaa ggacagctgg ctggtgggca agctgaactg ggccagccag    1620
atctacgccg gcatcaaggt gaagcagctg atcctgaagg agcccgtgca cggcgtgtac    1680
gagcccatcg tgggcgccga gaccttctac gtggacggcg ccgccaaccg cgccggcaac    1740
ctgtgggtga ccgtgtacta cggcgtgccc gtgtggaagg aggccaccac caccctggtg    1800
gagcgctacc tgcgcgacca gcagctgctg ggcatctggg gctgcgcctg cacccctac    1860 gacatcaacc agatgctgcg cggccctggc cgcgccttcg tgaccatccg ccagggcagc    1920
ctggcggccg tgttagacaa atgggaaaaa attcggttaa ggccaggggg aaagaaaaaa    1980
tatcaattaa acatatagt atgggcaagc agggagctag aacgattcgc agttaatcct    2040
ggcctgttag aaacatcaga aggctgtaga cagataatgg gacagctaca accgtcccctt    2100 cagacaggat cagaagaact tagatcatta tataatacag tagcaaccct ctattgtgtg    2160
catcaaaaga tagaggtaaa agacaccaag gaagctttag acaaggtaga ggaagagcaa    2220
aacaacagta agaaaaggc acagcaagaa gcagctgacg caggaaacag aaaccaggtc    2280
agccaaaatt accctatagt gcaaaaccta caggggacaaa tggtacatca ggccatatca    2340
cctagaactt taaatgcatg ggtaaaagta gtggaagaga aggctttcag cccagaagta    2400
atacccatgt tttcagcatt atcagaagga gccacccca agatttaaaa ccatgcta    2460 aacacagtgg ggggacatca agcagccatg caaatgttaa agaaaccat caatgaggaa    2520 gctgcagaat gggatagatt gcacccagtg catgcagggc ctattgcacc aggccagatg    2580
agagaaccaa ggggaagtga catagcagga actactagta cccttcagga caaatagga    2640 tggatgacaa ataatccacc tatcccagta ggagaaatat ataagagatg gataatcctg    2700
ggattaaata aaatagtaag aatgtatagc cctaccagca ttctggatat aaaacaagga    2760
ccaaaagaac ccctttagaga ttatgtagac cggttctata aaaccctaag agccgagcaa    2820
gctacacagg aagtaaaaaa ttggatgaca gaaaccttgt tggtccaaaa tgcgaatcca    2880
gattgtaaga ctatttttaaa agcattagga ccagcagcta cactagaaga aatgatgaca    2940
gcatgtcagg gagtgggggg acccggccat aaagcaagag ttttggctga agcaatgagc    3000
caagtaacag gttcagctgc cataatgatg cagagaggca attttaggaa ccaaagaaag    3060
actgttaagt gtttcaattg tggcaaagaa gggcacatag ccagaaattg cagggcccct    3120
aggaaaaagg gctgttggaa atgtggaaag gaaggacatc aaatgaagga ttgcacagaa    3180
agacaggcta attag                                                    3195

<210> SEQ ID NO 19
<211> LENGTH: 3195
<212> TYPE: DNA
<213> ORGANISM: Artificial Sequence
<220> FEATURE:
<223> OTHER INFORMATION: Hybrid protein cds comprised of Tat-Rev-Nef,
      truncated Gag protein and CTL (TRN-dgag-CTL)

<400> SEQUENCE: 19
atggagccag tagatcctag actagagccc tggaagcatc caggaagtca gcctaggacc     60
```

-continued

```
ccttgtacca attgctattg taaaaagtgt tgccttcatt gccaagtttg tttcacaaga    120
aaaggcttag gcatctccta tggcaggaag aagcggagac agcgacgaag agctcctcaa    180
gacagtcaga ctcatcaagt ttctctacca aagcaaccct cctcccagca acgaggggac    240
ccgacaggcc cgaagaaatc gaagaagaag gtggagagag agacagaggc agatccgttc    300
gatactagtg caggaagaag cggagacagc gacgaagagc tcctcaagac agtcagactc    360
atcaagtttc tctaccaaag caaccctcct cccagcaacg aggggacccg acaggcccga    420
agaaatcgaa gaagaggtg gagagagaga cagaggcaga tccgttcgat tagtgagcgg    480
attcttagca cttttctggg acgacctgcg gagcctgtgc ctcttcagct accgccgctt    540
gagagactta ctcttgattg tagcgaagat tgtggaaact ctgggacgca ggggtggga    600
agtcctcaag tattggtgga atctcctgca gtattggagc caggaactaa agaaaagctt    660
gtgggcaagt ggtcaaaatg tagtggatgg cctactgtaa gggaaagaat gaaacaagct    720
gagcctgagc cagcagcaga tggggtggga gcagcatctc gagacctgga aaaacatgga    780
gcaatcacaa gtagcaatac agcaactaat aacgctgctt gtgcctggct agaagcacaa    840
gaggaagagg aagtgggttt tccagtcaga cctcaggtac ctttaagacc aatgacttac    900
aagggagctt tagatcttag ccactttta aaagaaaagg ggggactgga agggttaatt    960
tactccccaa aaagacaaga gatccttgat ctgtgggtct accacacaca aggctacttc   1020
cctgattggc agaactacac accagggcca ggggtcagat atccactgac ctttggatgg   1080
tgcttcaagt tagtaccagt tgaaccagat gaagaagaga cagcagcct gttacaccct   1140
gcgagcctgc atgggacaga ggacacggag agagaagtgt taaagtggaa gtttgacagc   1200
catctagcat ttcatcacaa ggcccgagag ctgcatccgg agtactacaa agactgcgcg   1260
gccgtgttag acaaatggga aaaaattcgg ttaaggccag ggggaaagaa aaaatatcaa   1320
ttaaaacata tagtatgggc aagcaggag ctagaacgat tcgcagttaa tcctggcctg   1380
ttagaaacat cagaaggctg tagacagata tgggacagc tacaaccgtc ccttcagaca   1440
ggatcagaag aacttagatc attatataat acagtagcaa ccctctattg tgtgcatcaa   1500
aagatagagg taaaagacac caaggaagct ttagacaagg tagaggaaga gcaaaacaac   1560
agtaagaaaa aggcacagca agaagcagct gacgcaggaa acagaaacca ggtcagccaa   1620
aattacccta tagtgcaaaa cctacaggga caaatggtac atcaggccat atcacctaga   1680
actttaaatg catgggtaaa agtagtgaa gagaaggctt tcagcccaga gtaataccc    1740
atgttttcag cattatcaga aggagccacc ccacaagatt aaacaccat gctaaacaca   1800
gtggggggac atcaagcagc catgcaaatg ttaaaagaaa ccatcaatga ggaagctgca   1860
gaatgggata gattgcaccc agtgcatgca gggcctattg caccaggcca gatgagagaa   1920
ccaaggggaa gtgacatagc aggaactact agtacccttc aggaacaaat aggatggatg   1980
acaaataatc cacctatccc agtaggagaa atatataaga gatggataat cctgggatta   2040
aataaaatag taagaatgta tagccctacc agcattctgg atataaaaca aggaccaaaa   2100
gaacccttta gagattatgt agaccggttc tataaaaccc taagagccga gcaagctaca   2160
caggaagtaa aaaattggat gacagaaacc ttgttggtcc aaaatgcgaa tccagattgt   2220
aagactattt taaaagcatt aggaccagca gctacactag aagaaatgat gacagcatgt   2280
cagggagtgg ggggacccgg ccataaagca agagttttgg ctgaagcaat gagccaagta   2340
acaggttcag ctgccataat gatgcagaga ggcaatttta ggaaccaaag aaagactgtt   2400
```

-continued

```
aagtgtttca attgtggcaa agaagggcac atagccagaa attgcagggc ccctaggaaa      2460
aagggctgtt ggaaatgtgg aaaggaagga catcaaatga aggattgcac agaaagacag      2520
gctaatgcgg ccgtcatcac cctgtgcag cgcccctgg tggccctgat cgagatctgc       2580
accgagatgg agaaggaggg caagatcagc aagatcggcc ccgccggcct gaagaagaag      2640
aagagcgtga ccgtgctgga cgtgggcgac gcctacttca gcgtgccct ggataaggac       2700 ttccgcaagt acaccgcctt caccatcccc agcatctgga agggcagccc cgccatcttc      2760
cagagcagca tgaccaagaa gcagaacccc gacatcgtga tctaccagta catggacgac      2820
ctgtacgtgc ccatcgtgct gcccgagaag acagctggc tggtgggcaa gctgaactgg       2880
gccagccaga tctacgccgg catcaaggtg aagcagctga tcctgaagga gcccgtgcac      2940
ggcgtgtacg agcccatcgt gggcgccgag accttctacg tggacggcgc cgccaaccgc     3000
gccggcaacc tgtgggtgac cgtgtactac ggcgtgcccg tgtggaagga ggccaccacc     3060
accctggtgg agcgctacct gcgcgaccag cagctgctgg catctggg ctgcgcctgc        3120 accccctacg acatcaacca gatgctgcgc ggccctggcc gcgccttcgt gaccatccgc     3180
cagggcagcc tgtag                                                        3195

<210> SEQ ID NO 20
<211> LENGTH: 3195
<212> TYPE: DNA
<213> ORGANISM: Artificial Sequence
<220> FEATURE:
<223> OTHER INFORMATION: Hybrid protein cds comprised of Rev-Nef-Tat,
      truncated Gag protein and CTL (RNT-dgag-CTL)

<400> SEQUENCE: 20
atggcaggaa gaagcggaga cagcgacgaa gagctcctca agacagtcag actcatcaag        60
tttctctacc aaagcaaccc tcctcccagc aacgaggga cccgacaggc ccgaagaaat        120
cgaagaagaa ggtggagaga gagacagagg cagatccgtt cgattagtga gcggattctt       180 agcactttc tgggacgacc tgcggagcct gtgcctcttc agctaccgcc gcttgagaga        240
cttactcttg attgtagcga agattgtgga aactctggga cgcagggggt gggaagtcct       300
caagtattgg tggaatctcc tgcagtattg gagccaggaa ctaaagaaac tagtgtgggc       360
aagtggtcaa atgtagtgg atggcctact gtaaggaaa gaatgaaaca agctgagcct       420
gagccagcag cagatggggt gggagcagca tctcgagacc tggaaaaaca tggagcaatc       480
acaagtagca atacagcaac taataacgct gcttgtgcct ggctagaagc acaagaggaa      540
gaggaagtgg gttttccagt cagacctcag gtacctttaa gaccaatgac ttacaaggga      600
gctttagatc ttagccactt ttaaaagaa aagggggggac tggaagggtt aatttactcc       660
ccaaaaagac aagagatcct tgatctgtgg gtctaccaca caaaggcta cttccctgat        720 tggcagaact acacaccagg gccagggtc agatatccac tgacctttgg atggtgcttc       780
aagttagtac cagttgaacc agatgaagaa gagaacagca gcctgttaca ccctgcgagc      840
ctgcatggga cagaggacac ggagagaa gtgttaaagt ggaagtttga cagccatcta         900
gcatttcatc acaaggcccg agagctgcat ccggagtact acaaagactg caagcttgag      960
ccagtagatc ctagactaga gcctggaag catccaggaa gtcagcctag gacccttgt         1020 accaattgct attgtaaaaa gtgttgcctt cattgccaag tttgtttcac aagaaaaggc       1080
ttaggcatct cctatggcag gaagaagcgg agacagcgac gaagagctcc tcaagacagt      1140
cagactcatc aagtttctct accaaagcaa ccctcctccc agcaacgagg ggaccccgaca     1200
```

```
ggcccgaaga aatcgaagaa gaaggtggag agagagacag aggcagatcc gttcgatgcg   1260
gccgtgttag acaaatggga aaaaattcgg ttaaggccag ggggaaagaa aaatatcaa    1320 ttaaaacata tagtatgggc aagcaggag ctagaacgat tcgcagttaa tcctggcctg    1380
ttagaaacat cagaaggctg tagacagata atgggacagc tacaaccgtc ccttcagaca   1440
ggatcagaag aacttagatc attatataat acagtagcaa ccctctattg tgtgcatcaa   1500
aagatagagg taaaagacac caaggaagct ttagacaagg tagaggaaga gcaaaacaac   1560
agtaagaaaa aggcacagca agaagcagct gacgcaggaa acagaaacca ggtcagccaa   1620
aattacccta tagtgcaaaa cctacaggga caaatggtac atcaggccat atcacctaga   1680
actttaaatg catgggtaaa agtagtggaa gagaaggctt tcagcccaga agtaataccc   1740
atgttttcag cattatcaga aggagccacc ccacaagatt taaacaccat gctaaacaca   1800 gtgggggac atcaagcagc catgcaaatg ttaaaagaaa ccatcaatga ggaagctgca   1860
gaatgggata gattgcaccc agtgcatgca gggcctattg caccaggcca gatgagagaa   1920
ccaaggggaa gtgacatagc aggaactact agtacccttc aggaacaaat aggatggatg   1980
acaaataatc cacctatccc agtaggagaa atatataaga gatggataat cctgggatta   2040
aataaaatag taagaatgta tagccctacc agcattctgg atataaaaca aggaccaaaa   2100
gaacccttta gagattatgt agaccggttc tataaaaccc taagagccga gcaagctaca   2160
caggaagtaa aaaattggat gacagaaacc ttgttggtcc aaaatgcgaa tccagattgt   2220
aagactattt taaaagcatt aggaccagca gctacactag aagaaatgat gacagcatgt   2280
cagggagtgg ggggacccgg ccataaagca agagttttgg ctgaagcaat gagccaagta   2340
acaggttcag ctgccataat gatgcagaga ggcaatttta ggaaccaaag aaagactgtt   2400
aagtgtttca attgtggcaa agaagggcac atagccagaa attgcagggc ccctaggaaa   2460
aagggctgtt ggaaatgtgg aaaggaagga catcaaatga aggattgcac agaaagacag   2520
gctaatgcgg ccgtcatcac cctgtggcag cgccccctgg tggccctgat cgagatctgc   2580
accgagatgg agaaggaggg caagatcagc aagatcggcc ccgccggcct gaagaagaag   2640
aagagcgtga ccgtgctgga cgtgggcgac gcctacttca gcgtgcccct ggataaggac   2700
ttccgcaagt acaccgcctt caccatcccc agcatctgga agggcagccc cgccatcttc   2760
cagagcagca tgaccaagaa gcagaacccc gacatcgtga tctaccagta catggacgac   2820
ctgtacgtgc ccatcgtgct gccccgagaag gacagctggc tggtgggcaa gctgaactgg   2880
gccagccaga tctacgccgg catcaaggtg aagcagctga cctgaagga gcccgtgcac   2940 ggcgtgtacg agcccatcgt gggcgccgag accttctacg tggacggcgc cgccaaccgc   3000
gccggcaacc tgtgggtgac cgtgtactac ggcgtgcccg tgtggaagga ggccaccacc   3060
accctggtgg agcgctacct gcgcgaccag cagctgctgg gcatctgggg ctgcgcctgc   3120 acccctacg acatcaacca gatgctgcgc ggccctggcc gcgccttcgt gaccatccgc   3180
cagggcagcc tgtag                                                   3195
```

<210> SEQ ID NO 21
<211> LENGTH: 3020
<212> TYPE: DNA
<213> ORGANISM: Artificial Sequence
<220> FEATURE:
<223> OTHER INFORMATION: Hybrid protein cds comprised of Tat-Rev-Nef,
       truncated Gag protein and CTL (TRN-optp17/24-CTL)

<400> SEQUENCE: 21

```
atggagccag tagatcctag actagagccc tggaagcatc caggaagtca gcctaggacc    60
ccttgtacca attgctattg taaaaagtgt tgccttcatt gccaagtttg tttcacaaga   120
aaaggcttag gcatctccta tggcaggaag aagcggagac agcgacgaag agctcctcaa   180
gacagtcaga ctcatcaagt ttctctacca aagcaaccct cctcccagca acgaggggac   240
ccgacaggcc cgaagaaatc gaagaagaag gtggagagag agacagaggc agatccgttc   300
gatactagtg caggaagaag cggagacagc gacgaagagc tcctcaagac agtcagactc   360
atcaagtttc tctaccaaag caaccctcct cccagcaacg ggggacccg acaggcccga   420
agaaatcgaa gaagaaggtg gagagagaga cagaggcaga tccgttcgat tagtgagcgg   480
attcttagca ctttttctggg acgacctgcg gagcctgtgc ctcttcagct accgccgctt   540
gagagactta ctcttgattg tagcgaagat tgtggaaact ctgggacgca ggggtggga   600
agtcctcaag tattggtgga atctcctgca gtattggagc caggaactaa agaaaagctt   660
gttggcaagt ggtcaaaatg tagtggatgg cctactgtaa gggaagaat gaaacaagct   720
gagcctgagc cagcagcaga tggggtggga gcagcatctc gagacctgga aaaacatgga   780
gcaatcacaa gtagcaatac agcaactaat aacgctgctt gtgcctggct agaagcacaa   840
gaggaagagg aagtgggttt ccagtcaga cctcaggtac ctttaagacc aatgacttac   900
aagggagctt tagatcttag ccactttta aagaaaagg ggggactgga agggttaatt   960
tactccccaa aaagacaaga gatccttgat ctgtgggtct accacacaca aggctacttc  1020
cctgattggc agaactacac accagggcca ggggtcagat atccactgac ctttggatgg  1080
tgcttcaagt tagtaccagt tgaaccagat gaagaagaga acagcagcct gttacaccct  1140
gcgagcctgc atgggacaga ggacacggag agagaagtgt taaagtggaa gtttgacagc  1200
catctagcat ttcatcacaa ggcccgagag ctgcatccgg agtactacaa agactgcgcg  1260
gccgtgggcg caagagcctc cgtgctgagc ggcggagagc tggacaagtg ggagaagatc  1320
cgcctgcgcc ccggcggcaa gaagaagtac cagctgaagc acatcgtgtg ggccagccgc  1380
gagctggagc gcttcgccgt gaaccccggc ctgctcgaga ccagcgaagg ctgccgccag  1440
atcatgggcc agctccagcc cagcctccag accggcagcg aggagctgcg cagcctgtac  1500
aacaccgtgg ccaccctgta ctgcgtgcac cagaagatcg aggtaaagga caccaaggag  1560
gccctggaca aggtggagga ggagcagaac aacagcaaga agaaggccca gcaggaggcc  1620
gccgacgccg gcaaccgcaa ccaagtcagc cagaactacc ccatcgtgca gaacctgcag  1680
ggccagatgg tgcaccaggc catcagcccc cgcacactga acgcctgggt gaaggtggtg  1740
gaggagaagg ccttcagccc cgaggtgatc cccatgttca gcgccctaag cgagggcgct  1800
accccccagg acctgaacac catgctgaac accgtgggcg ccaccaggc cgccatgcag  1860
atgctgaagg agaccatcaa cgaggaggcc gccgagtggg accgcctgca ccccgtgcac  1920
gccgggccca tcgcccccgg ccagatgcgc gagcccgcg cagcgacat cgccggcacc  1980
accagcaccc tccaggagca gatcggctgg atgaccaaca ccccccat cccgtgggc  2040
gagatctaca gcgctggat catcctgggc ctgaacaaga tcgtccgcat gtacagcccc  2100
accagcatcc tggacatcaa gcagggcccc aaggagccct tccgcgacta cgtggaccgc  2160
ttctacaaga ccctgcgcgc cgagcaggcc acccaggagg tgaagaactg gatgaccgag  2220
accctgctgg tgcagaacgc caaccccgac tgcaagacca tcctcaaggc cctgggaccc  2280
gccgccaccc tggaggagat gatgaccgcc tgccaaggcg tgggcggccc cggccacaag  2340
gcccgcgtgc tggcggccgt catcacccct tggcagcgcc ccctggtggc cctgatcgag  2400
```

```
atctgcaccg agatggagaa ggagggcaag atcagcaaga tcggccccgc cggcctgaag   2460
aagaagaaga gcgtgaccgt gctggacgtg ggcgacgcct acttcagcgt gcccctggat   2520
aaggacttcc gcaagtacac cgccttcacc atccccagca tctggaaggg cagccccgcc   2580
atcttccaga gcagcatgac caagaagcag aaccccgaca tcgtgatcta ccagtacatg   2640
gacgacctgt acgtgcccat cgtgctgccc gagaaggaca gctggctggt gggcaagctg   2700
aactgggcca gccagatcta cgccggcatc aaggtgaagc agctgatcct gaaggagccc   2760
gtgcacggcg tgtacgagcc catcgtgggc gccgagacct cctacgtgga cggcgccgcc   2820
aaccgcgccg gcaacctgtg ggtgaccgtg tactacggcg tgcccgtgtg aaggaggcc   2880 accaccaccc tggtggagcg ctacctgcgc gaccagcagc tgctgggcat ctggggctgc   2940
gcctgcaccc cctacgacat caaccagatg ctgcgcggcc ctggccgcgc ctcgtgacca   3000
tccgccaggg cagcctgtag                                                3020
```

<210> SEQ ID NO 22
<211> LENGTH: 3021
<212> TYPE: DNA
<213> ORGANISM: Artificial Sequence
<220> FEATURE:
<223> OTHER INFORMATION: Hybrid protein cdscomprised of Tat-Rev-Nef,
      CTL and truncated Gag protein (TRN-CTL-optp17/24)

<400> SEQUENCE: 22

```
atggagccag tagatcctag actagagccc tggaagcatc caggaagtca gcctaggacc     60
ccttgtacca attgctattg taaaaagtgt tgccttcatt gccaagtttg tttcacaaga    120
aaaggcttag gcatctccta tggcaggaag aagcggagac agcgacgaag agctcctcaa    180
gacagtcaga ctcatcaagt ttctctacca aagcaaccct cctcccagca acgaggggac    240
ccgacaggcc cgaagaaatc gaagaagaag gtggagagag agacagaggc agatccgttc    300
gatactagtg caggaagaag cggagacagc gacgaagagc tcctcaagac agtcagactc    360
atcaagtttc tctaccaaag caaccctcct cccagcaacg aggggacccg acaggcccga    420
agaaatcgaa gaaggtg gagagagaga cagaggcaga tccgttcgat tagtgagcgg    480
attcttagca ctttttctggg acgacctgcg gagcctgtgc ctcttcagct accgccgctt    540
gagagactta ctcttgattg tagcgaagat tgtggaaact ctgggacgca ggggtggga    600 agtcctcaag tattggtgga atctcctgca gtattggagc caggaactaa gaaaagctt    660 gtgggcaagt ggtcaaaatg tagtggatgg cctactgtaa gggaaagaat gaaacaagct    720
gagcctgagc cagcagcaga tggggtggga gcagcatctc gagacctgga aaaacatgga    780
gcaatcacaa gtagcaatac agcaactaat aacgctgctt gtgcctggct agaagcacaa    840
gaggaagagg aagtgggttt tccagtcaga cctcaggtac ctttaagacc aatgacttac    900
aagggagctt tagatcttag ccacttttta aagaaaagg ggggactgga agggttaatt    960
tactccccaa aaagacaaga gatccttgat ctgtgggtct accacacaca aggctacttc    1020
cctgattggc agaactacac accagggcca ggggtcagat atccactgac ctttggatgg    1080
tgcttcaagt tagtaccagt tgaaccagat aagaagaga cagcagcct gttacaccct    1140 gcgagcctgc atgggacaga ggacacggag agagaagtgt taaagtggaa gtttgacagc    1200
catctagcat ttcatcacaa ggcccgagag ctgcatccgg agtactacaa agactgcgcg    1260
gccgtcatca cccctgtggca gcgcccctg gtgcccctga tcgagatctg caccgagatg    1320
gagaaggagg gcaagatcag caagatcggc cccgccggcc tgaagaagaa gaagagcgtg    1380
```

```
accgtgctgg acgtgggcga cgcctacttc agcgtgcccc tggataagga cttccgcaag    1440
tacaccgcct tcaccatccc cagcatctgg aagggcagcc ccgccatctt ccagagcagc    1500
atgaccaaga agcagaaccc cgacatcgtg atctaccagt acatggacga cctgtacgtg    1560
cccatcgtgc tgcccgagaa ggacagctgg ctggtgggca agctgaactg ggccagccag    1620
atctacgccg gcatcaaggt gaagcagctg atcctgaagg agcccgtgca cggcgtgtac    1680
gagcccatcg tgggcgccga gaccttctac gtggacggcg ccgccaaccg cgccggcaac    1740
ctgtgggtga ccgtgtacta cggcgtgccc gtgtggaagg aggccaccac caccctggtg    1800
gagcgctacc tgcgcgacca gcagctgctg ggcatctggg gctgcgcctg cacccctac    1860 gacatcaacc agatgctgcg cggccctggc cgcgccttcg tgaccatccg ccagggcagc    1920
ctggcggccg tgggcgcaag agcctccgtg ctgagcggcg agagctgga caagtgggag    1980 aagatccgcc tgcgccccgg cggcaagaag aagtaccagc tgaagcacat cgtgtgggcc    2040
agccgcgagc tggagcgctt cgccgtgaac cccggcctgc tcgagaccag cgaaggctgc    2100
cgccagatca tgggccagct ccagcccagc ctccagaccg gcagcgagga gctgcgcagc    2160
ctgtacaaca ccgtggccac cctgtactgc gtgcaccaga gatcgaggt gaaggacacc    2220 aaggaggccc tggacaaggt ggaggaggag cagaacaaca gcaagaagaa ggcccagcag    2280
gaggccgccg acgccggcaa ccgcaaccaa gtcagccaga actaccccat cgtgcagaac    2340
ctgcagggcc agatggtgca ccaggccatc agccccgca ccctgaacgc ctgggtgaag    2400
gtggtggagg agaaggcctt cagccccgag gtgatcccca tgttcagcgc cctgagcgag    2460
ggcgctaccc ccaggacct gaacaccatg ctgaacaccg tgggcggcca ccaggccgcc    2520
atgcagatgc tgaaggagac catcaacgag gaggccgccg agtgggaccg cctgcacccc    2580
gtgcacgccg ggcccatcgc ccccggccag atgcgcgagc ccgcggcag cgacatcgcc    2640 ggcaccacca gcaccctcca ggagcagatc ggctggatga ccaacaaccc ccccatcccc    2700
gtgggcgaga tctacaagcg ctggatcatc ctgggcctga acaagatcgt ccgcatgtac    2760
agccccacca gcatcctgga catcaagcag ggccccaagg agcccttccg cgactacgtg    2820
gaccgcttct acaagaccct gcgcgccgag caggccaccc aggaggtgaa gaactggatg    2880
accgagaccc tgctggtgca gaacgccaac cccgactgca gaccatcct caaggccctg    2940 ggacccgccg ccaccctgga ggagatgatg accgcctgcc aaggcgtggg cggccccggc    3000
cacaaggccc gcgtgctgtg a                                             3021

<210> SEQ ID NO 23
<211> LENGTH: 3021
<212> TYPE: DNA
<213> ORGANISM: Artificial Sequence
<220> FEATURE:
<223> OTHER INFORMATION: Hybrid protein cds comprised of Rev-Nef-Tat,
      CTL and truncated Gag protein (RNT-CTL-optp17/24)

<400> SEQUENCE: 23
atggcaggaa gaagcggaga cagcgacgaa gagctcctca agacagtcag actcatcaag      60
tttctctacc aaagcaaccc tcctcccagc aacgagggga cccgacaggc ccgaagaaat     120
cgaagaagaa ggtggagaga gagacagagg cagatccgtt cgattagtga gcggattctt     180 agcactttc tggacgacc tgcggagcct gtgcctcttc agctaccgcc gcttgagaga     240
cttactcttg attgtagcga agattgtgga aactctggga cgcagggggt gggaagtcct     300
caagtattgg tggaatctcc tgcagtattg gagccaggaa ctaaagaaac tagtgtgggc     360
```

```
aagtggtcaa aatgtagtgg atggcctact gtaagggaaa gaatgaaaca agctgagcct    420
gagccagcag cagatggggt gggagcagca tctcgagacc tggaaaaaca tggagcaatc    480
acaagtagca atacagcaac taataacgct gcttgtgcct ggctagaagc acaagaggaa    540
gaggaagtgg gttttccagt cagacctcag gtacctttaa gaccaatgac ttacaaggga    600
gctttagatc ttagccactt tttaaaagaa aaggggggac tggaagggtt aatttactcc    660
ccaaaaagac aagagatcct tgatctgtgg gtctaccaca cacaaggcta cttccctgat    720
tggcagaact acacaccagg gccagggtc agatatccac tgacctttgg atggtgcttc     780
aagttagtac cagttgaacc agatgaagaa gagaacagca gcctgttaca ccctgcgagc    840
ctgcatggga cagaggacac ggagagaaa gtgttaaagt ggaagtttga cagccatcta     900
gcatttcatc acaaggcccg agagctgcat ccggagtact acaaagactg caagcttgag    960
ccagtagatc ctagactaga gccctggaag catccaggaa gtcagcctag gacccttgt    1020 accaattgct attgtaaaaa gtgttgcctt cattgccaag tttgtttcac aagaaaaggc    1080
ttaggcatct cctatggcag gaagaagcgg agacagcgac gaagagctcc tcaagacagt    1140
cagactcatc aagtttctct accaaagcaa ccctcctccc agcaacgagg ggaccccgaca   1200 ggcccgaaga atcgaagaa gaaggtggag agagagacag aggcagatcc gttcgatgcg     1260
gccgtcatca ccctgtggca gcgccccctg gtggccctga tcgagatctg caccgagatg    1320
gagaaggagg gcaagatcag caagatcggc cccgccggcc tgaagaagaa gaagagcgtg    1380
accgtgctgg acgtgggcga cgcctacttc agcgtgcccc tggataagga cttccgcaag    1440
tacaccgcct tcaccatccc cagcatctgg aagggcagcc ccgccatctt ccagagcagc    1500
atgaccaaga agcagaaccc cgacatcgtg atctaccagt acatggacga cctgtacgtg    1560
cccatcgtgc tgcccgagaa ggacagctgg ctggtgggca agctgaactg gccagccag    1620 atctacgccg gcatcaaggt gaagcagctg atcctgaagg agcccgtgca cggcgtgtac    1680
gagcccatcg tgggcgccga gccttctac gtggacggcg ccgccaaccg cgccggcaac    1740
ctgtgggtga ccgtgtacta cggcgtgccc gtgtggaagg aggccaccac caccctggtg    1800
gagcgctacc tgcgcgacca gcagctgctg ggcatctggg gctgcgcctg cacccctac     1860 gacatcaacc agatgctgcg cggccctggc cgcgccttcg tgaccatccg ccagggcagc    1920
ctggcggccg tgggcgcaag agcctccgtg ctgagcggcg gagagctgga caagtgggag    1980
aagatccgcc tgcgccccgg cggcaagaag aagtaccagc tgaagcacat cgtgtgggcc    2040
agccgcgagc tggagcgctt cgccgtgaac cccggcctgc tcgagaccag cgaaggctgc    2100
cgccagatca tgggccagct ccagcccagc ctccagaccg cagcgagga gctgcgcagc     2160 ctgtacaaca ccgtggccac cctgtactgc gtgcaccaga gatcgaggt gaaggacacc     2220 aaggaggccc tggacaaggt ggaggaggag cagaacaaca gcaagaagaa ggcccagcag    2280
gaggccgccg acgccggcaa ccgcaaccaa gtcagccaga actacccat cgtgcagaac     2340 ctgcaggcc agatggtgca ccaggccatc agccccgca ccctgaacgc ctgggtgaag      2400
gtggtggagg agaaggcctt cagccccgag gtgatccca tgttcagcgc cctgagcgag    2460
ggcgctaccc cccaggacct gaacaccatg ctgaacaccg tggcggcca ccaggccgcc    2520 atgcagatgc tgaaggagac catcaacgag gaggccgccg agtgggaccg cctgcacccc    2580
gtgcacgccg gcccatcgc ccccggccag atgcgcgagc cccgcggcag cgacatcgcc    2640
ggcaccacca gcacactcca ggagcagatc ggctggatga ccaacaaccc ccccatcccc    2700
```

```
gtgggcgaga tctacaagcg ctggatcatc ctgggcctga caagatcgt ccgcatgtac      2760 agccccacca gcatcctgga catcaagcag ggccccaagg agcccttccg cgactacgtg      2820
gaccgcttct acaagaccct gcgcgccgag caggccaccc aggaggtgaa gaactggatg      2880
accgagaccc tgctggtgca gaacgccaac cccgactgca gaccatcct caaggccctg      2940 ggacccgccg ccaccctgga ggagatgatg accgcctgcc aaggcgtggg cggccccggc      3000
cacaaggccc gcgtgctgtg a                                               3021

<210> SEQ ID NO 24
<211> LENGTH: 3021
<212> TYPE: DNA
<213> ORGANISM: Artificial Sequence
<220> FEATURE:
<223> OTHER INFORMATION: Hybrid protein cds comprised of Rev-Nef-Tat,
      truncated Gag protein and CTL (RNT-optp17/24-CTL)

<400> SEQUENCE: 24
atggcaggaa gaagcggaga cagcgacgaa gagctcctca agacagtcag actcatcaag        60
tttctctacc aaagcaaccc tcctcccagc aacgagggga cccgacaggc ccgaagaaat       120
cgaagaagaa ggtggagaga gagacagagg cagatccgtt cgattagtga gcggattctt       180
agcacttttc tgggacgacc tgcggagcct gtgcctcttc agctaccgcc gcttgagaga       240
cttactcttg attgtagcga agattgtgga aactctggga cgcaggggt gggaagtcct       300 caagtattgg tggaatctcc tgcagtattg gagccaggaa ctaaagaaac tagtgtgggc       360
aagtggtcaa aatgtagtgg atggcctact gtaagggaaa gaatgaaaca agctgagcct       420
gagccagcag cagatggggt gggagcagca tctcgagacc tggaaaaaca tggagcaatc       480
acaagtagca atacagcaac taataacgct gcttgtgcct ggctagaagc acaagaggaa       540
gaggaagtgg gttttccagt cagacctcag gtacctttaa gaccaatgac ttacaaggga       600
gctttagatc ttagccactt tttaaaagaa aagggggga tggaagggtt aatttactcc       660
ccaaaaagac aagagatcct tgatctgtgg gtctaccaca cacaaggcta cttccctgat       720
tggcagaact acacaccagg gccagggtc agatatccac tgacctttgg atggtgcttc       780
aagttagtac cagttgaacc agatgaagaa gagaacagca gcctgttaca ccctgcgagc       840
ctgcatggga cagaggacac ggagagaaa gtgttaaagt ggaagtttga cagccatcta       900
gcatttcatc acaaggcccg agagctgcat ccggagtact acaaagactg caagcttgag       960
ccagtagatc ctagactaga gccctggaag catccaggaa gtcagcctag acccccttgt      1020
accaattgct attgtaaaaa gtgttgcctt cattgccaag tttgtttcac aagaaaaggc      1080
ttaggcatct cctatggcag gaagaagcgg agacagcgac gaagagctcc tcaagacagt      1140
cagactcatc aagtttctct accaaagcaa ccctcctccc agcaacgagg ggacccgaca      1200
ggcccgaaga atcgaagaa gaaggtggag agagagacag aggcagatcc gttcgatgcg      1260
gccgtgggcg caagagcctc cgtgctgagc ggcggagagc tggacaagtg ggagaagatc      1320
cgcctgcgcc ccggcggcaa gaagaagtac cagctgaagc acatcgtgtg gccagccgc      1380 gagctggagc gcttcgccgt gaaccccggc ctgctcgaga ccagcgaagg ctgccgccag      1440
atcatgggcc agctccagcc cagcctccag accggcagcg aggagctgcg cagcctgtac      1500
aacaccgtgg ccaccctgta ctgcgtgcac cagaagatcg aggtgaagga caccaaggag      1560
gccctggaca aggtggagga ggagcagaac aacagcaaga agaaggccca gcaggaggcc      1620
gccgacgccg gcaaccgcaa ccaagtcagc cagaactacc ccatcgtgca gaacctgcag      1680
```

-continued

```
ggccagatgg tgcaccaggc catcagcccc cgcaccctga acgcctgggt gaaggtggtg    1740
gaggagaagg ccttcagccc cgaggtgatc cccatgttca gcgccctaag cgagggcgct    1800
accccccagg acctgaacac catgctgaac accgtgggcg ccaccaggc cgccatgcag     1860 atgctgaagg agaccatcaa cgaggaggcc gccgagtggg accgcctgca ccccgtgcac    1920
gccgggccca tcgccccccgg ccagatgcgc gagccccgcg cagcgacat cgccggcacc    1980 accagcaccc tccaggagca gatcggctgg atgaccaaca ccccccccat ccccgtgggc    2040
gagatctaca gcgctggat catcctgggc ctgaacaaga tcgtccgcat gtacagcccc    2100
accagcatcc tggacatcaa gcagggcccc aaggagccct ccgcgacta cgtggaccgc    2160 ttctacaaga ccctgcgcgc cgagcaggcc acccaggagg tgaagaactg gatgaccgag    2220
accctgctgg tgcagaacgc caaccccgac tgcaagacca tcctcaaggc cctgggaccc    2280
gccgccaccc tggaggagat gatgaccgcc tgccaaggcg tgggcggccc cggccacaag    2340
gcccgcgtgc tggcggccgt catcaccctg tggcagcgcc ccctggtggc cctgatcgag    2400
atctgcaccg agatggagaa ggagggcaag atcagcaaga tcggccccgc cggcctgaag    2460
aagaagaaga gcgtgaccgt gctggacgtg ggcgacgcct acttcagcgt gcccctggat    2520
aaggacttcc gcaagtacac cgccttcacc atccccagca tctggaaggg cagccccgcc    2580
atcttccaga gcagcatgac caagaagcag aaccccgaca tcgtgatcta ccagtacatg    2640
gacgacctgt acgtgcccat cgtgctgccc gagaaggaca gctggctggt gggcaagctg    2700
aactgggcca gccagatcta cgccggcatc aaggtgaagc agctgatcct gaaggagccc    2760
gtgcacggcg tgtacgagcc catcgtgggc gccgagacct tctacgtgga cggcgccgcc    2820
aaccgcgccg gcaacctgtg ggtgaccgtg tactacggcg tgcccgtgtg gaaggaggcc    2880
accaccaccc tggtggagcg ctacctgcgc gaccagcagc tgctgggcat ctggggctgc    2940
gcctgcaccc cctacgacat caaccagatg ctgcgcggcc ctggccgcgc cttcgtgacc    3000
atccgccagg gcagcctgta g                                              3021
```

<210> SEQ ID NO 25
<211> LENGTH: 419
<212> TYPE: PRT
<213> ORGANISM: Artificial Sequence
<220> FEATURE:
<223> OTHER INFORMATION: Hybrid protein comprised of Nef-Tat-Rev (NTR)

<400> SEQUENCE: 25

```
Met Val Gly Lys Trp Ser Lys Cys Ser Gly Trp Pro Thr Val Arg Glu
1               5                   10                  15

Arg Met Lys Gln Ala Glu Pro Glu Pro Ala Ala Asp Gly Val Gly Ala
            20                  25                  30

Ala Ser Arg Asp Leu Glu Lys His Gly Ala Ile Thr Ser Ser Asn Thr
        35                  40                  45

Ala Thr Asn Asn Ala Ala Cys Ala Trp Leu Glu Ala Gln Glu Glu Glu
    50                  55                  60

Glu Val Gly Phe Pro Val Arg Pro Gln Val Pro Leu Arg Pro Met Thr
65                  70                  75                  80

Tyr Lys Gly Ala Leu Asp Leu Ser His Phe Leu Lys Glu Lys Gly Gly
                85                  90                  95

Leu Glu Gly Leu Ile Tyr Ser Pro Lys Arg Gln Glu Ile Leu Asp Leu
            100                 105                 110

Trp Val Tyr His Thr Gln Gly Tyr Phe Pro Asp Trp Gln Asn Tyr Thr
        115                 120                 125
```

```
Pro Gly Pro Gly Val Arg Tyr Pro Leu Thr Phe Gly Trp Cys Phe Lys
        130                 135                 140

Leu Val Pro Val Glu Pro Asp Glu Glu Glu Asn Ser Ser Leu Leu His
145                 150                 155                 160

Pro Ala Ser Leu His Gly Thr Glu Asp Thr Glu Arg Glu Val Leu Lys
                165                 170                 175

Trp Lys Phe Asp Ser His Leu Ala Phe His His Lys Ala Arg Glu Leu
                180                 185                 190

His Pro Glu Tyr Tyr Lys Asp Cys Thr Ser Ala Gly Arg Ser Gly Asp
            195                 200                 205

Ser Asp Glu Glu Leu Leu Lys Thr Val Arg Leu Ile Lys Phe Leu Tyr
        210                 215                 220

Gln Ser Asn Pro Pro Ser Asn Glu Gly Thr Arg Gln Ala Arg Arg
225                 230                 235                 240

Asn Arg Arg Arg Arg Trp Arg Glu Arg Gln Arg Gln Ile Arg Ser Ile
                245                 250                 255

Ser Glu Arg Ile Leu Ser Thr Phe Leu Gly Arg Pro Ala Glu Pro Val
                260                 265                 270

Pro Leu Gln Leu Pro Pro Leu Glu Arg Leu Thr Leu Asp Cys Ser Glu
            275                 280                 285

Asp Cys Gly Asn Ser Gly Thr Gln Gly Val Gly Ser Pro Gln Val Leu
        290                 295                 300

Val Glu Ser Pro Ala Val Leu Glu Pro Gly Thr Lys Glu Lys Leu Glu
305                 310                 315                 320

Pro Val Asp Pro Arg Leu Glu Pro Trp Lys His Pro Gly Ser Gln Pro
                325                 330                 335

Arg Thr Pro Cys Thr Asn Cys Tyr Cys Lys Lys Cys Cys Leu His Cys
                340                 345                 350

Gln Val Cys Phe Thr Arg Lys Gly Leu Gly Ile Ser Tyr Gly Arg Lys
            355                 360                 365

Lys Arg Arg Gln Arg Arg Ala Pro Gln Asp Ser Gln Thr His Gln
370                 375                 380

Val Ser Leu Pro Lys Gln Pro Ser Ser Gln Arg Gly Asp Pro Thr
385                 390                 395                 400

Gly Pro Lys Lys Ser Lys Lys Lys Val Glu Arg Glu Thr Glu Ala Asp
                405                 410                 415

Pro Phe Asp

<210> SEQ ID NO 26
<211> LENGTH: 419
<212> TYPE: PRT
<213> ORGANISM: Artificial Sequence
<220> FEATURE:
<223> OTHER INFORMATION: Hybrid protein comprised of Tat-Rev-Nef (TRN)

<400> SEQUENCE: 26

Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
                20                  25                  30

His Cys Gln Val Cys Phe Thr Arg Lys Gly Leu Gly Ile Ser Tyr Gly
            35                  40                  45

Arg Lys Lys Arg Arg Gln Arg Arg Arg Ala Pro Gln Asp Ser Gln Thr
        50                  55                  60
```

```
His Gln Val Ser Leu Pro Lys Gln Pro Ser Ser Gln Arg Gly Asp
 65                  70                  75                  80

Pro Thr Gly Pro Lys Ser Lys Lys Val Glu Arg Glu Thr Glu
                 85                  90                  95

Ala Asp Pro Phe Asp Thr Ser Ala Gly Arg Ser Gly Asp Ser Asp Glu
            100                 105                 110

Glu Leu Leu Lys Thr Val Arg Leu Ile Lys Phe Leu Tyr Gln Ser Asn
        115                 120                 125

Pro Pro Pro Ser Asn Glu Gly Thr Arg Gln Ala Arg Arg Asn Arg Arg
    130                 135                 140

Arg Arg Trp Arg Glu Arg Gln Arg Gln Ile Arg Ser Ile Ser Glu Arg
145                 150                 155                 160

Ile Leu Ser Thr Phe Leu Gly Arg Pro Ala Glu Pro Val Pro Leu Gln
                165                 170                 175

Leu Pro Pro Leu Glu Arg Leu Thr Leu Asp Cys Ser Glu Asp Cys Gly
            180                 185                 190

Asn Ser Gly Thr Gln Gly Val Gly Ser Pro Gln Val Leu Val Glu Ser
        195                 200                 205

Pro Ala Val Leu Glu Pro Gly Thr Lys Glu Lys Leu Val Gly Lys Trp
    210                 215                 220

Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
                245                 250                 255

Glu Lys His Gly Ala Ile Thr Ser Ser Asn Thr Ala Thr Asn Asn Ala
            260                 265                 270

Ala Cys Ala Trp Leu Glu Ala Gln Glu Glu Glu Val Gly Phe Pro
        275                 280                 285

Val Arg Pro Gln Val Pro Leu Arg Pro Met Thr Tyr Lys Gly Ala Leu
    290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
                325                 330                 335

Gln Gly Tyr Phe Pro Asp Trp Gln Asn Tyr Thr Pro Gly Pro Gly Val
            340                 345                 350

Arg Tyr Pro Leu Thr Phe Gly Trp Cys Phe Lys Leu Val Pro Val Glu
        355                 360                 365

Pro Asp Glu Glu Glu Asn Ser Ser Leu Leu His Pro Ala Ser Leu His
    370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
                405                 410                 415

Lys Asp Cys

<210> SEQ ID NO 27
<211> LENGTH: 419
<212> TYPE: PRT
<213> ORGANISM: Artificial Sequence
<220> FEATURE:
<223> OTHER INFORMATION: Hybrid protein comprised of Rev-Tat-Nef (RTN)

<400> SEQUENCE: 27

Met Ala Gly Arg Ser Gly Asp Ser Asp Glu Glu Leu Leu Lys Thr Val
```

-continued

```
1               5                   10                  15
Arg Leu Ile Lys Phe Leu Tyr Gln Ser Asn Pro Pro Ser Asn Glu
                20                  25                  30
Gly Thr Arg Gln Ala Arg Arg Asn Arg Arg Arg Trp Arg Glu Arg
                35                  40                  45
Gln Arg Gln Ile Arg Ser Ile Ser Glu Arg Ile Leu Ser Thr Phe Leu
                50                  55                  60
Gly Arg Pro Ala Glu Pro Val Pro Leu Gln Leu Pro Pro Leu Glu Arg
65                  70                  75                  80
Leu Thr Leu Asp Cys Ser Glu Asp Cys Gly Asn Ser Gly Thr Gln Gly
                85                  90                  95
Val Gly Ser Pro Gln Val Leu Val Glu Ser Pro Ala Val Leu Glu Pro
                100                 105                 110
Gly Thr Lys Glu Thr Ser Glu Pro Val Asp Pro Arg Leu Glu Pro Trp
                115                 120                 125
Lys His Pro Gly Ser Gln Pro Arg Thr Pro Cys Thr Asn Cys Tyr Cys
                130                 135                 140
Lys Lys Cys Cys Leu His Cys Gln Val Cys Phe Thr Arg Lys Gly Leu
145                 150                 155                 160
Gly Ile Ser Tyr Gly Arg Lys Lys Arg Arg Gln Arg Arg Ala Pro
                165                 170                 175
Gln Asp Ser Gln Thr His Gln Val Ser Leu Pro Lys Gln Pro Ser Ser
                180                 185                 190
Gln Gln Arg Gly Asp Pro Thr Gly Pro Lys Ser Lys Lys Val
                195                 200                 205
Glu Arg Glu Thr Glu Ala Asp Pro Phe Asp Lys Leu Val Gly Lys Trp
                210                 215                 220
Ser Lys Cys Ser Gly Trp Pro Thr Val Arg Glu Arg Met Lys Gln Ala
225                 230                 235                 240
Glu Pro Glu Pro Ala Ala Asp Gly Val Gly Ala Ala Ser Arg Asp Leu
                245                 250                 255
Glu Lys His Gly Ala Ile Thr Ser Ser Asn Thr Ala Thr Asn Asn Ala
                260                 265                 270
Ala Cys Ala Trp Leu Glu Ala Gln Glu Glu Glu Val Gly Phe Pro
                275                 280                 285
Val Arg Pro Gln Val Pro Leu Arg Pro Met Thr Tyr Lys Gly Ala Leu
                290                 295                 300
Asp Leu Ser His Phe Leu Lys Glu Lys Gly Gly Leu Glu Gly Leu Ile
305                 310                 315                 320
Tyr Ser Pro Lys Arg Gln Glu Ile Leu Asp Leu Trp Val Tyr His Thr
                325                 330                 335
Gln Gly Tyr Phe Pro Asp Trp Gln Asn Tyr Thr Pro Gly Pro Gly Val
                340                 345                 350
Arg Tyr Pro Leu Thr Phe Gly Trp Cys Phe Lys Leu Val Pro Val Glu
                355                 360                 365
Pro Asp Glu Glu Glu Asn Ser Ser Leu Leu His Pro Ala Ser Leu His
                370                 375                 380
Gly Thr Glu Asp Thr Glu Arg Glu Val Leu Lys Trp Lys Phe Asp Ser
385                 390                 395                 400
His Leu Ala Phe His His Lys Ala Arg Glu Leu His Pro Glu Tyr Tyr
                405                 410                 415
Lys Asp Cys
```

<210> SEQ ID NO 28
<211> LENGTH: 419
<212> TYPE: PRT
<213> ORGANISM: Artificial Sequence
<220> FEATURE:
<223> OTHER INFORMATION: Hybrid protein comprised of Tat-Nef-Rev (TNR)

<400> SEQUENCE: 28

```
Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
            20                  25                  30

His Cys Gln Val Cys Phe Thr Arg Lys Gly Leu Gly Ile Ser Tyr Gly
        35                  40                  45

Arg Lys Lys Arg Arg Gln Arg Arg Ala Pro Gln Asp Ser Gln Thr
50                  55                  60

His Gln Val Ser Leu Pro Lys Gln Pro Ser Ser Gln Arg Gly Asp
65                  70                  75                  80

Pro Thr Gly Pro Lys Lys Ser Lys Lys Val Glu Arg Glu Thr Glu
                85                  90                  95

Ala Asp Pro Phe Asp Thr Ser Val Gly Lys Trp Ser Lys Cys Ser Gly
            100                 105                 110

Trp Pro Thr Val Arg Glu Arg Met Lys Gln Ala Glu Pro Glu Pro Ala
        115                 120                 125

Ala Asp Gly Val Gly Ala Ala Ser Arg Asp Leu Glu Lys His Gly Ala
130                 135                 140

Ile Thr Ser Ser Asn Thr Ala Thr Asn Asn Ala Ala Cys Ala Trp Leu
145                 150                 155                 160

Glu Ala Gln Glu Glu Glu Val Gly Phe Pro Val Arg Pro Gln Val
                165                 170                 175

Pro Leu Arg Pro Met Thr Tyr Lys Gly Ala Leu Asp Leu Ser His Phe
            180                 185                 190

Leu Lys Glu Lys Gly Gly Leu Glu Gly Leu Ile Tyr Ser Pro Lys Arg
        195                 200                 205

Gln Glu Ile Leu Asp Leu Trp Val Tyr His Thr Gln Gly Tyr Phe Pro
210                 215                 220

Asp Trp Gln Asn Tyr Thr Pro Gly Pro Gly Val Arg Tyr Pro Leu Thr
225                 230                 235                 240

Phe Gly Trp Cys Phe Lys Leu Val Pro Val Glu Pro Asp Glu Glu
                245                 250                 255

Asn Ser Ser Leu Leu His Pro Ala Ser Leu His Gly Thr Glu Asp Thr
            260                 265                 270

Glu Arg Glu Val Leu Lys Trp Lys Phe Asp Ser His Leu Ala Phe His
        275                 280                 285

His Lys Ala Arg Glu Leu His Pro Glu Tyr Tyr Lys Asp Cys Lys Leu
290                 295                 300

Ala Gly Arg Ser Gly Asp Ser Asp Glu Glu Leu Leu Lys Thr Val Arg
305                 310                 315                 320

Leu Ile Lys Phe Leu Tyr Gln Ser Asn Pro Pro Ser Asn Glu Gly
                325                 330                 335

Thr Arg Gln Ala Arg Arg Asn Arg Arg Arg Trp Arg Glu Arg Gln
            340                 345                 350

Arg Gln Ile Arg Ser Ile Ser Glu Arg Ile Leu Ser Thr Phe Leu Gly
        355                 360                 365
```

-continued

```
Arg Pro Ala Glu Pro Val Pro Leu Gln Leu Pro Pro Leu Glu Arg Leu
    370                 375                 380

Thr Leu Asp Cys Ser Glu Asp Cys Gly Asn Ser Gly Thr Gln Gly Val
385                 390                 395                 400

Gly Ser Pro Gln Val Leu Val Glu Ser Pro Ala Val Leu Glu Pro Gly
                405                 410                 415

Thr Lys Glu

<210> SEQ ID NO 29
<211> LENGTH: 419
<212> TYPE: PRT
<213> ORGANISM: Artificial Sequence
<220> FEATURE:
<223> OTHER INFORMATION: Hybrid protein comprised of Rev-Nef-Tat (RNT)

<400> SEQUENCE: 29

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30

Gly Thr Arg Gln Ala Arg Arg Asn Arg Arg Arg Arg Trp Arg Glu Arg
        35                  40                  45

Gln Arg Gln Ile Arg Ser Ile Ser Glu Arg Ile Leu Ser Thr Phe Leu
    50                  55                  60

Gly Arg Pro Ala Glu Pro Val Pro Leu Gln Leu Pro Pro Leu Glu Arg
65                  70                  75                  80

Leu Thr Leu Asp Cys Ser Glu Asp Cys Gly Asn Ser Gly Thr Gln Gly
                85                  90                  95

Val Gly Ser Pro Gln Val Leu Val Glu Ser Pro Ala Val Leu Glu Pro
            100                 105                 110

Gly Thr Lys Glu Thr Ser Val Gly Lys Trp Ser Lys Cys Ser Gly Trp
        115                 120                 125

Pro Thr Val Arg Glu Arg Met Lys Gln Ala Glu Pro Glu Pro Ala Ala
    130                 135                 140

Asp Gly Val Gly Ala Ala Ser Arg Asp Leu Glu Lys His Gly Ala Ile
145                 150                 155                 160

Thr Ser Ser Asn Thr Ala Thr Asn Asn Ala Ala Cys Ala Trp Leu Glu
                165                 170                 175

Ala Gln Glu Glu Glu Glu Val Gly Phe Pro Val Arg Pro Gln Val Pro
            180                 185                 190

Leu Arg Pro Met Thr Tyr Lys Gly Ala Leu Asp Leu Ser His Phe Leu
        195                 200                 205

Lys Glu Lys Gly Gly Leu Glu Gly Leu Ile Tyr Ser Pro Lys Arg Gln
    210                 215                 220

Glu Ile Leu Asp Leu Trp Val Tyr His Thr Gln Gly Tyr Phe Pro Asp
225                 230                 235                 240

Trp Gln Asn Tyr Thr Pro Gly Pro Gly Val Arg Tyr Pro Leu Thr Phe
                245                 250                 255

Gly Trp Cys Phe Lys Leu Val Pro Val Glu Pro Asp Glu Glu Asn
            260                 265                 270

Ser Ser Leu Leu His Pro Ala Ser Leu His Gly Thr Glu Asp Thr Glu
        275                 280                 285

Arg Glu Val Leu Lys Trp Lys Phe Asp Ser His Leu Ala Phe His His
    290                 295                 300

Lys Ala Arg Glu Leu His Pro Glu Tyr Tyr Lys Asp Cys Lys Leu Glu
```

-continued

```
              305                 310                 315                 320

Pro Val Asp Pro Arg Leu Glu Pro Trp Lys His Pro Gly Ser Gln Pro
                325                 330                 335

Arg Thr Pro Cys Thr Asn Cys Tyr Cys Lys Lys Cys Cys Leu His Cys
                340                 345                 350

Gln Val Cys Phe Thr Arg Lys Gly Leu Gly Ile Ser Tyr Gly Arg Lys
                355                 360                 365

Lys Arg Arg Gln Arg Arg Ala Pro Gln Asp Ser Gln Thr His Gln
                370                 375                 380

Val Ser Leu Pro Lys Gln Pro Ser Ser Gln Arg Gly Asp Pro Thr
385                 390                 395                 400

Gly Pro Lys Lys Ser Lys Lys Val Glu Arg Glu Thr Glu Ala Asp
                405                 410                 415

Pro Phe Asp

<210> SEQ ID NO 30
<211> LENGTH: 387
<212> TYPE: PRT
<213> ORGANISM: Artificial Sequence
<220> FEATURE:
<223> OTHER INFORMATION: Protein comprised of Immunodominant parts of
      the Nef-Tat-Rev(NTR)

<400> SEQUENCE: 30

Met Gly Trp Pro Thr Val Arg Glu Arg Met Lys Gln Ala Glu Pro Glu
1               5                   10                  15

Pro Ala Ala Asp Gly Val Gly Ala Ala Ser Arg Asp Leu Glu Lys His
                20                  25                  30

Gly Ala Ile Thr Ser Ser Asn Thr Ala Thr Asn Asn Ala Ala Cys Ala
                35                  40                  45

Trp Leu Glu Ala Gln Glu Glu Glu Val Gly Phe Pro Val Arg Pro
                50                  55                  60

Gln Val Pro Leu Arg Pro Met Thr Tyr Lys Gly Ala Leu Asp Leu Ser
65              70                  75                  80

His Phe Leu Lys Glu Lys Gly Gly Leu Glu Gly Leu Ile Tyr Ser Pro
                85                  90                  95

Lys Arg Gln Glu Ile Leu Asp Leu Trp Val Tyr His Thr Gln Gly Tyr
                100                 105                 110

Phe Pro Asp Trp Gln Asn Tyr Thr Pro Gly Pro Gly Val Arg Tyr Pro
                115                 120                 125

Leu Thr Phe Gly Trp Cys Phe Lys Leu Val Pro Val Glu Pro Asp Glu
                130                 135                 140

Glu Glu Asn Ser Ser Leu Leu His Pro Ala Ser Leu His Gly Thr Glu
145                 150                 155                 160

Asp Thr Glu Arg Glu Val Leu Lys Trp Lys Phe Asp Ser His Leu Ala
                165                 170                 175

Phe His His Lys Ala Arg Glu Leu His Pro Glu Tyr Tyr Lys Asp Cys
                180                 185                 190

Ala Leu Ala Ala Val Glu Pro Val Asp Pro Arg Leu Glu Pro Trp Lys
                195                 200                 205

His Pro Gly Ser Gln Pro Arg Thr Pro Cys Thr Asn Cys Tyr Cys Lys
                210                 215                 220

Lys Cys Cys Leu His Cys Gln Val Cys Phe Thr Arg Lys Gly Leu Gly
225                 230                 235                 240

Ile Ser Tyr Gly Arg Lys Lys Arg Arg Gln Arg Arg Ala Pro Gln
```

-continued

```
                245                 250                 255
Asp Ser Gln Thr His Gln Val Ser Leu Pro Lys Gln Pro Ser Ser Gln
            260                 265                 270
Gln Arg Gly Asp Pro Thr Gly Pro Lys Lys Ser Gly Leu Ala Ile Leu
        275                 280                 285
Leu Ser Asp Glu Glu Leu Leu Lys Thr Val Arg Leu Ile Lys Phe Leu
    290                 295                 300
Tyr Gln Ser Asn Pro Pro Ser Asn Glu Gly Thr Arg Gln Ala Arg
305                 310                 315                 320
Arg Asn Arg Arg Arg Trp Arg Glu Arg Gln Arg Gln Ile Arg Ser
                325                 330                 335
Ile Ser Glu Arg Ile Leu Ser Thr Phe Leu Gly Arg Pro Ala Glu Pro
            340                 345                 350
Val Pro Leu Gln Leu Pro Pro Leu Glu Arg Leu Thr Leu Asp Cys Ser
        355                 360                 365
Glu Asp Cys Gly Asn Ser Gly Thr Gln Gly Val Gly Ser Pro Gln Val
    370                 375                 380
Leu Val Glu
385

<210> SEQ ID NO 31
<211> LENGTH: 390
<212> TYPE: PRT
<213> ORGANISM: Artificial Sequence
<220> FEATURE:
<223> OTHER INFORMATION: Protein comprised of Immunodominant parts of
      the Nef-Tat-Rev separated by protease sites(NTR)

<400> SEQUENCE: 31

Met Gly Trp Pro Thr Val Arg Glu Arg Met Lys Gln Ala Glu Pro Glu
1               5                   10                  15
Pro Ala Ala Asp Gly Val Gly Ala Ala Ser Arg Asp Leu Glu Lys His
            20                  25                  30
Gly Ala Ile Thr Ser Ser Asn Thr Ala Thr Asn Asn Ala Ala Cys Ala
        35                  40                  45
Trp Leu Glu Ala Gln Glu Glu Glu Val Gly Phe Pro Val Arg Pro
    50                  55                  60
Gln Val Pro Leu Arg Pro Met Thr Tyr Lys Gly Ala Leu Asp Leu Ser
65                  70                  75                  80
His Phe Leu Lys Glu Lys Gly Gly Leu Glu Gly Leu Ile Tyr Ser Pro
                85                  90                  95
Lys Arg Gln Glu Ile Leu Asp Leu Trp Val Tyr His Thr Gln Gly Tyr
            100                 105                 110
Phe Pro Asp Trp Gln Asn Tyr Thr Pro Gly Pro Gly Val Arg Tyr Pro
        115                 120                 125
Leu Thr Phe Gly Trp Cys Phe Lys Leu Val Pro Val Glu Pro Asp Glu
    130                 135                 140
Glu Glu Asn Ser Ser Leu Leu His Pro Ala Ser Leu His Gly Thr Glu
145                 150                 155                 160
Asp Thr Glu Arg Glu Val Leu Lys Trp Lys Phe Asp Ser His Leu Ala
                165                 170                 175
Phe His His Lys Ala Arg Glu Leu His Pro Glu Tyr Tyr Lys Asp Cys
            180                 185                 190
Ala Leu Ala Phe Lys Arg Val Glu Pro Val Asp Pro Arg Leu Glu Pro
        195                 200                 205
```

-continued

```
Trp Lys His Pro Gly Ser Gln Pro Arg Thr Pro Cys Thr Asn Cys Tyr
    210                 215                 220
Cys Lys Lys Cys Cys Leu His Cys Gln Val Cys Phe Thr Arg Lys Gly
225                 230                 235                 240
Leu Gly Ile Ser Tyr Gly Arg Lys Lys Arg Arg Gln Arg Arg Arg Ala
                245                 250                 255
Pro Gln Asp Ser Gln Thr His Gln Val Ser Leu Pro Lys Gln Pro Ser
            260                 265                 270
Ser Gln Gln Arg Gly Asp Pro Thr Gly Pro Lys Lys Ser Val Arg Glu
        275                 280                 285
Lys Arg Leu Leu Ser Asp Glu Leu Leu Lys Thr Val Arg Leu Ile
    290                 295                 300
Lys Phe Leu Tyr Gln Ser Asn Pro Pro Ser Asn Glu Gly Thr Arg
305                 310                 315                 320
Gln Ala Arg Arg Asn Arg Arg Arg Trp Arg Glu Arg Gln Arg Gln
                325                 330                 335
Ile Arg Ser Ile Ser Glu Arg Ile Leu Ser Thr Phe Leu Gly Arg Pro
            340                 345                 350
Ala Glu Pro Val Pro Leu Gln Leu Pro Pro Leu Glu Arg Leu Thr Leu
        355                 360                 365
Asp Cys Ser Glu Asp Cys Gly Asn Ser Gly Thr Gln Gly Val Gly Ser
    370                 375                 380
Pro Gln Val Leu Val Glu
385                 390

<210> SEQ ID NO 32
<211> LENGTH: 386
<212> TYPE: PRT
<213> ORGANISM: Artificial Sequence
<220> FEATURE:
<223> OTHER INFORMATION: Protein comprised of Immunodominant parts of
      the regulatory proteins Nef-Tat-Rev started from aa1 of Nef(N11TR)

<400> SEQUENCE: 32

Met Trp Pro Thr Val Arg Glu Arg Met Lys Gln Ala Glu Pro Glu Pro
1               5                   10                  15
Ala Ala Asp Gly Val Gly Ala Ala Ser Arg Asp Leu Glu Lys His Gly
            20                  25                  30
Ala Ile Thr Ser Ser Asn Thr Ala Thr Asn Ala Ala Cys Ala Trp
        35                  40                  45
Leu Glu Ala Gln Glu Glu Glu Val Gly Phe Pro Val Arg Pro Gln
    50                  55                  60
Val Pro Leu Arg Pro Met Thr Tyr Lys Gly Ala Leu Asp Leu Ser His
65                  70                  75                  80
Phe Leu Lys Glu Lys Gly Gly Leu Glu Gly Leu Ile Tyr Ser Pro Lys
                85                  90                  95
Arg Gln Glu Ile Leu Asp Leu Trp Val Tyr His Thr Gln Gly Tyr Phe
            100                 105                 110
Pro Asp Trp Gln Asn Tyr Thr Pro Gly Pro Gly Val Arg Tyr Pro Leu
        115                 120                 125
Thr Phe Gly Trp Cys Phe Lys Leu Val Pro Val Glu Pro Asp Glu Glu
    130                 135                 140
Glu Asn Ser Ser Leu Leu His Pro Ala Ser Leu His Gly Thr Glu Asp
145                 150                 155                 160
Thr Glu Arg Glu Val Leu Lys Trp Lys Phe Asp Ser His Leu Ala Phe
                165                 170                 175
```

```
His His Lys Ala Arg Glu Leu His Pro Glu Tyr Tyr Lys Asp Cys Ala
            180                 185                 190

Leu Ala Ala Val Glu Pro Val Asp Pro Arg Leu Glu Pro Trp Lys His
            195                 200                 205

Pro Gly Ser Gln Pro Arg Thr Pro Cys Thr Asn Cys Tyr Cys Lys Lys
            210                 215                 220

Cys Cys Leu His Cys Gln Val Cys Phe Thr Arg Lys Gly Leu Gly Ile
225                 230                 235                 240

Ser Tyr Gly Arg Lys Lys Arg Arg Gln Arg Arg Arg Ala Pro Gln Asp
                245                 250                 255

Ser Gln Thr His Gln Val Ser Leu Pro Lys Gln Pro Ser Ser Gln Gln
            260                 265                 270

Arg Gly Asp Pro Thr Gly Pro Lys Ser Gly Leu Ala Ile Leu Leu
            275                 280                 285

Ser Asp Glu Glu Leu Leu Lys Thr Val Arg Leu Ile Lys Phe Leu Tyr
            290                 295                 300

Gln Ser Asn Pro Pro Pro Ser Asn Glu Gly Thr Arg Gln Ala Arg Arg
305                 310                 315                 320

Asn Arg Arg Arg Arg Trp Arg Glu Arg Gln Arg Gln Ile Arg Ser Ile
                325                 330                 335

Ser Glu Arg Ile Leu Ser Thr Phe Leu Gly Arg Pro Ala Glu Pro Val
            340                 345                 350

Pro Leu Gln Leu Pro Pro Leu Glu Arg Leu Thr Leu Asp Cys Ser Glu
            355                 360                 365

Asp Cys Gly Asn Ser Gly Thr Gln Gly Val Gly Ser Pro Gln Val Leu
            370                 375                 380

Val Glu
385

<210> SEQ ID NO 33
<211> LENGTH: 389
<212> TYPE: PRT
<213> ORGANISM: Artificial Sequence
<220> FEATURE:
<223> OTHER INFORMATION: Protein comprised of Immunodominant parts of
      the regulatory proteins Nef-Tat-Rev started from aa1 of Nef
      separated by protease sites(N11TR)

<400> SEQUENCE: 33

Met Trp Pro Thr Val Arg Glu Arg Met Lys Gln Ala Glu Pro Glu Pro
1               5                   10                  15

Ala Ala Asp Gly Val Gly Ala Ala Ser Arg Asp Leu Glu Lys His Gly
            20                  25                  30

Ala Ile Thr Ser Ser Asn Thr Ala Thr Asn Ala Ala Cys Ala Trp
            35                  40                  45

Leu Glu Ala Gln Glu Glu Glu Val Gly Phe Pro Val Arg Pro Gln
            50                  55                  60

Val Pro Leu Arg Pro Met Thr Tyr Lys Gly Ala Leu Asp Leu Ser His
65                  70                  75                  80

Phe Leu Lys Glu Lys Gly Gly Leu Glu Gly Leu Ile Tyr Ser Pro Lys
                85                  90                  95

Arg Gln Glu Ile Leu Asp Leu Trp Val Tyr His Thr Gln Gly Tyr Phe
                100                 105                 110

Pro Asp Trp Gln Asn Tyr Thr Pro Gly Pro Gly Val Arg Tyr Pro Leu
            115                 120                 125
```

```
Thr Phe Gly Trp Cys Phe Lys Leu Val Pro Val Glu Pro Asp Glu Glu
    130                 135                 140

Glu Asn Ser Ser Leu Leu His Pro Ala Ser Leu His Gly Thr Glu Asp
145                 150                 155                 160

Thr Glu Arg Glu Val Leu Lys Trp Lys Phe Asp Ser His Leu Ala Phe
                165                 170                 175

His His Lys Ala Arg Glu Leu His Pro Glu Tyr Tyr Lys Asp Cys Ala
            180                 185                 190

Leu Ala Phe Lys Arg Val Glu Pro Val Asp Pro Arg Leu Glu Pro Trp
        195                 200                 205

Lys His Pro Gly Ser Gln Pro Arg Thr Pro Cys Thr Asn Cys Tyr Cys
    210                 215                 220

Lys Lys Cys Cys Leu His Cys Gln Val Cys Phe Thr Arg Lys Gly Leu
225                 230                 235                 240

Gly Ile Ser Tyr Gly Arg Lys Lys Arg Arg Gln Arg Arg Ala Pro
                245                 250                 255

Gln Asp Ser Gln Thr His Gln Val Ser Leu Pro Lys Gln Pro Ser Ser
            260                 265                 270

Gln Gln Arg Gly Asp Pro Thr Gly Pro Lys Lys Ser Val Arg Glu Lys
        275                 280                 285

Arg Leu Leu Ser Asp Glu Glu Leu Leu Lys Thr Val Arg Leu Ile Lys
    290                 295                 300

Phe Leu Tyr Gln Ser Asn Pro Pro Ser Asn Glu Gly Thr Arg Gln
305                 310                 315                 320

Ala Arg Arg Asn Arg Arg Arg Trp Arg Glu Arg Gln Ile
                325                 330                 335

Arg Ser Ile Ser Glu Arg Ile Leu Ser Thr Phe Leu Gly Arg Pro Ala
            340                 345                 350

Glu Pro Val Pro Leu Gln Leu Pro Pro Leu Glu Arg Leu Thr Leu Asp
        355                 360                 365

Cys Ser Glu Asp Cys Gly Asn Ser Gly Thr Gln Gly Val Gly Ser Pro
    370                 375                 380

Gln Val Leu Val Glu
385

<210> SEQ ID NO 34
<211> LENGTH: 220
<212> TYPE: PRT
<213> ORGANISM: Artificial Sequence
<220> FEATURE:
<223> OTHER INFORMATION: Protein comprised of Cytotoxic T-cell epitopes
      of Pol and Env genes(CTL)

<400> SEQUENCE: 34

Met Ile Thr Leu Trp Gln Arg Pro Leu Val Ala Leu Ile Glu Ile Cys
1               5                   10                  15

Thr Glu Met Glu Lys Glu Gly Lys Ile Ser Lys Ile Gly Pro Ala Gly
                20                  25                  30

Leu Lys Lys Lys Ser Val Thr Val Leu Asp Val Gly Asp Ala Tyr
            35                  40                  45

Phe Ser Val Pro Leu Asp Lys Asp Phe Arg Lys Tyr Thr Ala Phe Thr
        50                  55                  60

Ile Pro Ser Ile Trp Lys Gly Ser Pro Ala Ile Phe Gln Ser Ser Met
65                  70                  75                  80

Thr Lys Lys Gln Asn Pro Asp Ile Val Ile Tyr Gln Tyr Met Asp Asp
                85                  90                  95
```

```
Leu Tyr Val Pro Ile Val Leu Pro Glu Lys Asp Ser Trp Leu Val Gly
                100                 105                 110

Lys Leu Asn Trp Ala Ser Gln Ile Tyr Ala Gly Ile Lys Val Lys Gln
            115                 120                 125

Leu Ile Leu Lys Glu Pro Val His Gly Val Tyr Glu Pro Ile Val Gly
        130                 135                 140

Ala Glu Thr Phe Tyr Val Asp Gly Ala Ala Asn Arg Ala Gly Asn Leu
145                 150                 155                 160

Trp Val Thr Val Tyr Tyr Gly Val Pro Val Trp Lys Glu Ala Thr Thr
                165                 170                 175

Thr Leu Val Glu Arg Tyr Leu Arg Asp Gln Gln Leu Leu Gly Ile Trp
            180                 185                 190

Gly Cys Ala Cys Thr Pro Tyr Asp Ile Asn Gln Met Leu Arg Gly Pro
        195                 200                 205

Gly Arg Ala Phe Val Thr Ile Arg Gln Gly Ser Leu
    210                 215                 220

<210> SEQ ID NO 35
<211> LENGTH: 421
<212> TYPE: PRT
<213> ORGANISM: Artificial Sequence
<220> FEATURE:
<223> OTHER INFORMATION: Truncated Gag protein sequence(dgag)

<400> SEQUENCE: 35

Met Leu Asp Lys Trp Glu Lys Ile Arg Leu Arg Pro Gly Gly Lys Lys
1               5                   10                  15

Lys Tyr Gln Leu Lys His Ile Val Trp Ala Ser Arg Glu Leu Glu Arg
            20                  25                  30

Phe Ala Val Asn Pro Gly Leu Leu Glu Thr Ser Glu Gly Cys Arg Gln
        35                  40                  45

Ile Met Gly Gln Leu Gln Pro Ser Leu Gln Thr Gly Ser Glu Glu Leu
    50                  55                  60

Arg Ser Leu Tyr Asn Thr Val Ala Thr Leu Tyr Cys Val His Gln Lys
65                  70                  75                  80

Ile Glu Val Lys Asp Thr Lys Glu Ala Leu Asp Lys Val Glu Glu Glu
                85                  90                  95

Gln Asn Asn Ser Lys Lys Lys Ala Gln Gln Glu Ala Ala Asp Ala Gly
            100                 105                 110

Asn Arg Asn Gln Val Ser Gln Asn Tyr Pro Ile Val Gln Asn Leu Gln
        115                 120                 125

Gly Gln Met Val His Gln Ala Ile Ser Pro Arg Thr Leu Asn Ala Trp
    130                 135                 140

Val Lys Val Val Glu Glu Lys Ala Phe Ser Pro Glu Val Ile Pro Met
145                 150                 155                 160

Phe Ser Ala Leu Ser Glu Gly Ala Thr Pro Gln Asp Leu Asn Thr Met
                165                 170                 175

Leu Asn Thr Val Gly Gly His Gln Ala Ala Met Gln Met Leu Lys Glu
            180                 185                 190

Thr Ile Asn Glu Glu Ala Ala Glu Trp Asp Arg Leu His Pro Val His
        195                 200                 205

Ala Gly Pro Ile Ala Pro Gly Gln Met Arg Glu Pro Arg Gly Ser Asp
    210                 215                 220

Ile Ala Gly Thr Thr Ser Thr Leu Gln Glu Gln Ile Gly Trp Met Thr
225                 230                 235                 240
```

```
Asn Asn Pro Pro Ile Pro Val Gly Glu Ile Tyr Lys Arg Trp Ile Ile
                245                 250                 255

Leu Gly Leu Asn Lys Ile Val Arg Met Tyr Ser Pro Thr Ser Ile Leu
            260                 265                 270

Asp Ile Lys Gln Gly Pro Lys Glu Pro Phe Arg Asp Tyr Val Asp Arg
        275                 280                 285

Phe Tyr Lys Thr Leu Arg Ala Glu Gln Ala Thr Gln Glu Val Lys Asn
    290                 295                 300

Trp Met Thr Glu Thr Leu Leu Val Gln Asn Ala Asn Pro Asp Cys Lys
305                 310                 315                 320

Thr Ile Leu Lys Ala Leu Gly Pro Ala Ala Thr Leu Glu Glu Met Met
                325                 330                 335

Thr Ala Cys Gln Gly Val Gly Gly Pro Gly His Lys Ala Arg Val Leu
            340                 345                 350

Ala Glu Ala Met Ser Gln Val Thr Gly Ser Ala Ala Ile Met Met Gln
        355                 360                 365

Arg Gly Asn Phe Arg Asn Gln Arg Lys Thr Val Lys Cys Phe Asn Cys
    370                 375                 380

Gly Lys Glu Gly His Ile Ala Arg Asn Cys Arg Ala Pro Arg Lys Lys
385                 390                 395                 400

Gly Cys Trp Lys Cys Gly Lys Glu Gly His Gln Met Lys Asp Cys Thr
                405                 410                 415

Glu Arg Gln Ala Asn
            420

<210> SEQ ID NO 36
<211> LENGTH: 363
<212> TYPE: PRT
<213> ORGANISM: Artificial Sequence
<220> FEATURE:
<223> OTHER INFORMATION: Synthetic p17/24 protein of Gag gene(Syn 17/24)

<400> SEQUENCE: 36

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Lys Tyr Gln Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Met Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Lys Ile Glu Val Lys Asp
                85                  90                  95

Thr Lys Glu Ala Leu Asp Lys Val Glu Glu Gln Asn Asn Ser Lys
            100                 105                 110

Lys Lys Ala Gln Gln Glu Ala Ala Asp Ala Gly Asn Arg Asn Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175
```

```
Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Lys Gln Gly
            275                 280                 285

Pro Lys Glu Pro Phe Arg Asp Tyr Val Asp Arg Phe Tyr Lys Thr Leu
            290                 295                 300

Arg Ala Glu Gln Ala Thr Gln Glu Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu
            355                 360

<210> SEQ ID NO 37
<211> LENGTH: 363
<212> TYPE: PRT
<213> ORGANISM: Artificial Sequence
<220> FEATURE:
<223> OTHER INFORMATION: Synthetic p17/24 protein of Gag gene optimized
      for expression in eukaryotic cells(optp 17/24)

<400> SEQUENCE: 37

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Lys Tyr Gln Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Met Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Lys Ile Glu Val Lys Asp
                85                  90                  95

Thr Lys Glu Ala Leu Asp Lys Val Glu Glu Glu Gln Asn Asn Ser Lys
            100                 105                 110

Lys Lys Ala Gln Gln Glu Ala Ala Asp Ala Gly Asn Arg Asn Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
```

-continued

```
                165                 170                 175
Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Lys Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Thr Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu
        355                 360

<210> SEQ ID NO 38
<211> LENGTH: 641
<212> TYPE: PRT
<213> ORGANISM: Artificial Sequence
<220> FEATURE:
<223> OTHER INFORMATION: Hybrid protein comprised of Tat-Rev-Nef and
      CTL(TRN-CTL)

<400> SEQUENCE: 38

Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
            20                  25                  30

His Cys Gln Val Cys Phe Thr Arg Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Val Ser Leu Pro Lys Gln Pro Ser Ser Gln Arg Gly Asp
65                  70                  75                  80

Pro Thr Gly Pro Lys Lys Ser Lys Lys Val Glu Arg Glu Thr Glu
            85                  90                  95

Ala Asp Pro Phe Asp Thr Ser Ala Gly Arg Ser Gly Asp Ser Asp Glu
        100                 105                 110

Glu Leu Leu Lys Thr Val Arg Leu Ile Lys Phe Leu Tyr Gln Ser Asn
    115                 120                 125

Pro Pro Pro Ser Asn Glu Gly Thr Arg Gln Ala Arg Arg Asn Arg Arg
    130                 135                 140

Arg Arg Trp Arg Glu Arg Gln Arg Gln Ile Arg Ser Ile Ser Glu Arg
145                 150                 155                 160
```

-continued

```
Ile Leu Ser Thr Phe Leu Gly Arg Pro Ala Glu Pro Val Pro Leu Gln
            165                 170                 175

Leu Pro Pro Leu Glu Arg Leu Thr Leu Asp Cys Ser Glu Asp Cys Gly
            180                 185                 190

Asn Ser Gly Thr Gln Gly Val Gly Ser Pro Gln Val Leu Val Glu Ser
            195                 200                 205

Pro Ala Val Leu Glu Pro Gly Thr Lys Glu Lys Leu Val Gly Lys Trp
            210                 215                 220

Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
            245                 250                 255

Glu Lys His Gly Ala Ile Thr Ser Ser Asn Thr Ala Thr Asn Asn Ala
            260                 265                 270

Ala Cys Ala Trp Leu Glu Ala Gln Glu Glu Glu Val Gly Phe Pro
            275                 280                 285

Val Arg Pro Gln Val Pro Leu Arg Pro Met Thr Tyr Lys Gly Ala Leu
            290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
            325                 330                 335

Gln Gly Tyr Phe Pro Asp Trp Gln Asn Tyr Thr Pro Gly Pro Gly Val
            340                 345                 350

Arg Tyr Pro Leu Thr Phe Gly Trp Cys Phe Lys Leu Val Pro Val Glu
            355                 360                 365

Pro Asp Glu Glu Glu Asn Ser Ser Leu Leu His Pro Ala Ser Leu His
            370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
            405                 410                 415

Lys Asp Cys Ala Ala Val Ile Thr Leu Trp Gln Arg Pro Leu Val Ala
            420                 425                 430

Leu Ile Glu Ile Cys Thr Glu Met Glu Lys Glu Gly Lys Ile Ser Lys
            435                 440                 445

Ile Gly Pro Ala Gly Leu Lys Lys Lys Ser Val Thr Val Leu Asp
450                 455                 460

Val Gly Asp Ala Tyr Phe Ser Val Pro Leu Asp Lys Asp Phe Arg Lys
465                 470                 475                 480

Tyr Thr Ala Phe Thr Ile Pro Ser Ile Trp Lys Gly Ser Pro Ala Ile
            485                 490                 495

Phe Gln Ser Ser Met Thr Lys Lys Gln Asn Pro Asp Ile Val Ile Tyr
            500                 505                 510

Gln Tyr Met Asp Asp Leu Tyr Val Pro Ile Val Leu Pro Glu Lys Asp
            515                 520                 525

Ser Trp Leu Val Gly Lys Leu Asn Trp Ala Ser Gln Ile Tyr Ala Gly
            530                 535                 540

Ile Lys Val Lys Gln Leu Ile Leu Lys Glu Pro Val His Gly Val Tyr
545                 550                 555                 560

Glu Pro Ile Val Gly Ala Glu Thr Phe Tyr Val Asp Gly Ala Ala Asn
            565                 570                 575

Arg Ala Gly Asn Leu Trp Val Thr Val Tyr Tyr Gly Val Pro Val Trp
```

-continued

```
                580                 585                 590
Lys Glu Ala Thr Thr Thr Leu Val Glu Arg Tyr Leu Arg Asp Gln Gln
            595                 600                 605

Leu Leu Gly Ile Trp Gly Cys Ala Cys Thr Pro Tyr Asp Ile Asn Gln
            610                 615                 620

Met Leu Arg Gly Pro Gly Arg Ala Phe Val Thr Ile Arg Gln Gly Ser
625                 630                 635                 640

Leu

<210> SEQ ID NO 39
<211> LENGTH: 641
<212> TYPE: PRT
<213> ORGANISM: Artificial Sequence
<220> FEATURE:
<223> OTHER INFORMATION: Hybrid protein comprised of Rev-Nef-Tat and
      CTL(RNT-CTL)

<400> SEQUENCE: 39

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30

Gly Thr Arg Gln Ala Arg Arg Asn Arg Arg Arg Trp Arg Glu Arg
            35                  40                  45

Gln Arg Gln Ile Arg Ser Ile Ser Glu Arg Ile Leu Ser Thr Phe Leu
            50                  55                  60

Gly Arg Pro Ala Glu Pro Val Pro Leu Gln Leu Pro Pro Leu Glu Arg
65                  70                  75                  80

Leu Thr Leu Asp Cys Ser Glu Asp Cys Gly Asn Ser Gly Thr Gln Gly
                85                  90                  95

Val Gly Ser Pro Gln Val Leu Val Glu Ser Pro Ala Val Leu Glu Pro
            100                 105                 110

Gly Thr Lys Glu Thr Ser Val Gly Lys Trp Ser Lys Cys Ser Gly Trp
            115                 120                 125

Pro Thr Val Arg Glu Arg Met Lys Gln Ala Glu Pro Glu Pro Ala Ala
            130                 135                 140

Asp Gly Val Gly Ala Ala Ser Arg Asp Leu Glu Lys His Gly Ala Ile
145                 150                 155                 160

Thr Ser Ser Asn Thr Ala Thr Asn Asn Ala Ala Cys Ala Trp Leu Glu
                165                 170                 175

Ala Gln Glu Glu Glu Glu Val Gly Phe Pro Val Arg Pro Gln Val Pro
            180                 185                 190

Leu Arg Pro Met Thr Tyr Lys Gly Ala Leu Asp Leu Ser His Phe Leu
            195                 200                 205

Lys Glu Lys Gly Gly Leu Glu Gly Leu Ile Tyr Ser Pro Lys Arg Gln
            210                 215                 220

Glu Ile Leu Asp Leu Trp Val Tyr His Thr Gln Gly Tyr Phe Pro Asp
225                 230                 235                 240

Trp Gln Asn Tyr Thr Pro Gly Pro Gly Val Arg Tyr Pro Leu Thr Phe
                245                 250                 255

Gly Trp Cys Phe Lys Leu Val Pro Val Glu Pro Asp Glu Glu Glu Asn
            260                 265                 270

Ser Ser Leu Leu His Pro Ala Ser Leu His Gly Thr Glu Asp Thr Glu
            275                 280                 285

Arg Glu Val Leu Lys Trp Lys Phe Asp Ser His Leu Ala Phe His His
```

-continued

```
                290                 295                 300
Lys Ala Arg Glu Leu His Pro Glu Tyr Tyr Lys Asp Cys Lys Leu Glu
305                 310                 315                 320
Pro Val Asp Pro Arg Leu Glu Pro Trp Lys His Pro Gly Ser Gln Pro
                325                 330                 335
Arg Thr Pro Cys Thr Asn Cys Tyr Cys Lys Lys Cys Cys Leu His Cys
                340                 345                 350
Gln Val Cys Phe Thr Arg Lys Gly Leu Gly Ile Ser Tyr Gly Arg Lys
                355                 360                 365
Lys Arg Arg Gln Arg Arg Ala Pro Gln Asp Ser Gln Thr His Gln
370                 375                 380
Val Ser Leu Pro Lys Gln Pro Ser Ser Gln Arg Gly Asp Pro Thr
385                 390                 395                 400
Gly Pro Lys Lys Ser Lys Lys Val Glu Arg Glu Thr Glu Ala Asp
                405                 410                 415
Pro Phe Asp Ala Ala Val Ile Thr Leu Trp Gln Arg Pro Leu Val Ala
                420                 425                 430
Leu Ile Glu Ile Cys Thr Glu Met Glu Lys Glu Gly Lys Ile Ser Lys
                435                 440                 445
Ile Gly Pro Ala Gly Leu Lys Lys Lys Ser Val Thr Val Leu Asp
450                 455                 460
Val Gly Asp Ala Tyr Phe Ser Val Pro Leu Asp Lys Asp Phe Arg Lys
465                 470                 475                 480
Tyr Thr Ala Phe Thr Ile Pro Ser Ile Trp Lys Gly Ser Pro Ala Ile
                485                 490                 495
Phe Gln Ser Ser Met Thr Lys Lys Gln Asn Pro Asp Ile Val Ile Tyr
                500                 505                 510
Gln Tyr Met Asp Asp Leu Tyr Val Pro Ile Val Leu Pro Glu Lys Asp
                515                 520                 525
Ser Trp Leu Val Gly Lys Leu Asn Trp Ala Ser Gln Ile Tyr Ala Gly
530                 535                 540
Ile Lys Val Lys Gln Leu Ile Leu Lys Glu Pro Val His Gly Val Tyr
545                 550                 555                 560
Glu Pro Ile Val Gly Ala Glu Thr Phe Tyr Val Asp Gly Ala Ala Asn
                565                 570                 575
Arg Ala Gly Asn Leu Trp Val Thr Val Tyr Gly Val Pro Val Trp
                580                 585                 590
Lys Glu Ala Thr Thr Thr Leu Val Glu Arg Tyr Leu Arg Asp Gln Gln
                595                 600                 605
Leu Leu Gly Ile Trp Gly Cys Ala Cys Thr Pro Tyr Asp Ile Asn Gln
                610                 615                 620
Met Leu Arg Gly Pro Gly Arg Ala Phe Val Thr Ile Arg Gln Gly Ser
625                 630                 635                 640
Leu
```

<210> SEQ ID NO 40
<211> LENGTH: 842
<212> TYPE: PRT
<213> ORGANISM: Artificial Sequence
<220> FEATURE:
<223> OTHER INFORMATION: Hybrid protein cds comprised of Tat-Rev-Nef and truncated Gag protein(TRN-dgag)

<400> SEQUENCE: 40

Met Glu Pro Val Asp Pro Arg Leu Glu Pro Trp Lys His Pro Gly Ser

-continued

```
1               5                   10                  15
Gln Pro Arg Thr Pro Cys Thr Asn Cys Tyr Cys Lys Lys Cys Cys Leu
                20                  25                  30

His Cys Gln Val Cys Phe Thr Arg Lys Gly Leu Gly Ile Ser Tyr Gly
            35                  40                  45

Arg Lys Lys Arg Arg Gln Arg Arg Ala Pro Gln Asp Ser Gln Thr
        50                  55                  60

His Gln Val Ser Leu Pro Lys Gln Pro Ser Ser Gln Gln Arg Gly Asp
65                  70                  75                  80

Pro Thr Gly Pro Lys Lys Ser Lys Lys Val Glu Arg Glu Thr Glu
                85                  90                  95

Ala Asp Pro Phe Asp Thr Ser Ala Gly Arg Ser Gly Asp Ser Asp Glu
                100                 105                 110

Glu Leu Leu Lys Thr Val Arg Leu Ile Lys Phe Leu Tyr Gln Ser Asn
            115                 120                 125

Pro Pro Pro Ser Asn Glu Gly Thr Arg Gln Ala Arg Arg Asn Arg Arg
        130                 135                 140

Arg Arg Trp Arg Glu Arg Gln Arg Gln Ile Arg Ser Ile Ser Glu Arg
145                 150                 155                 160

Ile Leu Ser Thr Phe Leu Gly Arg Pro Ala Glu Pro Val Pro Leu Gln
                165                 170                 175

Leu Pro Pro Leu Glu Arg Leu Thr Leu Asp Cys Ser Glu Asp Cys Gly
                180                 185                 190

Asn Ser Gly Thr Gln Gly Val Gly Ser Pro Gln Val Leu Val Glu Ser
            195                 200                 205

Pro Ala Val Leu Glu Pro Gly Thr Lys Glu Lys Leu Val Gly Lys Trp
        210                 215                 220

Ser Lys Cys Ser Gly Trp Pro Thr Val Arg Glu Arg Met Lys Gln Ala
225                 230                 235                 240

Glu Pro Glu Pro Ala Asp Gly Val Gly Ala Ala Ser Arg Asp Leu
                245                 250                 255

Glu Lys His Gly Ala Ile Thr Ser Ser Asn Thr Ala Thr Asn Asn Ala
            260                 265                 270

Ala Cys Ala Trp Leu Glu Ala Gln Glu Glu Glu Val Gly Phe Pro
        275                 280                 285

Val Arg Pro Gln Val Pro Leu Arg Pro Met Thr Tyr Lys Gly Ala Leu
        290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
                325                 330                 335

Gln Gly Tyr Phe Pro Asp Trp Gln Asn Tyr Thr Pro Gly Pro Gly Val
            340                 345                 350

Arg Tyr Pro Leu Thr Phe Gly Trp Cys Phe Lys Leu Val Pro Val Glu
        355                 360                 365

Pro Asp Glu Glu Glu Asn Ser Ser Leu Leu His Pro Ala Ser Leu His
        370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
                405                 410                 415

Lys Asp Cys Ala Ala Val Leu Asp Lys Trp Glu Lys Ile Arg Leu Arg
                420                 425                 430
```

-continued

```
Pro Gly Gly Lys Lys Lys Tyr Gln Leu Lys His Ile Val Trp Ala Ser
        435                 440                 445

Arg Glu Leu Glu Arg Phe Ala Val Asn Pro Gly Leu Leu Glu Thr Ser
    450                 455                 460

Glu Gly Cys Arg Gln Ile Met Gly Gln Leu Gln Pro Ser Leu Gln Thr
465                 470                 475                 480

Gly Ser Glu Glu Leu Arg Ser Leu Tyr Asn Thr Val Ala Thr Leu Tyr
                485                 490                 495

Cys Val His Gln Lys Ile Glu Val Lys Asp Thr Lys Glu Ala Leu Asp
            500                 505                 510

Lys Val Glu Glu Glu Gln Asn Ser Lys Lys Lys Ala Gln Gln Glu
        515                 520                 525

Ala Ala Asp Ala Gly Asn Arg Asn Gln Val Ser Gln Asn Tyr Pro Ile
    530                 535                 540

Val Gln Asn Leu Gln Gly Gln Met Val His Gln Ala Ile Ser Pro Arg
545                 550                 555                 560

Thr Leu Asn Ala Trp Val Lys Val Val Glu Glu Lys Ala Phe Ser Pro
                565                 570                 575

Glu Val Ile Pro Met Phe Ser Ala Leu Ser Glu Gly Ala Thr Pro Gln
            580                 585                 590

Asp Leu Asn Thr Met Leu Asn Thr Val Gly Gly His Gln Ala Ala Met
        595                 600                 605

Gln Met Leu Lys Glu Thr Ile Asn Glu Glu Ala Ala Glu Trp Asp Arg
    610                 615                 620

Leu His Pro Val His Ala Gly Pro Ile Ala Pro Gly Gln Met Arg Glu
625                 630                 635                 640

Pro Arg Gly Ser Asp Ile Ala Gly Thr Thr Ser Thr Leu Gln Glu Gln
                645                 650                 655

Ile Gly Trp Met Thr Asn Asn Pro Pro Ile Pro Val Gly Glu Ile Tyr
            660                 665                 670

Lys Arg Trp Ile Ile Leu Gly Leu Asn Lys Ile Val Arg Met Tyr Ser
        675                 680                 685

Pro Thr Ser Ile Leu Asp Ile Lys Gln Gly Pro Lys Glu Pro Phe Arg
    690                 695                 700

Asp Tyr Val Asp Arg Phe Tyr Lys Thr Leu Arg Ala Glu Gln Ala Thr
705                 710                 715                 720

Gln Glu Val Lys Asn Trp Met Thr Glu Thr Leu Leu Val Gln Asn Ala
                725                 730                 735

Asn Pro Asp Cys Lys Thr Ile Leu Lys Ala Leu Gly Pro Ala Ala Thr
            740                 745                 750

Leu Glu Glu Met Met Thr Ala Cys Gln Gly Val Gly Gly Pro Gly His
        755                 760                 765

Lys Ala Arg Val Leu Ala Glu Ala Met Ser Gln Val Thr Gly Ser Ala
    770                 775                 780

Ala Ile Met Met Gln Arg Gly Asn Phe Arg Asn Gln Arg Lys Thr Val
785                 790                 795                 800

Lys Cys Phe Asn Cys Gly Lys Glu Gly His Ile Ala Arg Asn Cys Arg
                805                 810                 815

Ala Pro Arg Lys Lys Gly Cys Trp Lys Cys Gly Lys Glu Gly His Gln
            820                 825                 830

Met Lys Asp Cys Thr Glu Arg Gln Ala Asn
        835                 840
```

<210> SEQ ID NO 41
<211> LENGTH: 1064
<212> TYPE: PRT
<213> ORGANISM: Artificial Sequence
<220> FEATURE:
<223> OTHER INFORMATION: Hybrid protein cds comprised of Tat-Rev-Nef,
      CTL and truncated Gag protein(TRN-TCL-dgag)

<400> SEQUENCE: 41

```
Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
            20                  25                  30

His Cys Gln Val Cys Phe Thr Arg Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Val Ser Leu Pro Lys Gln Pro Ser Gln Gln Arg Gly Asp
65                  70                  75                  80

Pro Thr Gly Pro Lys Lys Ser Lys Lys Val Glu Arg Glu Thr Glu
                85                  90                  95

Ala Asp Pro Phe Asp Thr Ser Ala Gly Arg Ser Gly Asp Ser Asp Glu
            100                 105                 110

Glu Leu Leu Lys Thr Val Arg Leu Ile Lys Phe Leu Tyr Gln Ser Asn
        115                 120                 125

Pro Pro Pro Ser Asn Glu Gly Thr Arg Gln Ala Arg Arg Asn Arg Arg
    130                 135                 140

Arg Arg Trp Arg Glu Arg Gln Arg Gln Ile Arg Ser Ile Ser Glu Arg
145                 150                 155                 160

Ile Leu Ser Thr Phe Leu Gly Arg Pro Ala Glu Pro Val Pro Leu Gln
                165                 170                 175

Leu Pro Pro Leu Glu Arg Leu Thr Leu Asp Cys Ser Glu Asp Cys Gly
            180                 185                 190

Asn Ser Gly Thr Gln Gly Val Gly Ser Pro Gln Val Leu Val Glu Ser
        195                 200                 205

Pro Ala Val Leu Glu Pro Gly Thr Lys Glu Lys Leu Val Gly Lys Trp
    210                 215                 220

Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
                245                 250                 255

Glu Lys His Gly Ala Ile Thr Ser Ser Asn Thr Ala Thr Asn Asn Ala
            260                 265                 270

Ala Cys Ala Trp Leu Glu Ala Gln Glu Glu Glu Val Gly Phe Pro
        275                 280                 285

Val Arg Pro Gln Val Pro Leu Arg Pro Met Thr Tyr Lys Gly Ala Leu
    290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
                325                 330                 335

Gln Gly Tyr Phe Pro Asp Trp Gln Asn Tyr Thr Pro Gly Pro Gly Val
            340                 345                 350

Arg Tyr Pro Leu Thr Phe Gly Trp Cys Phe Lys Leu Val Pro Val Glu
        355                 360                 365
```

```
Pro Asp Glu Glu Glu Asn Ser Ser Leu Leu His Pro Ala Ser Leu His
    370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
                405                 410                 415

Lys Asp Cys Ala Ala Val Ile Thr Leu Trp Gln Arg Pro Leu Val Ala
            420                 425                 430

Leu Ile Glu Ile Cys Thr Glu Met Glu Lys Glu Gly Lys Ile Ser Lys
            435                 440                 445

Ile Gly Pro Ala Gly Leu Lys Lys Lys Ser Val Thr Val Leu Asp
    450                 455                 460

Val Gly Asp Ala Tyr Phe Ser Val Pro Leu Asp Lys Asp Phe Arg Lys
465                 470                 475                 480

Tyr Thr Ala Phe Thr Ile Pro Ser Ile Trp Lys Gly Ser Pro Ala Ile
                485                 490                 495

Phe Gln Ser Ser Met Thr Lys Lys Gln Asn Pro Asp Ile Val Ile Tyr
            500                 505                 510

Gln Tyr Met Asp Asp Leu Tyr Val Pro Ile Val Leu Pro Glu Lys Asp
        515                 520                 525

Ser Trp Leu Val Gly Lys Leu Asn Trp Ala Ser Gln Ile Tyr Ala Gly
    530                 535                 540

Ile Lys Val Lys Gln Leu Ile Leu Lys Glu Pro Val His Gly Val Tyr
545                 550                 555                 560

Glu Pro Ile Val Gly Ala Glu Thr Phe Tyr Val Asp Gly Ala Ala Asn
                565                 570                 575

Arg Ala Gly Asn Leu Trp Val Thr Val Tyr Tyr Gly Val Pro Val Trp
            580                 585                 590

Lys Glu Ala Thr Thr Thr Leu Val Glu Arg Tyr Leu Arg Asp Gln Gln
            595                 600                 605

Leu Leu Gly Ile Trp Gly Cys Ala Cys Thr Pro Tyr Asp Ile Asn Gln
    610                 615                 620

Met Leu Arg Gly Pro Gly Arg Ala Phe Val Thr Ile Arg Gln Gly Ser
625                 630                 635                 640

Leu Ala Ala Val Leu Asp Lys Trp Glu Lys Ile Arg Leu Arg Pro Gly
                645                 650                 655

Gly Lys Lys Lys Tyr Gln Leu Lys His Ile Val Trp Ala Ser Arg Glu
            660                 665                 670

Leu Glu Arg Phe Ala Val Asn Pro Gly Leu Leu Glu Thr Ser Glu Gly
        675                 680                 685

Cys Arg Gln Ile Met Gly Gln Leu Gln Pro Ser Leu Gln Thr Gly Ser
    690                 695                 700

Glu Glu Leu Arg Ser Leu Tyr Asn Thr Val Ala Thr Leu Tyr Cys Val
705                 710                 715                 720

His Gln Lys Ile Glu Val Lys Asp Thr Lys Glu Ala Leu Asp Lys Val
                725                 730                 735

Glu Glu Glu Gln Asn Asn Ser Lys Lys Ala Gln Gln Glu Ala Ala
            740                 745                 750

Asp Ala Gly Asn Arg Asn Gln Val Ser Gln Asn Tyr Pro Ile Val Gln
        755                 760                 765

Asn Leu Gln Gly Gln Met Val His Gln Ala Ile Ser Pro Arg Thr Leu
    770                 775                 780
```

```
Asn Ala Trp Val Lys Val Val Glu Glu Lys Ala Phe Ser Pro Glu Val
785                 790                 795                 800

Ile Pro Met Phe Ser Ala Leu Ser Glu Gly Ala Thr Pro Gln Asp Leu
                805                 810                 815

Asn Thr Met Leu Asn Thr Val Gly Gly His Gln Ala Ala Met Gln Met
            820                 825                 830

Leu Lys Glu Thr Ile Asn Glu Glu Ala Ala Glu Trp Asp Arg Leu His
        835                 840                 845

Pro Val His Ala Gly Pro Ile Ala Pro Gly Gln Met Arg Glu Pro Arg
    850                 855                 860

Gly Ser Asp Ile Ala Gly Thr Thr Ser Thr Leu Gln Glu Gln Ile Gly
865                 870                 875                 880

Trp Met Thr Asn Asn Pro Pro Ile Pro Val Gly Glu Ile Tyr Lys Arg
                885                 890                 895

Trp Ile Ile Leu Gly Leu Asn Lys Ile Val Arg Met Tyr Ser Pro Thr
                900                 905                 910

Ser Ile Leu Asp Ile Lys Gln Gly Pro Lys Glu Pro Phe Arg Asp Tyr
        915                 920                 925

Val Asp Arg Phe Tyr Lys Thr Leu Arg Ala Glu Gln Ala Thr Gln Glu
    930                 935                 940

Val Lys Asn Trp Met Thr Glu Thr Leu Leu Val Gln Asn Ala Asn Pro
945                 950                 955                 960

Asp Cys Lys Thr Ile Leu Lys Ala Leu Gly Pro Ala Ala Thr Leu Glu
                965                 970                 975

Glu Met Met Thr Ala Cys Gln Gly Val Gly Gly Pro Gly His Lys Ala
                980                 985                 990

Arg Val Leu Ala Glu Ala Met Ser  Gln Val Thr Gly Ser  Ala Ala Ile
            995                 1000                1005

Met Met  Gln Arg Gly Asn Phe  Arg Asn Gln Arg Lys   Thr Val Lys
    1010                1015                1020

Cys Phe  Asn Cys Gly Lys Glu   Gly His Ile Ala Arg   Asn Cys Arg
    1025                1030                1035

Ala Pro  Arg Lys Lys Gly Cys   Trp Lys Cys Gly Lys   Glu Gly His
    1040                1045                1050

Gln Met  Lys Asp Cys Thr Glu   Arg Gln Ala Asn
    1055                1060

<210> SEQ ID NO 42
<211> LENGTH: 1064
<212> TYPE: PRT
<213> ORGANISM: Artificial Sequence
<220> FEATURE:
<223> OTHER INFORMATION: Hybrid protein comprised of Tat-Rev-Nef, CTL
      and truncated Gag protein(TRN-CTL-dgag)

<400> SEQUENCE: 42

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30

Gly Thr Arg Gln Ala Arg Arg Asn Arg Arg Arg Trp Arg Glu Arg
            35                  40                  45

Gln Arg Gln Ile Arg Ser Ile Ser Glu Arg Ile Leu Ser Thr Phe Leu
    50                  55                  60

Gly Arg Pro Ala Glu Pro Val Pro Leu Gln Leu Pro Pro Leu Glu Arg
65                  70                  75                  80
```

-continued

```
Leu Thr Leu Asp Cys Ser Glu Asp Cys Gly Asn Ser Gly Thr Gln Gly
             85                  90                  95
Val Gly Ser Pro Gln Val Leu Val Glu Ser Pro Ala Val Leu Glu Pro
            100                 105                 110
Gly Thr Lys Glu Thr Ser Val Gly Lys Trp Ser Lys Cys Ser Gly Trp
            115                 120                 125
Pro Thr Val Arg Glu Arg Met Lys Gln Ala Glu Pro Glu Pro Ala Ala
            130                 135                 140
Asp Gly Val Gly Ala Ala Ser Arg Asp Leu Glu Lys His Gly Ala Ile
145                 150                 155                 160
Thr Ser Ser Asn Thr Ala Thr Asn Asn Ala Ala Cys Ala Trp Leu Glu
                165                 170                 175
Ala Gln Glu Glu Glu Val Gly Phe Pro Val Arg Pro Gln Val Pro
            180                 185                 190
Leu Arg Pro Met Thr Tyr Lys Gly Ala Leu Asp Leu Ser His Phe Leu
            195                 200                 205
Lys Glu Lys Gly Gly Leu Glu Gly Leu Ile Tyr Ser Pro Lys Arg Gln
            210                 215                 220
Glu Ile Leu Asp Leu Trp Val Tyr His Thr Gln Gly Tyr Phe Pro Asp
225                 230                 235                 240
Trp Gln Asn Tyr Thr Pro Gly Pro Gly Val Arg Tyr Pro Leu Thr Phe
                245                 250                 255
Gly Trp Cys Phe Lys Leu Val Pro Val Glu Pro Asp Glu Glu Glu Asn
            260                 265                 270
Ser Ser Leu Leu His Pro Ala Ser Leu His Gly Thr Glu Asp Thr Glu
            275                 280                 285
Arg Glu Val Leu Lys Trp Lys Phe Asp Ser His Leu Ala Phe His His
            290                 295                 300
Lys Ala Arg Glu Leu His Pro Glu Tyr Tyr Lys Asp Cys Lys Leu Glu
305                 310                 315                 320
Pro Val Asp Pro Arg Leu Glu Pro Trp Lys His Pro Gly Ser Gln Pro
            325                 330                 335
Arg Thr Pro Cys Thr Asn Cys Tyr Cys Lys Lys Cys Cys Leu His Cys
            340                 345                 350
Gln Val Cys Phe Thr Arg Lys Gly Leu Gly Ile Ser Tyr Gly Arg Lys
            355                 360                 365
Lys Arg Arg Gln Arg Arg Arg Ala Pro Gln Asp Ser Gln Thr His Gln
            370                 375                 380
Val Ser Leu Pro Lys Gln Pro Ser Ser Gln Gln Arg Gly Asp Pro Thr
385                 390                 395                 400
Gly Pro Lys Lys Ser Lys Lys Lys Val Glu Arg Glu Thr Glu Ala Asp
            405                 410                 415
Pro Phe Asp Ala Ala Val Ile Thr Leu Trp Gln Arg Pro Leu Val Ala
            420                 425                 430
Leu Ile Glu Ile Cys Thr Glu Met Glu Lys Glu Gly Lys Ile Ser Lys
            435                 440                 445
Ile Gly Pro Ala Gly Leu Lys Lys Lys Ser Val Thr Val Leu Asp
            450                 455                 460
Val Gly Asp Ala Tyr Phe Ser Val Pro Leu Asp Lys Asp Phe Arg Lys
465                 470                 475                 480
Tyr Thr Ala Phe Thr Ile Pro Ser Ile Trp Lys Gly Ser Pro Ala Ile
                485                 490                 495
```

-continued

```
Phe Gln Ser Ser Met Thr Lys Lys Gln Asn Pro Asp Ile Val Ile Tyr
                500                 505                 510

Gln Tyr Met Asp Asp Leu Tyr Val Pro Ile Val Leu Pro Glu Lys Asp
            515                 520                 525

Ser Trp Leu Val Gly Lys Leu Asn Trp Ala Ser Gln Ile Tyr Ala Gly
        530                 535                 540

Ile Lys Val Lys Gln Leu Ile Leu Lys Glu Pro Val His Gly Val Tyr
545                 550                 555                 560

Glu Pro Ile Val Gly Ala Glu Thr Phe Tyr Val Asp Gly Ala Ala Asn
                565                 570                 575

Arg Ala Gly Asn Leu Trp Val Thr Val Tyr Tyr Gly Val Pro Val Trp
            580                 585                 590

Lys Glu Ala Thr Thr Thr Leu Val Glu Arg Tyr Leu Arg Asp Gln Gln
        595                 600                 605

Leu Leu Gly Ile Trp Gly Cys Ala Cys Thr Pro Tyr Asp Ile Asn Gln
        610                 615                 620

Met Leu Arg Gly Pro Gly Arg Ala Phe Val Thr Ile Arg Gln Gly Ser
625                 630                 635                 640

Leu Ala Ala Val Leu Asp Lys Trp Glu Lys Ile Arg Leu Arg Pro Gly
                645                 650                 655

Gly Lys Lys Lys Tyr Gln Leu Lys His Ile Val Trp Ala Ser Arg Glu
            660                 665                 670

Leu Glu Arg Phe Ala Val Asn Pro Gly Leu Leu Glu Thr Ser Glu Gly
        675                 680                 685

Cys Arg Gln Ile Met Gly Gln Leu Gln Pro Ser Leu Gln Thr Gly Ser
        690                 695                 700

Glu Glu Leu Arg Ser Leu Tyr Asn Thr Val Ala Thr Leu Tyr Cys Val
705                 710                 715                 720

His Gln Lys Ile Glu Val Lys Asp Thr Lys Glu Ala Leu Asp Lys Val
                725                 730                 735

Glu Glu Glu Gln Asn Asn Ser Lys Lys Lys Ala Gln Gln Glu Ala Ala
            740                 745                 750

Asp Ala Gly Asn Arg Asn Gln Val Ser Gln Asn Tyr Pro Ile Val Gln
        755                 760                 765

Asn Leu Gln Gly Gln Met Val His Gln Ala Ile Ser Pro Arg Thr Leu
        770                 775                 780

Asn Ala Trp Val Lys Val Val Glu Glu Lys Ala Phe Ser Pro Glu Val
785                 790                 795                 800

Ile Pro Met Phe Ser Ala Leu Ser Glu Gly Ala Thr Pro Gln Asp Leu
                805                 810                 815

Asn Thr Met Leu Asn Thr Val Gly Gly His Gln Ala Ala Met Gln Met
            820                 825                 830

Leu Lys Glu Thr Ile Asn Glu Glu Ala Ala Glu Trp Asp Arg Leu His
        835                 840                 845

Pro Val His Ala Gly Pro Ile Ala Pro Gly Gln Met Arg Glu Pro Arg
        850                 855                 860

Gly Ser Asp Ile Ala Gly Thr Thr Ser Thr Leu Gln Glu Gln Ile Gly
865                 870                 875                 880

Trp Met Thr Asn Asn Pro Pro Ile Pro Val Gly Glu Ile Tyr Lys Arg
                885                 890                 895

Trp Ile Ile Leu Gly Leu Asn Lys Ile Val Arg Met Tyr Ser Pro Thr
            900                 905                 910

Ser Ile Leu Asp Ile Lys Gln Gly Pro Lys Glu Pro Phe Arg Asp Tyr
```

```
                915                 920                 925

Val Asp Arg Phe Tyr Lys Thr Leu Arg Ala Glu Gln Ala Thr Gln Glu
    930                 935                 940

Val Lys Asn Trp Met Thr Glu Thr Leu Leu Val Gln Asn Ala Asn Pro
945                 950                 955                 960

Asp Cys Lys Thr Ile Leu Lys Ala Leu Gly Pro Ala Ala Thr Leu Glu
                965                 970                 975

Glu Met Met Thr Ala Cys Gln Gly Val Gly Gly Pro Gly His Lys Ala
            980                 985                 990

Arg Val Leu Ala Glu Ala Met Ser Gln Val Thr Gly Ser Ala Ala Ile
        995                 1000                1005

Met Met Gln Arg Gly Asn Phe Arg Asn Gln Arg Lys Thr Val Lys
    1010                1015                1020

Cys Phe Asn Cys Gly Lys Glu Gly His Ile Ala Arg Asn Cys Arg
    1025                1030                1035

Ala Pro Arg Lys Lys Gly Cys Trp Lys Cys Gly Lys Glu Gly His
    1040                1045                1050

Gln Met Lys Asp Cys Thr Glu Arg Gln Ala Asn
    1055                1060
```

<210> SEQ ID NO 43
<211> LENGTH: 1064
<212> TYPE: PRT
<213> ORGANISM: Artificial Sequence
<220> FEATURE:
<223> OTHER INFORMATION: Hybrid protein comprised of Tat-Rev-Nef,
      truncated Gag protein and CTL (TRN-dgag-CTL)

<400> SEQUENCE: 43

```
Met Glu Pro Val Asp Pro Arg Leu Glu Pro Trp Lys His Pro Gly Ser
1               5                   10                  15

Gln Pro Arg Thr Pro Cys Thr Asn Cys Tyr Cys Lys Lys Cys Cys Leu
            20                  25                  30

His Cys Gln Val Cys Phe Thr Arg Lys Gly Leu Gly Ile Ser Tyr Gly
        35                  40                  45

Arg Lys Lys Arg Arg Gln Arg Arg Ala Pro Gln Asp Ser Gln Thr
    50                  55                  60

His Gln Val Ser Leu Pro Lys Gln Pro Ser Ser Gln Gln Arg Gly Asp
65                  70                  75                  80

Pro Thr Gly Pro Lys Lys Ser Lys Lys Lys Val Glu Arg Glu Thr Glu
                85                  90                  95

Ala Asp Pro Phe Asp Thr Ser Ala Gly Arg Ser Gly Asp Ser Asp Glu
            100                 105                 110

Glu Leu Leu Lys Thr Val Arg Leu Ile Lys Phe Leu Tyr Gln Ser Asn
        115                 120                 125

Pro Pro Pro Ser Asn Glu Gly Thr Arg Gln Ala Arg Arg Asn Arg Arg
    130                 135                 140

Arg Arg Trp Arg Glu Arg Gln Arg Gln Ile Arg Ser Ile Ser Glu Arg
145                 150                 155                 160

Ile Leu Ser Thr Phe Leu Gly Arg Pro Ala Glu Pro Val Pro Leu Gln
                165                 170                 175

Leu Pro Pro Leu Glu Arg Leu Thr Leu Asp Cys Ser Glu Asp Cys Gly
            180                 185                 190

Asn Ser Gly Thr Gln Gly Val Gly Ser Pro Gln Val Leu Val Glu Ser
        195                 200                 205
```

```
Pro Ala Val Leu Glu Pro Gly Thr Lys Glu Lys Leu Val Gly Lys Trp
    210                 215                 220

Ser Lys Cys Ser Gly Trp Pro Thr Val Arg Glu Arg Met Lys Gln Ala
225                 230                 235                 240

Glu Pro Glu Pro Ala Ala Asp Gly Val Gly Ala Ala Ser Arg Asp Leu
                    245                 250                 255

Glu Lys His Gly Ala Ile Thr Ser Ser Asn Thr Ala Thr Asn Asn Ala
                260                 265                 270

Ala Cys Ala Trp Leu Glu Ala Gln Glu Glu Glu Val Gly Phe Pro
            275                 280                 285

Val Arg Pro Gln Val Pro Leu Arg Pro Met Thr Tyr Lys Gly Ala Leu
    290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
                325                 330                 335

Gln Gly Tyr Phe Pro Asp Trp Gln Asn Tyr Thr Pro Gly Pro Gly Val
                340                 345                 350

Arg Tyr Pro Leu Thr Phe Gly Trp Cys Phe Lys Leu Val Pro Val Glu
                355                 360                 365

Pro Asp Glu Glu Glu Asn Ser Ser Leu Leu His Pro Ala Ser Leu His
    370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
                405                 410                 415

Lys Asp Cys Ala Ala Val Leu Asp Lys Trp Glu Lys Ile Arg Leu Arg
                420                 425                 430

Pro Gly Gly Lys Lys Lys Tyr Gln Leu Lys His Ile Val Trp Ala Ser
            435                 440                 445

Arg Glu Leu Glu Arg Phe Ala Val Asn Pro Gly Leu Leu Glu Thr Ser
    450                 455                 460

Glu Gly Cys Arg Gln Ile Met Gly Gln Leu Gln Pro Ser Leu Gln Thr
465                 470                 475                 480

Gly Ser Glu Glu Leu Arg Ser Leu Tyr Asn Thr Val Ala Thr Leu Tyr
                485                 490                 495

Cys Val His Gln Lys Ile Glu Val Lys Asp Thr Lys Glu Ala Leu Asp
                500                 505                 510

Lys Val Glu Glu Glu Gln Asn Asn Ser Lys Lys Ala Gln Gln Glu
    515                 520                 525

Ala Ala Asp Ala Gly Asn Arg Asn Gln Val Ser Gln Asn Tyr Pro Ile
530                 535                 540

Val Gln Asn Leu Gln Gly Gln Met Val His Gln Ala Ile Ser Pro Arg
545                 550                 555                 560

Thr Leu Asn Ala Trp Val Lys Val Val Glu Glu Lys Ala Phe Ser Pro
                565                 570                 575

Glu Val Ile Pro Met Phe Ser Ala Leu Ser Glu Gly Ala Thr Pro Gln
                580                 585                 590

Asp Leu Asn Thr Met Leu Asn Thr Val Gly Gly His Gln Ala Ala Met
                595                 600                 605

Gln Met Leu Lys Glu Thr Ile Asn Glu Glu Ala Ala Glu Trp Asp Arg
    610                 615                 620

Leu His Pro Val His Ala Gly Pro Ile Ala Pro Gly Gln Met Arg Glu
```

-continued

```
            625                 630                 635                 640
Pro Arg Gly Ser Asp Ile Ala Gly Thr Thr Ser Thr Leu Gln Glu Gln
                    645                 650                 655
Ile Gly Trp Met Thr Asn Asn Pro Pro Ile Pro Val Gly Glu Ile Tyr
                    660                 665                 670
Lys Arg Trp Ile Ile Leu Gly Leu Asn Lys Ile Val Arg Met Tyr Ser
                    675                 680                 685
Pro Thr Ser Ile Leu Asp Ile Lys Gln Gly Pro Lys Glu Pro Phe Arg
                    690                 695                 700
Asp Tyr Val Asp Arg Phe Tyr Lys Thr Leu Arg Ala Glu Gln Ala Thr
705                 710                 715                 720
Gln Glu Val Lys Asn Trp Met Thr Glu Thr Leu Leu Val Gln Asn Ala
                    725                 730                 735
Asn Pro Asp Cys Lys Thr Ile Leu Lys Ala Leu Gly Pro Ala Ala Thr
                    740                 745                 750
Leu Glu Glu Met Met Thr Ala Cys Gln Gly Val Gly Gly Pro Gly His
                    755                 760                 765
Lys Ala Arg Val Leu Ala Glu Ala Met Ser Gln Val Thr Gly Ser Ala
                    770                 775                 780
Ala Ile Met Met Gln Arg Gly Asn Phe Arg Asn Gln Arg Lys Thr Val
785                 790                 795                 800
Lys Cys Phe Asn Cys Gly Lys Glu Gly His Ile Ala Arg Asn Cys Arg
                    805                 810                 815
Ala Pro Arg Lys Lys Gly Cys Trp Lys Cys Gly Lys Glu Gly His Gln
                    820                 825                 830
Met Lys Asp Cys Thr Glu Arg Gln Ala Asn Ala Ala Val Ile Thr Leu
                    835                 840                 845
Trp Gln Arg Pro Leu Val Ala Leu Ile Glu Ile Cys Thr Glu Met Glu
                    850                 855                 860
Lys Glu Gly Lys Ile Ser Lys Ile Gly Pro Ala Gly Leu Lys Lys Lys
865                 870                 875                 880
Lys Ser Val Thr Val Leu Asp Val Gly Asp Ala Tyr Phe Ser Val Pro
                    885                 890                 895
Leu Asp Lys Asp Phe Arg Lys Tyr Thr Ala Phe Thr Ile Pro Ser Ile
                    900                 905                 910
Trp Lys Gly Ser Pro Ala Ile Phe Gln Ser Ser Met Thr Lys Lys Gln
                    915                 920                 925
Asn Pro Asp Ile Val Ile Tyr Gln Tyr Met Asp Asp Leu Tyr Val Pro
                    930                 935                 940
Ile Val Leu Pro Glu Lys Asp Ser Trp Leu Val Gly Lys Leu Asn Trp
945                 950                 955                 960
Ala Ser Gln Ile Tyr Ala Gly Ile Lys Val Lys Gln Leu Ile Leu Lys
                    965                 970                 975
Glu Pro Val His Gly Val Tyr Glu Pro Ile Val Gly Ala Glu Thr Phe
                    980                 985                 990
Tyr Val Asp Gly Ala Ala Asn Arg  Ala Gly Asn Leu Trp  Val Thr Val
                    995                 1000                1005
Tyr Tyr  Gly Val Pro Val Trp  Lys Glu Ala Thr  Thr Leu Val
                    1010                1015                1020
Glu Arg  Tyr Leu Arg Asp Gln  Gln Leu Leu Gly Ile  Trp Gly Cys
                    1025                1030                1035
Ala Cys  Thr Pro Tyr Asp Ile  Asn Gln Met Leu Arg  Gly Pro Gly
                    1040                1045                1050
```

-continued

```
Arg Ala  Phe Val Thr Ile Arg  Gln Gly Ser Leu
    1055             1060

<210> SEQ ID NO 44
<211> LENGTH: 1064
<212> TYPE: PRT
<213> ORGANISM: Artificial Sequence
<220> FEATURE:
<223> OTHER INFORMATION: Hybrid protein comprised of Rev-Nef-Tat,
      truncated Gag protein and CTL(RNT-dgag-CTL)

<400> SEQUENCE: 44

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30

Gly Thr Arg Gln Ala Arg Arg Asn Arg Arg Arg Trp Arg Glu Arg
            35                  40                  45

Gln Arg Gln Ile Arg Ser Ile Ser Glu Arg Ile Leu Ser Thr Phe Leu
    50                  55                  60

Gly Arg Pro Ala Glu Pro Val Pro Leu Gln Leu Pro Pro Leu Glu Arg
65                  70                  75                  80

Leu Thr Leu Asp Cys Ser Glu Asp Cys Gly Asn Ser Gly Thr Gln Gly
                85                  90                  95

Val Gly Ser Pro Gln Val Leu Val Glu Ser Pro Ala Val Leu Glu Pro
            100                 105                 110

Gly Thr Lys Glu Thr Ser Val Gly Lys Trp Ser Lys Cys Ser Gly Trp
            115                 120                 125

Pro Thr Val Arg Glu Arg Met Lys Gln Ala Glu Pro Glu Pro Ala Ala
    130                 135                 140

Asp Gly Val Gly Ala Ala Ser Arg Asp Leu Glu Lys His Gly Ala Ile
145                 150                 155                 160

Thr Ser Ser Asn Thr Ala Thr Asn Asn Ala Ala Cys Ala Trp Leu Glu
                165                 170                 175

Ala Gln Glu Glu Glu Val Gly Phe Pro Val Arg Pro Gln Val Pro
            180                 185                 190

Leu Arg Pro Met Thr Tyr Lys Gly Ala Leu Asp Leu Ser His Phe Leu
    195                 200                 205

Lys Glu Lys Gly Gly Leu Glu Gly Leu Ile Tyr Ser Pro Lys Arg Gln
    210                 215                 220

Glu Ile Leu Asp Leu Trp Val Tyr His Thr Gln Gly Tyr Phe Pro Asp
225                 230                 235                 240

Trp Gln Asn Tyr Thr Pro Gly Pro Gly Val Arg Tyr Pro Leu Thr Phe
                245                 250                 255

Gly Trp Cys Phe Lys Leu Val Pro Val Glu Pro Asp Glu Glu Glu Asn
            260                 265                 270

Ser Ser Leu Leu His Pro Ala Ser Leu His Gly Thr Glu Asp Thr Glu
            275                 280                 285

Arg Glu Val Leu Lys Trp Lys Phe Asp Ser His Leu Ala Phe His His
    290                 295                 300

Lys Ala Arg Glu Leu His Pro Glu Tyr Tyr Lys Asp Cys Lys Leu Glu
305                 310                 315                 320

Pro Val Asp Pro Arg Leu Glu Pro Trp Lys His Pro Gly Ser Gln Pro
                325                 330                 335

Arg Thr Pro Cys Thr Asn Cys Tyr Cys Lys Lys Cys Cys Leu His Cys
```

-continued

```
            340                 345                 350
Gln Val Cys Phe Thr Arg Lys Gly Leu Gly Ile Ser Tyr Gly Arg Lys
                355                 360                 365
Lys Arg Arg Gln Arg Arg Ala Pro Gln Asp Ser Gln Thr His Gln
    370                 375                 380
Val Ser Leu Pro Lys Gln Pro Ser Ser Gln Arg Gly Asp Pro Thr
385                 390                 395                 400
Gly Pro Lys Lys Ser Lys Lys Val Glu Arg Glu Thr Glu Ala Asp
                405                 410                 415
Pro Phe Asp Ala Ala Val Leu Asp Lys Trp Glu Lys Ile Arg Leu Arg
            420                 425                 430
Pro Gly Gly Lys Lys Lys Tyr Gln Leu Lys His Ile Val Trp Ala Ser
            435                 440                 445
Arg Glu Leu Glu Arg Phe Ala Val Asn Pro Gly Leu Leu Glu Thr Ser
    450                 455                 460
Glu Gly Cys Arg Gln Ile Met Gly Gln Leu Gln Pro Ser Leu Gln Thr
465                 470                 475                 480
Gly Ser Glu Glu Leu Arg Ser Leu Tyr Asn Thr Val Ala Thr Leu Tyr
                485                 490                 495
Cys Val His Gln Lys Ile Glu Val Lys Asp Thr Lys Glu Ala Leu Asp
                500                 505                 510
Lys Val Glu Glu Glu Gln Asn Asn Ser Lys Lys Lys Ala Gln Gln Glu
            515                 520                 525
Ala Ala Asp Ala Gly Asn Arg Asn Gln Val Ser Gln Asn Tyr Pro Ile
    530                 535                 540
Val Gln Asn Leu Gln Gly Gln Met Val His Gln Ala Ile Ser Pro Arg
545                 550                 555                 560
Thr Leu Asn Ala Trp Val Lys Val Val Glu Glu Lys Ala Phe Ser Pro
                565                 570                 575
Glu Val Ile Pro Met Phe Ser Ala Leu Ser Glu Gly Ala Thr Pro Gln
                580                 585                 590
Asp Leu Asn Thr Met Leu Asn Thr Val Gly Gly His Gln Ala Ala Met
            595                 600                 605
Gln Met Leu Lys Glu Thr Ile Asn Glu Glu Ala Ala Glu Trp Asp Arg
    610                 615                 620
Leu His Pro Val His Ala Gly Pro Ile Ala Pro Gly Gln Met Arg Glu
625                 630                 635                 640
Pro Arg Gly Ser Asp Ile Ala Gly Thr Thr Ser Thr Leu Gln Glu Gln
                645                 650                 655
Ile Gly Trp Met Thr Asn Asn Pro Pro Ile Pro Val Gly Glu Ile Tyr
                660                 665                 670
Lys Arg Trp Ile Ile Leu Gly Leu Asn Lys Ile Val Arg Met Tyr Ser
            675                 680                 685
Pro Thr Ser Ile Leu Asp Ile Lys Gln Gly Pro Lys Glu Pro Phe Arg
    690                 695                 700
Asp Tyr Val Asp Arg Phe Tyr Lys Thr Leu Arg Ala Glu Gln Ala Thr
705                 710                 715                 720
Gln Glu Val Lys Asn Trp Met Thr Glu Thr Leu Leu Val Gln Asn Ala
                725                 730                 735
Asn Pro Asp Cys Lys Thr Ile Leu Lys Ala Leu Gly Pro Ala Ala Thr
            740                 745                 750
Leu Glu Glu Met Met Thr Ala Cys Gln Gly Val Gly Gly Pro Gly His
            755                 760                 765
```

```
Lys Ala Arg Val Leu Ala Glu Ala Met Ser Gln Val Thr Gly Ser Ala
    770                 775                 780
Ala Ile Met Met Gln Arg Gly Asn Phe Arg Asn Gln Arg Lys Thr Val
785                 790                 795                 800
Lys Cys Phe Asn Cys Gly Lys Glu Gly His Ile Ala Arg Asn Cys Arg
                805                 810                 815
Ala Pro Arg Lys Lys Gly Cys Trp Lys Cys Gly Lys Glu Gly His Gln
            820                 825                 830
Met Lys Asp Cys Thr Glu Arg Gln Ala Asn Ala Ala Val Ile Thr Leu
        835                 840                 845
Trp Gln Arg Pro Leu Val Ala Leu Ile Glu Ile Cys Thr Glu Met Glu
    850                 855                 860
Lys Glu Gly Lys Ile Ser Lys Ile Gly Pro Ala Gly Leu Lys Lys Lys
865                 870                 875                 880
Lys Ser Val Thr Val Leu Asp Val Gly Asp Ala Tyr Phe Ser Val Pro
                885                 890                 895
Leu Asp Lys Asp Phe Arg Lys Tyr Thr Ala Phe Thr Ile Pro Ser Ile
            900                 905                 910
Trp Lys Gly Ser Pro Ala Ile Phe Gln Ser Ser Met Thr Lys Lys Gln
        915                 920                 925
Asn Pro Asp Ile Val Ile Tyr Gln Tyr Met Asp Asp Leu Tyr Val Pro
    930                 935                 940
Ile Val Leu Pro Glu Lys Asp Ser Trp Leu Val Gly Lys Leu Asn Trp
945                 950                 955                 960
Ala Ser Gln Ile Tyr Ala Gly Ile Lys Val Lys Gln Leu Ile Leu Lys
                965                 970                 975
Glu Pro Val His Gly Val Tyr Glu Pro Ile Val Gly Ala Glu Thr Phe
            980                 985                 990
Tyr Val Asp Gly Ala Ala Asn Arg Ala Gly Asn Leu Trp Val Thr Val
        995                 1000                1005
Tyr Tyr Gly Val Pro Val Trp Lys Glu Ala Thr Thr Thr Leu Val
    1010                1015                1020
Glu Arg Tyr Leu Arg Asp Gln Gln Leu Leu Gly Ile Trp Gly Cys
    1025                1030                1035
Ala Cys Thr Pro Tyr Asp Ile Asn Gln Met Leu Arg Gly Pro Gly
    1040                1045                1050
Arg Ala Phe Val Thr Ile Arg Gln Gly Ser Leu
    1055                1060

<210> SEQ ID NO 45
<211> LENGTH: 1006
<212> TYPE: PRT
<213> ORGANISM: Artificial Sequence
<220> FEATURE:
<223> OTHER INFORMATION: Hybrid protein cds comprised of Tat-Rev-Nef,
      truncated Gag protein and CTL(TRN-optp17/24-CTL )

<400> SEQUENCE: 45

Met Glu Pro Val Asp Pro Arg Leu Glu Pro Trp Lys His Pro Gly Ser
1               5                   10                  15
Gln Pro Arg Thr Pro Cys Thr Asn Cys Tyr Cys Lys Lys Cys Cys Leu
                20                  25                  30
His Cys Gln Val Cys Phe Thr Arg Lys Gly Leu Gly Ile Ser Tyr Gly
            35                  40                  45
Arg Lys Lys Arg Arg Gln Arg Arg Arg Ala Pro Gln Asp Ser Gln Thr
```

```
                 50                   55                    60
His Gln Val Ser Leu Pro Lys Gln Pro Ser Gln Gln Arg Gly Asp
 65                   70                    75                    80

Pro Thr Gly Pro Lys Lys Ser Lys Lys Val Glu Arg Glu Thr Glu
                     85                    90                    95

Ala Asp Pro Phe Asp Thr Ser Ala Gly Arg Ser Gly Asp Ser Asp Glu
                    100                   105                   110

Glu Leu Leu Lys Thr Val Arg Leu Ile Lys Phe Leu Tyr Gln Ser Asn
                    115                   120                   125

Pro Pro Pro Ser Asn Glu Gly Thr Arg Gln Ala Arg Arg Asn Arg Arg
130                   135                   140

Arg Arg Trp Arg Glu Arg Gln Arg Gln Ile Arg Ser Ile Ser Glu Arg
145                   150                   155                   160

Ile Leu Ser Thr Phe Leu Gly Arg Pro Ala Glu Pro Val Pro Leu Gln
                    165                   170                   175

Leu Pro Pro Leu Glu Arg Leu Thr Leu Asp Cys Ser Glu Asp Cys Gly
                    180                   185                   190

Asn Ser Gly Thr Gln Gly Val Gly Ser Pro Gln Val Leu Val Glu Ser
                    195                   200                   205

Pro Ala Val Leu Glu Pro Gly Thr Lys Glu Lys Leu Val Gly Lys Trp
210                   215                   220

Ser Lys Cys Ser Gly Trp Pro Thr Val Arg Glu Arg Met Lys Gln Ala
225                   230                   235                   240

Glu Pro Glu Pro Ala Ala Asp Gly Val Gly Ala Ala Ser Arg Asp Leu
                    245                   250                   255

Glu Lys His Gly Ala Ile Thr Ser Ser Asn Thr Ala Thr Asn Asn Ala
                    260                   265                   270

Ala Cys Ala Trp Leu Glu Ala Gln Glu Glu Glu Val Gly Phe Pro
                    275                   280                   285

Val Arg Pro Gln Val Pro Leu Arg Pro Met Thr Tyr Lys Gly Ala Leu
                    290                   295                   300

Asp Leu Ser His Phe Leu Lys Glu Lys Gly Gly Leu Glu Gly Leu Ile
305                   310                   315                   320

Tyr Ser Pro Lys Arg Gln Glu Ile Leu Asp Leu Trp Val Tyr His Thr
                    325                   330                   335

Gln Gly Tyr Phe Pro Asp Trp Gln Asn Tyr Thr Pro Gly Pro Gly Val
                    340                   345                   350

Arg Tyr Pro Leu Thr Phe Gly Trp Cys Phe Lys Leu Val Pro Val Glu
                    355                   360                   365

Pro Asp Glu Glu Glu Asn Ser Ser Leu Leu His Pro Ala Ser Leu His
                    370                   375                   380

Gly Thr Glu Asp Thr Glu Arg Glu Val Leu Lys Trp Lys Phe Asp Ser
385                   390                   395                   400

His Leu Ala Phe His His Lys Ala Arg Glu Leu His Pro Glu Tyr Tyr
                    405                   410                   415

Lys Asp Cys Ala Ala Val Gly Ala Arg Ala Ser Val Leu Ser Gly Gly
                    420                   425                   430

Glu Leu Asp Lys Trp Glu Lys Ile Arg Leu Arg Pro Gly Gly Lys Lys
                    435                   440                   445

Lys Tyr Gln Leu Lys His Ile Val Trp Ala Ser Arg Glu Leu Glu Arg
                    450                   455                   460

Phe Ala Val Asn Pro Gly Leu Leu Glu Thr Ser Glu Gly Cys Arg Gln
465                   470                   475                   480
```

```
Ile Met Gly Gln Leu Gln Pro Ser Leu Gln Thr Gly Ser Glu Glu Leu
            485                 490                 495

Arg Ser Leu Tyr Asn Thr Val Ala Thr Leu Tyr Cys Val His Gln Lys
            500                 505                 510

Ile Glu Val Lys Asp Thr Lys Glu Ala Leu Asp Lys Val Glu Glu Glu
            515                 520                 525

Gln Asn Asn Ser Lys Lys Ala Gln Gln Ala Ala Asp Ala Gly
            530                 535                 540

Asn Arg Asn Gln Val Ser Gln Asn Tyr Pro Ile Val Gln Asn Leu Gln
545                 550                 555                 560

Gly Gln Met Val His Gln Ala Ile Ser Pro Arg Thr Leu Asn Ala Trp
            565                 570                 575

Val Lys Val Val Glu Glu Lys Ala Phe Ser Pro Glu Val Ile Pro Met
            580                 585                 590

Phe Ser Ala Leu Ser Glu Gly Ala Thr Pro Gln Asp Leu Asn Thr Met
            595                 600                 605

Leu Asn Thr Val Gly Gly His Gln Ala Ala Met Gln Met Leu Lys Glu
            610                 615                 620

Thr Ile Asn Glu Glu Ala Ala Glu Trp Asp Arg Leu His Pro Val His
625                 630                 635                 640

Ala Gly Pro Ile Ala Pro Gly Gln Met Arg Glu Pro Arg Gly Ser Asp
            645                 650                 655

Ile Ala Gly Thr Thr Ser Thr Leu Gln Glu Gln Ile Gly Trp Met Thr
            660                 665                 670

Asn Asn Pro Pro Ile Pro Val Gly Glu Ile Tyr Lys Arg Trp Ile Ile
            675                 680                 685

Leu Gly Leu Asn Lys Ile Val Arg Met Tyr Ser Pro Thr Ser Ile Leu
            690                 695                 700

Asp Ile Lys Gln Gly Pro Lys Glu Pro Phe Arg Asp Tyr Val Asp Arg
705                 710                 715                 720

Phe Tyr Lys Thr Leu Arg Ala Glu Gln Ala Thr Gln Glu Val Lys Asn
            725                 730                 735

Trp Met Thr Glu Thr Leu Leu Val Gln Asn Ala Asn Pro Asp Cys Lys
            740                 745                 750

Thr Ile Leu Lys Ala Leu Gly Pro Ala Ala Thr Leu Glu Glu Met Met
            755                 760                 765

Thr Ala Cys Gln Gly Val Gly Gly Pro Gly His Lys Ala Arg Val Leu
            770                 775                 780

Ala Ala Val Ile Thr Leu Trp Gln Arg Pro Leu Val Ala Leu Ile Glu
785                 790                 795                 800

Ile Cys Thr Glu Met Glu Lys Glu Gly Lys Ile Ser Lys Ile Gly Pro
            805                 810                 815

Ala Gly Leu Lys Lys Lys Ser Val Thr Val Leu Asp Val Gly Asp
            820                 825                 830

Ala Tyr Phe Ser Val Pro Leu Asp Lys Asp Phe Arg Lys Tyr Thr Ala
            835                 840                 845

Phe Thr Ile Pro Ser Ile Trp Lys Gly Ser Pro Ala Ile Phe Gln Ser
            850                 855                 860

Ser Met Thr Lys Lys Gln Asn Pro Asp Ile Val Ile Tyr Gln Tyr Met
865                 870                 875                 880

Asp Asp Leu Tyr Val Pro Ile Val Leu Pro Glu Lys Asp Ser Trp Leu
            885                 890                 895
```

-continued

```
Val Gly Lys Leu Asn Trp Ala Ser Gln Ile Tyr Ala Gly Ile Lys Val
                900             905                 910
Lys Gln Leu Ile Leu Lys Glu Pro Val His Gly Val Tyr Glu Pro Ile
            915                 920                 925
Val Gly Ala Glu Thr Phe Tyr Val Asp Gly Ala Ala Asn Arg Ala Gly
        930                 935                 940
Asn Leu Trp Val Thr Val Tyr Tyr Gly Val Pro Val Trp Lys Glu Ala
945                 950                 955                 960
Thr Thr Thr Leu Val Glu Arg Tyr Leu Arg Asp Gln Leu Leu Gly
                965                 970                 975
Ile Trp Gly Cys Ala Cys Thr Pro Tyr Asp Ile Asn Gln Met Leu Arg
            980                 985                 990
Gly Pro Gly Arg Ala Phe Val Thr Ile Arg Gln Gly Ser Leu
        995                 1000                1005
```

<210> SEQ ID NO 46
<211> LENGTH: 1006
<212> TYPE: PRT
<213> ORGANISM: Artificial Sequence
<220> FEATURE:
<223> OTHER INFORMATION: Hybrid protein cdscomprised of Tat-Rev-Nef, CTL
      and truncated Gag protein (TRN-CTL-optp17/24)

<400> SEQUENCE: 46

```
Met Glu Pro Val Asp Pro Arg Leu Glu Pro Trp Lys His Pro Gly Ser
1               5                   10                  15
Gln Pro Arg Thr Pro Cys Thr Asn Cys Tyr Cys Lys Lys Cys Cys Leu
            20                  25                  30
His Cys Gln Val Cys Phe Thr Arg Lys Gly Leu Gly Ile Ser Tyr Gly
        35                  40                  45
Arg Lys Lys Arg Arg Gln Arg Arg Ala Pro Gln Asp Ser Gln Thr
    50                  55                  60
His Gln Val Ser Leu Pro Lys Gln Pro Ser Gln Gln Arg Gly Asp
65                  70                  75                  80
Pro Thr Gly Pro Lys Lys Ser Lys Lys Val Glu Arg Glu Thr Glu
                85                  90                  95
Ala Asp Pro Phe Asp Thr Ser Ala Gly Arg Ser Gly Asp Ser Asp Glu
            100                 105                 110
Glu Leu Leu Lys Thr Val Arg Leu Ile Lys Phe Leu Tyr Gln Ser Asn
        115                 120                 125
Pro Pro Pro Ser Asn Glu Gly Thr Arg Gln Ala Arg Arg Asn Arg Arg
    130                 135                 140
Arg Arg Trp Arg Glu Arg Gln Arg Gln Ile Arg Ser Ile Ser Glu Arg
145                 150                 155                 160
Ile Leu Ser Thr Phe Leu Gly Arg Pro Ala Glu Pro Val Pro Leu Gln
                165                 170                 175
Leu Pro Pro Leu Glu Arg Leu Thr Leu Asp Cys Ser Glu Asp Cys Gly
            180                 185                 190
Asn Ser Gly Thr Gln Gly Val Gly Ser Pro Gln Val Leu Val Glu Ser
        195                 200                 205
Pro Ala Val Leu Glu Pro Gly Thr Lys Glu Lys Leu Val Gly Lys Trp
    210                 215                 220
Ser Lys Cys Ser Gly Trp Pro Thr Val Arg Glu Arg Met Lys Gln Ala
225                 230                 235                 240
Glu Pro Glu Pro Ala Ala Asp Gly Val Gly Ala Ala Ser Arg Asp Leu
                245                 250                 255
```

-continued

```
Glu Lys His Gly Ala Ile Thr Ser Ser Asn Thr Ala Thr Asn Asn Ala
        260                 265                 270

Ala Cys Ala Trp Leu Glu Ala Gln Glu Glu Glu Val Gly Phe Pro
    275                 280                 285

Val Arg Pro Gln Val Pro Leu Arg Pro Met Thr Tyr Lys Gly Ala Leu
    290                 295                 300

Asp Leu Ser His Phe Leu Lys Glu Lys Gly Gly Leu Glu Gly Leu Ile
305                 310                 315                 320

Tyr Ser Pro Lys Arg Gln Glu Ile Leu Asp Leu Trp Val Tyr His Thr
                325                 330                 335

Gln Gly Tyr Phe Pro Asp Trp Gln Asn Tyr Thr Pro Gly Pro Gly Val
            340                 345                 350

Arg Tyr Pro Leu Thr Phe Gly Trp Cys Phe Lys Leu Val Pro Val Glu
        355                 360                 365

Pro Asp Glu Glu Glu Asn Ser Ser Leu Leu His Pro Ala Ser Leu His
    370                 375                 380

Gly Thr Glu Asp Thr Glu Arg Glu Val Leu Lys Trp Lys Phe Asp Ser
385                 390                 395                 400

His Leu Ala Phe His His Lys Ala Arg Glu Leu His Pro Glu Tyr Tyr
                405                 410                 415

Lys Asp Cys Ala Ala Val Ile Thr Leu Trp Gln Arg Pro Leu Val Ala
            420                 425                 430

Leu Ile Glu Ile Cys Thr Glu Met Glu Lys Glu Gly Lys Ile Ser Lys
        435                 440                 445

Ile Gly Pro Ala Gly Leu Lys Lys Lys Ser Val Thr Val Leu Asp
    450                 455                 460

Val Gly Asp Ala Tyr Phe Ser Val Pro Leu Asp Lys Asp Phe Arg Lys
465                 470                 475                 480

Tyr Thr Ala Phe Thr Ile Pro Ser Ile Trp Lys Gly Ser Pro Ala Ile
                485                 490                 495

Phe Gln Ser Ser Met Thr Lys Lys Gln Asn Pro Asp Ile Val Ile Tyr
            500                 505                 510

Gln Tyr Met Asp Asp Leu Tyr Val Pro Ile Val Leu Pro Glu Lys Asp
        515                 520                 525

Ser Trp Leu Val Gly Lys Leu Asn Trp Ala Ser Gln Ile Tyr Ala Gly
    530                 535                 540

Ile Lys Val Lys Gln Leu Ile Leu Lys Glu Pro Val His Gly Val Tyr
545                 550                 555                 560

Glu Pro Ile Val Gly Ala Glu Thr Phe Tyr Val Asp Gly Ala Ala Asn
                565                 570                 575

Arg Ala Gly Asn Leu Trp Val Thr Val Tyr Tyr Gly Val Pro Val Trp
            580                 585                 590

Lys Glu Ala Thr Thr Thr Leu Val Glu Arg Tyr Leu Arg Asp Gln Gln
        595                 600                 605

Leu Leu Gly Ile Trp Gly Cys Ala Cys Thr Pro Tyr Asp Ile Asn Gln
    610                 615                 620

Met Leu Arg Gly Pro Gly Arg Ala Phe Val Thr Ile Arg Gln Gly Ser
625                 630                 635                 640

Leu Ala Ala Val Gly Ala Arg Ala Ser Val Leu Ser Gly Gly Glu Leu
                645                 650                 655

Asp Lys Trp Glu Lys Ile Arg Leu Arg Pro Gly Gly Lys Lys Lys Tyr
            660                 665                 670
```

```
Gln Leu Lys His Ile Val Trp Ala Ser Arg Glu Leu Glu Arg Phe Ala
            675                 680                 685

Val Asn Pro Gly Leu Leu Glu Thr Ser Glu Gly Cys Arg Gln Ile Met
        690                 695                 700

Gly Gln Leu Gln Pro Ser Leu Gln Thr Gly Ser Glu Glu Leu Arg Ser
705                 710                 715                 720

Leu Tyr Asn Thr Val Ala Thr Leu Tyr Cys Val His Gln Lys Ile Glu
            725                 730                 735

Val Lys Asp Thr Lys Glu Ala Leu Asp Lys Val Glu Glu Glu Gln Asn
        740                 745                 750

Asn Ser Lys Lys Lys Ala Gln Gln Glu Ala Ala Asp Ala Gly Asn Arg
            755                 760                 765

Asn Gln Val Ser Gln Asn Tyr Pro Ile Val Gln Asn Leu Gln Gly Gln
        770                 775                 780

Met Val His Gln Ala Ile Ser Pro Arg Thr Leu Asn Ala Trp Val Lys
785                 790                 795                 800

Val Val Glu Glu Lys Ala Phe Ser Pro Glu Val Ile Pro Met Phe Ser
            805                 810                 815

Ala Leu Ser Glu Gly Ala Thr Pro Gln Asp Leu Asn Thr Met Leu Asn
        820                 825                 830

Thr Val Gly Gly His Gln Ala Ala Met Gln Met Leu Lys Glu Thr Ile
            835                 840                 845

Asn Glu Glu Ala Ala Glu Trp Asp Arg Leu His Pro Val His Ala Gly
850                 855                 860

Pro Ile Ala Pro Gly Gln Met Arg Glu Pro Arg Gly Ser Asp Ile Ala
865                 870                 875                 880

Gly Thr Thr Ser Thr Leu Gln Glu Gln Ile Gly Trp Met Thr Asn Asn
            885                 890                 895

Pro Pro Ile Pro Val Gly Glu Ile Tyr Lys Arg Trp Ile Ile Leu Gly
        900                 905                 910

Leu Asn Lys Ile Val Arg Met Tyr Ser Pro Thr Ser Ile Leu Asp Ile
            915                 920                 925

Lys Gln Gly Pro Lys Glu Pro Phe Arg Asp Tyr Val Asp Arg Phe Tyr
        930                 935                 940

Lys Thr Leu Arg Ala Glu Gln Ala Thr Gln Glu Val Lys Asn Trp Met
945                 950                 955                 960

Thr Glu Thr Leu Leu Val Gln Asn Ala Asn Pro Asp Cys Lys Thr Ile
            965                 970                 975

Leu Lys Ala Leu Gly Pro Ala Ala Thr Leu Glu Glu Met Met Thr Ala
        980                 985                 990

Cys Gln Gly Val Gly Gly Pro Gly  His Lys Ala Arg Val  Leu
        995                 1000                1005

<210> SEQ ID NO 47
<211> LENGTH: 1006
<212> TYPE: PRT
<213> ORGANISM: Artificial Sequence
<220> FEATURE:
<223> OTHER INFORMATION: Hybrid protein comprised of Rev-Nef-Tat, CTL
      and truncated Gag protein (RNT-CTL-optp17/24)

<400> SEQUENCE: 47

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30
```

-continued

```
Gly Thr Arg Gln Ala Arg Arg Asn Arg Arg Arg Trp Arg Glu Arg
         35                  40                  45
Gln Arg Gln Ile Arg Ser Ile Ser Glu Arg Ile Leu Ser Thr Phe Leu
 50                  55                  60
Gly Arg Pro Ala Glu Pro Val Pro Leu Gln Leu Pro Pro Leu Glu Arg
65                  70                  75                  80
Leu Thr Leu Asp Cys Ser Glu Asp Cys Gly Asn Ser Gly Thr Gln Gly
                 85                  90                  95
Val Gly Ser Pro Gln Val Leu Val Glu Ser Pro Ala Val Leu Glu Pro
                100                 105                 110
Gly Thr Lys Glu Thr Ser Val Gly Lys Trp Ser Lys Cys Ser Gly Trp
                115                 120                 125
Pro Thr Val Arg Glu Arg Met Lys Gln Ala Glu Pro Glu Pro Ala Ala
                130                 135                 140
Asp Gly Val Gly Ala Ala Ser Arg Asp Leu Glu Lys His Gly Ala Ile
145                 150                 155                 160
Thr Ser Ser Asn Thr Ala Thr Asn Asn Ala Ala Cys Ala Trp Leu Glu
                165                 170                 175
Ala Gln Glu Glu Glu Glu Val Gly Phe Pro Val Arg Pro Gln Val Pro
                180                 185                 190
Leu Arg Pro Met Thr Tyr Lys Gly Ala Leu Asp Leu Ser His Phe Leu
                195                 200                 205
Lys Glu Lys Gly Gly Leu Glu Gly Leu Ile Tyr Ser Pro Lys Arg Gln
                210                 215                 220
Glu Ile Leu Asp Leu Trp Val Tyr His Thr Gln Gly Tyr Phe Pro Asp
225                 230                 235                 240
Trp Gln Asn Tyr Thr Pro Gly Pro Gly Val Arg Tyr Pro Leu Thr Phe
                245                 250                 255
Gly Trp Cys Phe Lys Leu Val Pro Val Glu Pro Asp Glu Glu Glu Asn
                260                 265                 270
Ser Ser Leu Leu His Pro Ala Ser Leu His Gly Thr Glu Asp Thr Glu
                275                 280                 285
Arg Glu Val Leu Lys Trp Lys Phe Asp Ser His Leu Ala Phe His His
                290                 295                 300
Lys Ala Arg Glu Leu His Pro Glu Tyr Tyr Lys Asp Cys Lys Leu Glu
305                 310                 315                 320
Pro Val Asp Pro Arg Leu Glu Pro Trp Lys His Pro Gly Ser Gln Pro
                325                 330                 335
Arg Thr Pro Cys Thr Asn Cys Tyr Cys Lys Lys Cys Leu His Cys
                340                 345                 350
Gln Val Cys Phe Thr Arg Lys Gly Leu Gly Ile Ser Tyr Gly Arg Lys
                355                 360                 365
Lys Arg Arg Gln Arg Arg Ala Pro Gln Asp Ser Gln Thr His Gln
                370                 375                 380
Val Ser Leu Pro Lys Gln Pro Ser Ser Gln Arg Gly Asp Pro Thr
385                 390                 395                 400
Gly Pro Lys Lys Ser Lys Lys Val Glu Arg Glu Thr Glu Ala Asp
                405                 410                 415
Pro Phe Asp Ala Ala Val Ile Thr Leu Trp Gln Arg Pro Leu Val Ala
                420                 425                 430
Leu Ile Glu Ile Cys Thr Glu Met Glu Lys Glu Gly Lys Ile Ser Lys
                435                 440                 445
```

-continued

```
Ile Gly Pro Ala Gly Leu Lys Lys Lys Ser Val Thr Val Leu Asp
    450                 455                 460
Val Gly Asp Ala Tyr Phe Ser Val Pro Leu Asp Lys Asp Phe Arg Lys
465                 470                 475                 480
Tyr Thr Ala Phe Thr Ile Pro Ser Ile Trp Lys Gly Ser Pro Ala Ile
                485                 490                 495
Phe Gln Ser Ser Met Thr Lys Lys Gln Asn Pro Asp Ile Val Ile Tyr
            500                 505                 510
Gln Tyr Met Asp Asp Leu Tyr Val Pro Ile Val Leu Pro Glu Lys Asp
        515                 520                 525
Ser Trp Leu Val Gly Lys Leu Asn Trp Ala Ser Gln Ile Tyr Ala Gly
    530                 535                 540
Ile Lys Val Lys Gln Leu Ile Leu Lys Glu Pro Val His Gly Val Tyr
545                 550                 555                 560
Glu Pro Ile Val Gly Ala Glu Thr Phe Tyr Val Asp Gly Ala Ala Asn
                565                 570                 575
Arg Ala Gly Asn Leu Trp Val Thr Val Tyr Tyr Gly Val Pro Val Trp
            580                 585                 590
Lys Glu Ala Thr Thr Thr Leu Val Glu Arg Tyr Leu Arg Asp Gln Gln
        595                 600                 605
Leu Leu Gly Ile Trp Gly Cys Ala Cys Thr Pro Tyr Asp Ile Asn Gln
    610                 615                 620
Met Leu Arg Gly Pro Gly Arg Ala Phe Val Thr Ile Arg Gln Gly Ser
625                 630                 635                 640
Leu Ala Ala Val Gly Ala Arg Ala Ser Val Leu Ser Gly Gly Glu Leu
                645                 650                 655
Asp Lys Trp Glu Lys Ile Arg Leu Arg Pro Gly Gly Lys Lys Lys Tyr
            660                 665                 670
Gln Leu Lys His Ile Val Trp Ala Ser Arg Glu Leu Glu Arg Phe Ala
        675                 680                 685
Val Asn Pro Gly Leu Leu Glu Thr Ser Glu Gly Cys Arg Gln Ile Met
    690                 695                 700
Gly Gln Leu Gln Pro Ser Leu Gln Thr Gly Ser Glu Glu Leu Arg Ser
705                 710                 715                 720
Leu Tyr Asn Thr Val Ala Thr Leu Tyr Cys Val His Gln Lys Ile Glu
                725                 730                 735
Val Lys Asp Thr Lys Glu Ala Leu Asp Lys Val Glu Glu Gln Asn
            740                 745                 750
Asn Ser Lys Lys Lys Ala Gln Gln Glu Ala Ala Asp Ala Gly Asn Arg
        755                 760                 765
Asn Gln Val Ser Gln Asn Tyr Pro Ile Val Gln Asn Leu Gln Gly Gln
    770                 775                 780
Met Val His Gln Ala Ile Ser Pro Arg Thr Leu Asn Ala Trp Val Lys
785                 790                 795                 800
Val Val Glu Glu Lys Ala Phe Ser Pro Glu Val Ile Pro Met Phe Ser
                805                 810                 815
Ala Leu Ser Glu Gly Ala Thr Pro Gln Asp Leu Asn Thr Met Leu Asn
            820                 825                 830
Thr Val Gly Gly His Gln Ala Ala Met Gln Met Leu Lys Glu Thr Ile
        835                 840                 845
Asn Glu Glu Ala Ala Glu Trp Asp Arg Leu His Pro Val His Ala Gly
    850                 855                 860
Pro Ile Ala Pro Gly Gln Met Arg Glu Pro Arg Gly Ser Asp Ile Ala
```

-continued

```
                865                 870                 875                 880
Gly Thr Thr Ser Thr Leu Gln Glu Gln Ile Gly Trp Met Thr Asn Asn
                885                 890                 895

Pro Pro Ile Pro Val Gly Glu Ile Tyr Lys Arg Trp Ile Ile Leu Gly
            900                 905                 910

Leu Asn Lys Ile Val Arg Met Tyr Ser Pro Thr Ser Ile Leu Asp Ile
            915                 920                 925

Lys Gln Gly Pro Lys Glu Pro Phe Arg Asp Tyr Val Asp Arg Phe Tyr
    930                 935                 940

Lys Thr Leu Arg Ala Glu Gln Ala Thr Gln Glu Val Lys Asn Trp Met
945                 950                 955                 960

Thr Glu Thr Leu Leu Val Gln Asn Ala Asn Pro Asp Cys Lys Thr Ile
                965                 970                 975

Leu Lys Ala Leu Gly Pro Ala Ala Thr Leu Glu Glu Met Met Thr Ala
            980                 985                 990

Cys Gln Gly Val Gly Gly Pro Gly  His Lys Ala Arg Val  Leu
    995                 1000                1005

<210> SEQ ID NO 48
<211> LENGTH: 1006
<212> TYPE: PRT
<213> ORGANISM: Artificial Sequence
<220> FEATURE:
<223> OTHER INFORMATION: Hybrid protein comprised of Rev-Nef-Tat,
      truncated Gag protein and CTL (RNT-optp17/24-CTL)

<400> SEQUENCE: 48

Met Ala Gly Arg Ser Gly Asp Ser Asp Glu Glu Leu Leu Lys Thr Val
1               5                   10                  15

Arg Leu Ile Lys Phe Leu Tyr Gln Ser Asn Pro Pro Ser Asn Glu
            20                  25                  30

Gly Thr Arg Gln Ala Arg Arg Asn Arg Arg Arg Trp Arg Glu Arg
        35                  40                  45

Gln Arg Gln Ile Arg Ser Ile Ser Glu Arg Ile Leu Ser Thr Phe Leu
    50                  55                  60

Gly Arg Pro Ala Glu Pro Val Pro Leu Gln Leu Pro Pro Leu Glu Arg
65                  70                  75                  80

Leu Thr Leu Asp Cys Ser Glu Asp Cys Gly Asn Ser Gly Thr Gln Gly
                85                  90                  95

Val Gly Ser Pro Gln Val Leu Val Glu Ser Pro Ala Val Leu Glu Pro
            100                 105                 110

Gly Thr Lys Glu Thr Ser Val Gly Lys Trp Ser Lys Cys Ser Gly Trp
        115                 120                 125

Pro Thr Val Arg Glu Arg Met Lys Gln Ala Glu Pro Glu Pro Ala Ala
    130                 135                 140

Asp Gly Val Gly Ala Ala Ser Arg Asp Leu Glu Lys His Gly Ala Ile
145                 150                 155                 160

Thr Ser Ser Asn Thr Ala Thr Asn Asn Ala Ala Cys Ala Trp Leu Glu
                165                 170                 175

Ala Gln Glu Glu Glu Glu Val Gly Phe Pro Val Arg Pro Gln Val Pro
            180                 185                 190

Leu Arg Pro Met Thr Tyr Lys Gly Ala Leu Asp Leu Ser His Phe Leu
        195                 200                 205

Lys Glu Lys Gly Gly Leu Glu Gly Leu Ile Tyr Ser Pro Lys Arg Gln
    210                 215                 220
```

```
Glu Ile Leu Asp Leu Trp Val Tyr His Thr Gln Gly Tyr Phe Pro Asp
225                 230                 235                 240

Trp Gln Asn Tyr Thr Pro Gly Pro Gly Val Arg Tyr Pro Leu Thr Phe
            245                 250                 255

Gly Trp Cys Phe Lys Leu Val Pro Val Glu Pro Asp Glu Glu Glu Asn
                260                 265                 270

Ser Ser Leu Leu His Pro Ala Ser Leu His Gly Thr Glu Asp Thr Glu
            275                 280                 285

Arg Glu Val Leu Lys Trp Lys Phe Asp Ser His Leu Ala Phe His His
            290                 295                 300

Lys Ala Arg Glu Leu His Pro Glu Tyr Tyr Lys Asp Cys Lys Leu Glu
305                 310                 315                 320

Pro Val Asp Pro Arg Leu Glu Pro Trp Lys His Pro Gly Ser Gln Pro
                325                 330                 335

Arg Thr Pro Cys Thr Asn Cys Tyr Cys Lys Lys Cys Leu His Cys
                340                 345                 350

Gln Val Cys Phe Thr Arg Lys Gly Leu Gly Ile Ser Tyr Gly Arg Lys
            355                 360                 365

Lys Arg Arg Gln Arg Arg Ala Pro Gln Asp Ser Gln Thr His Gln
370                 375                 380

Val Ser Leu Pro Lys Gln Pro Ser Ser Gln Arg Gly Asp Pro Thr
385                 390                 395                 400

Gly Pro Lys Lys Ser Lys Lys Val Glu Arg Glu Thr Glu Ala Asp
            405                 410                 415

Pro Phe Asp Ala Ala Val Gly Ala Arg Ala Ser Val Leu Ser Gly Gly
                420                 425                 430

Glu Leu Asp Lys Trp Glu Lys Ile Arg Leu Arg Pro Gly Gly Lys Lys
            435                 440                 445

Lys Tyr Gln Leu Lys His Ile Val Trp Ala Ser Arg Glu Leu Glu Arg
450                 455                 460

Phe Ala Val Asn Pro Gly Leu Leu Glu Thr Ser Glu Gly Cys Arg Gln
465                 470                 475                 480

Ile Met Gly Gln Leu Gln Pro Ser Leu Gln Thr Gly Ser Glu Glu Leu
                485                 490                 495

Arg Ser Leu Tyr Asn Thr Val Ala Thr Leu Tyr Cys Val His Gln Lys
            500                 505                 510

Ile Glu Val Lys Asp Thr Lys Glu Ala Leu Asp Lys Val Glu Glu Glu
            515                 520                 525

Gln Asn Asn Ser Lys Lys Lys Ala Gln Gln Glu Ala Ala Asp Ala Gly
            530                 535                 540

Asn Arg Asn Gln Val Ser Gln Asn Tyr Pro Ile Val Gln Asn Leu Gln
545                 550                 555                 560

Gly Gln Met Val His Gln Ala Ile Ser Pro Arg Thr Leu Asn Ala Trp
                565                 570                 575

Val Lys Val Val Glu Glu Lys Ala Phe Ser Pro Glu Val Ile Pro Met
            580                 585                 590

Phe Ser Ala Leu Ser Glu Gly Ala Thr Pro Gln Asp Leu Asn Thr Met
            595                 600                 605

Leu Asn Thr Val Gly Gly His Gln Ala Ala Met Gln Met Leu Lys Glu
            610                 615                 620

Thr Ile Asn Glu Glu Ala Ala Glu Trp Asp Arg Leu His Pro Val His
625                 630                 635                 640

Ala Gly Pro Ile Ala Pro Gly Gln Met Arg Glu Pro Arg Gly Ser Asp
```

```
                     645                 650                 655
Ile Ala Gly Thr Thr Ser Thr Leu Gln Glu Gln Ile Gly Trp Met Thr
            660                 665                 670

Asn Asn Pro Pro Ile Pro Val Gly Glu Ile Tyr Lys Arg Trp Ile Ile
            675                 680                 685

Leu Gly Leu Asn Lys Ile Val Arg Met Tyr Ser Pro Thr Ser Ile Leu
            690                 695                 700

Asp Ile Lys Gln Gly Pro Lys Glu Pro Phe Arg Asp Tyr Val Asp Arg
705                 710                 715                 720

Phe Tyr Lys Thr Leu Arg Ala Glu Gln Ala Thr Gln Glu Val Lys Asn
                725                 730                 735

Trp Met Thr Glu Thr Leu Leu Val Gln Asn Ala Asn Pro Asp Cys Lys
            740                 745                 750

Thr Ile Leu Lys Ala Leu Gly Pro Ala Ala Thr Leu Glu Glu Met Met
            755                 760                 765

Thr Ala Cys Gln Gly Val Gly Gly Pro Gly His Lys Ala Arg Val Leu
            770                 775                 780

Ala Ala Val Ile Thr Leu Trp Gln Arg Pro Leu Val Ala Leu Ile Glu
785                 790                 795                 800

Ile Cys Thr Glu Met Glu Lys Glu Gly Lys Ile Ser Lys Ile Gly Pro
                805                 810                 815

Ala Gly Leu Lys Lys Lys Lys Ser Val Thr Val Leu Asp Val Gly Asp
            820                 825                 830

Ala Tyr Phe Ser Val Pro Leu Asp Lys Asp Phe Arg Lys Tyr Thr Ala
            835                 840                 845

Phe Thr Ile Pro Ser Ile Trp Lys Gly Ser Pro Ala Ile Phe Gln Ser
850                 855                 860

Ser Met Thr Lys Lys Gln Asn Pro Asp Ile Val Ile Tyr Gln Tyr Met
865                 870                 875                 880

Asp Asp Leu Tyr Val Pro Ile Val Leu Pro Glu Lys Asp Ser Trp Leu
                885                 890                 895

Val Gly Lys Leu Asn Trp Ala Ser Gln Ile Tyr Ala Gly Ile Lys Val
            900                 905                 910

Lys Gln Leu Ile Leu Lys Glu Pro Val His Gly Val Tyr Glu Pro Ile
            915                 920                 925

Val Gly Ala Glu Thr Phe Tyr Val Asp Gly Ala Ala Asn Arg Ala Gly
            930                 935                 940

Asn Leu Trp Val Thr Val Tyr Tyr Gly Val Pro Val Trp Lys Glu Ala
945                 950                 955                 960

Thr Thr Thr Leu Val Glu Arg Tyr Leu Arg Asp Gln Gln Leu Leu Gly
                965                 970                 975

Ile Trp Gly Cys Ala Cys Thr Pro Tyr Asp Ile Asn Gln Met Leu Arg
            980                 985                 990

Gly Pro Gly Arg Ala Phe Val Thr  Ile Arg Gln Gly Ser  Leu
            995                 1000                1005

<210> SEQ ID NO 49
<211> LENGTH: 7945
<212> TYPE: DNA
<213> ORGANISM: Bovine papillomavirus
<220> FEATURE:
<221> NAME/KEY: misc_feature
<222> LOCATION: 1205
<223> OTHER INFORMATION: n = A,T,C or G

<400> SEQUENCE: 49
```

```
gttaacaata atcacaccat caccgttttt tcaagcggga aaaatagcc agctaactat      60
aaaaagctgc tgacagaccc cggttttcac atggacctga aaccttttgc aagaaccaat    120
ccattctcag ggttggattg tctgtggtgc agagagcctc ttacagaagt tgatgctttt    180
aggtgcatgg tcaaagactt tcatgttgta attcgggaag gctgtagata tggtgcatgt    240
accatttgtc ttgaaaactg tttagctact gaaagaagac tttggcaagg tgttccagta    300
acaggtgagg aagctgaatt attgcatggc aaaacacttg ataggctttg cataagatgc    360
tgctactgtg ggggcaaact aacaaaaaat gaaaaacatc ggcatgtgct ttttaatgag    420
cctttctgca aaaccagagc taacataatt agaggacgct gctacgactg ctgcagacat    480
ggttcaaggt ccaaataccc atagaaactt ggatgattca cctgcaggac cgttgctgat    540
tttaagtcca tgtgcaggca cactaccag gtctcctgca gcacctgatg cacctgattt    600
cagacttccg tgccatttcg gccgtcctac taggaagcga ggtcccacta cccctccgct    660
ttcctctccc ggaaaactgt gtgcaacagg gccacgtcga gtgtattctg tgactgtctg    720
ctgtggaaac tgcggaaaag agctgacttt tgctgtgaag accagctcga cgtccctgct    780
tggatttgaa caccttttaa actcagattt agacctcttg tgtccacgtt gtgaatctcg    840
cgagcgtcat ggcaaacgat aaaggtagca attgggattc gggcttggga tgctcatatc    900
tgctgactga ggcagaatgt gaaagtgaca agagaatga ggaacccggg gcaggtgtag     960
aactgtctgt ggaatctgat cggtatgata gccaggatga ggattttgtt gacaatgcat   1020
cagtcttcca gggaaatcac ctggaggtct tccaggcatt agagaaaaag gcgggtgagg   1080
agcagatttt aaatttgaaa agaaaagtat tggggagttc gcaaaacagc agcggttccg   1140
aagcatctga aactccagtt aaaagacgga atcaggagc aaagcgaaga ttatttgctg    1200
aaaangaagc taaccgtgtt cttacgcccc tccaggtaca gggggagggg gagggaggc    1260
aagaacttaa tgaggagcag gcaattagtc atctacatct gcagcttgtt aaatctaaaa   1320
atgctacagt ttttaagctg gggctctta aatctttgtt cctttgtagc ttccatgata    1380
ttacgaggtt gtttaagaat gataagacca ctaatcagca atgggtgctg gctgtgtttg   1440
gccttgcaga ggtgtttttt gaggcgagtt tcgaactcct aaagaagcag tgtagttttc   1500
tgcagatgca aaaagatct catgaaggag gaacttgtgc agtttactta atctgcttta    1560
acacagctaa agcagagaa acagtccgga atctgatggc aaacacgcta atgtaagag     1620
aagagtgttt gatgctgcag ccagctaaaa ttcgaggact cagcgcagct ctattctggt   1680
ttaaaagtag tttgtcaccc gctacactta acatggtgc tttacctgag tggatacggg    1740
cgcaaactac tctgaacgag agcttgcaga ccgagaaatt cgacttcgga actatggtgc   1800
aatgggccta tgatcacaaa tatgctgagg agtctaaaat agcctatgaa tatgctttgg   1860
ctgcaggatc tgatagcaat gcacgggctt tttagcaac taacagccaa gctaagcatg    1920
tgaaggactg tgcaactatg gtaagacact atctaagagc tgaaacacaa gcattaagca   1980
tgcctgcata tattaaagct aggtgcaagc tggcaactgg ggaaggaagc tggaagtcta   2040
tcctaacttt ttttaactat cagaatattg aattaattac ctttattaat gctttaaagc   2100
tctggctaaa aggaattcca aaaaaaact gtttagcatt tattggccct ccaaacacag    2160
gcaagtctat gctctgcaac tcattaattc atttttggg tggtagtgtt ttatcttttg    2220
ccaaccataa aagtcacttt tggcttgctt ccctagcaga tactagagct gctttagtag   2280
atgatgctac tcatgcttgc tggaggtact ttgacacata cctcagaaat gcattggatg   2340
```

-continued

```
gctaccctgt cagtattgat agaaaacaca aagcagcggt tcaaattaaa gctccacccc    2400
tcctggtaac cagtaatatt gatgtgcagg cagaggacag atatttgtac ttgcatagtc    2460
gggtgcaaac ctttcgcttt gagcagccat gcacagatga atcgggtgag caaccttttta   2520 atattactga tgcagattgg aaatcttttt ttgtaaggtt atgggggcgt ttagacctga    2580
ttgacgagga ggaggatagt gaagaggatg gagacagcat gcgaacgttt acatgtagcg    2640
caagaaacac aaatgcagtt gattgagaaa agtagtgata agttgcaaga tcatatactg    2700
tactggactg ctgttagaac tgagaacaca ctgctttatg ctgcaaggaa aaaggggtg    2760 actgtcctag gacactgcag agtaccacac tctgtagttt gtcaagagag agccaagcag    2820
gccattgaaa tgcagttgtc tttgcaggag ttaagcaaaa ctgagtttgg ggatgaacca    2880
tggtctttgc ttgacacaag ctgggaccga tatatgtcag aacctaaacg gtgctttaag    2940
aaaggcgcca gggtggtaga ggtggagttt gatggaaatg caagcaatac aaactggtac    3000
actgtctaca gcaatttgta catgcgcaca gaggacggct ggcagcttgc gaaggctggg    3060
gctgacggaa ctgggctcta ctactgcacc atggccggtg ctggacgcat ttactattct    3120
cgctttggtg acgaggcagc cagatttagt acaacagggc attactctgt aagagatcag    3180
gacagagtgt atgctggtgt ctcatccacc tcttctgatt ttagagatcg cccagacgga    3240
gtctgggtcg catccgaagg acctgaagga gaccctgcag gaaaagaagc cgagccagcc    3300
cagcctgtct cttctttgct cggctccccc gcctgcggtc ccatcagagc aggcctcggt    3360
tgggtacggg acggtcctcg ctcgcacccc tacaattttc ctgcaggctc gggggctct    3420 attctccgct cttcctccac cccgtgcagg gcacggtacc ggtggacttg gcatcaaggc    3480
aggaagaaga ggagcagtcg cccgactcca cagaggaaga accagtgact ctcccaaggc    3540
gcaccaccaa tgatggattc cacctgttaa aggcaggagg gtcatgcttt gctctaattt    3600
caggaactgc taaccaggta aagtgctatc gctttcgggt gaaaaagaac catagacatc    3660
gctacgagaa ctgcaccacc acctggttca cagttgctga caacggtgct gaaagacaag    3720
gacaagcaca atactgatc acctttggat cgccaagtca aggcaagac tttctgaaac    3780 atgtaccact acctcctgga atgaacattt ccggctttac agccagcttg gacttctgat    3840
cactgccatt gcctttctt catctgactg gtgtactatg ccaaatctat ggtttctatt    3900
gttcttggga ctagttgctg caatgcaact gctgctatta ctgttcttac tcttgttttt    3960
tcttgtatac tgggatcatt ttgagtgctc ctgtacaggt ctgccctttt aatgccttta    4020
catcactggc tattggctgt gttttactg ttgtgtggat ttgatttgtt ttatatactg    4080
tatgaagttt tttcatttgt gcttgtattg ctgtttgtaa gttttttact agagtttgta    4140 ttcccccctgc tcagatttta tatggtttaa gctgcagcaa taaaaatgag tgcacgaaaa    4200
agagtaaaac gtgccagtgc ctatgacctg tacaggacat gcaagcaagc gggcacatgt    4260
ccaccagatg tgataccaaa ggtagaagga gatactatag cagataaaat tttgaaattt    4320
gggggtcttg caatctactt aggagggcta ggaataggaa catggtctac tggaagggtt    4380
gctgcaggtg atcaccaag gtacacacca ctccgaacag cagggtccac atcatcgctt    4440
gcatcaatag gatccagagc tgtaacagca gggacccgcc ccagtatagg tgcgggcatt    4500
cctttagaca cccttgaaac tcttgggccc ttgcgtccag gggtgtatga ggacactgtg    4560
ctaccagagg cccctgcaat agtcactcct gatgctgttc ctgcagattc agggcttgat    4620
gccctgtcca taggtacaga ctcgtccacg gagaccctca ttactctgct agagcctgag    4680
ggtcccgagg acatagcggt tcttgagctg caaccctgg accgtccaac ttggcaagta    4740
```

```
agcaatgctg ttcatcagtc ctctgcatac cacgcccctc tgcagctgca atcgtccatt   4800
gcagaaacat ctggtttaga aaatattttt gtaggaggct cgggtttagg ggatacagga   4860
ggagaaaaca ttgaactgac atacttcggg tccccacgaa caagcacgcc ccgcagtatt   4920
gcctctaaat cacgtggcat tttaaactgg ttcagtaaac ggtactacac acaggtgccc   4980
acggaagatc ctgaagtgtt ttcatcccaa acatttgcaa acccactgta tgaagcagaa   5040
ccagctgtgc ttaagggacc tagtggacgt gttggactca gtcaggttta taaacctgat   5100
acacttacaa cacgtagcgg gacagaggtg ggaccacagc tacatgtcag gtactcattg   5160
agtactatac atgaagatgt agaagcaatc ccctacacag ttgatgaaaa tacacaggga   5220
cttgcattcg tacccttgca tgaagagcaa gcaggttttg aggagataga attagatgat   5280
tttagtgaga cacatagact gctacctcag aacacctctt ctacacctgt tggtagtggt   5340
gtacgaagaa gcctcattcc aactcaggaa tttagtgcaa cacggcctac aggtgttgta   5400
acctatggct cacctgacac ttactctgct agcccagtta ctgaccctga ttctacctct   5460
cctagtctag ttatcgatga cactactact acaccaatca ttataattga tgggcacaca   5520
gttgatttgt acagcagtaa ctacaccttg catccctcct tgttgaggaa acgaaaaaaa   5580
cggaaacatg cctaattttt tttgcagatg gcgttgtggc aacaaggcca gaagctgtat   5640
ctccctccaa cccctgtaag caaggtgctt tgcagtgaaa cctatgtgca agaaaaagc    5700 attttttatc atgcagaaac ggagcgcctg ctaactatag gacatccata ttacccagtg   5760
tctatcgggg ccaaaactgt tcctaaggtc tctgcaaatc agtatagggt atttaaaata   5820
caactacctg atcccaatca atttgcacta cctgacagga ctgttcacaa cccaagtaaa   5880
gagcggctgg tgtgggcagt cataggtgtg caggtgtcca gagggcagcc tcttggaggt   5940
actgtaactg ggcaccccac ttttaatgct ttgcttgatg cagaaaatgt gaatagaaaa   6000
gtcaccaccc aaacaacaga tgacaggaaa caaacaggcc tagatgctaa gcaacaacag   6060
attctgttgc taggctgtac ccctgctgaa ggggaatatt ggacaacagc ccgtccatgt   6120
gttactgatc gtctagaaaa tggcgcctgc cctcctcttg aattaaaaaa caagcacata   6180
gaagatgggg atatgatgga aattgggttt ggtgcagcca acttcaaaga aattaatgca   6240
agtaaatcag atctacctct tgacattcaa aatgagatct gcttgtaccc agactacctc   6300
aaaatggctg aggacgctgc tggtaatagc atgttctttt ttgcaaggaa agaacaggtg   6360
tatgttagac acatctggac cagagggggc tcggagaaag aagcccctac cacagatttt   6420
tatttaaaga ataataaagg ggatgccacc cttaaaatac ccagtgtgca ttttggtagt   6480
cccagtggct cactagtctc aactgataat caaattttta atcggcccta ctggctattc   6540
cgtgcccagg gcatgaacaa tggaattgca tggaataatt tattgttttt aacagtgggg   6600
gacaatacac gtggtactaa tcttaccata agtgtagcct cagatggaac cccactaaca   6660
gagtatgata gctcaaaatt caatgtatac catagacata tggaagaata taagctagcc   6720
tttatattag agctatgctc tgtggaaatc acagctcaaa ctgtgtcaca tctgcaagga   6780
cttatgccct ctgtgcttga aaattgggaa ataggtgtgc agcctcctac ctcatcgata   6840
ttagaggaca cctatcgcta tatagagtct cctgcaacta atgtgcaag caatgtaatt    6900 cctgcaaaag aagacccttta tgcagggttt aagttttgga acatagatct taaagaaaag   6960 cttttctttgg acttagatca atttcccttg ggaagaagat ttttagcaca gcaaggggca   7020
ggatgttcaa ctgtgagaaa acgaagaatt agccaaaaaa cttccagtaa gcctgcaaaa   7080
```

-continued

```
aaaaaaaaaa aataaaagct aagtttctat aaatgttctg taaatgtaaa acagaaggta    7140
agtcaactgc acctaataaa aatcacttaa tagcaatgtg ctgtgtcagt tgtttattgg    7200
aaccacaccc ggtacacatc ctgtccagca tttgcagtgc gtgcattgaa ttattgtgct    7260
ggctagactt catggcgcct ggcaccgaat cctgccttct cagcgaaaat gaataattgc    7320
tttgttggca agaaactaag catcaatggg acgcgtgcaa agcaccggcg gcggtagatg    7380
cggggtaagt actgaatttt aattcgacct atcccggtaa agcgaaagcg acacgctttt    7440
ttttcacaca tagcgggacc gaacacgtta taagtatcga ttaggtctat ttttgtctct    7500
ctgtcggaac cagaactggt aaaagtttcc attgcgtctg gcttgtcta tcattgcgtc     7560 tctatggttt ttggaggatt agacggggcc accagtaatg gtgcatagcg gatgtctgta    7620
ccgccatcgg tgcaccgata taggtttggg gctccccaag ggactgctgg gatgacagct    7680
tcatattata ttgaatgggc gcataatcag cttaattggt gaggacaagc tacaagttgt    7740
aacctgatct ccacaaagta cgttgccggt cggggtcaaa ccgtcttcgg tgctcgaaac    7800
cgccttaaac tacagacagg tcccagccaa gtaggcggat caaaacctca aaaaggcggg    7860
agccaatcaa aatgcagcat tatattttaa gctcaccgaa accggtaagt aaagactatg    7920
tattttttcc cagtgaataa ttgtt                                          7945
```

<210> SEQ ID NO 50
<211> LENGTH: 306
<212> TYPE: PRT
<213> ORGANISM: bovine papillomavirus type 1

<400> SEQUENCE: 50

```
Met Glu Thr Ala Cys Glu Arg Leu His Val Ala Gln Glu Thr Gln Met
 1               5                  10                  15

Gln Leu Ile Glu Lys Ser Ser Asp Lys Leu Gln Asp His Ile Leu Tyr
            20                  25                  30

Trp Thr Ala Val Arg Thr Glu Asn Thr Leu Leu Tyr Ala Ala Arg Lys
        35                  40                  45

Lys Gly Val Thr Val Leu Gly His Cys Arg Val Pro His Ser Val Val
    50                  55                  60

Cys Gln Glu Arg Ala Lys Gln Ala Ile Glu Met Gln Leu Ser Leu Gln
65                  70                  75                  80

Glu Leu Ser Lys Thr Glu Phe Gly Asp Glu Pro Trp Ser Leu Leu Asp
                85                  90                  95

Thr Ser Trp Asp Arg Tyr Met Ser Glu Pro Lys Arg Cys Phe Lys Lys
            100                 105                 110

Gly Ala Arg Val Val Glu Val Glu Phe Asp Gly Asn Ala Ser Asn Thr
        115                 120                 125

Asn Trp Tyr Thr Val Tyr Ser Asn Leu Tyr Met Arg Thr Glu Asp Gly
    130                 135                 140

Trp Gln Leu Ala Lys Ala Gly Ala Asp Gly Thr Gly Leu Tyr Tyr Cys
145                 150                 155                 160

Thr Met Ala Gly Ala Gly Arg Ile Tyr Tyr Ser Arg Phe Gly Asp Glu
                165                 170                 175

Ala Ala Arg Phe Ser Thr Thr Gly His Tyr Ser Val Arg Asp Gln Asp
            180                 185                 190

Arg Val Tyr Ala Gly Val Ser Ser Thr Ser Ser Asp Phe Arg Asp Arg
        195                 200                 205

Pro Asp Gly Val Trp Val Ala Ser Glu Gly Pro Glu Gly Asp Pro Ala
    210                 215                 220
```

```
Gly Lys Glu Ala Glu Pro Ala Gln Pro Val Ser Ser Leu Leu Gly Ser
225                 230                 235                 240

Pro Ala Cys Gly Pro Ile Arg Ala Gly Leu Gly Trp Val Arg Asp Gly
            245                 250                 255

Pro Arg Ser His Pro Tyr Asn Phe Pro Ala Gly Ser Gly Ser Ile
            260                 265                 270

Leu Arg Ser Ser Ser Thr Pro Cys Arg Ala Arg Tyr Arg Trp Thr Trp
            275                 280                 285

His Gln Gly Arg Lys Lys Arg Ser Ser Arg Pro Thr Pro Gln Arg Lys
    290                 295                 300

Asn Gln
305

<210> SEQ ID NO 51
<211> LENGTH: 622
<212> TYPE: DNA
<213> ORGANISM: Human herpesvirus 4

<400> SEQUENCE: 51
gggtatcata tgctgactgt atatgcatga ggatagcata tgctacccgg atacagatta      60
ggatagcata tactacccag atatagatta ggatagcata tgctacccag atatagatta     120
ggatagccta tgctacccag atataaatta ggatagcata tactacccag atatagatta     180
ggatagcata tgctacccag atatagatta ggatagccta tgctacccag atatagatta     240
ggatagcata tgctacccag atatagatta ggatagcata tgctatccag atatttgggt     300
agtatatgct acccagatat aaattaggat agcatatact accctaatct ctattaggat     360
agcatatgct acccggatac agattaggat agcatatact acccagatat agattaggat     420
agcatatgct acccagatat agattaggat agcctatgct acccagatat aaattaggat     480
agcatatact acccagatat agattaggat agcatatgct acccagatat agattaggat     540
agcctatgct acccagatat agattaggat agcatatgct atccagatat ttgggtagta     600
tatgctaccc atggcaacat ta                                              622

<210> SEQ ID NO 52
<211> LENGTH: 641
<212> TYPE: PRT
<213> ORGANISM: Human herpesvirus 4

<400> SEQUENCE: 52

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Ser Gly Pro Gln
            20                  25                  30

Arg Arg Gly Gly Asp Asn His Gly Arg Gly Arg Gly Arg Gly Arg Gly
            35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly
            100                 105                 110

Gly Gly Ala Gly Gly Ala Gly Gly Ala Gly Gly Ala Gly Ala Gly Gly
```

```
                115                 120                 125
Gly Ala Gly Ala Gly Gly Ala Gly Ala Gly Gly Ala Gly Ala
    130                 135                 140
Gly Gly Gly Ala Gly Ala Gly Gly Ala Gly Ala Gly Ala Gly
145                 150                 155                 160
Gly Gly Ala Gly Gly Ala Gly Ala Gly Ala Gly Gly Ala Gly
                165                 170                 175
Ala Gly Gly Gly Ala Gly Gly Ala Gly Ala Gly Gly Ala Gly
                180                 185                 190
Ala Gly Gly Ala Gly Ala Gly Gly Ala Gly Ala Gly Gly Ala Gly
                195                 200                 205
Gly Ala Gly Gly Ala Gly Ala Gly Gly Ala Gly Ala Gly Gly Ala
    210                 215                 220
Gly Gly Ala Gly Gly Ala Gly Ala Gly Gly Ala Gly Ala Gly Ala
225                 230                 235                 240
Gly Ala Gly Gly Ala Gly Ala Gly Gly Ala Gly Ala Gly Ala Gly
                245                 250                 255
Gly Ala Gly Gly Ala Gly Ala Gly Gly Ala Gly Ala Gly Ala Gly
            260                 265                 270
Gly Gly Ala Gly Gly Ala Gly Ala Gly Gly Ala Gly Gly Ala Gly
        275                 280                 285
Ala Gly Gly Ala Gly Gly Ala Gly Ala Gly Gly Ala Gly Ala Gly
    290                 295                 300
Ala Gly Gly Ala Gly Gly Ala Gly Ala Gly Gly Ala Gly Ala Gly
305                 310                 315                 320
Gly Ala Gly Ala Gly Gly Gly Gly Arg Gly Arg Gly Gly Ser Gly Gly
                325                 330                 335
Arg Gly Arg Gly Gly Ser Gly Gly Arg Gly Arg Gly Gly Ser Gly Gly
                340                 345                 350
Arg Arg Gly Arg Gly Arg Glu Arg Ala Arg Gly Gly Ser Arg Glu Arg
            355                 360                 365
Ala Arg Gly Arg Gly Arg Gly Arg Gly Glu Lys Arg Pro Arg Ser Pro
    370                 375                 380
Ser Ser Gln Ser Ser Ser Gly Ser Pro Arg Arg Pro Pro Pro
385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
                420                 425                 430
Ala Ile Glu Gln Gly Pro Ala Asp Asp Pro Gly Glu Gly Pro Ser Thr
                435                 440                 445
Gly Pro Arg Gly Gln Gly Asp Gly Gly Arg Arg Lys Lys Gly Gly Trp
    450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
                500                 505                 510
Ser Lys Thr Ser Leu Tyr Asn Leu Arg Arg Gly Thr Ala Leu Ala Ile
            515                 520                 525
Pro Gln Cys Arg Leu Thr Pro Leu Ser Arg Leu Pro Phe Gly Met Ala
    530                 535                 540
```

```
                                          -continued

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
            580                 585                 590

Ile Arg Val Thr Val Cys Ser Phe Asp Asp Gly Val Asp Leu Pro Pro
        595                 600                 605

Trp Phe Pro Pro Met Val Glu Gly Ala Ala Ala Glu Gly Asp Asp Gly
        610                 615                 620

Asp Asp Gly Asp Glu Gly Gly Asp Gly Asp Glu Gly Glu Glu Gly Gln
625                 630                 635                 640

Glu
```